US012431216B2

(12) United States Patent
Shmakov et al.

(10) Patent No.: US 12,431,216 B2
(45) Date of Patent: Sep. 30, 2025

(54) METHODS FOR IDENTIFYING CLASS 2 CRISPR-CAS SYSTEMS

(71) Applicants: THE BROAD INSTITUTE, INC., Cambridge, MA (US); MASSACHUSETTS INSTITUTE OF TECHNOLOGY, Cambridge, MA (US); RUTGERS, THE STATE UNIVERSITY OF NEW JERSEY, New Brunswick, NJ (US); THE UNITED STATES OF AMERICA, AS REPRESENTED BY THE SECRETARY, DEPARTMENT OF HEALTH AND HUMAN SERVICES, Bethesda, MD (US)

(72) Inventors: Sergey Shmakov, Moscow (RU); Kira S. Makarova, Bethesda, MD (US); Yuri I. Wolf, Bethesda, MD (US); Aaron Smargon, Cambridge, MA (US); Neena Pyzocha, Cambridge, MA (US); David Cox, Cambridge, MA (US); Winston Yan, Brookline, MA (US); David Scott, Cambridge, MA (US); Konstantin Severinov, Piscataway, NJ (US); Feng Zhang, Cambridge, MA (US); Eugene V. Koonin, Bethesda, MD (US)

(73) Assignees: Broad Institute, Inc., Cambridge, MA (US); Massachusetts Institute of Technology, Cambridge, MA (US); Rutgers, The State University of New Jersey, New Brunswick, NJ (US); The United States of America, as represented by the Secretary, Department of Health and Human Services, Bethesda, MD (US)

( * ) Notice: Subject to any disclaimer, the term of this patent is extended or adjusted under 35 U.S.C. 154(b) by 318 days.

(21) Appl. No.: 16/326,132

(22) PCT Filed: Aug. 16, 2017

(86) PCT No.: PCT/US2017/047193
§ 371 (c)(1),
(2) Date: Feb. 15, 2019

(87) PCT Pub. No.: WO2018/035250
PCT Pub. Date: Feb. 22, 2018

(65) Prior Publication Data

US 2021/0166783 A1 Jun. 3, 2021

Related U.S. Application Data

(60) Provisional application No. 62/376,387, filed on Aug. 17, 2016.

(51) Int. Cl.
*C12N 9/22* (2006.01)
*C12N 15/11* (2006.01)
(Continued)

(52) U.S. Cl.
CPC ............... *G16B 20/20* (2019.02); *C12N 9/22* (2013.01); *C12N 15/11* (2013.01); *G16B 30/10* (2019.02);
(Continued)

(58) Field of Classification Search
None
See application file for complete search history.

(56) References Cited

U.S. PATENT DOCUMENTS 8,697,359 B1 4/2014 Zhang
8,771,945 B1 7/2014 Zhang
(Continued)

FOREIGN PATENT DOCUMENTS

EP 2 784 162 A1 10/2014
EP 2 771 468 B1 2/2015
(Continued)

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
(Continued)

*Primary Examiner* — Richard G Hutson
(74) *Attorney, Agent, or Firm* — F. Brent Nix, Esq.; Johnson, Marocu, Isaacs & Nix, LLC; Drew P. Harding

(57) ABSTRACT

Disclosed here is a method of identifying novel CRISPR effectors, comprising: identifying sequences in a genomic or
(Continued)

metagenomic database encoding a CRISPR array; identifying one or more Open Reading Frames (ORFs) in said selected sequences within 10 kb of the CRISPR array; discarding all loci encoding proteins which are assigned to known CRISPR-Cas subtypes and, optionally, all loci encoding a protein of less than 700 amino acids; and identifying putative novel CRISPR effectors, and optionally classifying them based on structure analysis.

6 Claims, 25 Drawing Sheets

Specification includes a Sequence Listing.

(51) Int. Cl.

| | |
|---|---|
| ***G16B 20/20*** | (2019.01) |
| ***G16B 30/10*** | (2019.01) |
| ***G16B 40/30*** | (2019.01) |

(52) U.S. Cl.

CPC .......... *G16B 40/30* (2019.02); *C12N 2310/20* (2017.05); *C12N 2800/80* (2013.01)

(56) References Cited

U.S. PATENT DOCUMENTS

| | | | |
|---|---|---|---|
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |
| 8,999,641 | B2 | 4/2015 | Zhang et al. |
| 10,815,730 | B2 | 10/2020 | Liu et al. |
| 11,041,173 | B2 | 6/2021 | Zhang et al. |
| 2004/0171156 | A1 | 9/2004 | Hartley et al. |
| 2011/0265198 | A1 | 10/2011 | Gregory et al. |
| 2012/0017290 | A1 | 1/2012 | Cui et al. |
| 2013/0236946 | A1 | 9/2013 | Gouble |
| 2014/0170753 | A1 | 6/2014 | Zhang |
| 2014/0179006 | A1 | 6/2014 | Zhang |
| 2014/0179770 | A1 | 6/2014 | Zhang et al. |
| 2014/0186843 | A1 | 7/2014 | Zhang et al. |
| 2014/0186919 | A1 | 7/2014 | Zhang et al. |
| 2014/0186958 | A1 | 7/2014 | Zhang et al. |
| 2014/0189896 | A1 | 7/2014 | Zhang et al. |
| 2014/0227787 | A1 | 8/2014 | Zhang |
| 2014/0234972 | A1 | 8/2014 | Zhang |
| 2014/0242664 | A1 | 8/2014 | Zhang et al. |
| 2014/0242699 | A1 | 8/2014 | Zhang |
| 2014/0242700 | A1 | 8/2014 | Zhang et al. |
| 2014/0248702 | A1 | 9/2014 | Zhang et al. |
| 2014/0256046 | A1 | 9/2014 | Zhang et al. |
| 2014/0273231 | A1 | 9/2014 | Zhang et al. |
| 2014/0273232 | A1 | 9/2014 | Zhang et al. |
| 2014/0273234 | A1 | 9/2014 | Zhang et al. |
| 2014/0287938 | A1 | 9/2014 | Zhang et al. |
| 2014/0310830 | A1 | 10/2014 | Zhang et al. |
| 2015/0247150 | A1 | 9/2015 | Zhang et al. |
| 2015/0291965 | A1 | 10/2015 | Zhang et al. |
| 2016/0251648 | A1 | 9/2016 | Wang et al. |
| 2017/0198269 | A1 | 7/2017 | Zhang et al. |
| 2017/0349894 | A1 | 12/2017 | Dahlman et al. |
| 2017/0349914 | A1 | 12/2017 | Cox et al. |
| 2018/0010134 | A1 | 1/2018 | Sharp et al. |
| 2018/0044662 | A1 | 2/2018 | Platt et al. |
| 2018/0057810 | A1 | 3/2018 | Zhang et al. |
| 2019/0203212 | A1 | 7/2019 | Zhang et al. |
| 2019/0330605 | A1 | 10/2019 | Zhang et al. |
| 2020/0318123 | A1 | 10/2020 | Zhang |
| 2020/0354751 | A1 | 11/2020 | Zhang et al. |

FOREIGN PATENT DOCUMENTS

| | | | | |
|---|---|---|---|---|
| EP | 2 764 103 | B1 | 8/2015 | |
| WO | WO-2012164565 | A1 * | 12/2012 | .......... C07K 14/195 |
| WO | 2014/018423 | A2 | 1/2014 | |
| WO | 2014/093595 | A1 | 6/2014 | |
| WO | 2014/093622 | A2 | 6/2014 | |
| WO | 2014/093635 | A1 | 6/2014 | |
| WO | 2014/093655 | A2 | 6/2014 | |
| WO | 2014/093661 | A2 | 6/2014 | |
| WO | 2014/093694 | A1 | 6/2014 | |
| WO | 2014/093701 | A1 | 6/2014 | |
| WO | 2014/093709 | A1 | 6/2014 | |
| WO | 2014/093712 | A1 | 6/2014 | |
| WO | 2014/093718 | A1 | 6/2014 | |
| WO | 2014/204723 | A1 | 12/2014 | |
| WO | 2014/204724 | A1 | 12/2014 | |
| WO | 2014/204725 | A1 | 12/2014 | |
| WO | 2014/204726 | A1 | 12/2014 | |
| WO | 2014/204727 | A1 | 12/2014 | |
| WO | 2014/204728 | A1 | 12/2014 | |
| WO | 2014/204729 | A1 | 12/2014 | |
| WO | 2015/065964 | A1 | 5/2015 | |
| WO | 2018/035250 | A1 | 2/2018 | |

OTHER PUBLICATIONS

Stella et al. (Nature Structural & Molecular Biology, vol. 24 No. 11, pp. 882-892, Nov. 2017).*

Doggett et al., GenBank: AFQ19722.1. Jul. 26, 2016.*

Database EMBL [OnLine], "*Synechococcus* sp. JA-3-3Ab ISSoc2, transposase", Feb. 7, 2006, XP055423485, retrieved from EBI accession No. EMBL:ABC98938, 2 pages.

Rahmatabadi et al., "Studying the features of 57 confirmed CRISPR loci in 29 strains of *Escherichia coli*", Journal of Basic Microbiology 2016, vol. 56, No. 6, Feb. 12, 2016, pp. 645-653.

Shmakov et al., "Discovery and Functional Characterization of Diverse Class 2 CRISPR-Cas Systems", Molecular Cell, vol. 60, No. 3, Nov. 1, 2015, pp. 385-397.

The Broad Institute, Inc., "Communication pursuant to Article 94(3) EPC for EP 17764475.4", May 14, 2021, 3 pages.

The Broad Institute, Inc., "Communication Pursuant to Rule 164(2)(b) and Article 94(3) EPC for EP 17764475.4", Jun. 25, 2020, 8 pages.

Shmakov, et al., "Diversity and Evolution of Class 2 CRISPR-Cas Systems", Nature Reviews, Microbiology, vol. 15, No. 3, Mar. 2017, pp. 169-182.

Shmakov, et al., "Supplementary Information S3 (figure). Multiple Alignment of Representatives from Five V-U Families", Nature Reviews, Microbiology, vol. 15, No. 3, Jan. 2017, 17 pages.

The Broad Institute, Inc. "International Preliminary Report on Patentability received in PCT Application No. PCT/US2017/047193", mailed on Feb. 28, 2019, 11 pages.

The Broad Institute, Inc. "International Search Report & Written Opinion received in PCT Application No. PCT/US2017/047193", mailed on Nov. 18, 2018, 15 pages.

Chung, et al., "Polycistronic RNA polymerase II Expression Vectors for RNA Interference Based on BIC/miR-155", Nucleic Acids Research, vol. 34, No. 7, e53, Apr. 13, 2006, 14 pages.

Shmakov, et al., "Discovery and functional characterization of diverse Class 2 CRISPR-Cas systems", Mol Cell. 60(3), 2015, pp. 385-397.

Gao, et al., "Type V CRISPR-Cas Cpf1 endonuclease employs a unique mechanism for crRNA-mediated target DNA recognition", Cell Res 2016, 26, 901-913.

* cited by examiner

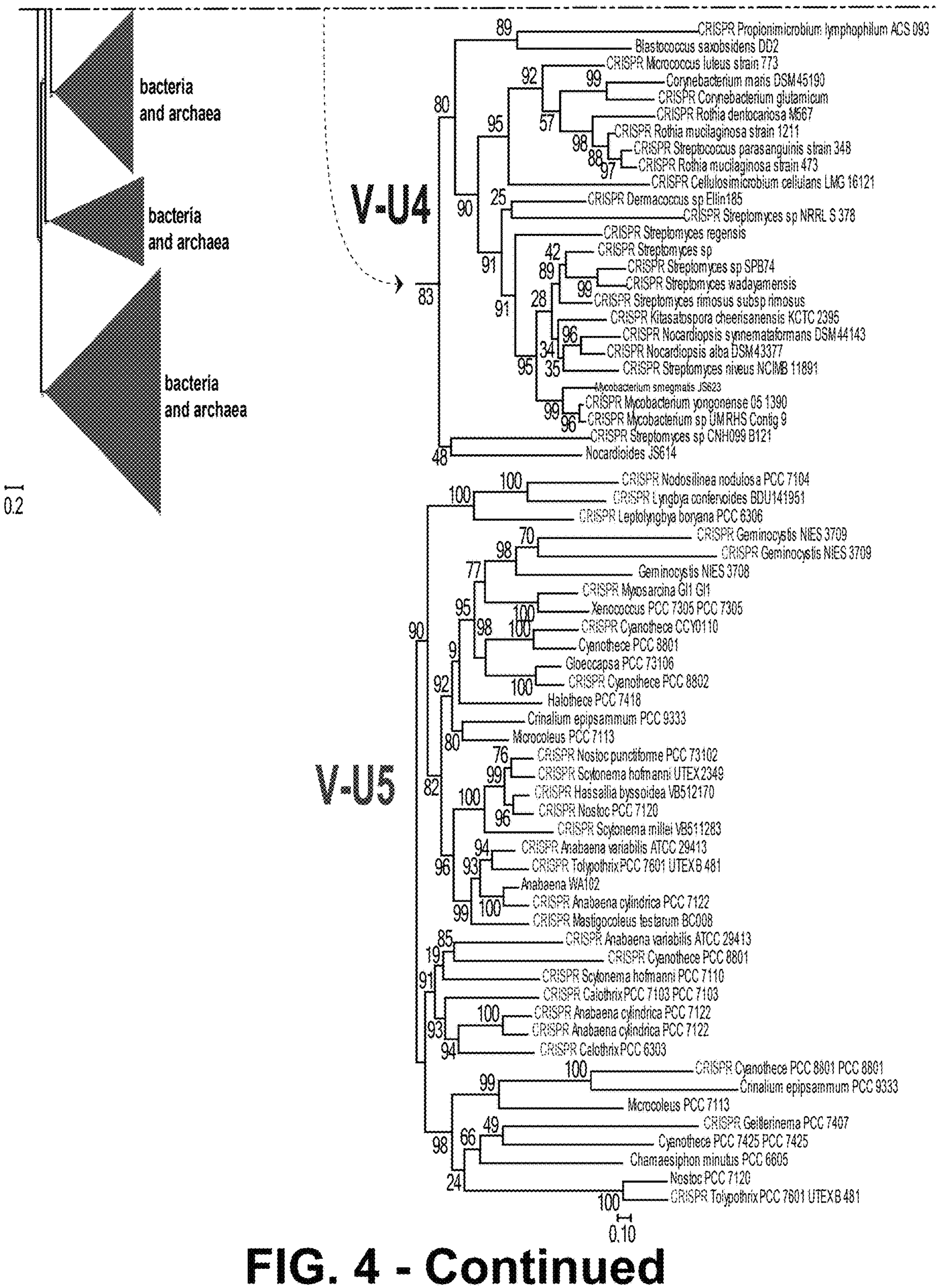
FIG. 4 - Continued

| | | nuclease domains | tracrRNA | PAM | substrate | cleavage pattern |
|---|---|---|---|---|---|---|
| Type II Cas9 |  | TnpB/ RuvC+HNH | yes | 3′, GC-rich | dsDNA | blunt ends |
| Type V-A Cas12a (Cpf1) |  | TnpB/ RuvC+Nuc | no | 5′, AT-rich | dsDNA | staggered ends, 5′ overhangs |
| Type V-B Cas12b (C2c1) |  | TnpB/ RuvC+? | yes | 5′, AT-rich | dsDNA | ? |
| Type VI-A Cas13a (C2c2) |  | 2xHEPN | no | 5′, non-G PFSa | ssRNA | cleaves ssRNA near uracil + collateral activity |

V-U1 family

```
1903609002 -----------------------------------------------------MT 2
1024922355 -----------------------------------------------------MT 2
1096423661 ------------------------------------------------------M 1
 118577413 MKRVTITIDGEQTKGIVIGTIAANHTAAEWLLTASVSAKSAKVRFDFEEAVAETS---SL 57
1003450287 ---------------------------------------MPFGKKARHVKAY---QF 15
1507071745 -------------------------------------------METAATKNYLALSF 14
 488601079 -------------------------------------------------------- 0
 297565028 -------------------------------------------------------- 0
 257060308 -------------------------------------------------------- 0

1903609002 TMTVHTMGVHY-----------------------KW----QIPEVLRQQLWLAHNLRE 33
1024922355 RVTVQTAGVHY-----------------------KW----QMPDQLTQQLRLAHDLRE 33
1096423661 AITVHTAGVHY-----------------------RW--TDNPPEQLMRQLRLAHDLRE 34
 118577413 VMIAPTRTEKYLYLVPDEQVQPVTTIVRKYGLLSPLDWDCPDYFAGDAFEHLFLQNKLWN 117
1003450287 GADAPQEGMEAV---------------------------------LEQHRLRTDYYN 39
1507071745 GCLSPTRGEEYL---------------------------------LDQIKKKHDLWN 38
 488601079 -------------------------------------------------------- 0
 297565028 -------------------------------------------------------- 0
 257060308 -------------------------------------------------------- 0

1903609002 DLVSLQLAYDDDLKAIWSCYPDVAQAEDTMAAAEADAVALSERVKQARIEARSKKISTE- 92
1024922355 DLVTLEYEYEDAVKAVWSCYPAVAALEAQVAELDERASELASTVKEEKSRQRTKRPSHP- 92
1096423661 DLVTLQLDYETAKAGIWSCYPAVAAAETELADAESAAEQAAAAVSEERTKLRTKRITGP- 93
 118577413 DLVTIEREHRAKYRELIGCDEETAQMDTEIASIKDRLSVLDEGRKKLRVEHRKKKCPEID 177
1003450287 ALVEMELRQREE-RTALLCNLAAES------GLESPNQVYERLKAA--GEKGIRKHPEYV 90
1507071745 KLVEKDREHREKVRQVMVFESETTK------KIKELEEELNSLREEIKNQRKTKRTGKVD 92
 488601079 ---------------MLICYRFRIYPS---------------------------------- 12
 297565028 --------------MSLLCVKCKLIPDA---------ST-------------------- 16
 257060308 ---------------MLECQPITVACKL---------QV-------------------- 15

1903609002 ---LTQQLRDAKKRLKDARQARRDAIAVVKDDAAERRKARSDQLAADQKACYGQYCRDGD 149
1024922355 ---AVAQLAETRAQLKAAKASRREAIASVRDEATERLRTISDERYAAQKQCYRDYCTDGL 149
1096423661 ---LAQKLTAARKRVKEARSTRRAAISEVHEEAKGRLVDASDALKAQQKACYKTYCQDGD 150
 118577413 CLDENIKKL--KSELKAVASKAKETRAAAKDRIRAAGNDIENLEKDRQAACIKAYN-NSG 234
1003450287 AARERQKALYGHPRLLELQSRQREERN---------------------ACRRSFG-AKG 127
1507071745 LTDQKARIEEIKPQLKQLKEKFKEERSFI---FEARKQELAQLEKER-WACVKELGKGSG 148
 488601079 -----------------------------------------KTVQAKCNEQLELC-- 26
 297565028 ----------------------------------------AEKLSRTCNQFANAC-- 31
 257060308 ------------------------------------ANTLAKEIDETCMVFACAC-- 34

1903609002 LYCASFNTVLDHHKTAVKRIAAQRASGKPATLCHHRFD-GSGTIAVQLQRQAGAPPRTPM 208
1024922355 LYCATFNAVLDHHKTAVKRIAAHRKQGRAAQLCHHRWD-GTGTISVQLQRQATDPARTPA 208
1096423661 LFCATFNDVLDHHKAAVKRIGQMRAAGQPAQLCHHRFD-GTGSIAVQLQRQAGQPQRTPE 209
 118577413 LWCGNYNAVLESYKKA--RIKA---LKDGAELCYHRFD-GSGRFTNQIQG--GMSVQD-- 264
1003450287 LYSSNYLDVERAFDKA--RQSP---------ELCFRRYSPHEGRLAVLYTE--GLPMRE-- 173
1507071745 LYCCNLEDVVNSYDIG--KKKA---KAAGGEMCFHRWD-GTGKVTVRFQK--GLPVNE-- 198
 488601079 -RC-LYNRLLSEVNKA-----------RKEGRCIRRED--TQSLIVRIKR-----EEKPE 66
 297565028 -NC-------ALQVARR-----------DNIWNCF---A--LQRAVYADLR-----AEY-- 61
 257060308 -DC--------VNQNTP-----------EKMTNCT---A--MQSLVYQDVR-----VNF-- 63

1903609002 VLADEA-GKYRNVLH------I---------------PGWTDPDVWEQMTRSQCRQSGRV 246
```

FIG. 9

```
1024922355 IIADADTGKWRSSLI------V---------------P-WVNPDVWDTMDRASRRKAGRV 246
1096423661 LIADVD-GKYGRVLS------V---------------P-WVQPDRWERIFRRERRMIGRV 246
 118577413 LL-----EGNRNVAS------LRLVSSGELGDISGKKF--PSLDLQSVGSRRDSREYGIL 331
1003450287 IG-----SDTRVQL-----------------------P--LPDPIIYRD-RATRRKHQRV 202
1507071745 MF-----SCTNNLLQ------I--------------DP--VDKDAWYNPVRAIRRKKSRT 231
 488601079 LS-----KVYSKVLQMVNYQLRSNISSLNELKKKGVKVGWLRYKTSPNSFXTLNFNQSGF 121
 297565028 ----------GLSANLAIRAI------ARVGKRKGHKAGGFKATSVDYDQRILSVNVDTE 105
 257060308 ----------GLSSNLAIQAIRRVCANRKTAKQKGKKVKEFKPTSISYDARIFSFRESDW 113

1903609002 TXRMRCGST-----DGQPQW---IDLPXQVHRWLPADADITGAEXVVTXVXGIYRAKXCX 298
1024922355 VXRMRCGSSRNPDGTKTSEW---IDVPXQQHRMLPADADITAAQXTVRXEXADLRATXSX 303
1096423661 TXRMRAGQL-----SGEPQW---LDIPXQQHRMLPLDADITGARXTVTXTXGTLRAQXSX 298
 118577413 AXTLYTGTD-----EQSKKFRRTLSFPXILHRPLPEGATLKSLSXHRRXVXTDFVWSXVF 386
1003450287 LXKFRVRSV-----ERQPLW---ITVPXYLHRELPDG-VCREVSXHWHXVXDRLRWTXSX 253
1507071745 RXRLRACSE-----NKKPLF---IELPXVLHREIPEDALIRTASXIREXVXMRYRYKXNX 283
 488601079 KX-----D---FDRK-KLSLSKVGDIPXRLHRSI--GGKIKGVIXKRTXSX---KWYAIX 167
 297565028 TX-----SLSTVDGRVKVPMRIAG-YQRELLRTA--KSIQGGQ-XVRGXDX---SWYXHX 153
 257060308 TX-----SVKLLNSRQRIKL-LIGNYQXGLLXSK--NPTSAT--XVKRXSX---NYYXHX 160

1903609002 TARIGDTEPVT----SGP-TVXXHLGWRS-TEEGTAVXTWRSDAPLDIPFGLRTVMRVDA 352
1024922355 TAKIPDQGEVD----EGP-TIXXHLGWRS-SDHGTVVXTWRSTEPLDIPETLRGVITTQS 357
1096423661 TAKIPDPEPVT----DGP-DVXXHLGWRN-TDTGVRVXRWRSTEPIEVPFDFRDTLTVDF 352
 118577413 TFTTDCP-TYDQRSSTGN-RCXXNLGWKKQAGGGLRVXT-I-----------------YD 426
1003450287 VVEVEGP-PVA--SPTGRGAVXXDLGWRR-VEGGLRAXFWV-----------------GE 292
1507071745 VLEILGE-NTNRILPALEGTAXXDLGWRT-VKDGLRVXCLV-----------------DD 324
 488601079 QAEVDKQ-FLP---PTGK-AIXXDVGITH-------FCV-------------------DS 196
 297565028 WCEYDDP-PVL---DPQG-MLXXDLGIVN-------IXT-------------------DS 182
 257060308 TLDEPTQ-PEA---KTDK-VLXXDLGRTD-------IXT-------------------TS 189

1903609002 AXTS-GIIVVPATXERRLTXTE-NIASSRSLALDALRDKXVGWXSDNDA---PTYRDAPL 407
1024922355 AERTVGSIVVPHRXEQRVHXHA-TVASHRDLAVDSIRDTXVAWXTEHGPQPHP-YDGDPI 415
1096423661 GXRS-GEIFVPEAXPRRVEXAH-LIASHRADRMNELRARXVDYXAETGPRPHPSREGEEL 410
 118577413 GXDA-RHITLPQAXIDGLDYVNGDLQGRIDSAANENHAWXLEQWGG---DELP--ESLQE 480
1003450287 DXAG-GEIALSEGDLKQFSXVE-DLRSIRDQHLNALKEAXAAWXEA-PPAPLP--DWLAE 347
1507071745 KXHS-EELILDNDXLHEFNXIK-DLQSIRDNLFNETKAKXMELXKT---LELP--DEAKE 377
 488601079 DXNYFEH---PKYXDRTLEX----------------IKKXQKQXSRKQ---------K-- 226
 297565028 DXETYSG----KHXNSVRHX----------------HRRXRKKXQKKG------------ 210
 257060308 EXESWSG----KQXTAKRNX----------------YAKXRTTXQKKA---------SKG 220

1903609002 EAATVKQWK--SPQRFASLAHAWKDN----GTEISDILWAWFSLDRXQWAQQENGRRKAL 461
1024922355 TAASVQRWK--APRRFAWLALQWRDTPPPEGADIAETLEAWRRADKXLWLESEHGRGRAL 473
1096423661 GAGNVRMWK--SPNRFAWLARVWADDESV-STDIREALAQWRHQDWISWHHQEGGRRRSA 467
 118577413 LRSMLRRSKRPHPAKFAKAVIAWRNYPEYLGDARDEA-EQRRKATKXLTIEMAHKREKLL 539
1003450287 ETKTLPQWR--SPARFAALFRRWQSERVHADEAAYGLLEGWHKRDRXLWQYEANLREQMI 405
1507071745 RTSHMANWR--SQQKMLRLHQYWREMRLPGDDEVWEVLEYWRKREIXLYEWQENLRDQVL 435
 488601079 GSKN----------------------------------------REXVRIGLAKLYEKLE 246
 297565028 TKGA----------------------------------------RRX----LKKLSGKET 226
 257060308 TRSS----------------------------------------RPXCRQLLARLSGKER 240

1903609002 GHRDDLYXQIXAVISDQA----GHXLXXXTS-XAELSARA--MERT-ELPTEVQQKIDRR 513
1024922355 RHRTDLHXQVXAYFAGVA----GRXVXXXSD-XAQIAGTA---KHS-ELLTDVDRQIARR 524
1096423661 AQRLDVYXQVXAVLVSQA----GRXVXXXTS-YADIAQRSATTKTE-ELPNETAARINRR 521
 118577413 RRRMDFYXNTXKQLTSVY----DVXCXXKMD-X-R---RLALLEKGDGTPNELTKIARKQ 590
1003450287 LRRREQYXVLXATLARQY----DAXIYXXFN-X-R---AAAELDQG-G--SDLPDAARRY 453
1507071745 RRRKEIYXIFXAKITRKY----KTXVLXXFT-XNK---TVQKPNPEEGPAGTLP--ANRN 485
 488601079 NQRNDFLXKLXRYYVNNY----DIXVXXXLN-XKE---MA---EN--GSSTT----LNRH 289
 297565028 RFSNHVNXTLXKRIVAKAQRTERAXAXXXLQGXRE---RV---RL--RRPQ--------R 270
 257060308 RFQKHINXEIXRQLVNNAVTNKQAXAXXXLTGXRE---RT---N---RKPRS----KKDK 287

1903609002 RDHAXP--GGLRASXVAAMTRDGVPVTIVAAADFTRTHSRCGHVN---PADDRYLSNPVR 568
1024922355 RAIAXF--GMLRAAXVAAATRDEVPTTTVSHTGLSRVHAACGHEN---PADDRYLMQPVL 579
1096423661 RAHAXF--GELRQTXVAAADRDAVPVDTVSHTGVSVVHAKCGHEN---PSDGRFMSVVVA 576
 118577413 RQQAXI--SELRECXSKAAAKNGTQIEQVSTA-SSATCSACKGKM--EQVDGI----MWR 641
1003450287 RTIAXP--STLRDAXVNAFAQRGKPVRKXNPAHTTTDCHACGGALVGDPAKEL----RLY 507
```

FIG. 9 - Continued

```
1507071745 RFIANI--SEFRNECANACRKNHVEFTYVPAENTTITCHKCGHKEKFDAAAQI----IHT 539
488601079  ITDSNWSKFV--RLCCEKAEKAARTVVKVNPKNTSKRCAMCGYIVNNLKLHDR----TFT 343
297565028  ATLHNWAFFDLGQKCRYKAERAGVPLVFVDPRNTSRQCPACGHAERANRPTQA----LFR 326
257060308  RLGNNWAFYQLRQFCTYKCILAGVKLILVNPAYTSLSCHKCLVIGDR---KGK----GFS 340

1903609002 CDGCGAMYDQCRSFVTLWLRAHTAPSNP-------------------------------- 596
1024922355 CDGCGRTYDTCLSWTILWLQRHSAATSN-------------------------------- 607
1096423661 CDGCGEKYDQCESWLTHWLTRHVQSAA--------------------------------- 603
118577413  CRECRALVDQCINWAANWFREVL------------------------------------- 664
1003450287 CPTCERFYDQCENWARNWLRRHQEVQAQV------------------------------- 536
1507071745 CSTCGELWDQCYNWAKNWLAFHQKGGVK-------------------------------- 567
488601079  CPICGWEAHRCYNWSLNWLDVHMGRSRTPVEGEPLPCVISYR-EVIAGQVLSMKQEVPSV 402
297565028  CVACGYSGAACYVWAVNWAVKHWAAVNRP--YLGEASRVSLH------------GSVPGS 372
257060308  CNNCGNKCHACYNWAQNWKALHAIINRPG--GSGLSCKLKTNVQYIQLSLFEGLGLLKTS 398

1903609002 ---                                                          596
1024922355 ---                                                          607
1096423661 ---                                                          603
118577413  ---                                                          664
1003450287 ---                                                          536
1507071745 ---                                                          567
488601079  RAE                                                          405
297565028  PRL                                                          375
257060308  TSA                                                          401
```

V-U2 family

```
1046552329 ------------MAWKVFEFWIYPH---------KDFQEQFNRWAYGLKKFYNFCLQQFELL 41
1019491369 ------------MTWKVFEFWIYPK---------KEFQEQFNRWAYGLKKFYNFCLEQFELL 41
428311397  --------------WLTLEFWADFS---------LEQQAKIDRWLEINRSLWNMGLAALEDF 39
218248844  MFAIKSMSELVQHHITIQLWAYLS---------TTQTALFENWTDSLRPLYNLALGLLYEE 52
1030942420 --------------WKVLEFWIHPT---------EEQVSKIDQSLAACKLLWNLSIALKEES 39
1305565200 --------------WKTLEFWIYPT---------LAQSQTIDKWLDKLKWVWNTGLSLKLAG 39
488601079  -------------MWISYRFWIYPS---------KTVQAKLNEQLELCRWLYNRLLSEVNKA 40
297565028  ------------MSWLSVKCWLIPDAST----AEKLSRTVNQFANACNY-----ALQVARR 40
257060308  -------------MWESQPITVACKLQVANTLAKEIDETMMVFACACDW------VNQNTP 42

1046552329 DEYTYWDKLSKTRVPCCPVPWSLKLIETLDPN--PYLPELKNKHYVS-YSNLIAPQDIPV 98
1019491369 DEYTYWDKLSKTRVPCCPIPWNLKLIETEEPN--PYLPELKNKHYVS-YSNLIAPKDIPV 98
428311397  DDFYSYVKGQKEYAPCCPIQYEYRPLSEEEKACIPTHEKTSDRKYLAPFCRIISEKSRWY 99
218248844  QQ-RRWRTNQKF---------------------LKNYLDKSSLQTYLNEIENK---PDIYP 88
1030942420 KQ-RYYKKKHKF-----------------------------------DEF--S---PEIWG 59
1305565200 RQ-KYYREKEIG-----------------------------------DQV--I---PDGVV 59
488601079  R--KEGRRIRRE---------------------------------------DTQSLIV 57
297565028  D--NIWNKF------------------------------------------ALQRAVY 54
257060308  E--KMTNKT------------------------------------------AMQSLVY 56

1046552329 ----IRNAPEARQYTLKKGETA--KDVFKRVKNPDQIVVTTAKPESSGLDKWPRGWLGGV 152
1019491369 ----IRNAPEARQYTLKEGETA--KDVFKRVKNPDKIVVTMAKPESSGLDKWPRGWLGGV 152
428311397  ----VKKLP---IYKVPTPAEK--KDSWGWL------------PSNHDED---RKYSRCT 135
218248844  VEWHITKALFECDWLTKEENEVRKKDNTKSLA---CKTI----NRD--------GNFFT- 132
1030942420 LSY-------SGHYDEKEFKTLKDKEKKLLIGNPCCKIAYFKKTSN--------GKEYTF 104
1305565200 LQWKWRKVVTE----DKKGKSTEKWEKVRLVG---TGVI---RPKN--------GYPYC- 100
488601079  ---------------RIKREEKPELSKVYSKVLQ---MVN-------------------- 79
297565028  ---------------ADLRAEY-------GLSAN---LAI-------------------- 69
257060308  ---------------QDVRVNF-------GLSSN---LAI-------------------- 71

1046552329 GYSQPPKQ-------DYQPSLIKNFPNSEKTRDAGILVKKETLENSNLPDEIKKVILDWP 205
1019491369 GYSQPWKQ-------DYKPSLIKNFPNSEKTRDAGILVKKETLENSDLPDEIKKAILDWP 205
428311397  GYSCPWPRYGSVENPSWYEPMIRN-PTYKGSGGLSLVSKTE-----NLPQWMKDS--DWP 187
218248844  ----PWRPYWHLEEPQKLAKPKCF---TN-----QWLISCNLLTNYHLQKLL-----NWN 175
1030942420 LNSIPWKKFMNAENIDKDAVNYLN---RK-----K----LAFYFRENTAKFI----GEWE 148
1305565200 ----EWRQHLNIEDPDKYGQ-----------------CEFYRSDKIPDFM----ADWP 133
488601079  ---YQWRS-------------NISS---LNELRKKG-----------VKVGWLRYK--TSP 108
```

FIG. 9 - Continued

```
297565028  ---RAK----------------------ARVGKRKG------------HKAGGFKAT--SKD 92
257060308  ---QAKRR-------------VCAN---RKTAKQKG------------KKVKEFKPT--SKS 100

1046552329 YKFWSGTLA-MLCTSRQEYLKSRSGQKDLKRGKPKYKRYRDRIETIIHPNPNAGSSKPAS 264
1019491369 YKFWTGTLS-SLCTSRQEYMKSRTGQNDLKRGKPKYKRYRDRIETIIHPNPNAGSSKPAS 264
428311397  QRFWAGENG-QLDTARQEYLKSRYGQSEVKRGKPQYKRKRDKLQTLINTNPSANE----- 241
218248844  MKVWQSFISNNLMEARKKY--Q-----KGDFKKLKFKSKRNFVISLCN----KQT-N-RI 222
1030942420 TEFWKGFFKSVIKTARDAA--K-----KGIRGIPRFKGRRDKVETLVN----GQP-D-TI 195
1305565200 TKFWAGVID-SLKKSRKAYVTP-----KHPGRKPKFKGRNDKIKSLVNLNAGGKS-K-EL 185
488601079  NSFWTLNFN---QSGRKID-----------------------------FD----R-----K- 128
297565028  YDQWILSVN---VDTETVSLS------------------------TVD----G-----RV 116
257060308  YDAWIFSFR---ESDRTVSVK------------------------LLN----S-----RQ 124

1046552329 WDACRLEWDNILV-LPSFGKVKIKGLDKRFRDNDGS-IPRVKVVKWLR-WPSGWYWQWTA 321
1019491369 WDACRLEWDNILV-LPSFGKIKIKGLDRRFRDNDGS-IPRVKVVKWLR-WPSAWYWQWTA 321
428311397  ----RLVWNNIFAGIPKLGKVRCKGLDKRWRNPDGS-IPRVATYKWCR-WPDAWYWQWSG 295
218248844  WFD--PEWNNCQLLGKEFGLIEFRGLHNRH---QGQIQFRNG--SWTR-WADGWYWNWVF 274
1030942420 WIK-----SNGVIVSSKIGLLKVRGL-DRL---QGK-AFRMA--KWTR-WATGWYWQWTV 242
1305565200 WPEKIPGWNNGYVQFPKLGKIRVKGLFDRY---DWQ-EWGAA--PWVI-EPSGWYWHWCV 238
488601079  WLSLSKVW-DIPI------------RLHRSI----G---GKIKGVIWKWTWSGKWNAIWQA 169
297565028  WVPMRIAW--YQR------------HLLRTA----K---SIQGGQ-WVWGWDSSWYWHWWC 155
257060308  WIKL-LIW-NYQI------------GLLKSK----N---PTSAT--WVWRWSGNWYWHWTL 162

1046552329 WINKSNKLFKKPLGAWGWDTGLKEDNWITTDRFAVTKPWWYRESEEWLAWLQKELDAKKL 381
1019491369 WINKSNKLFKKPLGAWGWDTGLKEENWITTDRFSVTKPWWYRESEEWLAWLQRELDAKKL 381
428311397  WVQRSFSV-KATNASWGWDPGLQYELSL-SDGTRIQPQWFYRKSEEWRAWLQQRLAKKLT 353
218248844  QVEH--KPIPDSDLQWGWDPGLVTLLT-LSDGKCISNQWFLKENERWLTVLQKRLSRQT- 330
1030942420 WTDD--TIYKESDKCWGWDMGAVAIFT-DDLGRQSEANWYAKIQKKWLNWLQRQASRQK- 299
1305565200 WVPD--EPLPKSDKSWGWDPGLLSVIT-TDQGREVEPPWLFRKQQAWLRWLQRRASRQV- 294
488601079  WVDK--QPLPPTGRAWGWDVGITHFCV-DSDGNYFEHPWYLDRTLEWIKWWQKQLSKKQ- 225
297565028  WYDD--PPVLDPQGMWGWDLGIVNIAT-DSDGETYSG-WHLNSVRHWHRWLRKKLQKKG- 210
257060308  WEPT--QPEAKTDKVWGWDLGRTDIAT-TSEGESWSG-WQITAKRNWYAWLRTTIQKKA- 217

1046552329 QRVILWLNHPDNSIERIKTIFPSIAREALEKVKACKRPQYLHELVKNNELSTSGLNQLKH 441
1019491369 QRVILWLNHPENSTERIKEVFPGISKESIEKVKGCKRPQDLQDLVSNNELSTSGLNQLKH 441
428311397  ERLILWIRHPDRTIQEIRKNFFPISNESYEALRAAKTEAEVIK-----AIGASRLNTLKY 408
218248844  ------------------------------P-------------------GSKNWE-- 337
1030942420 ------------------------------D-------------------GSNNQR-- 305
1305565200 ------------------------------K-------------------GGCNQK-- 301
488601079  ------------------------------K-------------------GSKNRE-- 232
297565028  --------------------------------------------------TRGAKR-- 216
257060308  ------------------------------S----------------KG-TRSSKR-- 226

1046552329 FNFRDCEWVESCYLFDKLLSASNKEIELAQRWRWWHEWLKRRRRSHNQKQWTWWTRKY-- 499
1019491369 FNFRDCEWVESCYLFDKLLSVSNKEIELAERWGWWHEWNKRRRRSHNQKQWTWWTRKY-- 499
428311397  NIVPDAPPT----MKDKSPFSGAKQKALEKAWRWWDRWISLQRRNHDHKITTNWVRNY-- 462
218248844  -------WT--------------------KKAWAWWHKQTADHRKYYNHKVWTHWVNKY-- 369
1030942420 -------WT--------------------YANWAWWHEWIARQRKGRNAQLWHKWTSEY-- 337
1305565200 -------WT--------------------YRKWALHHEWIRRSRNAFNHKLWTKWVREY-- 333
488601079  -------WV--------------------RIGWAWWYEWLENQRNDFLHKLWRYYVNNI-- 264
297565028  -------W----------------------WKWWWSGWETRFSNHVNHTLWKPWVAKAQR 246
257060308  -------WC--------------------RQLWAWWSGWERRFQKHINHEIWRQWVNNAVT 260

1046552329 --SIWRWWDGL-QKNV---GKSKAKVSEDNRSFERNAQNSRTGMNKWVLDAAIGGFISLW 553
1019491369 --SIWRWWDGL-QKNV---GKSKAKISEDNRSFEKNAQNSRAGMNKWVLDAAIGGFISLW 553
428311397  --GFWAWWDGL-QDEKLR-KRTKPKEREDGQGYEQTGAKRKSGLSKWLADASPGKKIAFW 518
218248844  --GAWAWWDTK-LTNM-N-KRPKAEKREDGKGYEHNGAKAKAGLNQWFHDAGLGQLRAFW 424
1030942420 --QGWIWWDLK-LKNM-T-AAAKPKEREDGDGYKQNGKKRKSGLNKWLLDNAIGQLRTFW 392
1305565200 --SGWVWWDIK-IQNL-N-RKPKAKKREDGNGYEQNGAKRKAGLNKWFADSALGDLISKW 398
488601079  --DIWVWWDLN-VKEMAENGSSTTLN------------RHITDSAWWKF-----V--RLW 302
297565028  TERAWAWWDLQGIRERVRLRRPQ-----------------RATLHSWWFF-----DLGQKW 285
257060308  NKQAWAWWDLTGIRERTN-RKPRSKK------------DKRLGNNWWFY-----QLRQFW 302

1046552329 ESWSKE-WGRDFKPWKPGKGKAYSQR-CPVCH-RENKEQKDITNSQD--WNCSNCGFTHR 608
```

FIG. 9 - Continued

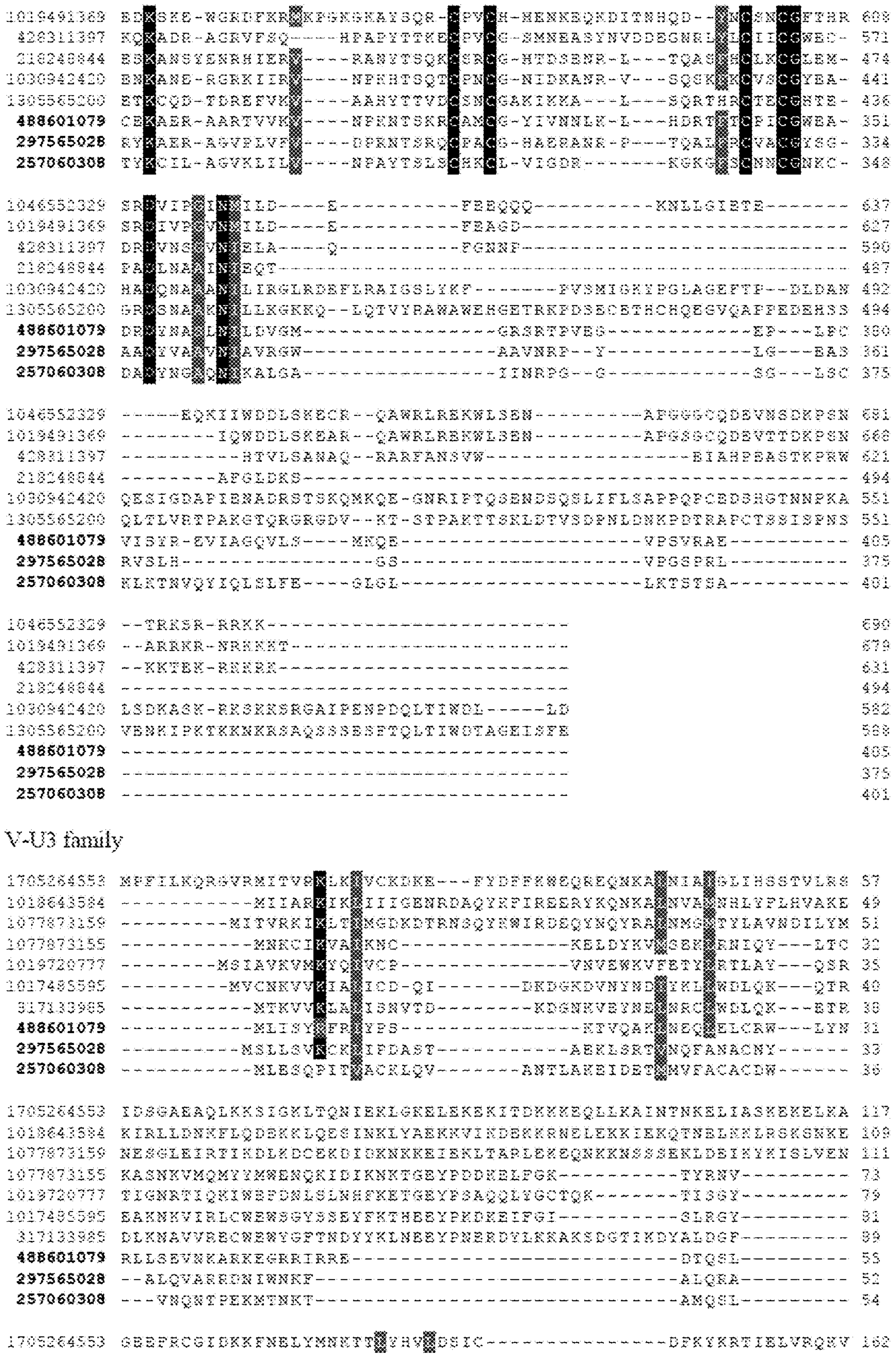
FIG. 9 - Continued

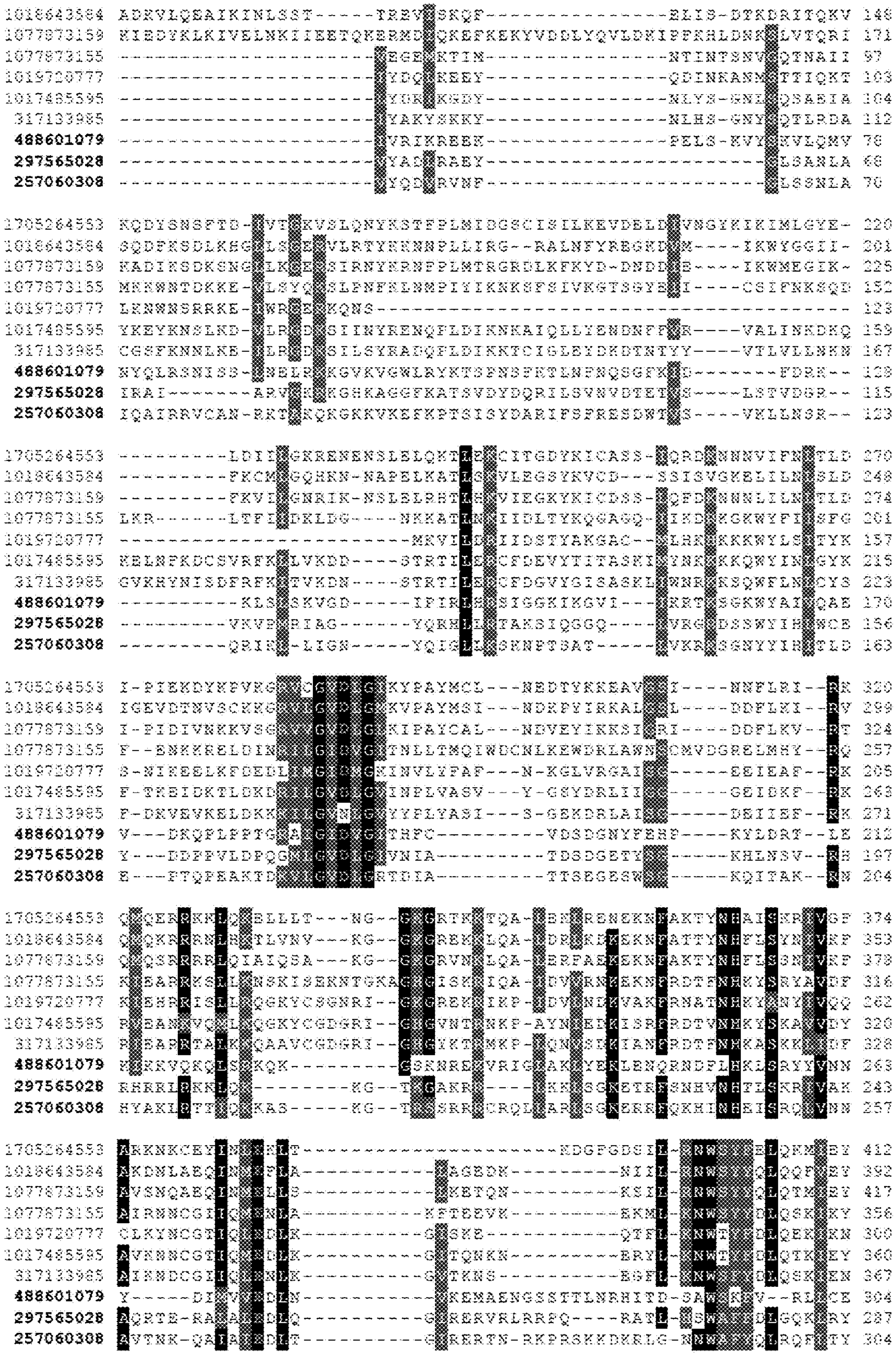

FIG. 9 - Continued

```
1705264553  ADRVLQEAIKINLSST-----TREV SKQF---------------ELIS-DTKDRITQKV 148
1018643584  KIEDYKLKIVELNKIIEETQKERXD QKEFKEKYVDDLYQVLDKIPFKHLDNK LVTQRI 171
1077873159  --------------------- EGE KTIN---------------NTINTSNV QTNAII 97
1077873155  --------------------- YDQ REEY---------------QDINKANM TTIQKT 103
1019720777  --------------------- YGK KGDY---------------NLYS-GNI QSABIA 104
1017485595  --------------------- YAKYSKKY---------------NLHS-GNY QTLRDA 112
317133985   --------------------- VRIKREEK---------------PELS-KVY KVLQNV 76
488601079   --------------------- YAS RAEY---------------------LSANLA 68
297565028   --------------------- YQD RVNF---------------------LSSNLA 70
257060308   

1705264553  KQDYSNSFTS- VT KVSLQNYKSTFPLNIDGSCISILKEVDBLD VNGYKIKIMLGYE- 220
1018643584  SQDFKSDLKSG LS E VLRTYKNNPLLIRG--RALNFYRBGKD M----IKWYGGII- 201
1077873159  KADIKSDKSNG LK E SIRNYKRNFPLMTRGRDLKFKYD-DNDL E----IKWMEGIK- 225
1077873155  MKKWNTDKKE- LSYQ DLPNFKLNMPIYIKNKSFSIVKGTSGYE I----CSIFNKSQD 152
1019720777  LKNWNSRKKE- WRE KQNS------------------------- 123
1017485595  YKEYKNSLKD- LR D SIINYRENQFLDIKNKAIQLLYENDNFP R----VALINKDKQ 159
317133985   CGSFKNNLKE- LR D SILSYRADQFLDIKKTCIGLEYDKDTNYY----VTLVLLNKN 167
488601079   NYQLRSNISS- NELP KGVKVGWLRYKTSPNSFKTLNPNQSGFK D-------FDRK-- 108
297565028   IRAI------APV E KGHKAGGFKATSVDYDQRILSVNVDTET S----LSTVDGR-- 115
257060308   IQAIRRVCAN-RKT RQKGKKVKEFKPTSISYDARIFSPRESDWT S----VKLLNSR-- 123

1705264553  ---------LDII GKRENENSLELQKTE CITGDYKICASS- QRD NNNVIFN TLD 270
1018643584  ---------FKCM GQRKN-NAPELKATI G VLEGSYKVCD---SSISVGKELILN SLD 248
1077873159  ---------FKVI GNRIK-NSLBLRHTI E VIEGKYKICDSS- QFD NNNLILN TLD 274
1077873155  LKR------LTFI DKLDG----NKKATIN IIDLTYKQGAGQ- IKD KKGKWYFI SFG 201
1019720777  ------------MKVIL IIDSTYAKGAC-- LRK KKKWYLS TYK 157
1017485595  KELNFKDCSVRFK LVKDD----STRTIL CFDEVYTITASKI YNK KKQWYIN GYK 215
317133985   GVKRYNISDFRFK TVKDN----STRTIL CFDGVYGISASKL WNR KSQWFLN CYS 223
488601079   ---------KLS SKVGD-----IPIRL SIGGKIKGVI---KRT SGKWYAI QAE 170
297565028   ---------VKVP PIAG------YQRHL TAKSIQGGQ----VRG DSSWYIH WCE 156
257060308   ---------QRIR -LIGN-----YQIGL SKNPTSAT-----VKR SGNYYIH TLD 163

1705264553  I-PIEKDYKPVRG VG P G KYPAYMCL---NEDTYKKEAV I----NNFLRI--RK 320
1018643584  IGEVDTNVSCKKG VG P G KVPAYMSI---NDRPYIRKAL L----DDFLKI--RV 299
1077873159  I-PIDIVNKKVSG VG V G KIPAYCAL---NDVEYIKKSI RI----DDFLKV--RT 324
1077873155  F--ENKKRELDIN IG R G TNLLTMQIWDCNLKEWDRLAWN CMVDGRELMHY--RQ 257
1019720777  S-NIKEELKFGEDL NG R G KINVLYPAF---N-KGLVRGAI -----EEIEAF--RK 205
1017485595  F-TKEIDKTLDKD IG R G INPLVASV---Y-GSYDRLII ------GEIDKF--RK 263
317133985   F-DKVEKELDKD IG N G YYPLYASI---S-GEKDRLAI ------KYLDRT--LE 271
488601079   V---DKQPLPFTG GI D G THPC--------VDSDGNYFBRF----KYLDRT--LE 212
297565028   Y---DDFPVLDPQG IG V G VNIA---------TDSDGETY -----KHLNSV--RH 197
257060308   E---FTQPEAKTD IG R GRTDIA----------TTSEGESW -----KQITAK--RN 204

1705264553  QQERRKKL Q ELLLT---NG--G GRTK TQA- E R ENEKN AKTYNHAI KR VGF 374
1018643584  Q QKRRANL H TLVNV---KG--G GREK LQA- DR KEMEKN ATTYNHF ISYN VRP 353
1077873159  Q QSRRRD QIAIQSA---KG--G GRVN LQA- E RFAEMEKN AKTYNHFISGN VRF 378
1077873155  K EARMSA L NSKISKRNTGKAEG ISK IQA- DV RNEKN PRDTFNHKYSRYA VDF 316
1019720777  K EHRRIS L QGKYCSGNRI-G GREK IKP- DV NIMVAK RNATNHKYANY VQQ 262
1017485595  R EANQ V QL L QGKYCGDGRI-G GVNT NKP-AYN EIKISR PDTVNHK YSKA VDY 320
317133985   R EAPRTA IK QAAVCGDGRI-G GYKT MKP- QN SIKIAN PRDTFNHKASKK DF 328
488601079   K RKVQKQ LS KQK-------- GSKNRE VRIG AK YERLENQRNDFLHKLSRYYVNN 263
297565028   RHRRL DKK LQ --------KG--T GAKR ----KK SGNETF SNHV NHTLSKR VAK 243
257060308   HYAKI DTT KK KAS-----KG--T SSKR CRQL AR SGNERF QKHN HEISRQ VNN 257

1705264553  ARKNKCEYI NW RLT-----------KDGPGDSIL- KNW ELQKM EY 412
1018643584  AKDMLAEQ IN WFLA---------MAGEDK------NII L KNW QQQF EY 392
1077873159  MVSNQAEQ IN WLLS---------DKETQN------KSIL KNW QTM EY 417
1077873155  AIRNNCGI H QMNLA---------KFTEEVK-----EKMI KNW DQSK KY 356
1019720777  CLKYNCGT IQ EDLK---------G SKE------QTFL KNW DLQEK RN 300
1017485595  AVRNNCGT IQ NDLK---------G TQNKN------ERYL KNW DLQTK EY 360
317133985   AIRNDCGI H QLNLK---------G TKNS------EGFL KNW DLQSK EN 367
488601079   Y-----DI KW EDLN---------DKEMAENGSSTLNRHID-SAW SKV--RL CE 304
297565028   AQRTE-RA A A EDLQ---------G RERVRLRRPQ----RATL NSW DLGQK RY 287
257060308   AVTNK-QA IA EDLT---------G RERTN-RKPRSKKDKRLG- NNW QIRQF TY 304
```

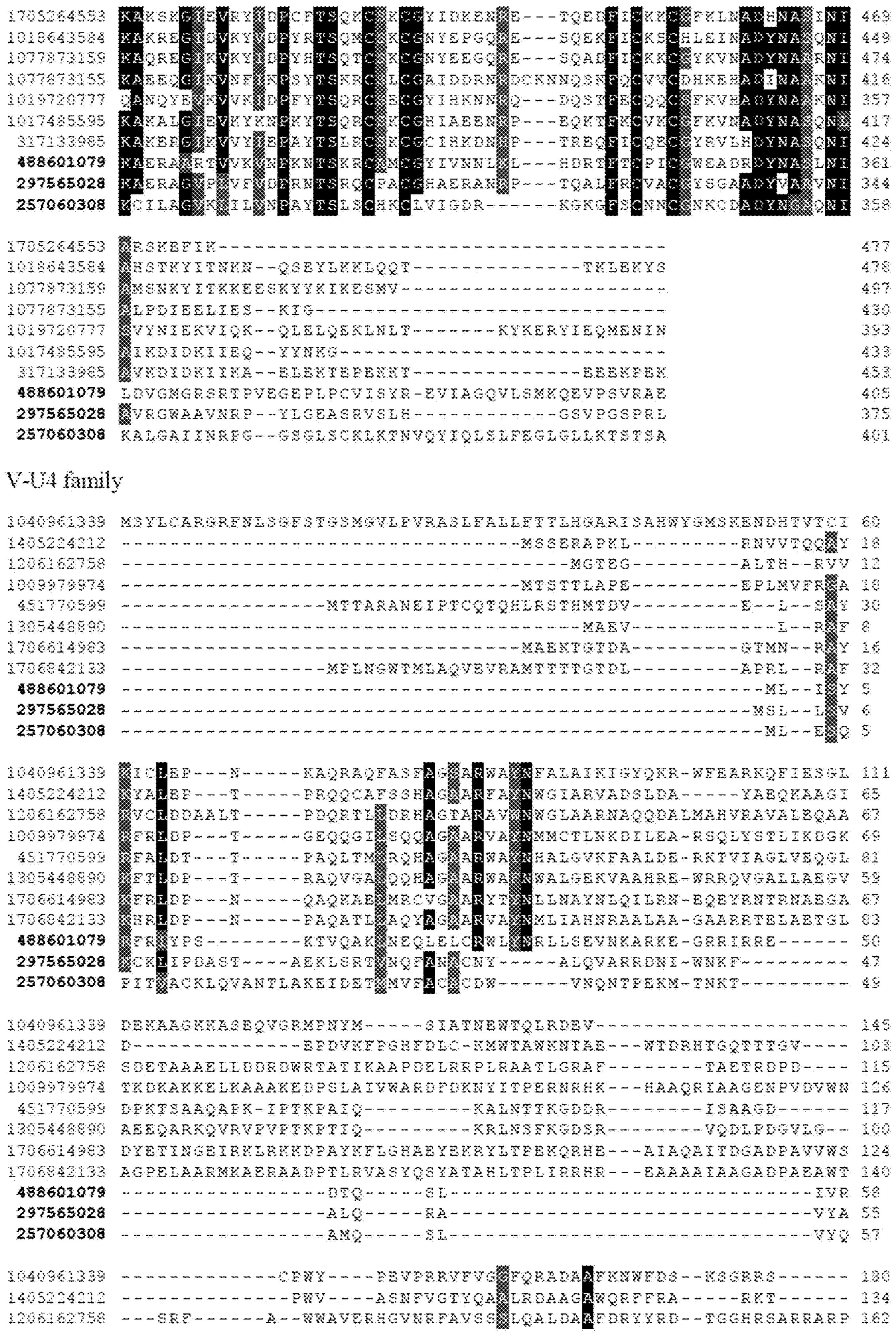

FIG. 9 - Continued

```
1705264553  KAKSK GEVRY DCFTSQE KCGYIDKEN E---TQEE ICKKC FKLNA ENA INI  469
1018643584  KAKRE GLVKY DFYRTSQW  KCGNYEPGQ E---SQEK ICKSC LEINA DYNA QNI  449
1077873159  KAQRE GLRVKY DFYHTSQTC KCGNYEEGQ E---SQAE FICKKC YKVNA DYNA RNI  474
1077873155  KAERE GRVNF KPSYTSKRC LCGAIDDRN DCKNNQSNF DCVWC HKEHA ENA RNI  416
1019720777  KANQYE ERVVK DPFYTSQRC ECGYIBKNN Q---DQST FECQQC FKVHA QYNA RNI  357
1017485595  KAKALG IEVVY KNPKYTSQEC KCGRIAEEN P---EQKT FKCVEC FKVMA QYNA QNI  417
317133985   KAKEFG IPVVY IEPAYTSLEC KCGCIRKDN P---TREQ FICQEC YRVLE DYNA QNI  424
488601079   KAERA KTVVK NPKNTSKRT QMCSYIVNNL L---HDRT FTTPIC WEADR DYNA LNI  361
297565028   KAERAG IPIVF DERNTSRQT PAEGHAERAN P---TQAL FRTVAC YSGAA DYVA VNI  344
257060308   KCILAG GKIL NPAYTSLSC HKCLVIGDR------KGKG PSCNNC NKCDA GYNA QNI  358

1705264553  RSKEFIK---------------------------------   477
1018643584  HSTKYITNEN--QSEYLKKLQQT------------TKLEKYS  478
1077873159  MSNKYITKKEESKYYKIKESMV-------------------  497
1077873155  LPDIEELIES---KIG-------------------------  430
1019720777  VYNIEKVIQK--QLELQEKLNLT------KYKERYIEQMENIN 393
1017485595  IKDIDKIIEQ--YYNKG------------------------  433
317133985   VKDIDKIIKA--ELEKTEPEKKY----------EEEKPEK   453
488601079   LDVGMGRSRTPVEGEPLPCVISYR-EVIAGQVLSMKQEVPSVRAE 405
297565028   VRGWAAVNRP--YLGEASRVSLH------------GSVPGSPRL 375
257060308   KALGAIINRPG--GSGLSCKLKTNVQYIQLSLFEGLGLLKTSTSA 401
```

V-U4 family

```
1040961339  MSYLCARGRFNLSGFSTGSMGVLPVRASLFALLFTTLHGARISAHWYGMSKENDHTVTCI 60
1405224212  ------------------------MSSERAPKL---------RNVVTQQEY 18
1206162758  ------------------------MGTEG---------ALTH--RVV 12
1009979974  ------------------------MTSTTLAPE---------EPLMVFREA 18
451770599   ------------MTTARANEIPTCQTQHLRSTHMTDV---------E--L--SEY 30
1305448890  ------------------------MAEV---------L--REF 8
1706614963  ------------------------MAEKTGTDA---------GTMN--REY 16
1706842133  ------------MPLNGWTMLAQVEVRAMTTTGTDL---------APRL--PEF 32
488601079   ------------------------ML--IEY 5
297565028   ------------------------MSL--LEV 6
257060308   ------------------------ML--EEQ 5

1040961339  ICLEP---N------KAQRAQFASFAG AGWA NFALAIKISYQKR-WFEARKQFIESGL 111
1405224212  YALEP---T------PRQQCAFSSHAG ARFA NWGIARVADSLDA-----YABQKAAGI 65
1206162758  VCLDDAALT------PDQRTL DRHAGTARAV NWGLAARNAQQDALMAHVRAVALEQAA 67
1009979974  FRLDP---T------GEQQGI SQQAG ARVA NMMCTLNKDILEA-RSQLYSTLIKDGK 69
451770599   EFALDT---T------PAQLTM RQHAG AEWA NHALGVKFAALDE-RKTVIAGLVEQGL 81
1305448890  FTLDP---T------RAQVGA QQHAG AEWA NWALGEKVAAHRE-WRRQVGALLAEGV 59
1706614963  FRLDP---N------QAQKAE MRCVG ARYT NLLNAYNLQILRN-EQEYRNTRNAEGA 67
1706842133  HRLDP---N------PAQATL AQYAG ARVA NMLIAHNRAALAA-GAARRTELAETGL 83
488601079   FRLYPS--------KTVQAK NEQLELC RWL NRLLGEVNKARKE-GRRIRRE------ 50
297565028   CKLIPDAST----AEKLSRT NQFAN CNY-----ALQVARRDNI-WNKF--------- 47
257060308   FITACKLQVANTLAKEIDET MVFAC CDW------VNQNTPEKM-TNKT--------- 49

1040961339  DEKAAGKKASEQVGRMPNYM-----GIATNEWTQLRDEV----------  145
1405224212  D-----------EPDVKFPGHFDLC-KMWTAWKNTAE---WTDRHTGQTTTGV----  103
1206162758  SDETAAAELLDDRDWRTATIKAAPDELREPLRAATLGRAF--------TAETRDPD----  115
1009979974  TKDKAKKELKAAAKEDPSLAIVWARDPDKNYITPERNRHK---HAAQRIAAGENPVDVWN 126
451770599   DFKTSAAQAFK-IPTKPAIQ---------KALNTTKGDDSR---------ISAAGD----  117
1305448890  AEEQARKQVRVPVFTKPTIQ---------KRLNSFKGDSR---------VQDLFDGVLG-- 100
1706614963  DYETINGEIRKLREKDPAYKFLGHAEYBKRYLTFEKQRHE---AIAQAITDGDPAVWS 124
1706842133  AGPELAARMKAERAADPTLRVASYQSYATAHLTPLIRRHR---EAAAAIAAGADPAEAWT 140
488601079   ---------------DTQ-----SL---------------IVR 58
297565028   ---------------ALQ-----RA---------------VYA 55
257060308   ---------------AMQ-----SL---------------VYQ 57

1040961339  ---------CPWY----PEVPRRVFVG FQRADA FKNWFDS--KSGRRS------ 180
1405224212  ---------PWV----ASNFVGTYQA LRDAAG WQRFFRA-----RKT------ 134
1206162758  ---SRF------A--WWAVERHGVNRFAVSS LQALDAA FDRYRD--TGGHRSARRARP 162
```

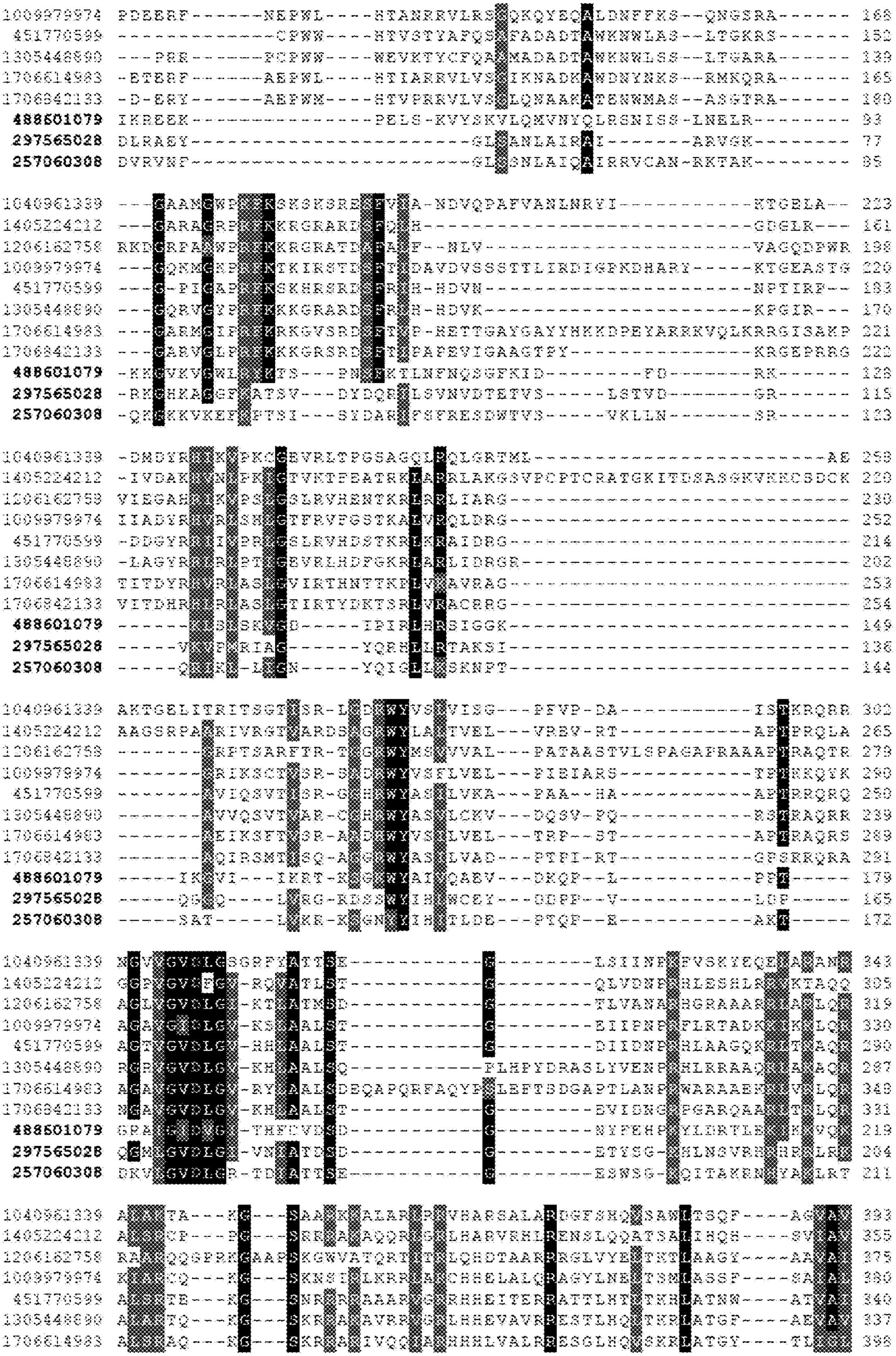
FIG. 9 - Continued

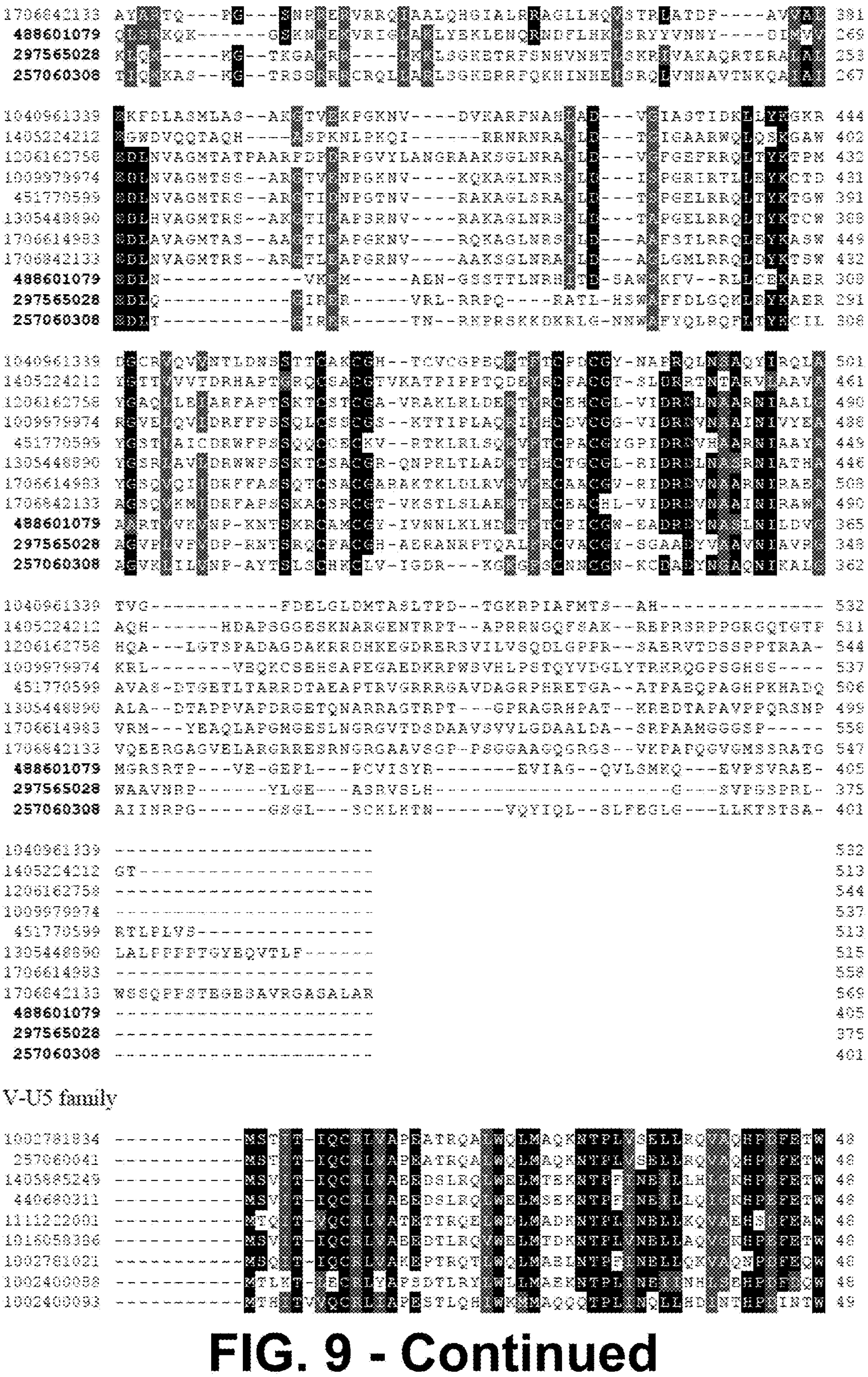
FIG. 9 - Continued

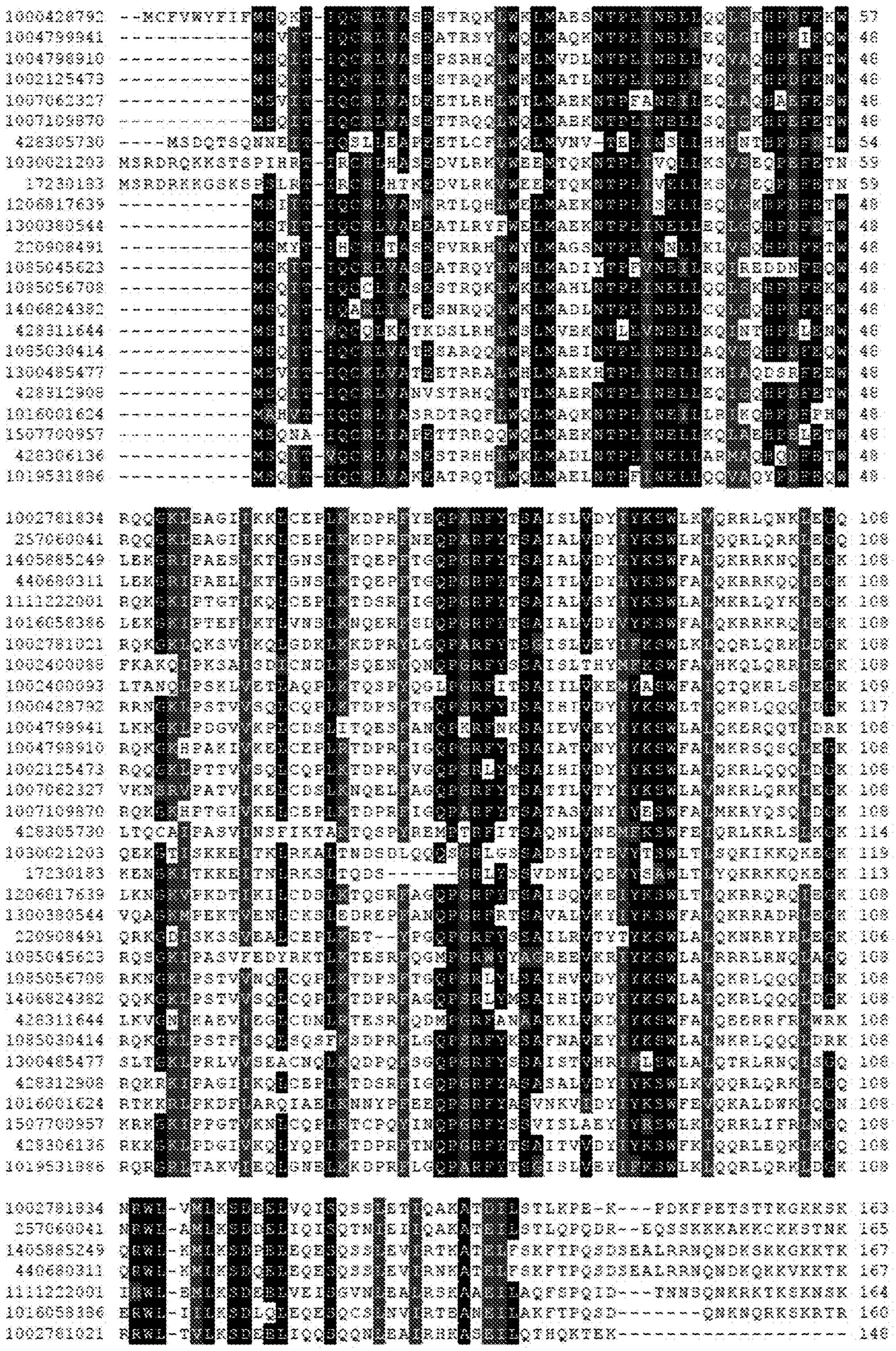
FIG. 9 - Continued

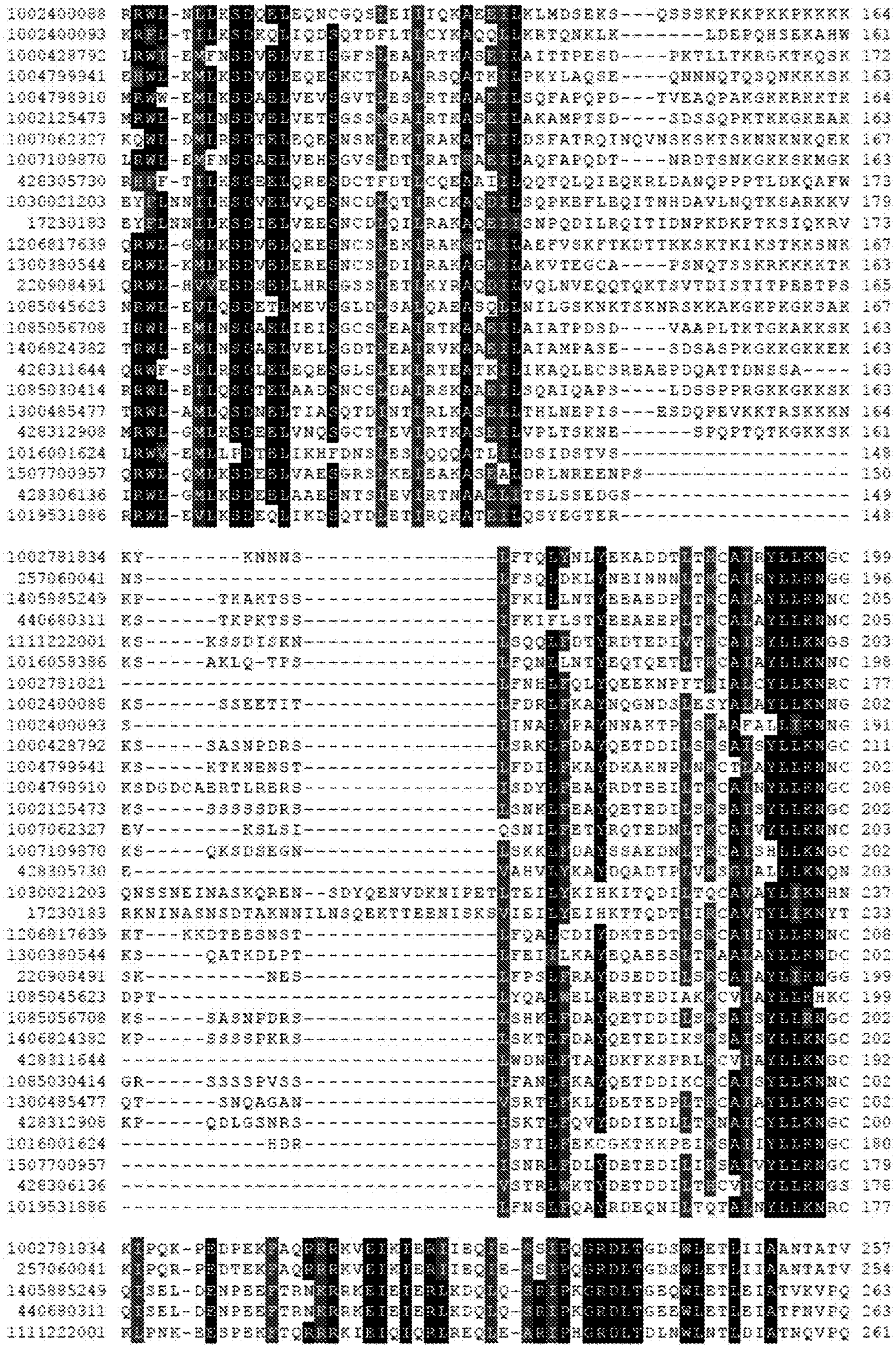
FIG. 9 - Continued

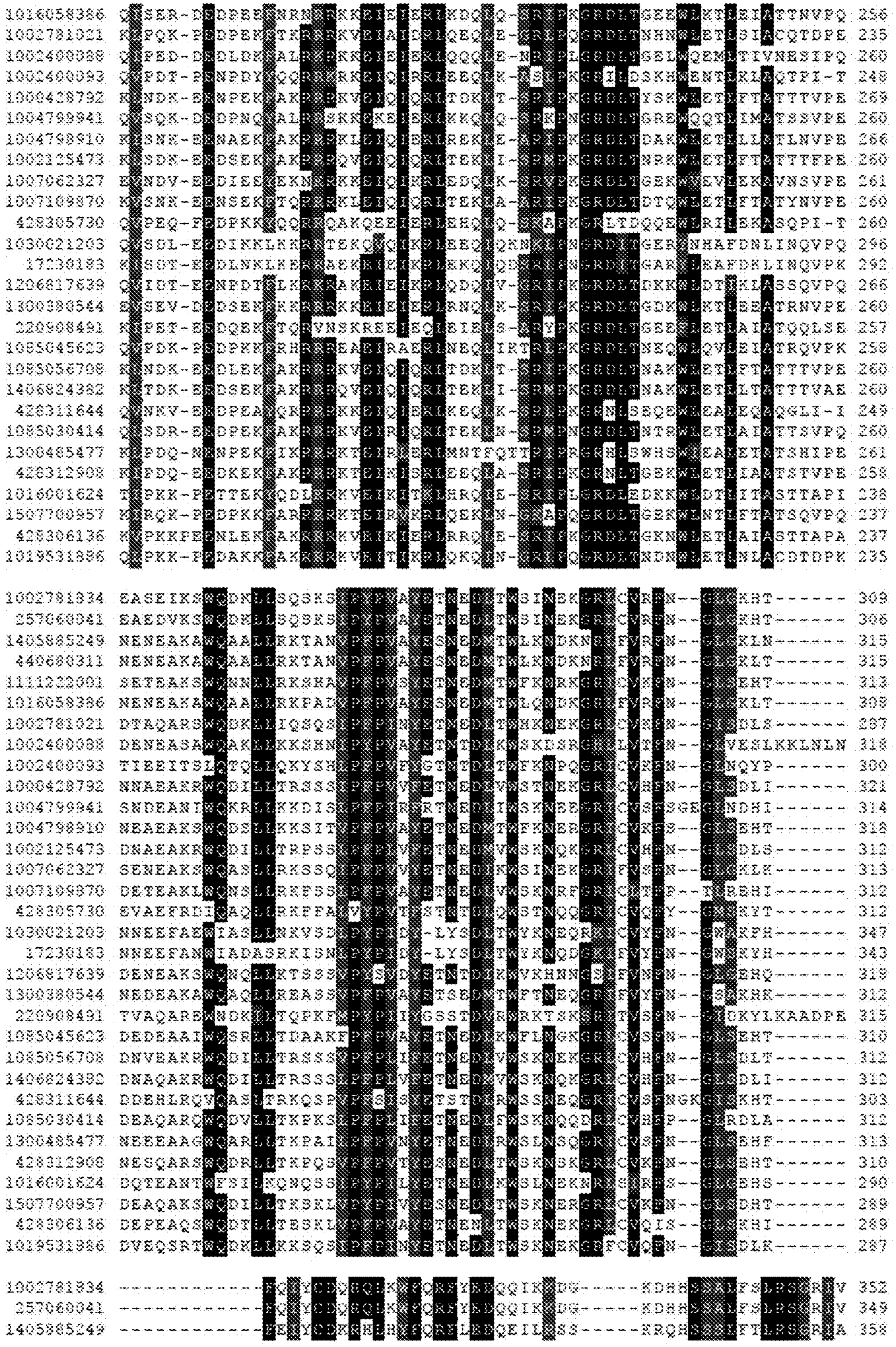
FIG. 9 - Continued

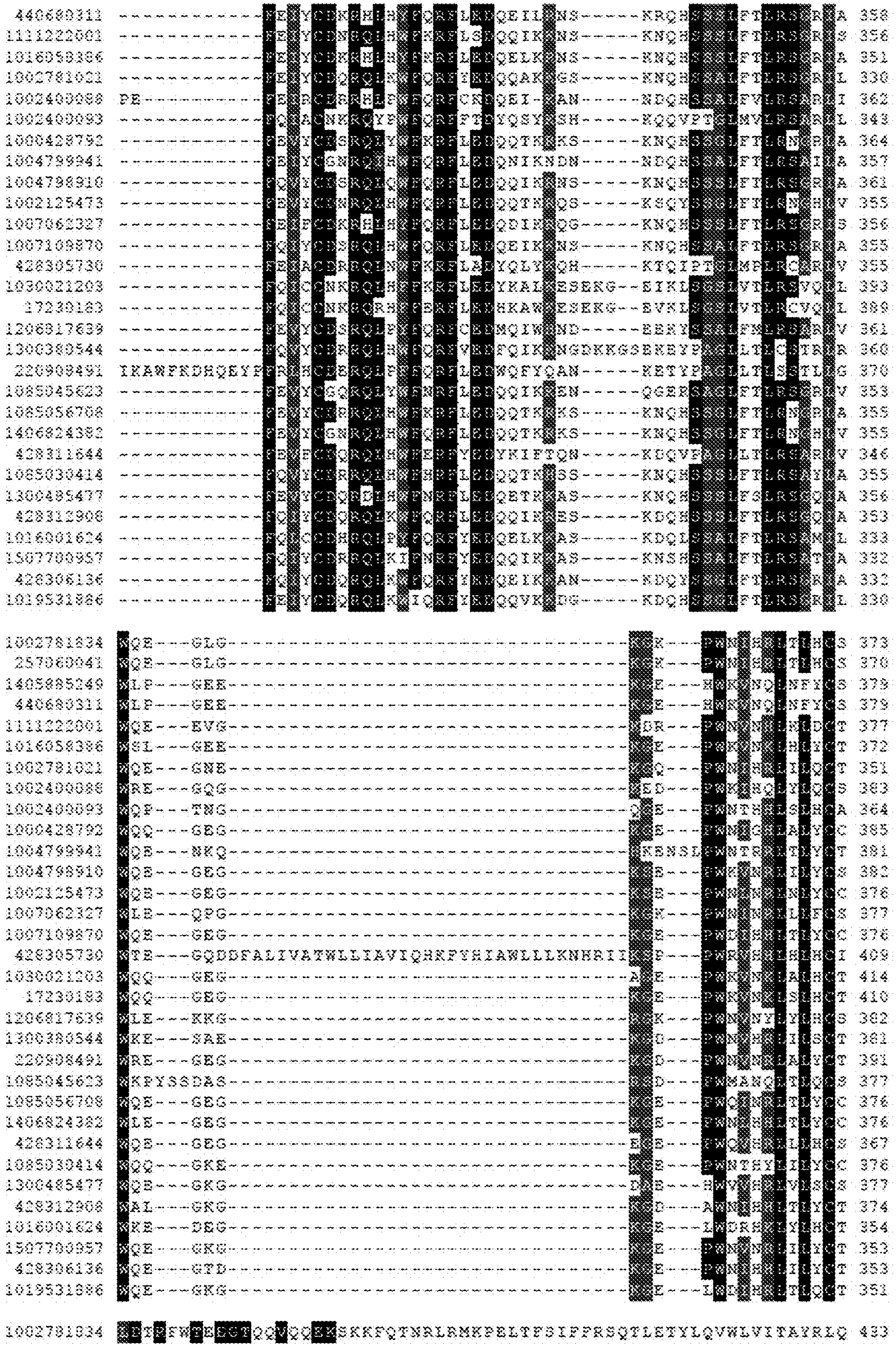
FIG. 9 - Continued

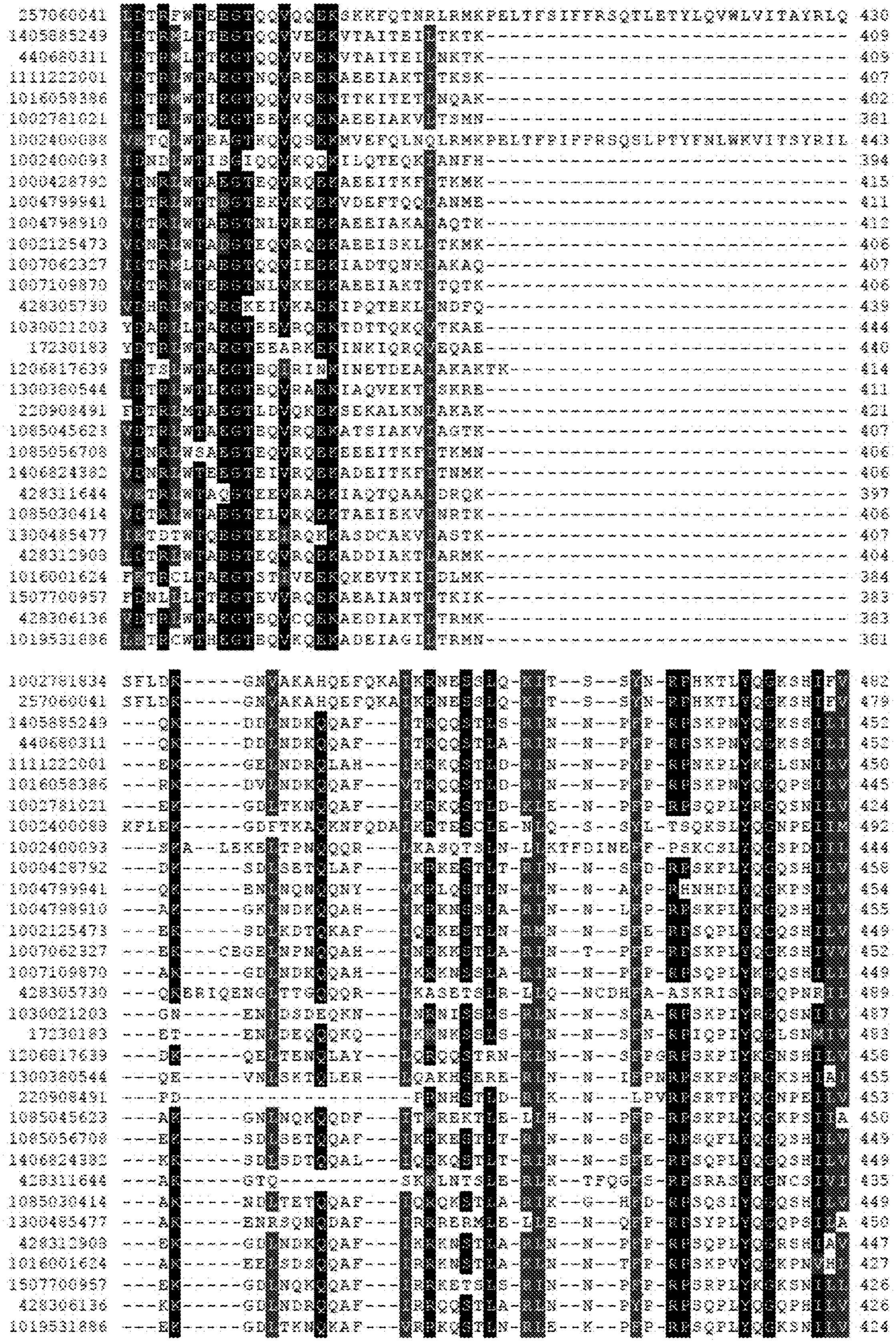
FIG. 9 - Continued

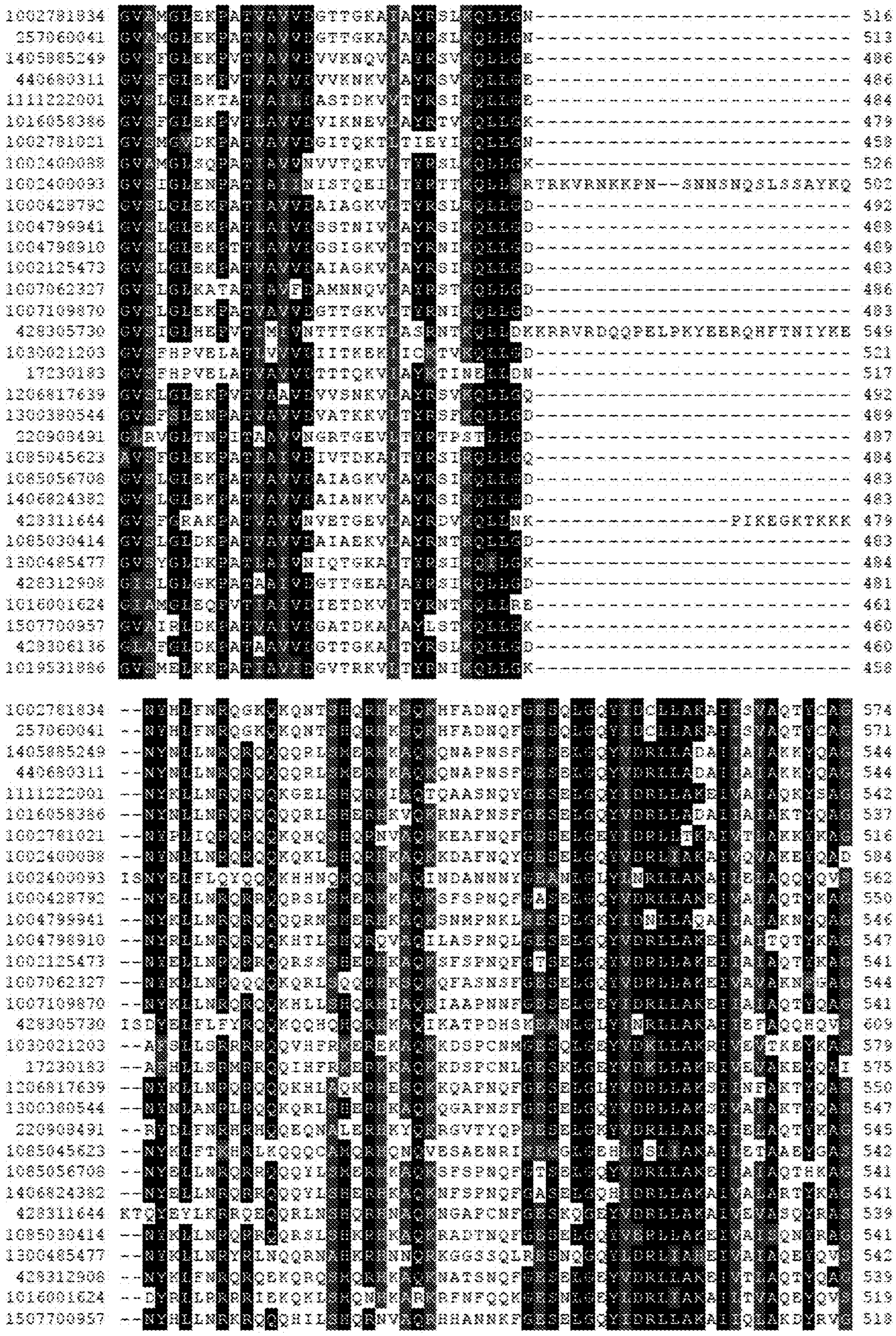
FIG. 9 - Continued

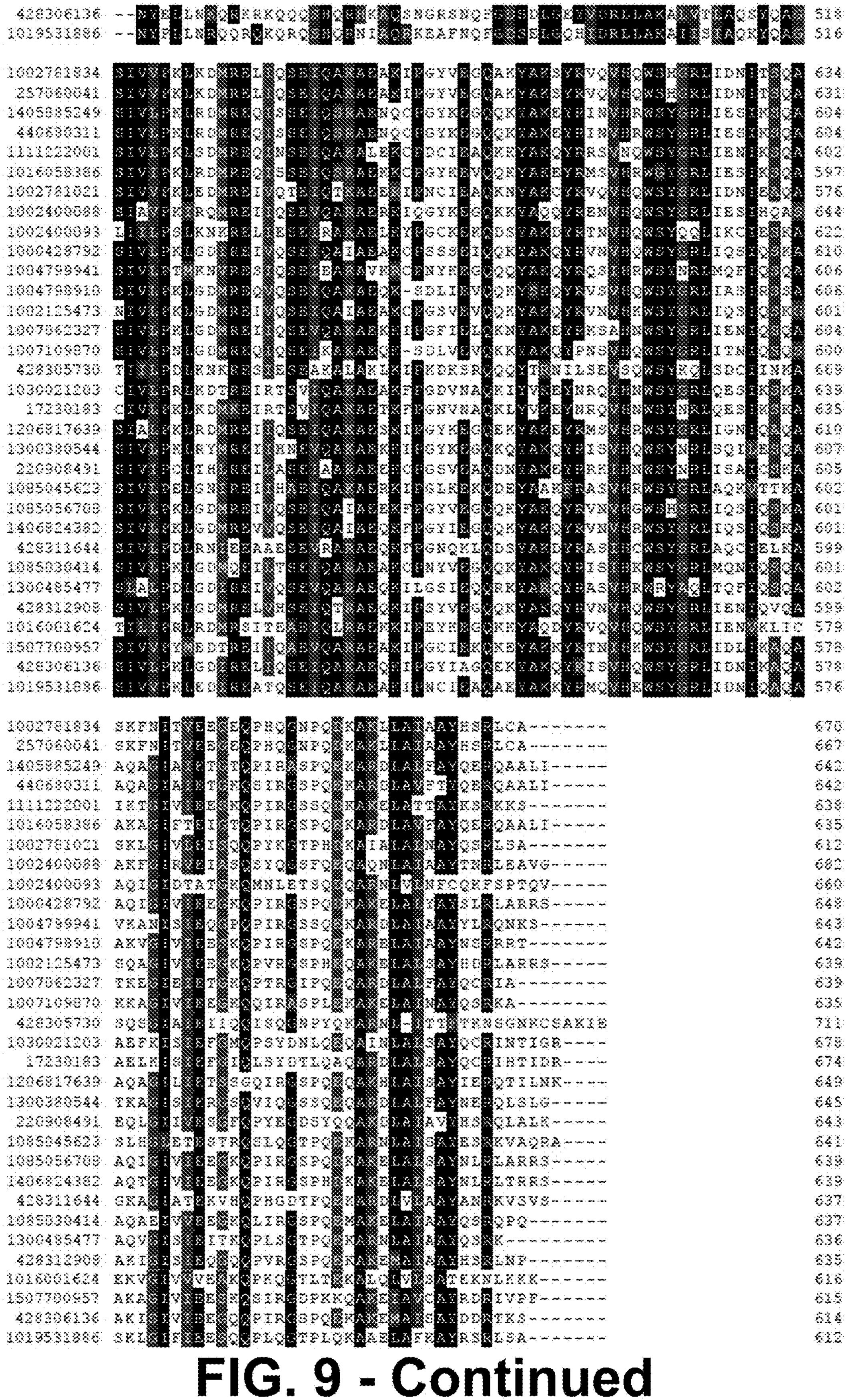
FIG. 9 - Continued

METHODS FOR IDENTIFYING CLASS 2 CRISPR-CAS SYSTEMS

CROSS REFERENCE TO RELATED APPLICATIONS

This application is a national phase of International Application No. PCT/US2017/047193, filed on Aug. 16, 2017, which claims priority to U.S. Provisional Application No. 62/376,387 filed on Aug. 17, 2016, each of which is incorporated herein by reference in its entirety.

STATEMENT AS TO FEDERALLY SPONSORED RESEARCH

This invention was made with government support under grant numbers MH100706 and MH110049 awarded by the National Institutes of Health. The government has certain rights in the invention.

The instant application contains a Sequence Listing which has been submitted electronically in ASCII format and is hereby incorporated by reference in its entirety. Said ASCII copy; created on Jun. 30, 2022, is named BROD-0700US and is 507,330 bytes in size.

BACKGROUND

The CRISPR-Cas systems embody adaptive immunity in archaea and bacteria. Similar to other defense mechanisms, CRISPR-Cas systems apparently evolve in the regime of incessant arms race with mobile genetic elements which results in extreme diversification of the Cas protein sequences and the architecture of the CRISPR-cas loci. Due to this diversity and the lack of universal cas genes, a comprehensive classification of the CRISPR-Cas systems cannot be generated in the form of a single phylogenetic tree but rather requires a multipronged approach combining identification of signature genes, trees and sequence similarity analysis for partially conserved cas genes, and quantitative comparison of the loci organization. The latest published CRISPR-Cas classification includes two classes that are subdivided into 5 types and 16 subtypes. The CRISPR-Cas systems are characterized by pronounced functional and evolutionary modularity. The module responsible for the first, adaptation step of the CRISPR response, i.e. spacer acquisition, shows limited variation among the diverse variants of CRISPR-Cas systems and consists of the essential cas1 and cas2 genes, often accompanied by the cas4 gene: in some variants, the cas2 gene is fused to cas3. By contrast, the CRISPR-Cas effector module involved in the maturation of the crRNAs as well as target recognition and cleavage, shows a far greater versatility in terms of the gene composition and locus architecture.

The two classes of CRISPR-Cas systems have been delineated on the basis of their fundamentally different organizations of the effector modules. The effector complexes of Class 1 systems (Types I, III and IV) consist of four to seven Cas protein subunits in an uneven stoichiometry as exemplified by the CRISPR-associated complex for antiviral defense (Cascade) of the Type I systems, and the Csm/Cmr complexes of the Type III systems. The majority of the subunits of the Class 1 effector complexes, in particular Cas5, Cas6 and Cas7, belong to the so-called RAMP (Repeat-Associated Mysterious Proteins) family of proteins containing the RNA-binding RRM (RNA Recognition Motif) domain. Although it is difficult to detect sequence similarity between individual subunits of Type I and Type III effector complexes, these complexes share similar overall architectures and probably evolved from a common ancestor.

The Class 1 systems are most common in bacteria and especially archaea, including all hyperthermophiles, and comprise about 90% of all identified CRISPR-Cas loci. The remaining 10% of the CRISPR-Cas systems belong to Class 2 (Types II and V) that are found almost exclusively in bacteria and never in hyperthermophiles. The signature feature of Class 2 systems is an effector module consisting of a single, multidomain protein. The relative architectural simplicity of the effector complex has made Class 2 CRISPR-cas systems the obvious choice for the new generation of genome-editing tools. The most common and best studied Class 2 effector is Cas9 (Type II), a CRISPR (cr) RNA-dependent endonuclease containing two unrelated nuclease domains, RuvC and HNH, which are responsible for the cleavage of the displaced (non-target) and target DNA strands, respectively, in the crRNA-target DNA complex. The Type II loci also encode a trans-acting CRISPR (tracr) RNA, a derivative of the corresponding CRISPR that is directly involved for pre-crRNA processing and target recognition in Type II systems.

The Cpf1 protein, the prototype Type V effector, contains only one readily detectable nuclease domain, RuvC. However, the structures of Cpf1 complexed with the crRNA or with both crRNA and target DNA reveal a second nuclease domain with a unique fold that, however, is functionally analogous to the HNH domain of Cas9, being inserted into the RuvC domain and responsible for the target strand cleavage. Remarkably, Cpf1 differs from Cas9 in that it is a single RNA-guided nuclease that does not require tracrRNA.

The discovery of two, distantly related Class 2 effector proteins, Cas9 and Cpf1, suggests that other, distinct variants of such systems could exist. We developed a computational pipeline to systematically identify novel Class 2 CRISPR-Cas loci in genomic and metagenomics sequences. Using Cas1, the most conserved Cas protein, as a seed, we identified 3 previously unknown Class 2 subtypes two of which contained effectors distantly related to Cpf1 and accordingly were included as additional subtypes in type V whereas the third one became the new type VI. The expression and interference activity of two of these proteins, denoted C2c1 and C2c2, has been experimentally demonstrated.

SUMMARY

We extended the search for novel Class 2 systems by using the CRISPR array itself as the seed, which yielded at least three new CRISPR-Cas subtypes.

At least one aspect of invention described herein relates to a method of identifying novel CRISPR effectors, comprising: a) identifying sequences in a genomic or metagenomic database encoding a CRISPR array: b) identifying one or more Open Reading Frames (ORFs) in said selected sequences within 10 kb of the CRISPR array: c) discarding all loci encoding proteins which are assigned to known CRISPR-Cas subtypes and, optionally, all loci encoding a protein of less than 700 amino acids; and d) identifying putative novel CRISPR effectors, and optionally classifying them based on structure analysis.

At least another aspect of invention described herein relates to a method for identifying putative CRISPR effectors comprising (a) identifying multiple CRISPR motifs using genome sequencing data: (b) extracting multiple features from said identified CRISPR motifs, such as protein elements, repeat structure, repeat sequence, spacer sequence and spacer mapping: (c) classifying CRISPR loci based on these features using unsupervised learning: (d) identifying conserved locus elements; and (e) selecting therefrom putative CRISPR effector based on structure analysis.

At least a further aspect of invention described herein relates to a method of identifying a Class 2 CRISPR effector, comprising: a) comparing sequences in a genomic and/or metagenomic database with at least one pre-identified seed sequence that encodes a CRISPR array, and selecting sequences comprising said seed sequence: b) identifying one or more Open Reading Frames (ORFs) in said selected sequences within 10 kb of the CRISPR array, wherein the ORF encode a protein of at least 300 amino acids and comprising one or more RuvC, HPN, and/or HEPN domains; and c) identifying putative novel CRISPR effectors, and optionally classifying them based on structure analysis.

At least an additional aspect of invention described herein relates to a recombinant nucleic acid comprising a nucleic acid sequence encoding a Class 2 CRISPR effector operably linked to a heterologous promoter, wherein the Class 2 CRISPR effector is not Cas9, Cpf1, C2c1, C2c2, C2c3, and C2c6.

Yet another aspect of invention described herein relates to an expression cassette comprising the recombinant nucleic acid. Yet a further aspect of invention described herein relates to a vector comprising the expression cassette. Yet an additional aspect of invention described herein relates to a cell transformed with the vector.

These and other features, together with the organization and manner of operation thereof, will become apparent from the following detailed description when taken in conjunction with the accompanying drawings.

BRIEF DESCRIPTION OF THE DRAWINGS

FIG. 9 shows multiple alignment of representatives from five V-U families. V-U1 and V-U4 families are aligned with regular TnpB, whose sequence IDs are shown in bold font. RuvC catalytic residues are highlighted by red letters.

DETAILED DESCRIPTION

Introduction

Figure 1:
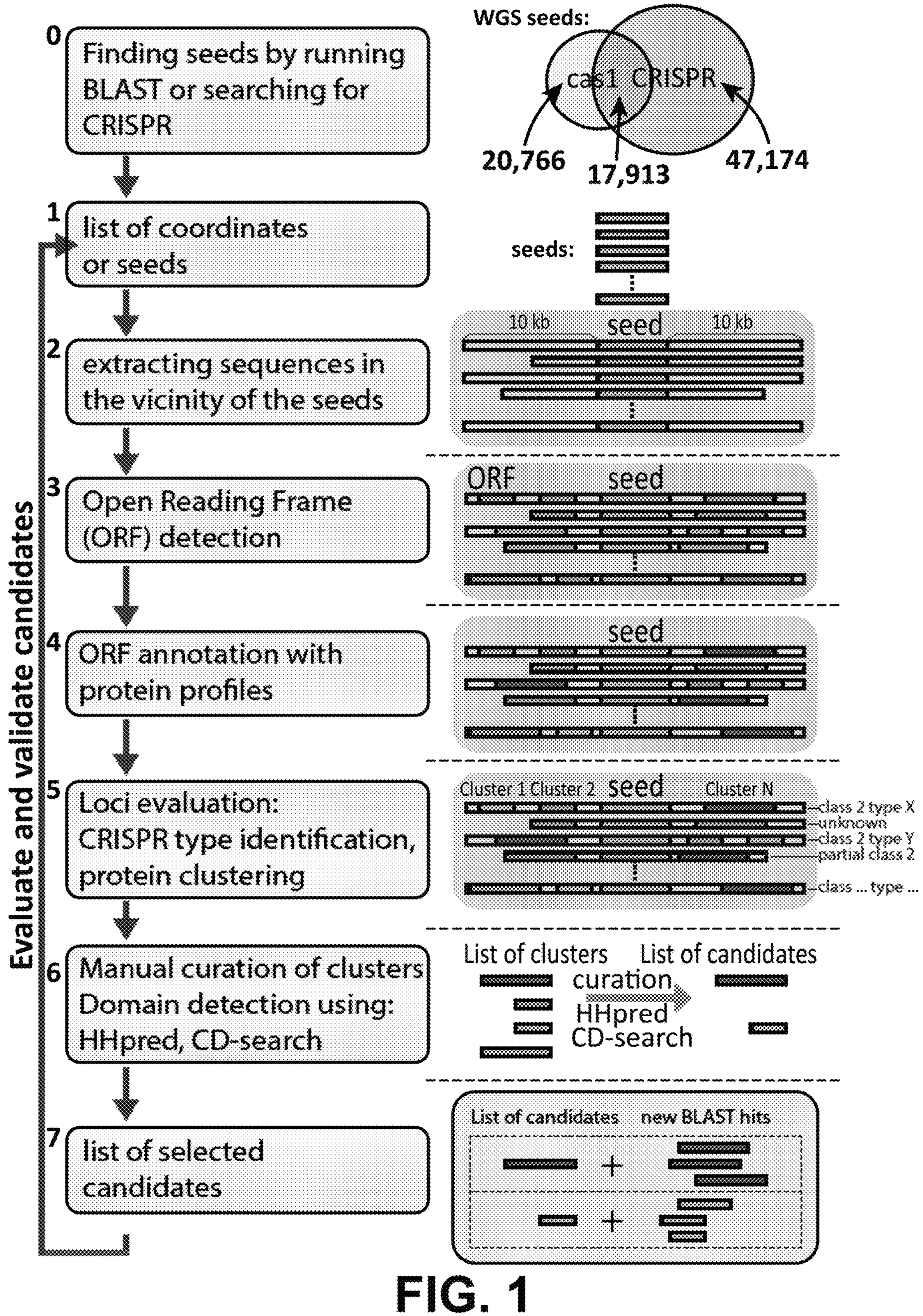
FIG. 1 shows a computational pipeline for the discovery of Class 2 CRISPR-Cas loci. The procedure begins with the identification of a 'seed' that signifies the likely presence of a CRISPR-Cas locus in a given nucleotide sequence. Previously, Cas1 was used as the seed. The Cas protein is most common in CRISPR-Cas systems and is most highly conserved at the sequence level. Here we update this part of the analysis by searching the current sequence databases. To ensure the maximum sensitivity of detection, the search was performed by comparing a Cas1 sequence profile to translated genomic and metagenomic sequences. After the cas1 genes were detected, the respective neighborhoods were examined for the presence of other cas genes by searching with approximately 400 previously developed profiles for Cas proteins and applying the criteria for the classification of the CRISPR-cas loci. In a complementary approach, to extend the search to non-autonomous CRISPR-Cas systems, the same procedures were repeated with the CRISPR array used as the seed. To ensure high sensitivity of the CRISPR array detection, the union of the predictions made using the PilerCR and CRISPRfinder methods was taken as the final CRISPR set. All loci that were assigned to known CRISPR-Cas subtypes through the Cas protein profile search were discarded from the subsequent analysis given that the search specifically aimed at the discovery of new subtypes. Among the remaining cas1 and CRISPR neighborhoods, those encoding large proteins (>500 amino acids) were chosen for detailed analysis given that Cas9 and Cpf1 are large proteins (typically, >1000 aa), and the respective protein structures suggest that this large size may be required to accommodate the complex of the crRNA with the target DNA. The sequences of such large proteins were then screened for known protein domains using sensitive profile-based methods such as HHpred, secondary structure prediction and manual examination of multiple alignments. Under the premise that Class 2 effector proteins contain nuclease domains, even if in some cases distantly related or unrelated to the known families of nucleases, the proteins containing domains deemed irrelevant in the context of the CRISPR-Cas function (e.g. membrane transporters or metabolic enzymes) were discarded. The retained proteins either contained readily identifiable nuclease domain or were complete unknowns. The sequences of these proteins were then analyzed using the most sensitive current methods for domain detection such as HHPred with a curated multiple alignment of the respective protein sequences used as the query. The use of maximally sensitive methods at this stage is essential because proteins involved in antivirus defense and the Cas proteins in particular typically evolve extremely fast. Note that the depicted procedure for discovery of Class 2 CRISPR-Cas systems, at least in principle, is expected to be exhaustive because all loci containing a gene encoding a large protein (that is, a putative Class 2 effector) in the vicinity of cas1 and/or CRISPR are analyzed in detail. The assumption on the structural requirements for a Class 2 effector underlying the protein size cutoff and the precision of cas1 and CRISPR detection are the only limitations of this approach.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US 2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 Jun. 10, 2014; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460) and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. application 62/091,462, 12 Dec. 2014, DEAD GUIDES FOR CRISPR TRANSCRIPTION FACTORS; U.S. application 62/096,324, 23 Dec. 2014, DEAD GUIDES FOR CRISPR TRANSCRIPTION FACTORS; U.S. application 62/091,456, 12 Dec. 2014, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014. ENGINEERING OF SYSTEMS. METHODS AND OPTIMIZED ENZYME AND GUIDE SCAFFOLDS FOR SEQUENCE MANIPULATION; U.S. application 62/098,059, 30 Dec. 2014. RNA-TARGETING SYSTEM; U.S. application 62/096,656, 24 Dec. 2014. CRISPR HAVING OR ASSOCIATED WITH DESTABILIZATION DOMAINS; U.S. application 62/096,697, 24 Dec. 2014. CRISPR HAVING OR ASSOCIATED WITH AAV; U.S. application 62/098,158, 30 Dec. 2014. ENGINEERED CRISPR COMPLEX INSERTIONAL TARGETING SYSTEMS; U.S. application 62/151,052, 22 Apr. 2015. CELLULAR TARGETING FOR EXTRACELLULAR EXOSOMAL REPORTING; U.S. application 62/054,490, 24 Sep. 2014. DELIVERY. USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 2014. SYSTEMS. METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS. METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014. DELIVERY. USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014. DELIVERY. USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; US application 62/0) 54.675, 24 Sep. 2014. DELIVERY. USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014. DELIVERY. USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014. DELIVERY. USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014. MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014. FUNCTIONAL SCREENING WITH OPTIMIZED FUNCTIONAL CRISPR-CAS SYSTEMS; U.S. application 62/055,487, 25 Sep. 2014. FUNCTIONAL SCREENING WITH OPTIMIZED FUNCTIONAL CRISPR-CAS SYSTEMS; U.S. application 62/087,546, 4 Dec. 2014, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference);

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A):

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi: 10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014 (2014);

Development and Applications of CRISPR-Cas9 for Genome Engineering, Hsu P D, Lander E S, Zhang F., Cell. June 5; 157(6):1262-78 (2014);

Genetic screens in human cells using the CRISPR/Cas9 system, Wang T, Wei J J, Sabatini D M, Lander E S., Science. January 3; 343(6166):80-84. doi: 10.1126/science. 1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015);

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260 Mar. 12, 2015 (multiplex screen in mouse); and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91 (2015);

Shalem et al., "High-throughput functional genomics using CRISPR-Cas9," Nature Reviews Genetics 16, 299-311 (May 2015);

Xu et al., "Sequence determinants of improved CRISPR sgRNA design," Genome Research 25, 1147-1157 (August 2015);

Parnas et al., "A Genome-wide CRISPR Screen in Primary Immune Cells to Dissect Regulatory Networks," Cell 162, 675-686 (Jul. 30, 2015);

Ramanan et al., "CRISPR/Cas9 cleavage of viral DNA efficiently suppresses hepatitis B virus," Scientific Reports 5:10833. doi: 10.1038/srep10833 (Jun. 2, 2015);

Nishimasu et al., "Crystal Structure of *Staphylococcus aureus* Cas9," Cell 162, 1113-1126 (Aug. 27, 2015);

Zetsche et al., "Cpf1 Is a Single RNA-Guided Endonuclease of a Class 2 CRISPR-Cas System," Cell 163, 1-13 (Oct. 22, 2015);

Shmakov et al., "Discovery and Functional Characterization of Diverse Class 2 CRISPR-Cas Systems," Molecular Cell 60, 1-13 (Available online Oct. 22, 2015)

each of which is incorporated herein by reference, may be considered in the practice of the instant invention, and discussed briefly below;

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA: Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multi-nucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Zetsche et al. (2015) reported the characterization of Cpf1, a putative class 2 CRISPR effector. It was demonstrated that Cpf1 mediates robust DNA interference with features distinct from Cas9. Identifying this mechanism of interference broadens our understanding of CRISPR-Cas systems and advances their genome editing applications.

Shmakov et al. (2015) reported the characterization of three distinct Class 2 CRISPR-Cas systems. The effectors of two of the identified systems, C2c1 and C2c3, contain RuvC like endonuclease domains distantly related to Cpf1. The third system, C2c2, contains an effector with two predicted HEPN RNase domains.

Methods for Identifying Class 2 Crispr-Cas Effectors

Many embodiments disclosed herein relates to a method of identifying novel CRISPR effectors, comprising: a) identifying sequences in a genomic or metagenomic database encoding a CRISPR array: b) identifying one or more Open Reading Frames (ORFs) in said selected sequences within 10 kb of the CRISPR array: c) discarding all loci encoding proteins which are assigned to known CRISPR-Cas subtypes and, optionally, all loci encoding a protein of less than 700 amino acids; and d) identifying putative novel CRISPR effectors, and optionally classifying them based on structure analysis.

In some embodiments, the CRISPR effector is a Class 2 CRISPR effector.

In some embodiments, step (a) comprises (i) comparing sequences in a genomic and/or metagenomic database with at least one pre-identified seed sequence that encodes a CRISPR array, and selecting sequences comprising said seed sequence; or (ii) identifying CRISPR arrays based on a CRISPR algorithm.

In some embodiments, step (d) comprises identifying nuclease domains.

In some embodiments, step (d) comprises identifying RuvC, HPN, and/or HEPN domains.

In some embodiments, within 10 kb of the CRISPR array no ORF encoding Cas1 or Cas2 is present.

In some embodiments, said ORF in step (b) encode a protein of at least 300 amino acids, preferably between 300 and 700 amino acids.

In some embodiments, putative novel CRISPR effectors obtained in step (d) are used as seed sequences for further comparing genomic and/or metagenomics sequences and subsequent selecting loci of interest as described in steps a) to d).

In some embodiments, the pre-identified seed sequence is obtained by a method comprising: (a) identifying CRISPR motifs in a genomic or metagenomic database, (b) extracting multiple features in said identified CRISPR motifs, (c) classifying the CRISPR loci using unsupervised learning, (d) identifying conserved locus elements based on said classification, and (e) selecting therefrom a putative CRISPR effector suitable as seed sequence.

In some embodiments, said features include protein elements, repeat structure, repeat sequence, spacer sequence and spacer mapping.

In some embodiments, said genomic and metagenomic databases are bacterial and/or archaeal genomes.

In some embodiments, said genomic and metagenomic sequences are obtained from the Ensembl and/or NCBI genome databases.

In some embodiments, the structure analysis in step (d) is based on secondary structure prediction and/or sequence alignments.

In some embodiments, step d) is achieved by clustering of the remaining loci based on the proteins they encode and manual curation of the obtained clusters.

In some embodiments, the clustering of the remaining loci and manual curation of the obtained clusters is performed by sensitive profile-based methods such as HHpred, secondary structure prediction and manual examination of multiple alignments and discarding the loci encoding protein domains deemed irrelevant in the context of the CRISPR-Cas function.

In some embodiments, loci encoding proteins (i) which match with low HHpred homology to any known protein domain, (ii) with minimal existing CRISPR classifications, (iii) which are located at 2 kb or less than 2 kb from the seed sequence, (iv) which have an identical orientation with respect to putative adjacent accessory proteins, (v) with consistent nature of CRISPR arrays nearby similar proteins, and (vi) with few neighboring annotated CRISPR proteins, are selected as candidate Class 2 CRISPR loci.

Moreover, many embodiments disclosed herein relates a method for identifying putative CRISPR effectors comprising (a) identifying multiple CRISPR motifs using genome sequencing data: (b) extracting multiple features from said identified CRISPR motifs, such as protein elements, repeat structure, repeat sequence, spacer sequence and spacer mapping: (c) classifying CRISPR loci based on these features using unsupervised learning: (d) identifying conserved locus elements; and (e) selecting therefrom putative CRISPR effector based on structure analysis.

Furthermore, many embodiments disclosed herein relates a method of identifying a Class 2 CRISPR effector, comprising: a) comparing sequences in a genomic and/or metagenomic database with at least one pre-identified seed sequence that encodes a CRISPR array, and selecting sequences comprising said seed sequence: b) identifying one or more Open Reading Frames (ORFs) in said selected sequences within 10 kb of the CRISPR array, wherein the ORF encode a protein of at least 300 amino acids and comprising one or more RuvC, HPN, and/or HEPN domains; and c) identifying putative novel CRISPR effectors, and optionally classifying them based on structure analysis.

Novel Class 2 Crispr-Cas Effectors

Many embodiments disclosed herein relates to novel Class 2 CRISPR effectors that have been newly identified.

In some embodiment, a recombinant nucleic acid is provided, which comprising a nucleic acid sequence encoding a Class 2 CRISPR effector operably linked to a heterologous promoter, wherein the Class 2 CRISPR effector is not Cas9, Cpf1, C2c1, C2c2, C2c3, and C2c6.

In some embodiments, the Class 2 CRISPR effector is a Type V CRISPR effector.

In some embodiments, the Class 2 CRISPR effector has about 300 and 700 amino acids.

In some embodiments, the Class 2 CRISPR effector comprises a RuvC-like nuclease domain.

In some embodiments, the Class 2 CRISPR effector is a nuclease adapted to break an DNA strand.

In some embodiments, the Class 2 CRISPR effector is an endogenous protein of *Clostridium botulinum* strain 713 CBOT 382, *Peptoclostridium difficile* P20, *Peptoclostridium difficile* DA00114, *Clostridium hiranonis* DSM 13275, *Cellulosilyticum ruminicola* JCM 14822, *Clostridium novyi* B str NCTC 9691, *Clostridium botulinum* strain AM1195 AM1195 7, *Clostridium ljungdahlii* DSM 13528, *Bacillus mycoides* Rock3 17, *Bacillus cereus* MC67, *Ruminococcus albus* 7, *Ruminococcus albus* SY3, *Eubacterium siraeum* DSM 15702, *Clostridium anorexicamassiliense* AP5, *Clostridium novyi* B str NCTC 9691, *Clostridium pasteurianum* BC1, *Thermincola ferriacetica, Syntrophomonas palmitatica* JCM 14374, *Bacillus cereus, Bacillus cereus* H308197, *Bacillus cereus* strain Lr 2 April LG48 098, *Bacillus thuringiensis* HD 771, *Sulfurihydrogenibium azorense* Az Ful, or *Hydrogenivirga* sp 128 5 R1 1.

In some embodiments, the Class 2 CRISPR effector is an endogenous protein of *Microcoleus* PCC 7113, *Lyngbya aestuarii* BL J, *Lyngbya* sp PCC 8106, Cyanothece PCC 8801, Cyanothece sp PCC 8802, *Chamaesiphon minutus* PCC 6605, *Microcystis aeruginosa* PCC 9432, or *Dolichospermum circinale* AWQC310F.

In some embodiments, the Class 2 CRISPR effector is an endogenous protein of *Mycobacterium conceptionense, Gordonia otitidis* NBRC 100426, *Mycobacterium mucogenicum* strain CCH10 A2, *Gordonia polyisoprenivorans* VH2, *Arthrospira platensis* NIES 39, Halothece PCC 7418, Halothece PCC 7418, *Stanieria cyanosphaera* PCC 7437, *Oscillatoria* PCC 7112, *Halorhodospira halophila* SLI, *Meiothermus silvanus* DSM 9946, *Pelobacter propionicus* DSM 2379, *Clostridiales bacterium* DRI 13 BR63.

In some embodiments, the Class 2 CRISPR effector is an endogenous protein of *Propionimicrobium lymphophilum* ACS 093, *Blastococcus saxobsidens* DD2, *Micrococcus luteus* strain 773, *Corynebacterium maris* DSM 45190, *Corynebacterium glutamicum, Rothia dentocariosa* M567, *Rothia mucilaginosa* strain 1211, *Streptococcus parasanguinis* strain 348, *Rothia mucilaginosa* strain 473, *Cellulosimicrobium cellulans* LMG 16121, *Dermacoccus* sp Ellin185, *Streptomyces* sp NRRL S 378, *Streptomyces regensis, Streptomyces* sp, *Streptomyces* sp SPB74, *Streptomyces wadayamensis, Streptomyces rimosus* subsp *rimosus, Kitasatospora cheerisanensis* KCTC 2395, *Nocardiopsis synnemataformans* DSM 44143, *Nocardiopsis alba* DSM 43377, *Streptomyces niveus* NCIMB 11891, *Mycobacterium smegmatis* JS623, *Mycobacterium yongonense* 05 1390, *Mycobacterium* sp UM RHS Contig 9. *Streptomyces* sp CNH099 B121, or *Nocardioides* JS614.

In some embodiments, the Class 2 CRISPR effector is an endogenous protein of *Nodosilinea nodulosa* PCC 7104, *Lyngbya confervoides* BDU141951, *Leptolyngbya boryana* PCC 6306, *Geminocystis* NIES 3709, *Geminocystis* NIES 3708, *Myxosarcina* GII GII, *Xenococcus* PCC 7305, Cyanothece CCY0110, Cyanothece PCC 8801, *Gloeocapsa* PCC 73106, Cyanothece PCC 8802, Halothece PCC 7418, *Crinalium epipsammum* PCC 9333, *Microcoleus* PCC 7113, *Nostoc punctiforme* PCC 73102, *Scytonema hofmanni* UTEX 2349, *Hassallia byssoidea* VB512170, *Nostoc* PCC 7120, *Scytonema millei* VB511283, *Anabaena variabilis* ATCC 29413, *Tolypothrix* PCC 7601 UTEX B 481, *Anabaena* WA102, *Anabaena cylindrica* PCC 7122, *Mastigocoleus testarum* BC008, Cyanothece PCC 8801, *Scytonema hofmanni* PCC 7110, *Calothrix* PCC 7103 PCC 7103, *Calothrix* PCC 6303, Cyanothece PCC 8801, *Crinalium epipsammum* PCC 9333, *Microcoleus* PCC 7113, Geitlerinema PCC 7407, Cyanothece PCC 7425, *Chamaesiphon minutus* PCC 6605, or *Tolypothrix* PCC 7601 UTEX B 481.

In some embodiments, the Class 2 CRISPR effector is a Type VI CRISPR effector.

In some embodiments, the Class 2 CRISPR effector comprises at least one HEPN nuclease domain.

In some embodiments, the Class 2 CRISPR effector comprises at least two HEPN nuclease domains.

In some embodiments, the Class 2 CRISPR effector is a nuclease adapted to break an RNA strand.

In some embodiments, the Class 2 CRISPR effector is an endogenous protein of *Fusobacterium perfoetens.*

In some embodiments, an expression cassette is provided, which comprises the recombinant nucleic acid.

In some embodiments, a vector is provided, which comprises the expression cassette.

In some embodiments, a cell is provided which has been transformed with the vector.

Additional Embodiments

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex. "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments, direct repeats may be identified in silico by searching for repetitive motifs that fulfill any or all of the following criteria: 1. found in a 2 Kb window of genomic sequence flanking the type II CRISPR locus: 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA, i.e. RNA capable of guiding Cas to a target genomic locus, are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies: available at www.novocraft.com), ELAND (Illumina, San Diego, CA), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In a classic CRISPR-Cas systems, the degree of complementarity between a guide sequence and its corresponding target sequence can be about or more than about 50%, 60%, 75%, 80%, 85%, 90%, 95%, 97.5%, 99%, or 100%: a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and advantageously tracr RNA is 30 or 50 nucleotides in length. However, an aspect of the invention is to reduce off-target interactions, e.g., reduce the guide interacting with a target sequence having low complementarity. Indeed, in the examples, it is shown that the invention involves mutations that result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in the context of the present invention the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In particularly preferred embodiments according to the invention, the guide RNA (capable of guiding Cas to a target locus) may comprise (1) a guide sequence capable of hybridizing to a genomic target locus in the eukaryotic cell: (2) a tracr sequence; and (3) a tracr mate sequence. All (1) to (3) may reside in a single RNA, i.e. an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence.

The methods according to the invention as described herein comprehend inducing one or more mutations in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s) RNA(s) or sgRNA(s). The mutations can include the introduction, deletion, or substitution of 1-75 nucleotides at each target sequence of said cell(s) via the guide(s) RNA(s) or sgRNA(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 40, 45, 50, 75, 100, 200, 300, 400 or 500 nucleotides at each target sequence of said cell(s) via the guide(s) RNA(s) or sgRNA(s).

For minimization of toxicity and off-target effect, it will be important to control the concentration of Cas mRNA and guide RNA delivered. Optimal concentrations of Cas mRNA and guide RNA can be determined by testing different concentrations in a cellular or non-human eukaryote animal model and using deep sequencing the analyze the extent of modification at potential off-target genomic loci. Alternatively, to minimize the level of toxicity and off-target effect, Cas nickase mRNA (for example *S. pyogenes* Cas9 with the D10A mutation) can be delivered with a pair of guide RNAs targeting a site of interest. Guide sequences and strategies to minimize toxicity and off-target effects can be as in WO 2014/093622 (PCT/US2013/074667); or, via mutation as herein.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory; the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

The nucleic acid molecule encoding a Cas is advantageously codon optimized Cas. An example of a codon optimized sequence is in this instance a sequence optimized for expression in a eukaryote, e.g., humans (i.e. being optimized for expression in humans), or for another eukaryote, animal or mammal as herein discussed: see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a Cas is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way how the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell: 159(2):440-455 (2014)), describing a Cas9 knock-in mouse, which is incorporated herein by reference. The Cas transgene can further comprise a Lox-Stop-poly A-Lox (LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus, such as for instance one or more oncogenic mutations, as for instance and without limitation described in Platt et al. (2014), Chen et al., (2014) or Kumar et al . . . (2009).

In some embodiments, the Cas sequence is fused to one or more nuclear localization sequences (NLSs), such as about or more than about 1, 2, 3, 4, 5, 6, 7, 8, 9, 10, or more NLSs. In some embodiments, the Cas comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the Cas comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 93); the NLS from nucleoplasmin (e.g. the nucleoplasmin bipartite NLS with the sequence KRPAATKKAGQAKKKK) (SEQ ID NO: 94); the c-myc NLS having the amino acid sequence PAAKRVKLD (SEQ ID NO: 95) or RQRRNELKRSP (SEQ ID NO: 96); the hRNPA1 M9 NLS having the sequence NQSSNFGPMKGGNFGGRSSGPYGGGGQYFAK-PRNQGGY (SEQ ID NO: 97); the sequence RMRIZFKNKGKDTAELRRRRVEVSVELRKAKKD-EQILKRRNV (SEQ ID NO: 98) of the IBB domain from importin-alpha; the sequences VSRKRPRP (SEQ ID NO: 99) and PPKKARED (SEQ ID NO: 100) of the myoma T protein; the sequence PQPKKKPL (SEQ ID NO: 101) of human p53; the sequence SALIKKKKKMAP (SEQ ID NO: 102) of mouse c-abl IV: the sequences DRLRR (SEQ ID NO: 103) and PKQKKRK (SEQ ID NO: 104) of the influenza virus NS1; the sequence RKLKKKIKKL (SEQ ID NO: 105) of the Hepatitis virus delta antigen; the sequence REKKKFLKRR (SEQ ID NO: 106) of the mouse Mx1 protein; the sequence KRKGDEVDGVDEVAKKKSKK (SEQ ID NO: 107) of the human poly(ADP-ribose) polymerase; and the sequence RKCLQAGMNLEARKTKK (SEQ ID NO: 108) of the steroid hormone receptors (human) glucocorticoid. In general, the one or more NLSs are of sufficient strength to drive accumulation of the Cas in a detectable amount in the nucleus of a eukaryotic cell. In general, strength of nuclear localization activity may derive from the number of NLSs in the Cas, the particular NLS(s) used, or a combination of these factors. Detection of accumulation in the nucleus may be performed by any suitable technique. For example, a detectable marker may be fused to the Cas, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry. Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or Cas enzyme activity), as compared to a control no exposed to the Cas or complex, or exposed to a Cas lacking the one or more NLSs.

In certain aspects the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded: nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s) (e.g., sgRNAs); and, when a single vector provides for more than 16 RNA(s) (e.g., sgRNAs), one or more promoter(s) can drive expression of more than one of the RNA(s) (e.g., sgRNAs), e.g., when there are 32 RNA(s) (e.g., sgRNAs), each promoter can drive expression of two RNA(s) (e.g., sgRNAs), and when there are 48 RNA(s) (e.g., sgRNAs), each promoter can drive expression of three RNA(s) (e.g., sgRNAs). By simple arithmetic and well established cloning protocols and the teachings in this disclosure one skilled in the art can readily practice the invention as to the RNA(s) (e.g., sgRNAs) for a suitable exemplary vector such as AAV, and a suitable promoter such as the U6 promoter, e.g., U6-sgRNAs. For example, the packaging limit of AAV is ~4.7 kb. The length of a single U6-sgRNA (plus restriction sites for cloning) is 361 bp. Therefore, the skilled person can readily fit about 12-16, e.g., 13 U6-sgRNA cassettes in a single vector. This can be assembled by any suitable means, such as a golden gate strategy used for TALE assembly (www.genome-engineering.org/taleffectors/). The skilled person can also use a tandem guide strategy to increase the number of U6-sgRNAs by approximately 1.5 times, e.g., to increase from 12-16, e.g., 13 to approximately 18-24, e.g., about 19 U6-sgRNAs. Therefore, one skilled in the art can readily reach approximately 18-24, e.g., about 19 promoter-RNAs, e.g., U6-sgRNAs in a single vector, e.g., an AAV vector. A further means for increasing the number of promoters and RNAs, e.g., sgRNA(s) in a vector is to use a single promoter (e.g., U6) to express an array of RNAs, e.g., sgRNAs separated by cleavable sequences. And an even further means for increasing the number of promoter-RNAs, e.g., sgRNAs in a vector, is to express an array of promoter-RNAs, e.g., sgRNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short, www.nature.com/mt/journal/v16/n9/abs/mt2008144a.html). In an advantageous embodiment, AAV may package U6 tandem sgRNA targeting up to about 50 genes. Accordingly, from the knowledge in the art and the teachings in this disclosure the skilled person can readily make and use vector(s), e.g., a single vector, expressing multiple RNAs or guides or sgRNAs under the control or operatively or functionally linked to one or more promoters-especially as to the numbers of RNAs or guides or sgRNAs discussed herein, without any undue experimentation.

The guide RNA(s), e.g., sgRNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

Ways to package Cas coding nucleic acid molecules, e.g., DNA, into vectors, e.g., viral vectors, to mediate genome modification in vivo include:

- To achieve NHEJ-mediated gene knockout:
  - Single virus vector:
    - Vector containing two or more expression cassettes:
    - Promoter-Cas coding nucleic acid molecule-terminator
    - Promoter-gRNA1-terminator
    - Promoter-gRNA2-terminator
    - Promoter-gRNA (N)-terminator (up to size limit of vector)
  - Double virus vector:
    - Vector 1 containing one expression cassette for driving the expression of Cas
    - Promoter-Cas coding nucleic acid molecule-terminator
    - Vector 2 containing one more expression cassettes for driving the expression of one or more guideRNAs
    - Promoter-gRNA1-terminator
    - Promoter-gRNA (N)-terminator (up to size limit of vector)
- To mediate homology-directed repair.
  - In addition to the single and double virus vector approaches described above, an additional vector is used to deliver a homology-direct repair template.

The promoter used to drive Cas coding nucleic acid molecule expression can include:

- AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce potential toxicity due to over expression of Cas.
- For ubiquitous expression, can use promoters: CMV, CAG, CBh, PGK, SV40, Ferritin heavy or light chains, etc.
- For brain or other CNS expression, can use promoters: SynapsinI for all neurons, CaMKIIalpha for excitatory neurons, GAD67 or GAD65 or VGAT for GABAergic neurons, etc.
- For liver expression, can use Albumin promoter.
- For lung expression, can use SP-B.
- For endothelial cells, can use ICAM.
- For hematopoietic cells can use IFNbeta or CD45.
- For Osteoblasts can use OG-2.

The promoter used to drive guide RNA can include:

- Pol III promoters such as U6 or H1.

Use of Pol II promoter and intronic cassettes to express gRNA.

Working Examples

Example 1—Computational Pipeline for the Discovery of Class 2 CRISPR-Cas Systems from Genomic and Metagenomic Sequences A pipeline that was developed for systematic detection of Class 2 CRISPR-Cas systems is shown in FIG. 1. The procedure begins with the identification of an 'seed' that signifies the presence of a CRISPR-Cas locus in a given nucleotide sequence. In the previously reported analysis, we used as the seed Cas1, the Cas protein that is most common in CRISPR-Cas systems and is most highly conserved at the sequence level. To ensure maximum sensitivity of detection, the search was performed by comparing a Cas1 sequence profile to translated genomic and metagenomic sequences. After the cas1 genes were detected, the neighborhoods were examined for the presence of other cas genes by searching with approximately 400 previously developed profiles for Cas proteins and applying the criteria for the classification of the CRISPR-cas loci. All loci that were assigned to known CRISPR-Cas subtypes by this procedure were discarded from the subsequent analysis. Among the remaining cas1 neighborhoods, those encoding large proteins (>500 amino acids) were chosen for detailed analysis under the premise that Cas9 and Cpf1 are large proteins (typically, >1000 aa), and the respective protein structures suggest that this large size is a requirement to accommodate the complex of the crRNA with the target DNA. The sequences of such large proteins were then screened for known protein domains using sensitive profile-based methods such as HHpred, secondary structure prediction and manual examination of multiple alignments. The proteins containing domains deemed irrelevant in the context of the CRISPR-Cas function (e.g. membrane transporters) were discarded. The use of maximally sensitive methods at this stage is essential because proteins involved in antivirus defense typically evolve extremely fast. This implementation of the pipeline led to the discovery of two subtype of type V (effectors contain a RuvC-like nuclease domains distantly related to that of Cas9) and the new type VI (putative effector contains two HEPN domains). To expand the search to non-autonomous CRISPR-Cas systems, we repeated the same procedures with the CRISPR array used as the seed. The second run of the pipeline resulted in the detection of an additional, heterogeneous subtype of putative type V systems and two subtypes of type VI. The setup of the search described here (see FIG. 1) whereby all large proteins encoded near a cas1 gene or a CRISPR array were analyzed in detail implies that the detected variants represent the complete diversity of CRISPR-Cas systems detectable in the currently available genomes.

Example 2—Putative Type V System

Figure 2:
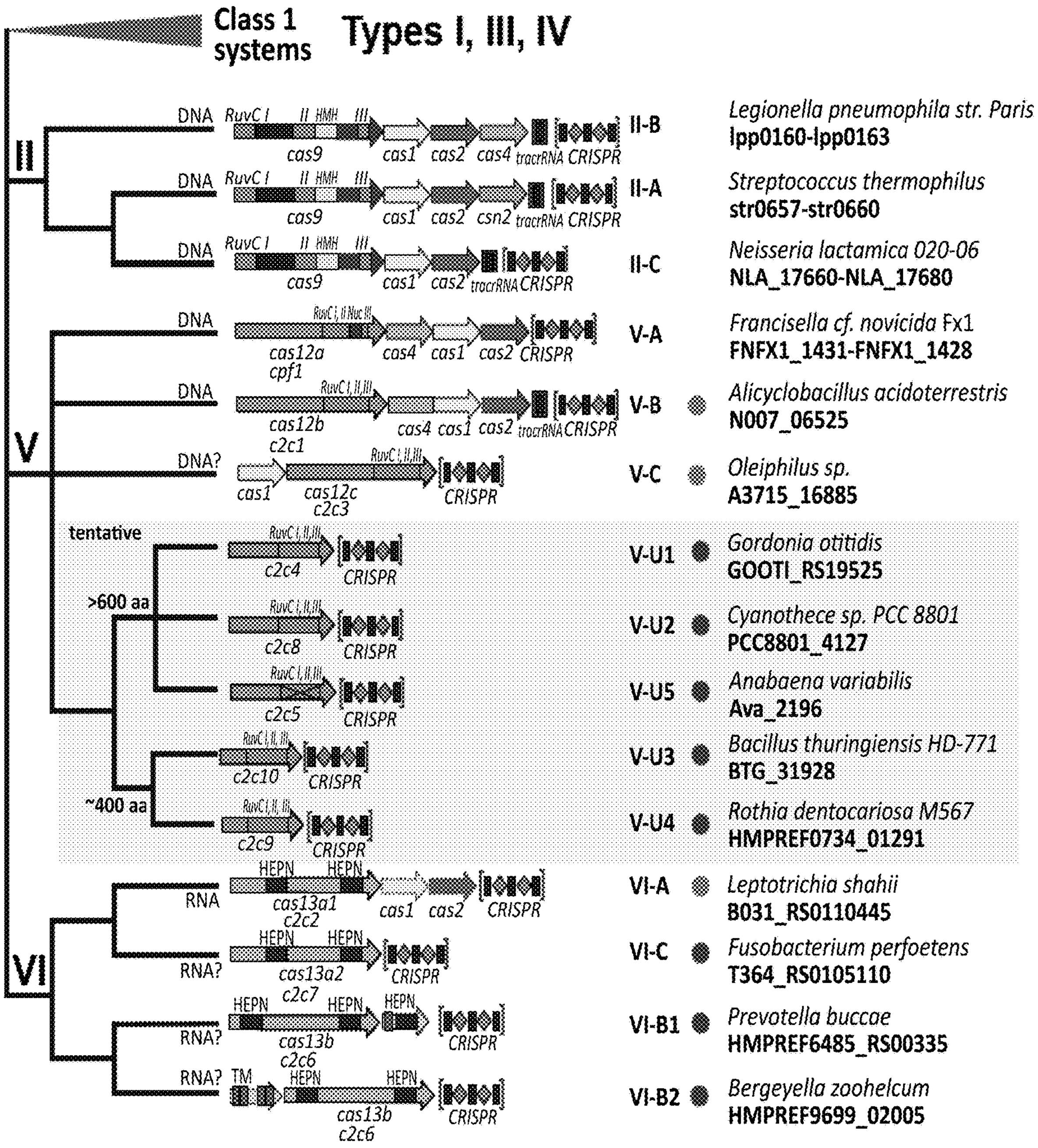
FIG. 2 shows a classification scheme for Class 2 CRISPR-cas systems. The Class 1 systems are collapsed. New Class 2 systems discovered using our computational pipeline (see FIG. 1) are shown by blue circles for those described previously or by red circles for those presented here for the first time. For each Class 2 subtype as well as 5 distinct variants of the provisional subtype V-U, the locus organization and the domain architecture organization of the effector proteins are schematically shown. For subtype VI-A, cas1 and cas2 are shown with dashed contours to indicate that only some of these loci include the adaptation module. For the V-U5 variant, the inactivation of the RuvC-like nucleases domain is indicated by a cross. RuvC I, II, III are the three distinct motifs that contribute to the nuclease catalytic center. TM, putative transmembrane helix. The putative target is indicated for each subtype.
Figure 3:
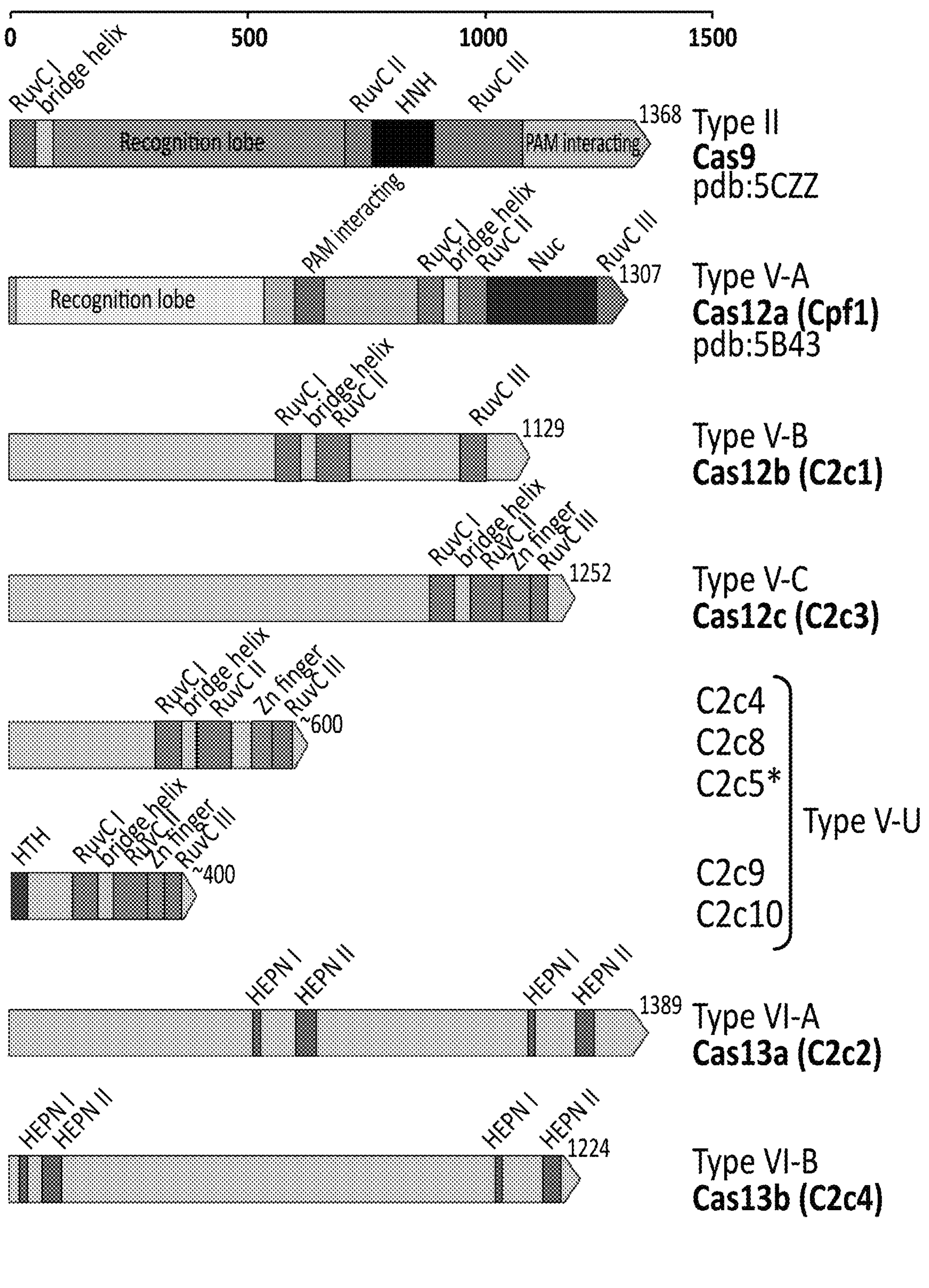
FIG. 3 shows domain architectures of the Class 2 CRISPR effector proteins. For the type II and subtype V-A effectors, the crystal structures (indicated by the Protein Databank (pdb) accession numbers) are available and accordingly the domain architectures are shown in detail. For the rest of the proteins, the grey areas indicate structurally and functionally uncharacterized portions of the proteins. RuvC I, II, III and HEPN I, II denote the respective catalytic motifs of the nuclease domains of the CRISPR effectors. The proteins are shown to scale. For each protein, the number of amino acids is indicated, and a ruler is shown on top of the figure to guide the eye. For the functionally characterized, full length effectors, the proposed new nomenclature (Cas12 and Cas13) is indicated whereas for the putative effectors of type V-U, only the 'candidate', provisional names are shown. The asterisks at C2c5 indicates that this putative effector protein contains replacements of the catalytic residues of the RuvC-like nuclease domain and lacks the Zn-finger.

The distinctive feature of type V CRISPR-Cas sequence is the presence, in the multidomain effector proteins, of RuvC-like nucleases domain. The type II systems share this domain but additionally possess the inserted HNH nuclease domain (FIG. 2). Other than the RuvC-like domain, the effector proteins of the four type V subtypes do not share any detectable sequence similarity to each other or to the Cas9 effectors of type II. However, the comparison of the two available Class 2 effector crystal structures, those of Cas9 and Cpf1, reveals a common structural framework. Both proteins form generally similar bilobed structures in which the RECognition (REC) and NUClease (NUC) lobes are joined through the positively charged bridge helix. Moreover, Cas9 and Cpf1 contain similarly (although not identically) positioned but unrelated domains inserted into the RuvC domain and responsible for the target strand cleavage. The structures of other (putative) large type V effectors discovered in complete CRISPR-Cas loci (i.e., by running the pipeline with the Cas1 seed) are not yet available but a robust interference activity has been demonstrated for subtype V-B. All these effectors share similar size and a single common domain, the RuvC-like endonuclease, although the actual sequence similarity between the effector proteins of different subtypes is extremely low. It appears likely that the type V effectors adopt similar bilobed structures that are required to hold together the crRNA and the target DNA although the effector proteins of different subtypes do not appear to be directly related.

Indeed, the search for likely ancestors of the type II and type V effectors showed that the RuvC-like nuclease domains are related to TnpB proteins, extremely abundant but poorly functionally characterized nucleases encoded by numerous autonomous and non-autonomous bacterial and archaeal transposons. In addition to the RuvC-like nuclease domain, the TnpB proteins contain a counterpart to the arginine-rich bridge helix suggesting the possibility that the TnpB protein bind RNA. For Cas9, the "smoking gun", the likely direct ancestor of the type II effectors, has been identified on the basis of highly significant sequence similarity and the presence of the HNH insert in the RuvC-like nuclease domain of a distinct family of TnpB proteins that has been denoted IscB (Insertion Sequences Cas9-like protein B). For the effector proteins of type V, the direct ancestry is difficult to identify given that the similarity between these proteins and TnpB is much lower than it is in the case of Cas9 and is largely limited to the RuvC-like nuclease catalytic motifs. Nevertheless, the effectors of the three subtypes of type V clearly show the highest similarity to different TnpB families leading to the hypothesis of independent origins of the type V effectors from the pool of tnpB genes. It has been proposed that the respective TnpB-encoding transposons initially integrated in the vicinity of an adaptation module and a CRISPR array, possibly displacing Class 1 effector modules. Such a scenario is compatible with the observations that the cas genes of different Class 2 subtypes are nested with different branches of Class 1.

The search for putative CRISPR-cas loci lacking the adaptation module (i.e. with a CRISPR used as the seed: see FIG. 1) yielded several additional variants of putative type V systems (FIG. 2) that might shed light on the evolutionary path from TnpB to full-fledged CRISPR-cas effectors. These proteins that we provisionally assigned to subtype V-U share two features that clearly distinguish them from the type II and type V effectors associated with complete CRISPR-cas loci. First, these proteins are much smaller than the effectors of complete Class2 systems, comprising between ca. 400) (the typical size of TnpB) and ca. 700 amino acids (roughly between the size of TnpB and the typical size of the bona fide Class 2 effectors). Second, these smaller TnpB homologs associated with CRISPR arrays show a much higher level of similarity to TnpB than the larger type I and type V effectors. In particular, 5 groups of these smaller TnpB homologs showed evolutionary coherence in terms of sequence conservation and consistent association with CRISPR arrays (FIG. 2). In view of the identification of these smaller CRISPR-associated TnpB homologs, we ran the pipeline (FIG. 1) in a modified form whereby the requirement for the minimal length of the protein adjacent to the CRISPR-array was lifted. The results were specifically searched for the presence of additional TnpB homologs. This analysis led to the detection of many CRISPR-associated TnpB homologs in the size range typical of the transposon-encoded TnpB, i.e. about 400 amino acids.

Figure 4:
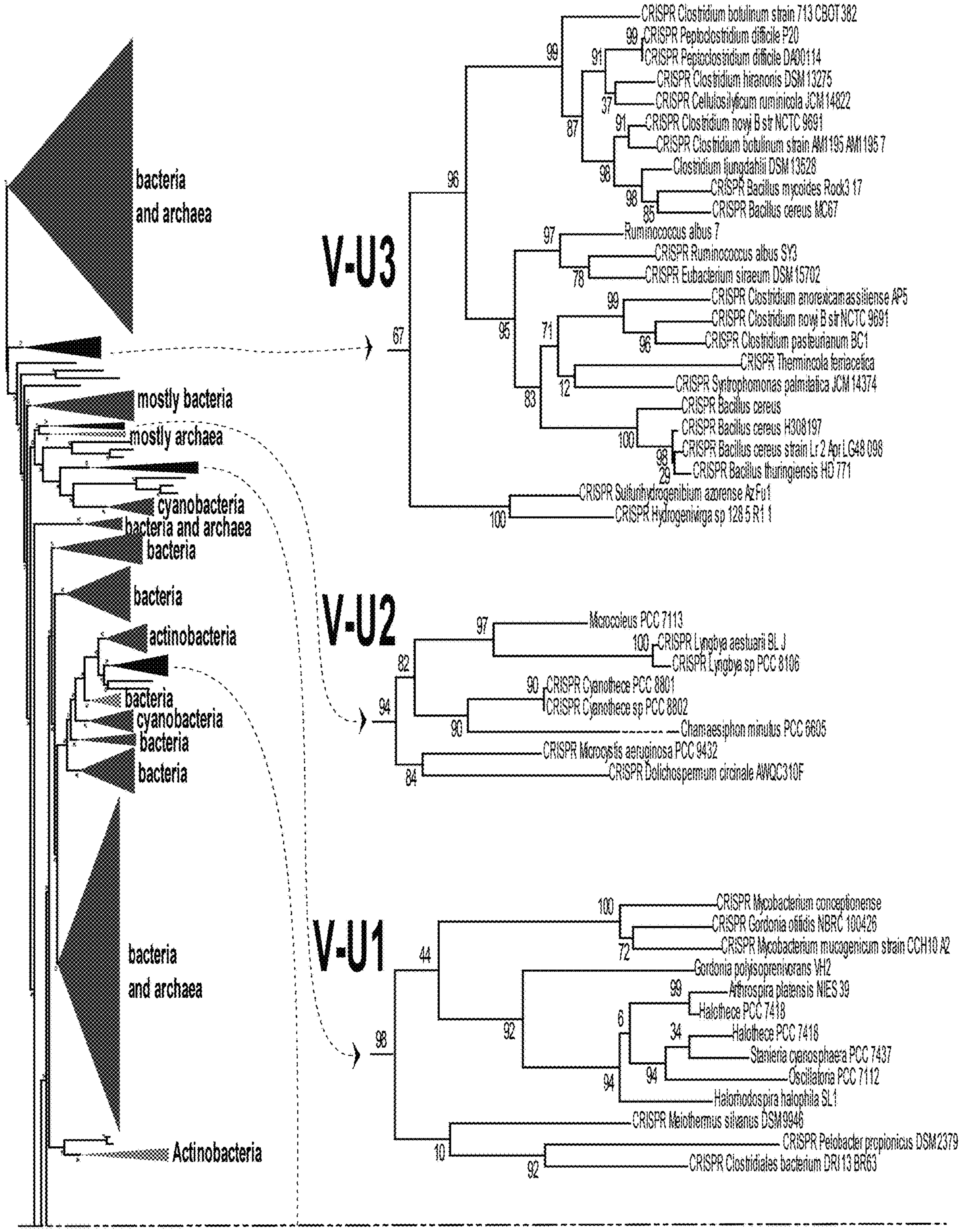
FIG. 4 shows phylogenetic tree of TnpB nucleases including type V-U effectors. The major families of TnpB proteins are collapsed and shown by blue triangles. The 4 distinct groups of CRISPR-associated TnpB homologs (putative subtype V-U effectors) are shown by red triangles and blown up to the species level resolution on the right. For these subtrees, bootstrap values (%) are shown at each internal branch. The V-B5 variant is provisionally added at the root of the tree. The presence of a CRISPR array next to the gene encoding a TnpB homolog is indicated for each locus. For the accession number of all sequences included in the tree.
Figure 5:
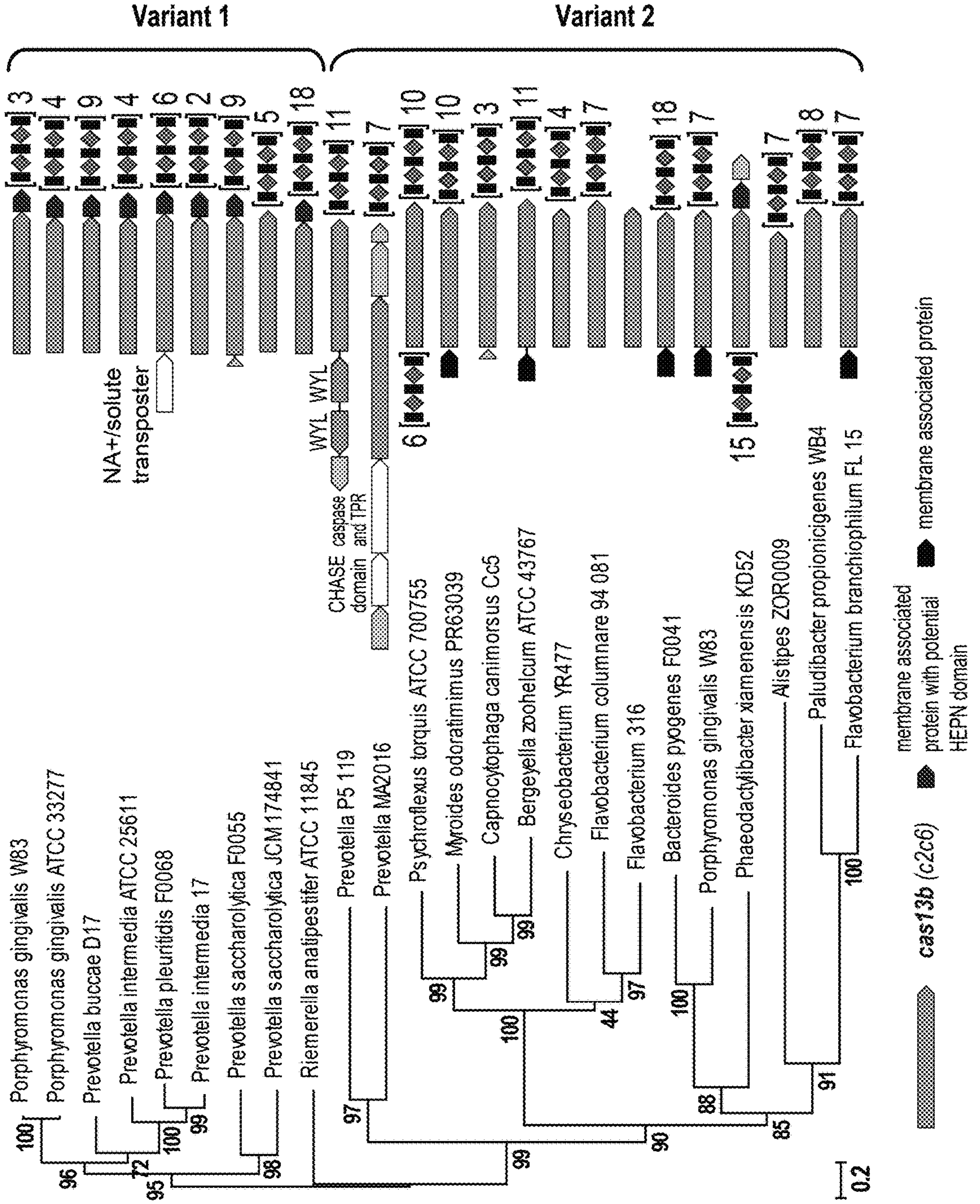
FIG. 5 shows phylogenetic tree of the subtype VI-B effector proteins, Cas13b. The tree was constructed as in FIG. 4, and the bootstrap values are indicated for each internal branch. The organization of each locus is schematically shown on the right, and the number of CRISPR units is indicated. TPR, tetratricopeptide repeats; WYL, putative ligand-binding domain associated with some CRISPR-Cas systems (named for the 3 conserved amino acid residues); CHASE, cyclase/histidine kinase-associated sensing extracellular domain.
Figure 6:
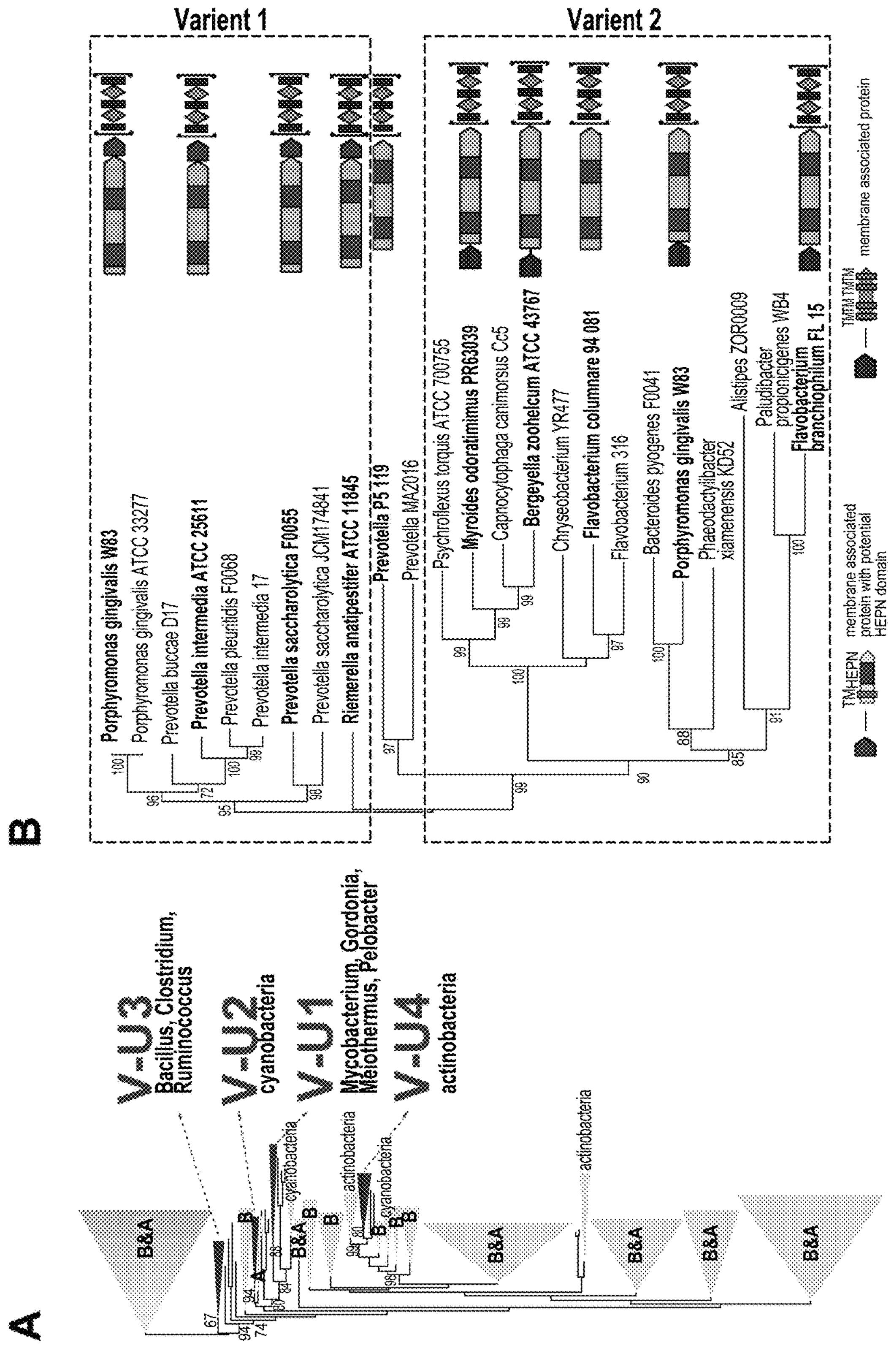
FIG. 6 shows phylogenies of the type V and type VI-B effectors. (A) Phylogenetic tree of TnpB nucleases including type V-U effectors with a putative active RuvC domain. The major subtrees of TnpB proteins are collapsed and shown by light blue triangles if they include representatives located next to a CRISPR array or by light yellow if no such representatives were identified in the respective branch. Dominant bacterial or archaeal lineages (if any) are indicated in the triangles. Abbreviations: A-diverse archaea; B, diverse bacteria. The 4 distinct groups of CRISPR-associated TnpB homologs (putative subtype V-U effectors) are shown by red triangles: for each of these, the classification and a list of major lineages is provided to the right of the tree. For these subtrees, bootstrap values (%) are shown for selected branches. (B) Phylogenetic tree of the subtype VI-B effector proteins, Cas13b. The tree was constructed as in (A), and the bootstrap values are indicated for selected internal branches. The organization of a typical cas13b locus for selected representatives (bold) is schematically shown on the right.

Whereas for the larger type V effectors, low sequence conservation precluded reliable phylogenetic analysis, a robust tree could be constructed for the smaller CRISPR-associated homologs and the typical TnpB. The topology of this tree clearly indicated that 4 of the 5 distinct variants of subtype V-U (hereinafter V-U1-5) originated from different TnpB families (FIG. 4), in agreement with the hypothesis on the independent evolution of the effectors of different Class 2 variants (subtypes) from transposon-encoded nucleases. In addition, a fifth group (V-U5) that is represented in a variety of Cyanobacteria consists of diverged TnpB homologs with multiple mutations in the catalytic motifs of the RuvC-like domain and was accordingly not included in the phylogeny. Of these 5 distinct variants, V-U1 is represented in diverse bacteria whereas the remaining ones are largely limited in their spread to a particular bacterial taxon (FIGS. 4 and 5). We further extended this evolutionary analysis to all (putative) type V effectors by building a cluster dendrogram based on the distances derived from profile to profile comparisons of the respective protein sequences. The results support the possibility that the effectors of each of the identified subtypes as well as several variants within the subtype V-U originated independently from different TnpB families.

The subtype V-U TnpB-like proteins appear to be too small to adopt the bilobed structure of sufficient size to accommodate the complex of the crRNA with the target DNA as the typical Class 2 effectors do, and therefore are unlikely to function in that capacity, at least not without additional partners. Nevertheless, the evolutionarily stable association of at least 5 distinct variants with CRISPR arrays implies that at least some of these proteins do perform CRISPR-dependent biological functions. Such functions might involve a typical CRISPR response aided by additional, non-Cas proteins. Remarkably, the CRISPR arrays associated with group V-U3 that is represented primarily in Bacilli and Clostridia contain multiple spacers that exactly match genomic sequences of bacteriophages infecting these bacteria. The presence of the phage-specific spacers implies that at least this variant within subtype V-U is a functional CRISPR-Cas system that is actively engaged in anti-phage adaptive immunity. The complete genomes containing the V-U3 (as well as V-U4) loci typically lack additional CRISPR-Cas systems. Alternatively, some of the V-U systems might be involved in distinct regulatory roles. This is particularly plausible for the V-U5 variant which appears to encompass a catalytically inactive TnpB homolog (FIG. 2). It is furthermore notable that in the complete genomes that contain the V-U2 and V-U5 loci along with other CRISPR-Cas systems, the CRISPR sequences associated with the former loci are unique, suggestive of distinct functions for these putative type V loci.

The locus architectures of the type V CRISPR-Cas systems are comparatively simple and resemble those of the type II loci (FIG. 2). Among the complete loci, subtype V-C is characterized by the simplest organization among the known systems, with the putative adaptation module consisting only of a distinct variety of Cas1 but no Cas2 protein. Subtypes V-A and V-B share the composition of the adaptation module that, in addition to Cas1 and Cas2, includes the Cas4 nuclease that in subtype V-B is encoded by a fusion gene with Cas1 (FIG. 2): the role of Cas4 in adaptation has been demonstrated for some type I systems. The subtype I-U loci lack any additional cas genes (FIG. 2). An important difference between the subtypes of type V is the requirement or lack thereof for a tracrRNA. Similar to type II, the type V-B systems have been shown to encode a tracrRNA. In contrast, Cpf1, the subtype V-A effector, has been characterized as a single RNA-guided nuclease that does not depend on tracrRNA which indeed does not appear to be encoded in the subtype V-A loci.

Newly discovered type V-U effectors are listed in Table 1. Multiple alignment of representative effectors from each of the five V-U subtypes are provided in FIG. 9.

TABLE 1

Type V-U CRISPR Effectors

| SEQ ID No | Local ID | Subfamily | Genome partition ID | Coordinates of the gene |
|---|---|---|---|---|
| 1 | 118577413 V-U1 | Pelobacter_propionicus_DSM_2379_uid58255 | NC_008607 | 189989 . . . 191983 |
| 2 | 1096423661 V-U1 | Mycobacterium conceptionense | LSKA01000495.1 | 6173 . . . 7963 |
| 3 | 1024922355 V-U1 | Gordonia otitidis NBRC 100426 | CP003591.1 | 3406549 . . . 3408810 |
| 4 | 1903609002 V-U1 | Mycobacterium mucogenicum strain CCH10-A2 CCH10-A2_contig531 | CP013015.1 | 1046310 . . . 1047626 |
| 5 | 1003450287 V-U1 | Meiothermus silvanus DSM 9946 | CP004310.1 | 7869 . . . 9053 |
| 6 | 1507071745 V-U1 | Clostridiales bacterium DRI-13 BR63DRAFT_scaffold00024.24_C | JHDU01000036.1 | 5392 . . . 6912 |
| 7 | 218248844 V-U2 | Cyanothece_PCC_8801_uid59027 | NC_011726 | 4331770 . . . 4333254 |
| 8 | 428311397 V-U2 | Microcoleus_PCC_7113_uid183114 | NC_019738 | 3704312 . . . 3706207 |
| 9 | 1046552329 V-U2 | Lyngbya aestuarii BL J | GG704699.1 | 234671 . . . 235915 |
| 10 | 1019491369 V-U2 | Lyngbya sp. PCC 8106 | CP001701.1 | 2289597 . . . 2291435 |
| 11 | 1002782830 V-U2 | Cyanothece sp. PCC 8802 | CM000744.1 | 5384706 . . . 5386142 |
| 12 | 1030942420 V-U2 | Microcystis aeruginosa PCC 9432 | AOLW01000047.1 | 195031 . . . 196203 |
| 13 | 1305565200 V-U2 | Dolichospermum circinale AWQC310F genomic scaffold 310F_Scaffold21 | JVFS01000043.1 | 149459 . . . 151135 |
| 14 | 402558454 V-U3 | Bacillus_thuringiensis_HD_771_uid173374 | NC_018501 | 43675 . . . 45027 |
| 15 | 300853273 V-U3 | Clostridium_ljungdahlii_DSM_13528_uid50583 | NC_014328 | 47093 . . . 48508 |
| 16 | 488769073 V-U3 | Clostridium_pasteurianum_BC1_uid201478 | NC_021182 | 86649 . . . 87935 |
| 17 | 317133985 V-U3 | Ruminococcus_albus_7_uid51721 | NC_014824 | 316073 . . . 317434 |
| 18 | 1705264553 V-U3 | Clostridium botulinum strain 713_CBOT 382_89760_1793432 | CP000239.1 | 731379 . . . 732659 |

TABLE 1-continued

Type V-U CRISPR Effectors

| | | | | | |
|---|---|---|---|---|---|
| 19 | 1043743222 | V-U3 | Peptoclostridium difficile P20 | AWWH01000158.1 | 23337 . . . 24521 |
| 20 | 1043409625 | V-U3 | Peptoclostridium difficile DA00114 | LN851177.1 | 607439 . . . 608656 |
| 21 | 1017733463 | V-U3 | Clostridium hiranonis DSM 13275 | CP001293.1 | 171333 . . . 172478 |
| 22 | 1804030309 | V-U3 | Cellulosilyticum ruminicola JCM 14822 DNA | JH930358.1 | 842544 . . . 844580 |
| 23 | 1077873159 | V-U3 | Clostridium novyi B str. NCTC 9691 | AAVU01000008.1 | 88984 . . . 90171 |
| 24 | 1905047130 | V-U3 | Clostridium botulinum strain AM1195 AM1195_7 | KI543234.1 | 99381 . . . 100637 |
| 25 | 1018643584 | V-U3 | Bacillus mycoides Rock3-17 | CP001287.1 | 3090392 . . . 3092440 |
| 26 | 1029128199 | V-U3 | Bacillus cereus MC67 | AP014821.1 | 690780 . . . 692630 |
| 27 | 1059072407 | V-U3 | Ruminococcus albus SY3 | AP017308.1 | 3158482 . . . 3159606 |
| 28 | 1017485595 | V-U3 | Eubacterium siraeum DSM 15702 | AAXW01000027.1 | 13366 . . . 15204 |
| 29 | 1077873155 | V-U3 | Clostridium novyi B str. NCTC 9691 | AAVU01000010.1 | 146528 . . . 147619 |
| 30 | 1100000271 | V-U3 | Thermincola ferriacetica | KK307111.1 | 94260 . . . 95639 |
| 31 | 1804024535 | V-U3 | Syntrophomonas palmitatica JCM 14374 DNA | JH930357.1 | 752813 . . . 753934 |
| 32 | 1122605119 | V-U3 | Bacillus cereus | AP017295.1 | 5092456 . . . 5094363 |
| 33 | 1019720777 | V-U3 | Bacillus cereus H3081.97 | GL892032.1 | 2978305 . . . 2979429 |
| 34 | 1700567090 | V-U3 | Bacillus cereus strain Lr 2-Apr LG48_098 | CP000240.1 | 605551 . . . 606744 |
| 35 | 529067778 | V-U4 | Corynebacterium_maris_DSM_45190_uid214081 | NC_021920 | 4967 . . . 6613 |
| 36 | 433644734 | V-U4 | Mycobacterium_smegmatis_JS623_uid184820 | NC_019959 | 39760 . . . 41247 |
| 37 | 451770599 | V-U4 | Mycobacterium_yongonense_05_1390_uid189649 | NC_020276 | 1603 . . . 3144 |
| 38 | 1706842133 | V-U4 | Micrococcus luteus strain 773_MLUT 184_13961_611621 | LGTE01000024.1 | 35698 . . . 37032 |
| 39 | 1009979974 | V-U4 | Corynebacterium glutamicum | LGVS01000034.1 | 22840 . . . 24252 |
| 40 | 1016662850 | V-U4 | Rothia dentocariosa M567 | KB899040.1 | 1248881 . . . 1250119 |
| 41 | 1705782714 | V-U4 | Rothia mucilaginosa strain 1211_RMUC 305_65084_1729696_109_ | BBCE01000017.1 | 52764 . . . 54257 |
| 42 | 1800346325 | V-U4 | Streptococcus parasanguinis strain 348_SPAR 455_33078_318375 | JQLJ01000001.1 | 1862742 . . . 1863920 |
| 43 | 1706614983 | V-U4 | Rothia mucilaginosa strain 473_RMUC 364_156967_2761259_266_ | LGTE01000024.1 | 32013 . . . 33293 |
| 44 | 1206162758 | V-U4 | Cellulosimicrobium cellulans LMG 16121 WGS project CAOI00000000 data | AVIV01000129.1 | 1206 . . . 2411 |
| 45 | 1095979361 | V-U4 | Streptomyces regensis | LFOD01000003.1 | 204245 . . . 206056 |
| 46 | 1305448890 | V-U4 | Streptomyces sp. CNS606 K304DRAFT_scaffold00043.43_C | JVYQ01000016.1 | 47267 . . . 48940 |
| 47 | 1017562432 | V-U4 | Streptomyces sp. SPB74 | CP001291.1 | 871333 . . . 872835 |
| 48 | 1075489406 | V-U4 | Streptomyces wadayamensis | AAVU01000062.1 | 13590 . . . 15629 |
| 49 | 1504922986 | V-U4 | Streptomyces rimosus subsp. rimosus strain NRRL WC-3927 contig19.1 | GG770539.1 | 3044316 . . . 3045845 |
| 50 | 1075265077 | V-U4 | Kitasatospora cheerisanensis KCTC 2395 | LATL02000229.1 | 28651 . . . 29838 |
| 51 | 1207200189 | V-U4 | Nocardiopsis synnemataformans DSM 44143 contig_9 | JYNK01000007.1 | 551994 . . . 553157 |
| 52 | 1207283968 | V-U4 | Nocardiopsis alba DSM 43377 contig_18 | KE150269.1 | 1355683 . . . 1357281 |
| 53 | 1048804328 | V-U4 | Streptomyces niveus NCIMB 11891 | CP002427.1 | 482416 . . . 483669 |
| 54 | 1401235120 | V-U4 | Mycobacterium sp. UM_RHS Contig_9 | KK073768.1 | 4862951 . . . 4864153 |
| 55 | 1040961339 | V-U4 | Propionimicrobium lymphophilum ACS-093-V-SCH5 | KK853997.1 | 2723615 . . . 2725093 |
| 56 | 1405224212 | V-U4 | Streptomyces sp. CNH099 B121DRAFT_scaffold_35.36_C | JH980292.1 | 654051 . . . 655259 |
| 57 | 440680311 | V-U5 | Anabaena cylindrica PCC 7122 | NC_019771 | 736937 . . . 738865 |
| 58 | 428305730 | V-U5 | Crinalium epipsammum PCC 9333 | NC_019753 | 2459484 . . . 2461619 |
| 59 | 428306136 | V-U5 | Crinalium epipsammum PCC 9333 | NC_019753 | 2911658 . . . 2913502 |
| 60 | 220908491 | V-U5 | Cyanothece sp. PCC 7425 | NC_011884 | 3086956 . . . 3088887 |
| 61 | 257060041 | V-U5 | Cyanothece sp. PCC 8802 | NC_013161 | 2226229 . . . 2228232 |
| 62 | 428776047 | V-U5 | Halothece sp. PCC 7418 | NC_019779 | 1563969 . . . 1565936 |
| 63 | 428311644 | V-U5 | Microcoleus sp. PCC 7113 | NC_019738 | 4021458 . . . 4023371 |
| 64 | 428312908 | V-U5 | Microcoleus sp. PCC 7113 | NC_019738 | 5618464 . . . 5620371 |
| 65 | 17230183 | V-U5 | Nostoc sp. PCC 7120 | NC_003272 | 3282086 . . . 3284110 |

TABLE 1-continued

Type V-U CRISPR Effectors

| | | | | | |
|---|---|---|---|---|---|
| 66 | 1019531886 | V-U5 | Cyanothece sp. CCY0110 | AEIQ01000064.1 | 599 . . . 2212 |
| 67 | 1111222001 | V-U5 | Mastigocoleus testarum BC008 | ANAW01000009.1 | 89276 . . . 90784 |
| 68 | 1406824382 | V-U5 | Tolypothrix Scytonema hofmanni UTEX 2349 genomic scaffold Tol9009DRAFT_TPD.8 | AUFD01000045.1 | 6273 . . . 7820 |
| 69 | 1206817639 | V-U5 | Calothrix sp. PCC 7103 genomic scaffold Cal7103DRAFT_CPM.1 | AVLX01000025.1 | 5639 . . . 6853 |
| 70 | 1007109870 | V-U5 | Anabaena cylindrica PCC 7122 | AYKZ01000007.1 | 13194 . . . 14723 |
| 71 | 1300380544 | V-U5 | Scytonema hofmanni PCC 7110 contig00008 | AZVL01000034.1 | 4057 . . . 5586 |
| 72 | 1002400088 | V-U5 | Cyanothece sp. PCC 8801 | BARH01000009.1 | 169965 . . . 171089 |
| 73 | 1007062327 | V-U5 | Calothrix sp. PCC 6303 | BBCG01000021.1 | 37618 . . . 38814 |
| 74 | 1002125473 | V-U5 | Nostoc punctiforme PCC 73102 | CP000117.1 | 2724972 . . . 2726903 |
| 75 | 1205733553 | V-U5 | Nodosilinea nodulosa PCC 7104 genomic scaffold Lepto7104DRAFT_LPD.2 | CP001037.1 | 6984000 . . . 6985919 |
| 76 | 1507700957 | V-U5 | Myxosarcina sp. GI1 contig_23 | CP001403.1 | 703203 . . . 704498 |
| 77 | 1000428792 | V-U5 | Nostoc sp. PCC 7120 | CP001785.1 | 691337 . . . 692632 |
| 78 | 1085030414 | V-U5 | Scytonema millei VB511283 | CP002044.1 | 109533 . . . 111143 |
| 79 | 1007036557 | V-U5 | Geitlerinema sp. PCC 7407 | CP002408.1 | 664453 . . . 665595 |
| 80 | 1004799941 | V-U5 | Anabaena variabilis ATCC 29413 | CP008811.1 | 36391 . . . 37491 |
| 81 | 1085045623 | V-U5 | Lyngbya confervoides BDU141951 | CP009520.1 | 3546198 . . . 3547451 |
| 82 | 1030021203 | V-U5 | Tolypothrix sp. PCC 7601 | CP011832.1 | 2453693 . . . 2454940 |
| 83 | 1016058386 | V-U5 | Nostoc sp. NIES-3756 | HG764817.1 | 5979713 . . . 5981140 |
| 84 | 1016001624 | V-U5 | Geminocystis sp. NIES-3709 | JENV01000018.1 | 78100 . . . 79593 |
| 85 | 1002781021 | V-U5 | Cyanothece sp. PCC 8802 | JH792114.1 | 681985 . . . 683475 |
| 86 | 1085056708 | V-U5 | Hassallia byssoidea VB512170 | JQNS01000003.1 | 410982 . . . 412205 |
| 87 | 1405885249 | V-U5 | Aphanizomenon flos-aquae NIES-81 genomic scaffold scaffold00002 | JVKQ01000122.1 | 24882 . . . 26570 |
| 88 | 1004798910 | V-U5 | Anabaena variabilis ATCC 29413 | KB217483.1 | 719459 . . . 721408 |
| 89 | 1002781834 | V-U5 | Cyanothece sp. PCC 8802 | KB976804.1 | 107528 . . . 108649 |
| 90 | 1300485477 | V-U5 | Leptolyngbya boryana PCC 6306 genomic scaffold LepboDRAFT_LPC.1 | KE384066.1 | 16736 . . . 17842 |
| 91 | 1016002403 | V-U5 | Geminocystis sp. NIES-3709 | KQ956191.1 | 3754 . . . 4848 |
| 92 | 1002400093 | V-U5 | Cyanothece sp. PCC 8801 | LIOK01000006.1 | 162536 . . . 163630 |

| SEQ ID No | Strand | Organism |
|---|---|---|
| 1 | − | Pelobacter_propionicus_DSM_2379_uid58255 |
| 2 | + | Mycobacterium_mucogenicum_CCH10_A2_GCA_001556905.1 |
| 3 | − | Geitlerinema_PCC_7407_PCC_7407_GCA_000317045.1 |
| 4 | + | delta_proteobacterium_HotSeep1_HS1_GCA_001577525.1 |
| 5 | + | Borrelia_crocidurae_DOU_GCA_000568715.1 |
| 6 | − | Streptomyces_wadayamensis_A23_GCA_000698945.1 |
| 7 | − | Cyanothece_PCC_8801_uid59027 |
| 8 | − | Microcoleus_PCC_7113_uid183114 |
| 9 | + | Lactobacillus_fermentum_28_3_CHN_GCA_000162395.1 |
| 10 | − | Cyanothece_PCC_8802_PCC_8802_GCA_000024045.1 |
| 11 | + | Bacillus_mycoides_Rock3_17_GCA_000161435.1 |
| 12 | + | Haloarcula_amylolytica_JCM_13557_GCA_000336615.1 |
| 13 | + | Rothia_mucilaginosa_473_RMUC_GCA_001065135.1 |
| 14 | + | Bacillus_thuringiensis_HD_771_uid173374 |
| 15 | + | Clostridium_ljungdahlii_DSM_13528_uid50583 |
| 16 | − | Clostridium_pasteurianum_BC1_uid201478 |
| 17 | + | Ruminococcus_albus_7_uid51721 |
| 18 | − | Synechococcus_JA_3_3Ab_JA_3_3Ab_GCA_000013205.1 |
| 19 | − | Lactobacillus_equi_DPC_6820_GCA_000504525.1 |
| 20 | − | Lactobacillus_agilis_Marseille_GCA_001243975.1 |
| 21 | − | Cyanothece_PCC_7424_PCC_7424_GCA_000021825.1 |
| 22 | + | Tolypothrix_PCC_7601_UTEX_B_481_GCA_000300115.1 |
| 23 | + | Lyngbya_PCC_8106_PCC_8106_GCA_000169095.1 |
| 24 | + | uncultured_archaeon_A07HR60_GCA_000496235.1 |
| 25 | + | Cyanothece_PCC_8801_PCC_8801_GCA_000021805.1 |
| 26 | − | Geminocystis_NIES_3709_NIES_3709_GCA_001548115.1 |
| 27 | − | Leptolyngbya_NIES_3755_NIES_3755_GCA_001548435.1 |
| 28 | − | Cyanothece_CCY0110_CCY0110_GCA_000169335.1 |
| 29 | − | Lyngbya_PCC_8106_PCC_8106_GCA_000169095.1 |
| 30 | − | Mycobacterium_tuberculosis_2228BH_GCA_000649295.1 |
| 31 | − | Tolypothrix_PCC_7601_UTEX_B_481_GCA_000300115.1 |
| 32 | − | Nostoc_NIES_3756_NIES_3756_GCA_001548375.1 |
| 33 | − | Desmospora_8437_8437_GCA_000213595.1 |
| 34 | + | Synechococcus_JA_2_3B_a_2_13_JA_2_3B_a_2_13_GCA_000013225.1 |
| 35 | − | Corynebacterium_maris_DSM_45190_uid214081 |
| 36 | − | Mycobacterium_smegmatis_JS623_uid184820 |

TABLE 1-continued

| Type V-U CRISPR Effectors | | |
|---|---|---|
| 37 | + | Mycobacterium_yongonense_05_1390_uid189649 |
| 38 | + | Thermincola_ferriacetica_Z_0001_GCA_001263415.1 |
| 39 | − | Clostridium_botulinum_48212_CD_GCA_001264515.1 |
| 40 | − | Coprothermobacter_platensis_DSM_11748_GCA_000378005.1 |
| 41 | − | Syntrophomonas_palmitatica_JCM_14374_GCA_001311885.1 |
| 42 | + | Thermus_scotoductus_KI2_GCA_000744155.1 |
| 43 | + | Thermincola_ferriacetica_Z_0001_GCA_001263415.1 |
| 44 | − | Peptoclostridium_difficile_DA00114_GCA_000449965.2 |
| 45 | − | Mycobacterium_conceptionense_MLE_GCA_001077745.1 |
| 46 | − | Rothia_mucilaginosa_1211_RMUC_GCA_001060545.1 |
| 47 | − | Cyanothece_PCC_7424_PCC_7424_GCA_000021825.1 |
| 48 | + | Lyngbya_PCC_8106_PCC_8106_GCA_000169095.1 |
| 49 | − | Streptomyces_SPB074_SPB074_GCA_000154905.1 |
| 50 | − | Limnoraphis_robusta_CS_951_GCA_000972705.2 |
| 51 | + | Peptoclostridium_difficile_ZJCDC_S82_GCA_000949855.1 |
| 52 | + | Propionimicrobium_lymphophilum_ACS_093_V_SCH5_GCA_000411175.1 |
| 53 | + | Lactobacillus_helveticus_H9_GCA_000525715.1 |
| 54 | − | Scytonema_hofmanni_UTEX_2349_GCA_000582685.1 |
| 55 | + | Kitasatospora_cheerisanensis_KCTC_2395_GCA_000696185.1 |
| 56 | − | Spirulina_subsalsa_PCC_9445_GCA_000314005.1 |
| 57 | + | Anabaena_cylindrica_PCC_7122_uid183339 |
| 58 | + | Crinalium_epipsammum_PCC_9333_uid183113 |
| 59 | + | Crinalium_epipsammum_PCC_9333_uid183113 |
| 60 | + | Cyanothece_PCC_7425_uid59435 |
| 61 | + | Cyanothece_PCC_8802_uid59143 |
| 62 | + | Halothece_PCC_7418_uid183338 |
| 63 | + | Microcoleus_PCC_7113_uid183114 |
| 64 | − | Microcoleus_PCC_7113_uid183114 |
| 65 | + | Nostoc_PCC_7120_uid57803 |
| 66 | − | Dermacoccus_Ellin185_Ellin185_GCA_000152185.2 |
| 67 | + | Nocardiopsis_synnemataformans_DSM_44143_GCA_000340945.1 |
| 68 | − | Streptomyces_CNS606_CNS606_GCA_000426325.1 |
| 69 | + | Peptoclostridium_difficile_P20_GCA_000451725.2 |
| 70 | + | Chloroflexi_bacterium_JGI_0000112_G22_JGI_0000112_G22_GCA_000494585.1 |
| 71 | − | Pseudomonas_URIL14HWK12_I6_URIL14HWK12_I6_GCA_000514195.1 |
| 72 | + | Anoxybacillus_flavithermus_NBRC_109594_GCA_000367505.1 |
| 73 | + | Cellulosilyticum_ruminicola_JCM_14822_GCA_001311925.1 |
| 74 | + | Anabaena_variabilis_ATCC_29413_GCA_000204075.1 |
| 75 | − | Nostoc_punctiforme_PCC_73102_GCA_000020025.1 |
| 76 | + | Sulfolobus_islandicus_Y_G_57_14_GCA_000022465.1 |
| 77 | + | Ammonifex_degensii_KC4_GCA_000024605.1 |
| 78 | − | Meiothermus_silvanus_DSM_9946_GCA_000092125.1 |
| 79 | + | Candidatus_Nitrososphaera_gargensis_Ga9_2_GCA_000303155.1 |
| 80 | − | Campylobacter_fetus_venerealis_97_608_GCA_000759515.1 |
| 81 | − | Methanosarcina_vacuolata_Z_761_GCA_000969905.1 |
| 82 | − | Geobacillus_12AMOR1_12AMOR1_GCA_001028085.1 |
| 83 | + | Clostridium_ultunense_Esp_GCA_000344075.2 |
| 84 | + | Clostridium_novyi_B_NCTC_9691_GCA_000724265.2 |
| 85 | + | Bacillus_cereus_MC67_GCA_000291155.1 |
| 86 | − | Methylobacter_whittenburyi_UCM_B_3033_GCA_000745375.1 |
| 87 | − | Streptococcus_parasanguinis_348_SPAR_GCA_001072395.1 |
| 88 | + | Calothrix_PCC_7103_PCC_7103_GCA_000331305.1 |
| 89 | + | Bacillus_cereus_VD140_GCA_000399545.1 |
| 90 | + | Pseudonocardia_asaccharolytica_DSM_44247_NBRC_16224_GCA_000423625.1 |
| 91 | − | Clostridium_perfringens_MJR7757A_GCA_001546355.1 |
| 92 | − | Anoxybacillus_suryakundensis_DSM_27374_GCA_001418025.1 |

Example 3—Putative Type VI System

The signature of type VI is an effector protein with two HEPN domains (FIG. 2). The HEPN domain are common in various defense systems in which the experimentally characterized ones, such as the toxins of numerous prokaryotic toxin-antitoxin systems or eukaryotic RNase L. Accordingly, once the putative type VI effector has been computationally identified, it has been predicted to function as an RNA-guided RNase. Subsequently, this prediction has been experimentally validated, and the protection by the type VI effector against the RNA bacteriophage MS2 has been demonstrated. In addition, a remarkable, novel feature of the type VI system has been discovered. Once primed with the cognate target RNA, the type VI effector (C2c2) turns into a promiscuous RNase that has a toxic, growth-inhibiting effect in bacteria. These findings demonstrate the coupling between adaptive immunity and programmed cell death (or dormancy induction) that has been previously predicted via comparative genomic analysis and mathematical modeling.

The new search for putative CRISPR-Cas loci (with the CRISPR seed) identified two additional large putative effectors each containing two HEPN domains and assigned to subtypes VI-B and VI-C, respectively (the C2c2-encoding loci accordingly became subtype VI-A). This classification is justified by the extremely low sequence similarity between the three groups of effectors, practically limited to the catalytic motif of the HEPN domain, the different positions of the HEPN domains with the large protein sequences, and additional features of the locus architecture in the case of subtype VI-B (FIGS. 2 and 5). Specifically, the two distinct variants of subtype VI-B both encode additional proteins containing confidently predicted transmembrane domains, 4 of these in the case of VI-B1 and a single one in VI-B2 (FIGS. 2 and 5). Phylogenetic analysis of the effector proteins clearly shows the split of the V-B1 and V-B2 variants in accordance with the distinct architectures of the associated (predicted) membrane proteins (FIG. 5). Thus, subtype VI-B is likely to represent membrane-associated, RNA-targeting systems, a novel twist in the biology of CRISPR-Cas. Furthermore, the single-transmembrane protein of VI-B2 encompasses an additional, derived HEPN domain, the third in this system (FIGS. 2 and 5).

Given that all (putative) type VI effectors so far discovered are similar in size to the active Class 2 effectors including subtype VI-A, it appears likely that the putative loci are functional CRISPR-Cas systems that rely on adaptation modules from other loci in the same genome. Moreover, given that RNA viruses only represent a minor component of the prokaryotic virome, it appears probable that activation of the toxin activity is the primary mechanism of action of these systems triggered by active transcription of foreign DNA. This mechanisms is likely not to be limited to type VI given the presence of HEPN domains in still poorly characterized Cas proteins present in many CRISPR-Cas systems and the experimental demonstration of the RNase activity of the Csm6 and Csx1 proteins in type III systems.

Example 4—Analysis of the Evolution of Class 2 CRISPR-Cas Systems

Figure 7:
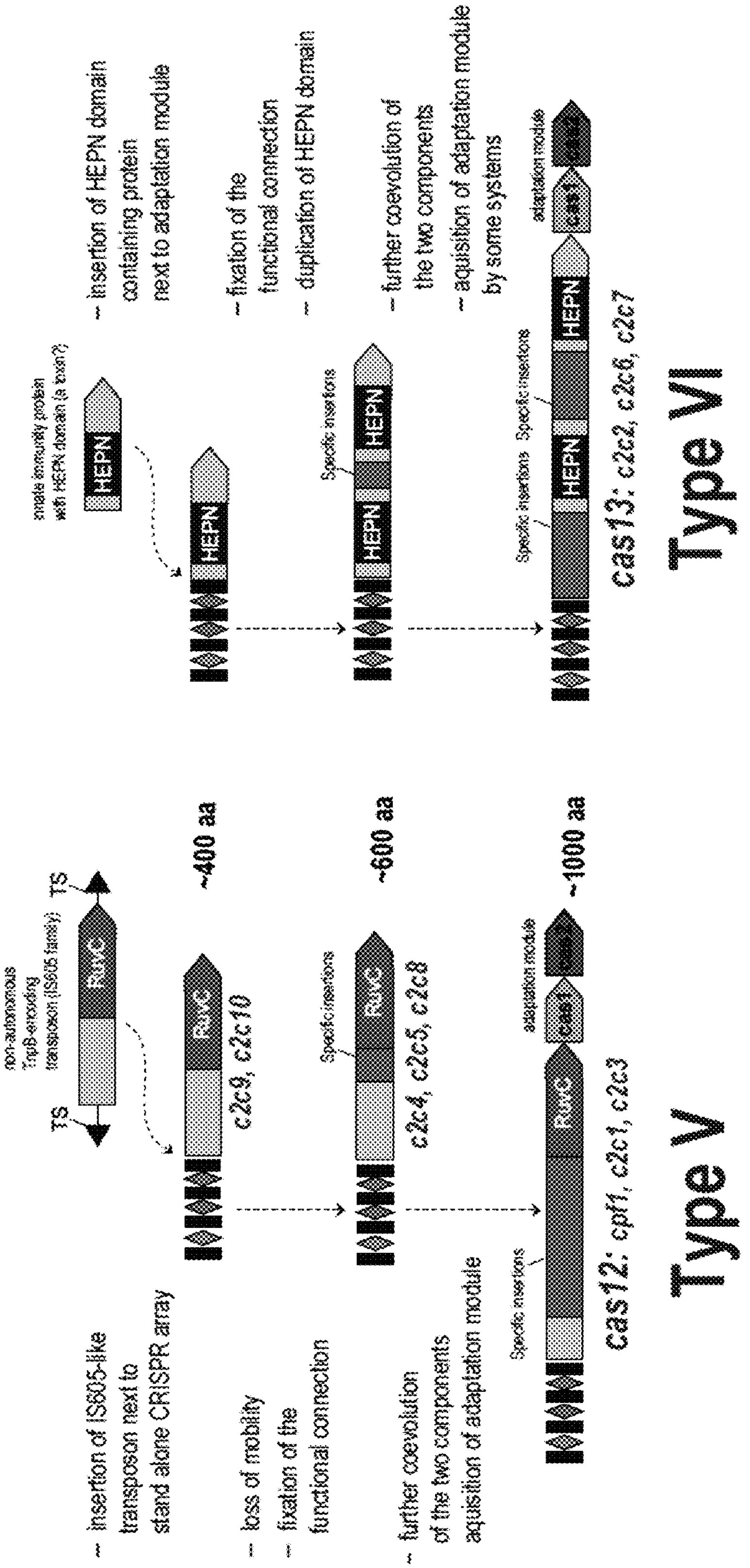
FIG. 7 shows evolutionary scenarios for Class 2 CRISPR-Cas systems. The figure depicts the path of 'maturation' of type II and type V systems that starts with random insertion of a TnpB encoding transposon next to a CRISPR cassette and a parallel path for type VI systems initiated by the insertion of a gene encoding a HEPN domain-containing protein, possibly a toxin.
Figure 8:
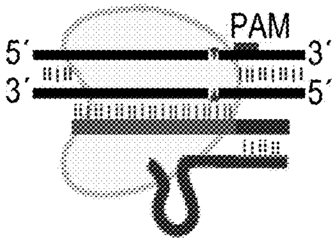
FIG. 8 shows functional diversity of the experimentally characterized Class 2 CRISPR-Cas systems.
Figure 8:
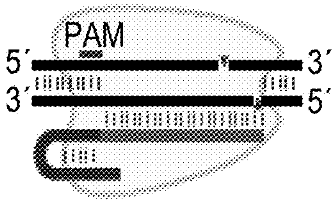
Figure 8:
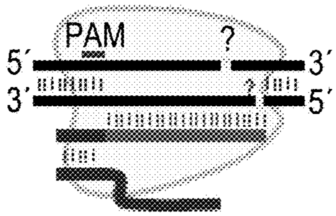
Figure 8:
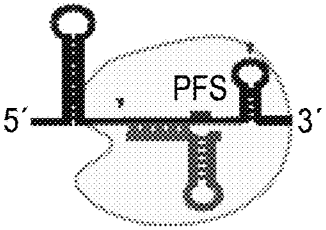

In extension of the previously proposed hypothesis on the independent origins of the effectors in different types and subtypes of Class 2, we harness the findings on incomplete type V loci to develop a more specific evolutionary scenario (FIG. 7). As discussed above, at least 5 distinct variants within subtype V-U show evolutionary coherence and stable association with CRISPR arrays, and typically contain TnpB homologs that are intermediate in size between the compact transposon-encoded TnpB's and the large Class 2 effectors (FIGS. 2 and 4), we consider these to be intermediate stages in independent paths to the emergence of new CRISPR-Cas variants. Other subtype V-U loci are not evolutionarily conserved and appear to reflect more or less random insertions of tnpB genes next to CRISPR arrays. These can be logically viewed as the earliest stages of evolution of CRISPR-Cas systems. Notably, all subtype V-U loci lack the adaptation modules suggesting that the first stage of evolution of new Class 2 CRISPR-Cas involves insertion of a TnpB-encoding element next to an orphan CRISPR array (FIG. 7). At the next step, the association between CRISPR and a TnpB derivative becomes fixed in the microbial population, conceivably due to the emergence of function the exact nature of which remains to be understood and accompanied by an increase in the size of the protein via internal duplications and/or insertion of additional domains (FIG. 7). The final steps include further growth of the effector protein resulting in the typical bilobed structure and, at least in some cases, association with an adaptation module through recombination with a different CRISPR-cas locus (FIG. 7).

A similar scenario could apply to the type VI systems (FIG. 7). In this case, the first step would involve insertion of a toxin-antitoxin module next to a CRISPR array, followed by a duplication of the HEPN-containing toxin gene accompanied by attenuation or masking of the toxicity and the loss of the antitoxin gene. Alternatively or additionally, and evolutionary connection between the type VI effectors and HEPN domain-containing proteins in other CRISPR-Cas variants cannot be ruled out. The subsequent evolution would include further expansion of the double-HEPN protein to the typical size of a Class 2 effector and acquisition of an adaptation module (FIG. 7).

Example 5—Amended Classification of Class 2 CRISPR-Cas Systems

The systematic search for novel Class 2 CRISPR-Cas loci described here has led to a major expansion of the known diversity of these systems. Instead of the two types and 4 subtypes included in the latest classification, there are now three types and at least 10 subtypes (FIG. 2). Despite the lack of functional data on subtype V-U, it appears likely that some variants in this provisional subtype, particularly V-U3, are eventually upgraded to the subtype status. Given the comprehensive character of the search described here (see FIG. 1), there may not be many new variants are discovered except for rare ones or possibly those that are restricted in their spread to particular groups of prokaryotes that are not adequately represented in current sequence databases. It should be noted, however, that the current subtype V-U is a heterogeneous assemblage of diverse loci that we provisionally kept together given the likely possibility that these are not typical, active CRISPR-Cas systems. Functional characterization of these variants will provide for a more granular classification.

Example 6—Functional Diversity of Class 2 CRISPR-Cas Systems

Although functional characterization of the Class 2 subtypes is not complete, even at this stage, remarkable functional diversity is apparent. The manifestations of this diversity include different target (dsDNA for types II and V, but RNA for type VI): the requirement for tracrRNA (type II and subtype V-B but not subtype V-A or type VI), the sequence of the protospacer-adjacent motif (PAM), and character of the cut introduced into the target nucleic acid (Table 2). This functional diversity is a major incentive for further characterization of different Class 2 systems as it creates opportunities for the development of various, specialized genome editing and engineering tools. In particular, effectors that do not depend on tracrRNA are attractive for their simplicity. The potential for the creation of new, conceivably, improved tools has already been demonstrated with the type V-A effector (Cpf1). Type VI systems could add a whole new dimension allowing for multiple RNA-targeting tools and possibly harnessing the programmed cell death-inducing capacity to kill cells expressing specific transcripts.

TABLE 2

Functional diversity of the Class 2 CRISPR-Cas systems

| | Nuclease domains | tracrRNA | PAM | Substrate | Target cut |
|---|---|---|---|---|---|
| Type II: Cas9 | TnpB/ RuvC + HNH | Yes | 3', GC-rich | dsDNA | Blunt ends |
| Type V-A: Cas12a/Cpf1 | TnpB/ RuvC + Nuc | No | 5', AT-rich | dsDNA | Staggered ends, 5' overhangs |
| Type V-B: Cas12b/C2c1 | TnpB/ RuvC + ? | Yes | 5', AT-rich | dsDNA | ? |

TABLE 2-continued

| Functional diversity of the Class 2 CRISPR-Cas systems | | | | | |
|---|---|---|---|---|---|
| | Nuclease domains | tracrRNA | PAM | Substrate | Target cut |
| Type VI-A: Cas13a/C2c2 | 2 × HEPN | No | 5', GC-rich | ssRNA | Unspecific RNA cuts + collateral RNA cleavage |

Example 7—Comprehensive Census of Class 2 CRISPR-Cas Loci in Bacterial and Archaeal Genomes The procedure that was employed here for the detection of the types and subtypes of Class 2 loci (see FIG. 1) can be expected to identify (nearly) all variants of such systems present in the currently available bacterial and archaeal genomes. Indeed, under the assumption that a functional Class2 effector has to be a large protein, we examined all such proteins encoded in the vicinity of CRISPR arrays and/or cas1 genes. We therefore were interested in a comprehensive census of Class 2 types and subtypes in the current set of complete bacterial and archaeal genomes. To this end, we constructed sequence profiles for the effectors of all identified Class 2 subtypes and compared these to the proteins encoded in the 5000 available complete prokaryotic genomes. This procedure ensured comprehensive detection of all instances of each effector including highly diverged variants. The neighborhoods of the respective genes were then examined for the presence of CRISPR arrays and additional cas genes as previously described.

The most striking observation is the dramatic dominance of type II which is represented in about 10% of bacterial genomes (Table 3). Both type V and type VI are more than an order of magnitude less abundant, in agreement with the expectation that the CRISPR-Cas types and subtypes remaining to be discovered are rare variants. An intriguing question is whether type II is in some fashion "more fit", i.e. more efficient in defense or incurs a lower cost, than other Class 2 variants. Most of the Class 2 subtypes are represented in taxonomically diverse bacteria which is indicative of horizontal gene transfer as the dominant process in CRISPR-Cas evolution. It is notable, however, that the relatively abundant subtype VI-B, the only CRISPR-Cas system that is predicted to be membrane-associated, appears to be restricted to the phylum Bacteroidetes, perhaps reflecting some unique aspect of the biology of these bacteria. Similarly, the V-U5 variant that encompasses an inactivated TnpB homolog is limited to Cyanobacteria, being perhaps involved in a unique regulatory pathway. A major puzzle that has been emphasized previously and becomes all the more striking with the present expansion of the diversity of Class 2 systems is that, apart from two instances of subtype V-A identified in mesophilic archaea, Class 2 systems are unique to bacteria. This exclusion of Class 2 systems from archaea implies a major functional distinction between the two classes of CRISPR-Cas systems the nature of which remains enigmatic.

TABLE 3

| A comprehensive census of Class 2 CRISPR-Cas systems in bacterial and archaeal genomes | | | | | | | |
|---|---|---|---|---|---|---|---|
| (Sub)type | II | V-A | V-B | V-U | VI-A | VI-B | VI-C |
| Effector | Cas9 | Cas12a (cpf1) | Cas12b (C2c1) | C2c4, C2c5; 5 distinct subgroups (V-U1-5) | Cas13a (C2c2) | Cas13b (C2c6) | Cas13c (C2c7) |
| Number of loci | 3822 2109 II-A 130 II-B 1573 II-C 10 unassigned | 70 | 18 | 92 | 30 | 94 | 6 |
| Representation | Diverse bacteria | Diverse bacteria + 2 archaea | Diverse bacteria | Diverse bacteria | Diverse bacteria | Bacteroidetes | Fusobacteria/ Clostridia |
| Other cas genes | 85% cas1 + cas2; 55% csn2; 3% cas4 | 70% cas1 + cas 255% cas4 | 65% cas1 + cas2 + cas4 | NONE | 25% cas1 + cas2 | NONE | NONE |
| % loci containing CRISPR array | 65% | 68% | 60% | ~50% | 73% | 90% | 83% |

The genomic analysis presented here substantially expands the diversity of Class 2 CRISPR-Cas systems. In particular, these new variants show unprecedented functional features, such as independence of a tracrRNA in subtype V-A as well as exclusive RNA targeting coupled with the induction of the toxic effect in subtype VI-A and likely in all type VI systems. The subtype V-U can be expected to show even more unusual properties. This functional diversity provides the potential for the development of new, versatile genome editing and regulation tools. We provide compelling evidence of independent origin of different Class 2 types and subtypes from mobile elements. The discovered remarkable diversity notwithstanding, it should be noted that the procedure applied here provides for a (near) exhaustive identification of Class 2 systems. Whatever additional variants remain to be found, they are likely either rare or confined to groups of bacteria that are currently unknown or poorly sampled.

In the foregoing description, it will be readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations, which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scopes of this invention.

What is claimed is:

1. An engineered, or non-naturally occurring composition comprising a Class 2, Type V-U Cas protein encoded by a sequence selected from SEQ ID NO: 14 and a guide RNA capable of forming a complex with the Class 2, Type V-U Cas protein and comprising a guide sequence heterologous to a naturally occurring guide sequence, wherein the guide sequence directs sequence-specific binding of the complex to a target sequence other than a naturally occurring protospacer of the Class 2, Type V-U Cas protein/guide RNA complex.

2. The composition of claim 1, wherein the Class 2, Type V-U Cas protein is a nuclease adapted to modify a DNA strand.

3. The composition of claim 1, wherein the Class 2, Type V-U Cas protein is a TnpB homolog.

4. The composition of claim 1, wherein the Class 2, Type V-U Cas protein is fused to one or more nuclear localization sequences.

5. The composition of claim 1, wherein the guide sequence further comprises a tracr sequence and a tracr mate sequence.

6. The composition of claim 1, wherein the guide sequence is about 10-30 nucleotides long.

* * * * *

SEQUENCE LISTING

```
<160> NUMBER OF SEQ ID NOS: 170

<210> SEQ ID NO 1
<211> LENGTH: 1995
<212> TYPE: DNA
<213> ORGANISM: Pelobacter propionicus

<400> SEQUENCE: 1

tcacaatacc tctcgaaaaa gattggctgc ggcgttgatg tcctgatcaa ccagtgcccg     60

gcattctcga cagcgccaca tgataccgtc aacctgctcc attttcccct tgcaggcgct    120

gcaggtggct gaggatgctg ttgatacctg ctcgatctgt gttccgtttt ttgcagcagc    180

cttggataaa cattccctga gttccgagat agccgcctgc tggcgctgtt tcctcgcgat    240

tttagtaagt tcgttgggcg tcccatcacc tttttccagc agcgccagac gacgcaagtc    300

cattttgtcg aggcaaatca catcatatac agacgtgagt tgcttcgctg tgttgcgata    360

aaagtccatt cgacgccgga gaagcttttc gcgcttatga gccatctcga tcgtaagccg    420

cttggttgcc ttgcgtctct gctcggcctc gtctcgtgca tctccgaggt attctggata    480

attgcgccag gcgataacgg ctttagcaaa tttcgccgga tgcggtcttt ttgagcggcg    540

cagcatggag cgcaactcct gcaacgattc cggcagctcg tcaccccccc attgctccag    600

caaccaggcg tgattctcgt tcgcagcaga gtcgattcgg ccctggagat cgccattaac    660

atagtcgagt ccgtcgatta ttgcctgtgg caacgtaata tgacgagcgt cggaaccatc    720

atatatcgtt gctacacgta agccgccgcc agcctgtttt ttccagccca ggttgagccc    780

acaacgatta ccagttgagg acctctgatc gtatgtaggg caatcagtgg tgaacgtaaa    840

aacgacagac cacacgaaat cagtcccgac tctttttcga tggacagata gcgacttgag    900

tgttgctcct tcaggcagtg ggcggtgcag aattaccggg aaacttaggg ttcgacggaa    960

ttttttactc tgttcatccg tcccggtgta cagggtgata gcgaggatac catactcccg   1020

cgagtcacgt cgactgccaa cactttgcag atcaagtgag ggcggttttt tcccgctgat   1080

gtctccgagt tcaccgctgg acaccaaccg gagcgatgcg acgttacggt tgccttctag   1140

cagatcttga acactcatgc caccctgaat ctgattggta aaacgcccgg agccgtcaaa   1200

ccggtggtat ttcagctcgg ctccatcctt gagcgctttt atgcgtgcct tcttgtacga   1260

ttccagcacg gcattgtagt tcccccacca gagacctgag ttattgtatg ccttaataac   1320

agcggcctgt cggtcttttt caagattctc aatatcattg ccggcggccc tgatccgatc   1380

ttttgccgcc gcccgggttt ctttggcctt gcttgcaaca gctttaagtt ccgacttgag   1440

ctttttttatg ttttcgtcca gacagtcaat ttccgggcat ttctttttcc ggtgctccac   1500

gcgcagtttt ttacgcccct catcgaggac actgagccgg tctttgatag aggcgatttc   1560

cgtatccatc tgagccgttt cttcgtctga tccgatcagt tccctgtatt ttgcgcgatg   1620

ctcgcgttca atggtgacca gatcgttcca gagtttgttt tggagaaaca gatgctcgaa   1680

ggcgtcacca gcagggtagt ccggacagtc ccagtctagt gggctgagca ggccatattt   1740
```

```
cctgacgatg gtcgtcactg gctggacctg ttcatcaggc acgagataca gatatttttc   1800

cgtgcgggtt ggagcaatca tgacaagact cgatgtttct gcaaccgctt cttccggatc   1860

aaagcgtacc ttggctgact ttgcggacac agatgcagtt agcagccatt cagctgcagt   1920

atggttcgcc gcaatagtgc caattactat acctttggtt tgctctccgt ctatcgtgat   1980

tgttactcgc ttcat                                                    1995


<210> SEQ ID NO 2
<211> LENGTH: 1791
<212> TYPE: DNA
<213> ORGANISM: Mycobacterium mucogenicum

<400> SEQUENCE: 2

atgaccacga tgaccgtgca caccatgggc gtgcactaca aatggcagat acctgaggta     60

ttgcgccagc aactgtggct cgcgcacaat ctgcgcgaag acctggtgag cttgcagctc    120

gcctacgacg acgacctcaa agccatctgg tcgtcctacc ccgatgtggc ccaggccgag    180

gacacgatgg ccgccgcaga agccgacgcc gtcgcgctgt ccgagcgggt caagcaggcg    240

cggatcgagg cccggagcaa gaaaatcagc accgaactga cccaacagct ccgcgacgcc    300

aagaagcggc tcaaggacgc tcgccaagcc cgccgcgacg ccatcgccgt cgtgaaagac    360

gatgccgctg aacgccgcaa agcgcgcagt gaccaactcg ccgccgacca gaaagcgctg    420

tacgggcaat actgccgtga cggcgacctg tactgggcca gcttcaacac ggtgctggac    480

catcacaaga ccgcagtcaa acgtattgcg gcgcaacggg catcggggaa gccggcgaca    540

ttgcgtcatc atcggttcga tggcagcggc accatcgccg tgcagctgca gcgccaggcc    600

ggagcgccgc cgcgcacccc catggttctc gccgacgagg ccggcaagta ccgcaacgtg    660

ttgcacattc ccggatggac agaccccgat gtgtgggaac agatgacccg ctcgcaatgc    720

cgccaatccg ggcgcgtcac ggtgcggatg cgctgcggca gcaccgacgg ccagccacag    780

tggatcgacc taccggtgca agtgcaccga tggctcccgg ccgacgccga catcaccggc    840

gccgaactcg tcgttacccg cgtcgccggc atctaccggg ccaagctgtg tgtcaccgcc    900

cgcatcggag acacagaacc cgtcaccagc ggaccgaccg tggccctcca cctgggctgg    960

cgatccaccg aggaaggcac cgcggtggcc acatggcgct cggacgcacc cctggacatc   1020

cctttcggcc tacgcaccgt gatgcgcgtc gatgcagcgg gtacgtcagg aatcatcgtg   1080

gtgcccgcca ccatcgagcg ccggctgaca cgcacagaaa acatcgcctc atcccgctca   1140

ctggcgctag atgccttacg cgacaaagtc gttgggtggc tatcggacaa tgacgcaccc   1200

acctatcggg acgcaccgct ggaagcggca acagtcaaac agtggaaatc gccacagcga   1260

ttcgcatccc tagcgcacgc ctggaaagac aacggcaccg aaatctccga catcctctgg   1320

gcctggttca gcctcgaccg aaagcaatgg gcccaacaag aaaacgggcg ccgcaaggca   1380

ctcggacacc gcgacgacct ctaccgccag atcgccgcgg tgatcagcga ccaggccggc   1440

cacgtcctcg tcgacgacac cagcgtggcc gaactcagcg cccgcgccat ggaacgcaca   1500

gagctcccaa ccgaagtgca acagaagatc gaccggcgcc gcgatcacgc cgccccaggt   1560

ggattacggg cctccgtcgt ggccgccatg acccgagacg gcgtacccgt aacgatcgtc   1620

gcagcagcgg atttcacacg gacacacagc cgatgcggcc acgtcaaccc cgcagacgac   1680

cggtacctgt ctaaccccgt gcgctgcgat ggctgcggag ccatgtacga ccaagaccgc   1740

tcctttgtca cactgatgct gcgagcggcc actgcaccat ccaatcccta g            1791
```

<210> SEQ ID NO 3
<211> LENGTH: 2262
<212> TYPE: DNA
<213> ORGANISM: Geitlerinema sp.

<400> SEQUENCE: 3

```
ctacctttcg gcagactctc gggtgtagta ggcagcttgg gcaaggtctt ttgccttgtc     60
ctgtaaatct ccagacaccg gttgccatgc tgtctcaatc aaaactccaa cacgggctgc    120
tttagagcga atggcggtat caagccgacc gtaactccat tgatgaaaac tgatccgaaa    180
ctctttagca tacttatcct gggcttcctt caaaccagga aatttctttt cagctcttgc    240
tcttatttca ctttcaacac tttcacgaat gttttcgatc tttggtagag taatactgcc    300
agctttccat ttgattgcta gctcgacaat tctagctgcc aaaagtctgt ccacatacag    360
acccagattt gtttctgatt tggattgctg gtacatacct cgacttcgct cttgattacg    420
acggcgcaat ctatttcgac gcaatcgttg atgacgacca accaacctat actgttgaaa    480
ctttaattga acaatagtct gatttcctct tttatcctgt accttccggt caaccagtaa    540
ttgacgcaca gtttgagttt ctagaatttt gtcctccttt gcatcccaca ctacagcagt    600
agcaggcttg tgtcggctaa aacttacccc aaccacgatg tcaggctgtc cttgataagg    660
tttttgcta gggcgtgaaa aagcagattt attattaagt cgagtcagtg tagatgattt     720
ccttttcctg tctgccattt gcccagcagt tagttcctga ttgtcagtaa ccgctttctt    780
ctttctggaa tcctttgaat cgccctccaa ctgtttaatg atctgaccaa tctcttcctg    840
ccgtacctcc tcagttcctt ctgcagtaag caagcgagta tcgatcgagc attgaagata    900
caaccgatga gtattccaag gttcagtttt tcggttgtct gaagaactgc caacattctt    960
gcccgatgcc actaccgcgt tatttttctg tttccctttc ttcttgcgaa ggcttttggg   1020
tggaacccga ttgtcctccc tccatatcaa acgagcagac cggagtaaaa atagactggc   1080
agagcacttc tctgagtcag cttttccttt cctgtccaac tcttggtacg ttttccagtc   1140
agttacaaac tgttgaaaat gtggtaactg acggcgatcg cacaggatct taaagctatg   1200
gtttttcaat ccctgaaaac ggacaatgat ttggtttctt ggtttgtttg ttttcttacc   1260
cttgagggtt ttacgctcct gtgtctcttg gaaccatcga agatcggtat tgctaccaaa   1320
actaattggg tagggtaaag attttggcaa tctcataaca gcaattcgtc tttgcccttc   1380
ttccgcattc catttaatga attctgagac atcctcttca gaagttgaaa gtttgcttgg   1440
caattcagta gcaaactcta aattcttctg gtactgcgtt ccaaaaggat ctcgcccctt   1500
tggcaattgg ctcttcagtt gttgatccaa acgctcaatt tcaattctgg ttttctcaat   1560
ctctaaagga atcttatctg gatcttcctc ttcattcact tgagaatgat ttctgaccag   1620
atgggcaatg gcacgtcgtg tcacagcatc cgttgaagag ttatacagtt tattcagctt   1680
gtatattgat ataaatttc tttcttcttg catttcttct gaatctgttt gagccttatc    1740
tttcttttt gtggcttttt tcctcctaac ttttttatct tccgacgttt cattggcttc    1800
ctttttcatc tcggacaaaa gttgagatag aatttcatga gcctttttta tgattgaatc   1860
cagttgagat tcatcatatt ccgtgagcaa atcgtcttct acgatatcta gccagagctg   1920
ctttctatta cgttgttgtt gccgtccatg ctgtaaggca agccatgatt tataagtagt   1980
ctggacggta gaaatcgctg atttataaaa tcgatcaggt agttggctga agcgtggctc   2040
taaaagcaac ggaggttctt cattacttga ttctttggca aggcgttcta cagcttttgc   2100
tggtaaattg ccagcactct gccatctttc aaaatctgga tgctgagcgg ctctttccaa   2160
```

aagctctctt acaaggactg catgctgcac cataagcgac catacatatt gacgagtctc 2220
ttcgctagca gccaataggc actcaacggt gatgataggc at 2262

<210> SEQ ID NO 4
<211> LENGTH: 1317
<212> TYPE: DNA
<213> ORGANISM: Candidatus Desulfofervidus auxilii

<400> SEQUENCE: 4
atgtcagtac ccagaaagaa aaataaagag cctgataata taattgagat tacacacaga 60
taccgggcat acttaacagc cctccaggaa tataaggcgg agagctggtt atatactctt 120
tgtaatctat acaattcagc cattaaagaa cgcagaaacg catatcgtac cgaaaaaaag 180
actataacct acagccaaca gcaaaatggc ttgctcttgc tcaaagattc agatcccaca 240
ttgaaaaaag tgcacagtca gctattgcag aactgtctcc agcgtgtgga tagggcctat 300
caaaaatttt ttgaggacct aaaacgaaag aagaatggaa aacatgtcaa ggtgggatat 360
cctcgtctga aaaaactatc caaatatcgt tcattcacct atccacaggt ctggatgaag 420
caaaagggag agctaaaaca agttatcaag ttcagacagg ataacaataa atttggcaca 480
actgtcctgc ctggtttcgg tgaggtaagg ataagggtac ataggccatt agactggaaa 540
caggccaaaa ccgttatact gaagcgggaa aaatcaggta agtggtatct ctgtatcacc 600
cttaaaaaag cagtagagct tcaacttcag gataacggta aatctacagg cattgacctt 660
ggactgaaaa aaatcgttaa cacttctgat accaattatc aagaacatcc gaaatttatc 720
tacaggtctg aagcccggat aaagagagcc cagaaaaggc tttcccgcaa acaaaaaggt 780
tcagcgaatt acgaaaaaca gagaatcagg ctggcaagat tacacgagaa agttgcgaat 840
cagcgcagag attttttaca caaactggcc ctatggctgg tggtaaacta cagctttatt 900
gcctttgaaa ggctaaacat aaggggaatg gtgaaaaatc atcatttagc aaaggcaata 960
cttgatgcag gatgggcaac tcttatcacc cttaccacct ataagagtgt catgctcagg 1020
ggtaatgagg tagtgagagt agatccaaga tatacgagcc aagagtgtag cgcctgtcat 1080
gctctcgttc caaaagcttt ggctgagagg atccacaaat gcccgtactg cgggatagaa 1140
ctcgaccgag ataccaatgc ggcaagggta atcgaacaga aagcattttt gagggagaca 1200 accccttta gaagccctag ggccggggcg gtccgaagtc acgcctgtgg agatcgagcc 1260
tctactcatc cctacgggaa tgggcaagct cggtcgctga agcaggaatc ccactag 1317

<210> SEQ ID NO 5
<211> LENGTH: 1185
<212> TYPE: DNA
<213> ORGANISM: Borrelia crocidurae

<400> SEQUENCE: 5
gtggagatga atttgcaacg caagttaaaa tattataaaa taacaaaaca tatgggtgct 60
aataaagctt ataagtacag aatatatcct aacgctaatc aaaagaaata cttttcaaaa 120
gtatttggat gcgtaagatt tttgtataac aaaatgttaa gtgataagag agactattat 180
gaaaagaata agaaaagtat tagcgttaat ccaagtaatt ataaaaatga atttccattt 240
ttaaaggaag ttgatagttt agctctttgt agcgcatgga ttgatttaaa ttctgcgtat 300
agtaattttt ttagagaaat taaaaaagga aatagaacac aaggatttcc taagtataaa 360
agtaagaaaa atagacaaac ctttagaact aataatcaaa aaaactcaat aagaatagaa 420
aatgattata taaagctacc taagatagga tttgtaaaat tagctctaca taggaatatt 480
aaaagcaatg aacttattaa aaatgtagta gtagaaaaag atactgatga taaatattat 540
atttcagtag cagttgagtg cttagatgtt aaaaataacg ataaaattaa atgcaataaa 600
aaagagatag ttggtattga tatgagcatg aggcattttt tagtaagtag tgagggtgag 660
aaaatcaatc atcccaaatg tttactaaaa aatgaacata aactcaagaa atgccaaaga 720
aaactatcaa aaaaacaaaa gggctctaaa aatagagcta aatctagatt aagagttgcc 780
aagttgcata ggaaaatttc aaatcaaaga aaagattttt tacataaatt atcttattat 840
tttgtagcta attataaaaa tatagtaata gaaagcctat caattaaaag tatgcaaaaa 900
ggaatgtttg gcaaaagtgt taatgatttg ggatggcatg agtttgtaag acaattatca 960
tataaattag agtggtctaa atcttatttg cataaagttg atagatattt tccatcaagc 1020
aagctatgca acaattgcgg tattaaaaat acaactctaa aattaagtga tattaggtgg 1080
agttgtagga gttgtaacac tttgcacgat agagatataa atgcagctct aaatcttaaa 1140
gcttattatt ataaggaaat aaaaactaag gcaggaactg cctga 1185

<210> SEQ ID NO 6
<211> LENGTH: 1521
<212> TYPE: DNA
<213> ORGANISM: Streptomyces wadayamensis

<400> SEQUENCE: 6
ttagaacagc tttgcctgtc cttggcgcgg gttggggggt gtcggcggat tgctccgccg 60
aggtggcacc ggcccgggag ggccggtgtc ttcccgcttc gtcgagccct gcttctccgc 120
ccgggggcgg gggagtctga cggttctcc acgggcgttt tgggtctccc ccgtaccgga 180
ggcgacctgt gttgcgtgct gctcgatgtt gcgggccgcg ttgaggtcgc ggtccagggt 240
gagtccgcac tgagcgcact cgaatacccg gtcggcgagc gtgaggcttg ggttttgcca 300
cccgcacgcc gagcaggtct tgctggaggg ccaccagcgg tcgaggaccg cgaggcggga 360
gccgtaccag gaagtcttgt aggtgatctg ccggcgggcc tcggccatgg aggcgtcgag 420
gatcgcgcgg ttaagcccgg ccttctgccg gaccttgcga cccggcttgt ccatcgtgcc 480
gcgggcgctc cgcgtcatcc cggagacgtg gaggtcctcg acggcgatcg tcgcgaaccg 540
cgtcgtgagg cgcttggtga tctggtgcag ggcgctctgg cgccggacgg cgacctcgtg 600
gtggaggcgg gcgacgcggc ggcgggcctt ctcccggcgg gcggagccct tctggcggcg 660
ggagagcgtc tgctgggcgc gcttgagccg gtgggcggcc ttggcgaggt gccgggggtt 720
gggcagcagg gtggactccg gccggtccgg gacgaggggc ttgctcaagg cggcgagggc 780
cttgacgccg aagtcgatgc cgaccgtgcc ggcggcctgc tgggagcgtg tggggcacga 840
gggcaggtcc atctcgacct tgcacagcac cgaggcgtac cagcggtggc ccgcgcggga 900
gaccgtgacc gactggacga gggccgtccc gcgatcgatc tgccggacca gcgtgcgcgc 960
ggagtcgtgc agccggacct caccgaaggt ggggaggcgc agccgccggt gggtggagaa 1020
ccggatggtc ggcttcgtca ccgtgtggtg caggcgaaat gcgtcgcggg cgcgcccgcg 1080
cttcttgaac cgcgggtagc cgacacggcg ccccttgcgc gtgcccttga aggagtcgag 1140
ccagttgttc caggcgcggt cggcgtcgat gaacgcggac tggaagacat gggtgttgat 1200
ctcgtgcgcc catgggcaga ccccatcgac cccttcgcgg gtgtcgccgc gttcggcgat 1260
gaacgccttg tacacagcgg gcttggtcgg cgtcttcggg cccgtgaccc gcttgcgggc 1320
caccggctcc ttgacgcccg acgtcacgag agcgtcgacc tgggcccgcc actcggtgtg 1380

-continued cgctgcacgc ttcgaggcca aggcgtagtt gaacgccagc cgagcgttcc cgcaccagcg 1440
gaggagctgc tgttcctggg cggccgtggg cgccagggtg aacttgaacg cgcgcagcac 1500
gacggtcttg gtgcttgcca c 1521

<210> SEQ ID NO 7
<211> LENGTH: 1485
<212> TYPE: DNA
<213> ORGANISM: Cyanothece sp.

<400> SEQUENCE: 7
ctaagatttg tcaagcccaa aagcagtctg ttcgatatta attgccgcgt ttaaatcggc 60
gggcatttct aacccacatt ttaagcaatg aaatgaagct tgagttaggc gattttcgct 120
atctgtatgc ccacagcgtg agcatttttg gctggtgtaa ttggctctta ccctctcaat 180
atgcctattc tcataggaat tagccttaga ttccaaaaat gctctaagtt gtccaagtcc 240
tgcatcgtgg aaggattgat tgagtcctgc tttagctttt gccccattat gttcatagcc 300
tttgccgtct tctctctttt cggcttttgg tcttttattc atattggtta gtttagtatc 360
ctcgatagcg atcgcaccgt atttattaac taaatgagtt gacactttat ggttatagta 420
tttacggtga tcagcagttt gtttatggat tttagctaaa gctttttttag tttttttccca 480 gtttttgctc ccaggggttt gtcttgataa ttttttttgt aatacagtca agtgtcgttc 540
attttctttt aaaaaccgtt gattagagat acatttacca tcacttaagg ttaacaaagt 600
gactaaccct ggatcaattc ccacttgtaa atcactatca ggaataggct tatgttctac 660
ttgaaagact aggttaagat agtagccatc agcttttttt gttaaacttc cattacgcgg 720
ttgaatttgt ccctgatgac gattatgaag acctctaaat tcaatcaatc caaattcttt 780
acccaataac tgacagttat tggcttctgg atcaaactta atcctatttg tctgtttgtt 840
gcataaagag ataacaggat tgcgttttga tttaaacttt aactttctaa agtctccttt 900
ttgatagcgt ttccaagctt ccattaagtt cattgaaatg aaagattgcc taactttcat 960
gttaacattt aacagttttt gaagatgata attagtcaaa agattacagc ttattaacca 1020
ttgattagta aagcatttaa acttagcaag tttttggggt tcttcaagat gccaataggg 1080
tctaatggga gtaaaaaaat taccatctcg attaatcgtt cgacaagcta aacttttagt 1140
attgtctttt ttacggactt cattttcttc ttttgttaac caatcacatt cgggtaaagc 1200
tttggtaata tgccattcaa cggggtaaat atcaggttta ttttctatct cattaagata 1260
agtttgtaaa gatgatttat caagataatt tttaagaaat ttctgattag tacgccatct 1320
tcgttgttgt tcttcataga gcaaccctaa agctaaatta tacagaggtc tcaaagaatc 1380
agtccagttt tcaaataaag cagtttgagt tgttgataaa tacgctttaa gttgaatagt 1440
aatatggtgt tgaacaagct ctgacataga ttttatggca aacat 1485

<210> SEQ ID NO 8
<211> LENGTH: 1896
<212> TYPE: DNA
<213> ORGANISM: Microcoleus sp.

<400> SEQUENCE: 8
ttatttcctt tttttgcgct tctcggtctt cttccaacgt ggttttgtcg aagcttctgg 60
atgggctatt tcccacacgc tattagcaaa tcttgcacgc tgagcgtttg ctgagagtac 120
cgtgtgcgga ttattgccaa actgagccaa ttcgatattg actcccgaat tgacatcgcg 180
atcgcattcc caaccacaaa taatgcatag ataaagacgg ttgccttcat catctacgtt 240

```
ataggatgcc tcattcattg agccgcaaac tggacactct tttgttgtgt agggtgcagg    300
gtgctgacta aataccctac cagctctgtc agccttctgt ttcaaaaaag caattttcct    360
tccaggtgat gcatcagcaa ggctcttact cagtcccgat ttacgttttg ctccggtttg    420
ttcgtaacct tgcccatctt cacgctcttt aggcttcgta cgttttctta gtttctcatc    480
ttgtaaacca tcttctacag caataaaacc atagttacga acaatcatag tggtaatttt    540
atgatcgtga tttcgccgtt gcaggctaat ttttcggtca agtttgcgga tagctttctc    600
aagagctttt tgctttgctc cagaaaatgg gcttttatcc ttcatcgttg gtggtgcatc    660
aggtacaata ttatatttca atgtattgag cctagaagct cctattgcct tgattacctc    720
agcctctgtt ttcgcagctc ttaaagcttc ataactctca ttgctaatag ggaaaaaatt    780
tttccgaatt tcttgaattg ttcgatcagg atgatgaatc cacagaatga gcctttccgt    840
taattttta gccagcttct gttgtagttt agctctacgt tcttccgact ttctataaaa    900
cttttgaggc tgaatacgag taccatctga aaggcttaat tcgtactgta gccctggatc    960
gattcctatt gaagcattgg tggctttgac agagaaactt cgttgcactt cacctgaaag   1020
ctgtatgtag tatgcatcgg gacgcttaca aattttgtat gtagcaactc taggaataga   1080
gccatcagga tttcgccatc tcttgtcaat tcctttacat cgaacttttc caagctttgg   1140
gattcctgca aagatattat tgcctactaa tctttcattt gcactaggat tggtgttgat   1200
taaggtctgt aatttatccc ttttacgctt gtactgtggc tttcctcttt taacttcgga   1260
ttgaccatac cgacttttca aatattcttg ccatgccgta tcgagttgcc ccatctctcc   1320
agcacggaat ctctgaggga tgtcgctatc tttcatccat tgagggagat tttcagtttt   1380
gcttactaaa cttaatccac cagaaccttt ataagtggga ttccgaatca taggctcata   1440
ccaacttgga ttttcgacag agccgtaacg aggtatggga caagaatatc ctgtacagtt   1500
agagtacttg cgatcttcat catgattcga cggtagccag ccccaactat ccttcttttc   1560
agcgggagta ggaactttat aaattggtag ctttttcaca taccaacgtg atttttcaga   1620
aataattcta caaaagggag ctaaatactt tcgatccgac gttttctcat gggttggaat   1680
gcaagctttc tcttcctcac tgagcggtcg atattcgtat tgaatgggac aacacggtgc   1740
gtactccttt tgtcctttaa cataactgta aaagtcatca aagtcttcta aagctgctaa   1800
ccccatattc caaagggatc tattaatctc aagccatcgg tcaatttttg cttgttgctc   1860
taggctgaaa tcagccttga actctagggt aagcat                             1896
```

<210> SEQ ID NO 9
<211> LENGTH: 1245
<212> TYPE: DNA
<213> ORGANISM: Lactobacillus fermentum

<400> SEQUENCE: 9

```
atgcaacaaa cgctaactgc taagattcga ctatatccaa cgcatgaaca aatagcgcta     60
tttaaggcgg tgactaagga atatcaacgc ctgtgcaata ttgtcagtca atggtatttc    120
gatggatatt ttaatgccaa tcaaaaggtc tttcagaaag acatgtacca ttatctgcga    180
aatgagtcgc caaagctcaa ctctcaaatg gtacagtcaa cctatagaac agttaaggca    240
cgatatgaca cggtaaggac acaattgtat cagcaccctt atcgttacga taccggactc    300
attgacgaaa agaccggtaa gcatatttgg gaatccattc cccgaacttt agagtggtta    360
tggaagccga ttcactttaa acgccctcag gcagattatg ttcatggctc taactattcc    420
```

-continued

```
ttcgttaagg aacgtacgat gatctcgctt aacgttttgg gcaagcgaat caaagtaccg    480
tttaaagcgg attatctgga agatttgttc gctaccaatg ccaaattagg aactgctaaa    540
ctagttcaac taaaaaaaca ctggttctta catgttccgg ttacgattga agttaacgaa    600
tggaaaaaaa tttgcaatca gcacattgtg ggtatcgacc gtggcttgcg tcagattatg    660
acgatctatg atgaacaagg gagaactaag tttttcaatg gtaaacgggt ggcctatcag    720
cgtaagaagt acgcccattt gcgcaaacaa ctgcaagctg ccggtaccaa atcagccaag    780
cgtcatctaa aacgactggc tggacgagag aaccgctgga tggaagatgt taaccatcgc    840
ctgtctaaga cactcgtaca gcactatgga gaaaataccc tattcgtttt ggaagtcttg    900
accaacgtat cgtttgatga aaagaatcaa agcactcgtg atcgtaaccg cgacctgcat    960
tcttggtcgt tctacgacct tcaagttaag ctgacgtaca aggcacaagc taagcaatca   1020
caagtattga tggtatccgc taaatacacc agtcaacgtt gccctaaatg cggtcagatt   1080
cgtaaagaaa atcgtaatca tgcactgcat cgctacgact gtgcatactg tggctttcga   1140
actaatgatg atcgcgttgg cgcaatgaac ctttacgaac tcggcaaaca atatcttgcc   1200
ggaaacgagc gtccaaagtt tgaattaaac aacgttgccg actga                   1245
```

```
<210> SEQ ID NO 10
<211> LENGTH: 1839
<212> TYPE: DNA
<213> ORGANISM: Cyanothece sp.

<400> SEQUENCE: 10

ttaagctgaa agacgcgatt gataagcatt taaagccaaa gcgatcgctt tatcatgggg     60
tgttcccttg tagggttgtt ggctaatttc aagaacaatc cctaattttg aggcttgtgc    120
ttcaatattg tcgataagtc tgctgtaact ccactgatgc acttgaacac ggtagcattt    180
agcatagttt ttttgtgctt caatgcagtt agggattctt tcctcagctt tggtttgaat    240
ctcagtttgc acaatttctc gcatatcctc taatttggga acaacgatgc ttcctgcttt    300
gtatttcttg gcaagagtaa cgatggcttt ggtcagtagg cgatcgatgt attcccctaa    360
ttctgagtct ccgaattgat taaaagcctc ttttcgttgc gcgacgttac gctgatggga    420
ctgatgctgt ttttgttggc gttgacgctg aattaaaggg taattattgc ctaaaagttg    480
tttaatatac tcgatagtaa gggtttttttg ggtaattcca tccacaacgg cgacagttgc    540
aggtttatct acccccattg ataccccaac gagaatattt gattgacccc gataaagggg    600
ttgactggga cgaggaaagg gattttctag cttatcaaga gttgattgtt tccgtttaat    660
gaaggcttgt tgatttttgg ttaaatcacc cttttcattc atagaagtga gaactttagc    720
gatttcctcg gctttttcct gtttgacttc ttctgtccct tcttgtgtcc ataaacgagt    780
gtctagggta cattgcagga ttaagcgatg aatgttccaa ggttgacctt tttcattccc    840
ttcttgccag agaatacgcc cagaacgtaa ggtaaataag gcactagaat gttgattttt    900
actgcctttc tttgcttgct ggtcttcata aaagcgttga aaccacttta attgtcgttg    960
atcacagtaa atttcaaagc ttaggtcact aatgccgtta aatttaacgc ataatcgtcc   1020
tttctcgttt ttatgccatg ttaagtcttc attggtttcg tagttgatag gaaatgggat   1080
agactgggat tggattaata gtttatcttg ccatgaacgg gcttgtgcgg tgtcttctgg   1140
gtcagtctga caggcaatag acagggtttc tagccaatta tgattggtta agtctctccc   1200
ttggggaaga cgaccttcta attgttcttg tagtctatca atggcaattt cgactttacg   1260
gcgacgtttt gtaaattttt cgggatcttc tggtttctga ggaagtttac agcgattttt   1320
```

gagcagataa cataaggcta tgtgggtgaa agggtttttt tcttcttgat aaagttgaaa 1380
gagatgatta aagagttttt ctgtcttttg atgggtttgg agaatttcag aggctttatg 1440
gcgaatagct tctaaatttt gctgactttg ctgaattaat tcttcatcac tttttaagac 1500
ggttaaccat cgtcttttac cgtcgagttt acgctgtaat cgttgttgga gttttagcca 1560
agatttgaag atgtattcta ctaagcttat cccagaggta taaaatcggg ctggttgtcc 1620
caaataacgg ggatcttttt ttaatttgtc tcctaattgc ttaataacac ttttttgaag 1680
ctttcctttt tgtctccatt gttcaaagtc gggattttgt gccacttttt gcagtaattc 1740
gttaataaat ggcgtgttta actctgccat cagttgccac agggtttgac gggtgggttc 1800
tttagcaacg agacgacatt gaatcgtgat ttgactcat 1839

<210> SEQ ID NO 11
<211> LENGTH: 1437
<212> TYPE: DNA
<213> ORGANISM: Bacillus mycoides

<400> SEQUENCE: 11
atgattatcg ctaggaaaat taagctgatt attattggtg aaaatcgtga tgcccagtat 60
aaatttattc gtgaagaacg gtataaacaa aataaagctc taaatgtagc aatgaatcac 120
ttgtactttc ttcatgttgc aaaagagaaa attcgattgc tagataataa atttttacag 180
gatgaaaaga aactacaaga aagcattaac aagctttatg ctgaaaagaa agtcataaaa 240
gatgagaaaa aaagaaatga actagaaaag aaaatagaga aacaaacaaa tgaattaaag 300
aagttgcgga gtaagagtaa taaagaagcg gataaggttt tacaagaagc gattaaaatt 360
aatctttcta gcacaacacg tgaagtaatc agtaaacagt ttgaattgat aagtgataca 420
aaagatcgga ttacacaaaa agtatcacaa gactttaaat ctgatttaaa acacggtcta 480
ttgagcggcg aacgtgtatt acgcacatat aaaaagaata atccattgtt aatacgaggg 540
cgtgcattga acttttatcg tgaagggaaa gatgtaatga ttaagtggta tggcggtatt 600
attttcaaat gtatgcttgg gcaacataaa aataatgctc cagaattaaa agcaacttta 660
agtaaagtgt tagagggatc ttataaggta tgtgatagca gtatttcagt aggaaaggaa 720
ctaattctta acttatcctt agatatagga gaagttgata caaatgtatc ctgcaaaaaa 780
ggacgtgttc taggtgttga tttaggtatg aaggtaccag cgtatatgtc tataaatgac 840
aaaccgtata ttcggaaggc attaggaagt ttagatgatt ttttaaaaat ccgtgtacaa 900
atgcaaaaaa gaagaagaaa tttacacaag acattagtga atgtaaaagg tggaaaaggt 960
agagaaaaga aattacaagc attagatcgc ttaaaagaca aagaaaagaa ctttgcaaca 1020
acttacaatc attttttgag ctataacatc gttaagttcg caaaagataa tcttgctgaa 1080
caaattaata tggaatttct tgcactagcg ggtgaagata aaaatataat tttaagaaac 1140
tggtcttatt atcagttgca acaatttgta gagtataaag ctaagcgaga aggaatcgat 1200
gtgaagtacg tagatccata ccgcacaagt caaatgtgct caaaatgtgg gaattatgaa 1260
ccaggacaaa gagaatcaca ggaaaagttt atttgtaaat catgtcattt ggaaatcaat 1320
gcagattata atgcatcaca aaatattgct catagtacaa aatatattac aaataaaaat 1380
caaagtgagt atttaaaaaa attgcagcaa accacaaaat tagaaaaata ctcatga 1437

<210> SEQ ID NO 12
<211> LENGTH: 1173
<212> TYPE: DNA

-continued

<213> ORGANISM: Haloarcula amylolytica

<400> SEQUENCE: 12
atgcagacca gcatcagtga gttcactgct ggcactgacg aactcgacat tacccggacg 60
atccggtgta agctcgccac cagcaacgag aaaaacgaga ctgtccgtcg tgggatcgag 120
gcctaccagc aggtcgccag ccacatggct gatgtgctgc cgtcctaccc cgcatatgag 180
tggaacctcc agaacacgca gatgtatcat caggccaagc gagcgctccc agatgatgat 240
gtgcggtata aaaccacgct cgcacagatg gccaagaacg atgtcgtcga gtcgttcacc 300
agctggcgcg aacgtggtga agacgggacg ttgcctcgtg gccagtacgg tgacgctgac 360
tacctcagcc tccggcatga cgactgcgag attcacgcga acgacaaggg ctggggtgtc 420
aagacgagct ttatcagcta caatccagtg tggttccaca ttcacgctgg agactatcag 480
cggcagtttc tcgaacgcgt gactgatgac gatgatccgg caagcgccgg gtctgccgaa 540
ctccatctcc acgacgacgg gacgctgtac ctccaccaga cgatcacatg gccagttgag 600
gtctaccagc ccgccgaggt aagtaccgtc gttggcgttg acctcaacga tgatccacta 660
gtctgtgcag ctgtcgtcga cgacggtgat gtcgtggctg tcgagttgga gtcgggtgcg 720
gagtatcgcc accatcgcga gcgggtgaag cgtcgccgga gcgaggcgat ggagcgcaac 780
gacctgaaag ccatcaagga cgctcgactc cagtacaagc gctacaccga tcacatcacc 840
aacgtcgcca gcaaacgtgt ggttgacgtc gctgaagagc atgctccggc agtaatccat 900
ttggaagatc tcacccacta tcgcgagact gccgaggacc caattcacga ctggcccttc 960
gccgagatcc aagagaagat cgcgtacaag gcccacgagg ctggcattcc agtccaggta 1020
atcgacccac gcaacacgag tgttacgtgc cgcaagtgtg gggaaaccaa tccagccatg 1080
cgggatggcg atgacttcga gtgttgggaa tgtggatacg aggtccatgc ggacgtgaat 1140
gccgcgatca acatcgcaaa tacagatcca tag 1173

<210> SEQ ID NO 13
<211> LENGTH: 1677
<212> TYPE: DNA
<213> ORGANISM: Rothia mucilaginosa

<400> SEQUENCE: 13
atggctgaga aaaccggcac cgatgctggc accatgaacc gcgcctataa attccgcctc 60
gaccccaacc aggcacaaaa agcagagctg atgcgctgtg taggcgcagc gcgctacacg 120
tacaacctcc tcaacgcata caatcttcaa attctccgaa acgaacagga atatcgaaac 180
acccgtaacg ccgaaggcgc agattacgag acgatcaacg gcgagattag gaaactacgt 240
aagaaggacc cggcctataa gttccttgga cacgctgagt acgaaaagcg atacctaacc 300
cctgagaaac agcgtcatga agctatcgcc caggctatta ctgacggcgc tgaccccgcc 360
gtggtctggt ctgaaactga acgattcgct gaaccttggt tgcacactat tgctcgacga 420
gtccttgttt ctgggataaa gaacgctgat aaggcttggg acaactacaa caaatcccgt 480
atgaagcaac gtgccggcgc ccgaatgggc atccctcgtt tcaagcgtaa gggcgtgagc 540
cgtgattcct tcacggttcc gcatgaaacc accggtgctt atggagctta ctatcataag 600
aaagacccag aatacgcacg tcgtaaggta caactgaagc gtcgaggtat tagtgcaaaa 660
ccgaccatca ctgactaccg ccacgtgcgc ctcgcatctt tgggtgttat ccgtactcat 720
aacaccacta aacctctggt gaaggccgtg cgtgctggcg ctgaaatcaa atcgttcact 780
gtctcccgtg ctgctgacca ctggtatgtc tccatcctcg tggagctcac ccgcccgtct 840

-continued

```
actgcccccta cgcgtgccca gcgttccgct ggtgctgtcg gtgtagacct gggcgtgcgc    900

tacctcgccg cgctctctga cgagcaggca ccacagcgct tcgcacagta cccctccctg    960

gagttcacca gtgacggtgc ccctacccctg gctaaccccc gctgggcacg tgccgctgag   1020

aagcgcctgg tacgtctgca acgtgccctc tcgcgtgccc agaagggctc taagcgtcgt   1080

gcccgcattg tgcagcagat tgcacggcac caccacctag tagccttgcg ccgcgaatcc   1140

gggttgcatc aggtctctaa gcgcctggcc accgggtaca ccctcatcgg gcttgaagac   1200

ttggctgtag cgggtatgac cgcctcagct gccggtacca tcgaggcacc gggcaaaaac   1260

gtgcgccaga aagccggact caaccggtcc attctggatg ccgcttttag tacgctgcgc   1320

cgccagctgg aatacaaggc cagctggtac ggctcgcagg tacagattat tgaccgcttc   1380

tttgcatcct ctcagacgtg tagcgcctgc ggagcacgag cgaaaaccaa gctcgacctt   1440

cgcgtgcgtg tctttgagtg cgcggcctgc ggtgtgcgga ttgatcgtga cgtgaatgcg   1500

gcacgtaata ttcgtgcgga ggctgtgcgg atgtatgagg cgcaactcgc cccggcatg    1560

ggggagagtc taaacggacg cggagttact gactctgatg ctgctgtttc ggtggtgttg   1620

ggggatgcgg cgttggatgc gtcaagacca gccgccatgg gcggcgggtc accgtag       1677
```

<210> SEQ ID NO 14
<211> LENGTH: 1353
<212> TYPE: DNA
<213> ORGANISM: Bacillus thuringiensis

<400> SEQUENCE: 14

```
ttgagtacag ttgtaaaagt catgaaatac caaatagttt gtcctgtaaa tatagagtgg     60

aaggcgtttg aaacgtattt acgtacacta tcgtatcaag ttaggacaat tggaaatcga    120

actatacaaa aactttggga ttttgacaat cagtcgttga atcattttag agaaaatggt    180

gtatatccga gtgcccaaca attatatgga tgtacccaaa aaacgataag cggatatatc    240

tatgatcagt taaaagagga atatcaggat attaataaag ccaatatgtc cacaactcta    300

caaaagacga ttaagacttg gaatagtaga aaaaaagaaa ttcgaagtgg tgaaatgtcc    360

attccttctt ttcgaaacaa tttaccaatc gatatccatg ggaactctat acagataaca    420

aaagaaaaaa gtggggatta tatcgcaagc ttatctctat tttcatcaaa ctttataaaa    480

gaaaataatt tgcctaacgg taaaatacag gtgaaattat caacgagaaa acaaaatagt    540

atgaaggtca ttttagatag aataattgaa aatacatatg ctaaaggtgc ttgcatgctt    600

cataagcaca aaaataaatg gtatttgtct atcatttata agccaactgt gaaggaagaa    660

cataaatttg aagaagattt agtcatgggt attgatatgg ggaaaataaa cgtactttat    720

tttgctttta ataaaggatg gataagaggg gcaattagtg gagaggaaat tgaggctttt    780

cggaaaaaaa ttgaacatag acgtataagt ttattgcgtc aaggtaaata ttgtagtgga    840

aacagggtgg ggaaagggcg agaaaagcga attaaaccca ttgatgtatt gaataataaa    900

gtagctaggt ttagaaatgc aacgaatcat aaatacgcaa attatatagt acaacagtgt    960

ctgaaatata attgtggcac tatacagtta gagaatttac aaggaataag caaggaacaa   1020

acattcctga aaaattggac gtattttgat ttgcaggaga aatcaagcaa gcaagctcat   1080

caatacggta ttaaagtagt tacaattgat ccctcatata caagtcaacg ttgtagtgaa   1140

tgtgggtata tccataaaaa taatcggcaa agtcaatcaa cttttgagtg tcagcaatgt   1200

aatctaaaag tacatgcaga ctataatgcg gcaaaaaata tatctatata caatattgaa   1260
```

-continued

```
aaagtgatac aaaaacagtt gaagttacag gagaagttga attctaagaa gtttacagaa   1320

cagtatatag aacagataga aaatattaat tag                                1353


<210> SEQ ID NO 15
<211> LENGTH: 1416
<212> TYPE: DNA
<213> ORGANISM: Clostridium ljungdahlii

<400> SEQUENCE: 15

gtgataactg ctagaaaagt aaagttaact ataactgaaa atagggaaga tgggtataat     60

tttatccaca atgaattaag agagcagaat caagctttga atatggcgat gaatcatttg    120

tactttaact atgtagcaag agaaaaaatt aaattagcag atgaaacaca taaaattaag    180

ttagcggaag atcaaggcta tttagatcaa aaatatacgg agcttaaaga ggttaagact    240

gataagaaaa aacaaaatat tagaaaatct attcaagctg ctaaaaaaag attggaaacg    300

ctaagaaaag ctgaaaataa acaagtagcg gagaaattca aagaaattat agctgcatca    360

gaaaaaacca atttaagaga ttttataacg gataacttta atttaactag tgatactaaa    420

gacaggttaa ctcagaaggt ttcagcagat tttaaaaatg atattgtaga tgttttaagg    480

ggtgaaagaa ctttaagaag atacaagaaa ggtaatccat tatatattcg cggtagaaat    540

ttaactttct atataaaaga tgaggagtat tatattaaat ggatgaagag tattgtattt    600

aaatgtgtac ttggagttaa aaagcagaat agtttagaac tgcaaaaaac tttagacaag    660

gttatagaag gaaaatataa ggtgtgtgat agtagtattg aatttaagca aaatagtctt    720

atacttaacc tgactttaaa tataccagtt tgtaacagtt ttgacaaggt tgaaggcaga    780

gtagttggag tagatttagg tatgaaaata ccagcttatg ttactttaaa tgatagtgat    840

tatattagaa gggcaatagg tagtatagat gatttcttaa aagttagaac gcaaatgcaa    900

agtagaagaa gaaatttaca gagggcattg aagagtacaa aaggtggcaa aggtagggaa    960

aaaaaattaa aagcattaaa tcaatttgaa gttaaggaga agaattttgc taaaacgtac   1020

aataatttta ttagcagcaa tatagttaag tttgcatcag ataacaaggc taaacaaatt   1080

aatatggaat ttttaagcct ttcagaaact caaaataaat ctgttttaag aaattggagc   1140

tattatcaac ttcagcaaat gattgaatat aaagctaata gagttggaat taaggttaag   1200

tatgttgatc catatcatac aagccagata tgcagtaagt gtggtcatta tgaagaaggg   1260

caaagagaaa agcaggaagt atttatttgt aagaatccag agtgtaaaaa tttcaatata   1320

gaagtaaatg cagattataa tgcatcaagg aatattgcta aaagtaataa gtatataact   1380

aaaaaagagg aaagtgagta ttacaaaatc aattga                             1416


<210> SEQ ID NO 16
<211> LENGTH: 1287
<212> TYPE: DNA
<213> ORGANISM: Clostridium pasteurianum

<400> SEQUENCE: 16

ttaaggtatt ttggcaaaat ttttaataag tttttctata ttaggaagtg ctatattttt     60

agcagcattg atatctgcat gttcctcata tccacaatta atacacttaa atattgattg    120

attattttta gaatctctat ttaatttatc tatgcaaccg catatactac atctttggct    180

tgttttgtat ggatttatta tttttatatc tattcctttt tctttagact tatacttaat    240

tttactttgc atatcaaaat atggccaaga cttaagaaaa ttattttcag gattaaagcc    300

tgttaaatct tctaattgta cagttccaca gttatgtttt actgcgaaat ctacaatata    360
```

```
ttttgaatac ttgtggttta atgtatctct aaaattattt attttatctc ctatatttga    420
tgcagatcta attttagttt tagtaccatg tccgcttctt ccgtcacctg caactttaca    480
ggagattaac atacttcttc ttctagcttc tactttttgt ctaaaatgaa ttgactcttt    540
accgtctaat atacattctc tatataataa tttatcccat ttttttcat tattgtccca     600
tatttgtaat gttgctgtgt ttgttattcc aagatctaca ccaagaattc tatttttgtc    660
taattcttta atgtctggaa caaaactaaa actaattata aaataccatt taccttttt     720
atcttgaatt atctgagcgg ctccctgctt atatatacca cttattattt tatttaaagt    780
aaccttttg ttgttatcta atttatcaat attaaaagtt acgtgcctta aatcttgttt     840
cttgttaaat atagctgcat ctatttcgta tccattattt ccttgtatta ttttataatt    900
tttattataa atataaattg gcatatttag cttgaaactt gctacagatt ttctgtagtt    960
taaaatgtct tgtttatcag aattccattt ttttaacaca aatgcatttg tttggcttac   1020
atttgatgta tttactatat tcattatttc cttcatatat ccttctacaa catttctata   1080
tgttttgcca aatagatcct tatctatagg atattgacca tttaattttt tataattcat   1140
tctttcatat tcccacatat agtacatttg catagcttta ttactggctt tacatgtcat   1200
atatcgaata ttacttaatg tcttattaat atttgtaaag tttaattgat tacaattttt   1260
tatggttatt tttatacatt tattcat                                       1287
```

<210> SEQ ID NO 17
<211> LENGTH: 1362
<212> TYPE: DNA
<213> ORGANISM: Ruminococcus albus

<400> SEQUENCE: 17

```
atgactaaag tagtaaaatt agcgttaata agcaatgtaa ccgataaaga tggaaacaaa     60
gttgaataca atgaattaaa cagatgccta tgggatcttc aaaaagaaac cagggacctg    120
aaaaatgctg tagtaagaga atgctgggaa tggtacggat tcaccaacga ttattataaa    180
cttaacgaag aatatccgaa tgaaagagat tatctgaaaa aggcaaagtc tgacggaacg    240
attaaagatt atgctttgga tggatttata tatgctaaat acagcaaaaa atacaatctt    300
cattcaggaa actattcaca aacattaaga gacgcctgcg gaagctttaa aaataatctc    360
aaagaaatat taagaggaga taagagcatt ttaagttata gagccgatca gcctctggat    420
atcaagaaga cctgtatcgg actggaatac gataaggaca caaacactta ttatgtaact    480
cttgttctgc taaacaaaaa tggcgtcaag cattataata tcagtgattt cagatttaag    540
ataaccgtaa aggataattc aacaagaacg atccttgaac gttgttttga tggagtatac    600
ggcataagcg caagtaagct tatctggaac agaaagaaga gtcagtggtt tttaaatctc    660
tgctattcat tcgataaagt agaggtaaag gaacttgaca agaaaaagat actgggagta    720
aatctcggtg tttactaccc tttatacgct tcaatatccg gagaaaagga tagactagcg    780
atctctggtg atgaaataat cgaattcagg aaacgaatag aggctagaag gacagctctg    840
aagaaacagg ctgctgtgtg cggagatgga aggataggtc atggttataa aaccaggatg    900
aaaccattac agaatgtctc tgataagata gcaaatttca gagatacctt taatcacaaa    960
gcaagtaaaa agctaattga ttttgcaatc aaaaatgatt gtgggatcat ccagctcgaa   1020
aatcttaaag gagtaacaaa aaattcagaa ggattcctca aaaactggtc tttttatgat   1080
cttcagagta agatcgaaaa taaggcgaaa gaaagaggga taaaagttgt ttatattgaa   1140
```

```
cctgcttaca caagcctgag atgctcaaaa tgcggatgta tacacaaaga taatcatccg   1200

accagagagc agtttatctg tcaagagtgt gggtataggg ttctgcatga ttacaatgcc   1260

agccagaaca ttgctgtcaa ggatatagac aagataataa aagctgaact tgaaaagacg   1320

gaaccggaaa agaaaacaga ggaagaaaag cccgagaagt aa                      1362
```

<210> SEQ ID NO 18
<211> LENGTH: 1281
<212> TYPE: DNA
<213> ORGANISM: Synechococcus sp.

<400> SEQUENCE: 18

```
ttacgctgaa cactgctgag cattactgct cagcggtgaa gcgatagcat tctgtccgtt     60

tccgttgtca ctacgcgatg ctgacgcgac cgcgctactc ggacggagtc caaacagaaa    120

ggcggtatcc cgcaaagccc tgagcataac acccagagcg ccttgccaat ctcgtggtag    180

cctatggttg cactttgggc atctaaacac ctttgcacca cccaacttgg tgtggatgtg    240

cccgcactta gtacaggttt tgctggtgta cgcttccgat acttccacga caaccacgtt    300

tttcttcttg gcttgaaact tcaggaactg cttgaaccga tagtgcgccc aggtgagcat    360

cgcccttgct gtcttgctac caaacttcct ccctgccttg gcaaccatct tggctgactc    420

gaaagtgggg aggaatatca atcggtagtt atccgttagg aacgccgcta ccttgcgatg    480

gcactcgtcc accaagttcc tgattctctc ccgcagacga aacgccgctt gccgcattcg    540

cctacgcttg ggtctcggtg ctttactcag cctagattgc agatcgtcta ggtggtagca    600

cagccgaacg atcctgccaa agtctccctt ggcgatatct acaaagcccg ccccatcaaa    660

ccctgtaagg aagcttctta ctccaggatc aagtgcgatc accccctttg ctaacgaaca    720

ctgctcgttc acgggctcag ggaagatggc ataccatctg tctttcaccc gcattagctc    780

agttccacgt gcccattctc tggcatctc ctcggatgca cggaacgcca aacctcgggt    840

gagtttcgga taccacgtcc cattgcgaaa gttgccggcg ttgaattgca gcgtatgcga    900

cctgtcccgc acactgcgaa acctcgcgtc tttgcttcgg cgaaacgcca accacgcctc    960

gacgaccgcg ttctgcttga tgtggcaggg ggcgtccttc acccacccgg gcaggtcgga   1020

gcgcaggatg atgtcccgca gctttctggc cgttcttgga gcaccatgct ggcgctgata   1080

ggcaatcgct tggttgtagc agtaccggca cgccgcttgc caccgcttcc aaactttagc   1140

cagcgctggc tccggataaa tccgtatctt tctcgattgc agcccggtat tttctgagtc   1200

cgtagagccg actgctgaag cagtgcagga tggtgaggat atcctcaacc agttcctgtt   1260

ggggagaaag gtgatcgtca t                                             1281
```

<210> SEQ ID NO 19
<211> LENGTH: 1185
<212> TYPE: DNA
<213> ORGANISM: Lactobacillus equi

<400> SEQUENCE: 19

```
ctactggata tttaattgtt ttagaccacg atttaagata tttaaactag cgtttatatc     60

tctatcgtgg tttttgtggc aataaggaca cgtccagttg cgtgtactta accattgcgc    120

ttgagttaaa ccatcaaact catgattctt cttaccgcaa tcagaacaaa tacgactggt    180

atttttaggg tctacaatta ctaattgttt accataccag ttacacttgt attcaagcat    240

tgacttaaaa gtataccaag catttgaact aactacatta gctagattat gatttttcat    300

catatttttt gatttaagat tttcaatcac aattacatca tattgcttaa ctaatttagt    360
```

-continued

```
cgttattttg tgaagctcat catttctttt gttagtaatt ttagcttgca atttagcttt    420
atttttcttt gctttttgcc aattagtgaa atcttctact tcaatatcat acagtctaga    480
tttatcatga ttatgagtag cgactatatt ttttacgtta tgcagtcttt tattatattt    540
tctttgccat agcctagctt tcttatctaa attcttaaat tgtagtttag aatatttaac    600
accatcagaa gtaattgcta aatcatgaac acccaagtcg atacctacta ctttacccgt    660
tttattgagc ttttggttct caaactcaac ttgcaagctc aaatagtagt tgccattagg    720
tgaatgttca acggtataac gtttgatttt acaatcattt aataagttag ttttacttgt    780
tttaacaatc cctaattttg gtatcttcat atatctagca ttggcaactt taattgttgc    840
tgacttacca gtatatgact gtttgtaagc tttacggcta tgaaatttag gtctaccatg    900
tttctttttg aagaacatta accacgcctg ataaagatta ttagtcacca cttgtaaact    960
ggagctatca ctttctttta gaaagtcata ttcttgctta agtggtttga gtaggtaatt   1020
catatcgtaa gctgacaaaa cctttaaact gggattgttt ttataccgtt ggttaattag   1080
atttaacatc tcattccaaa caaatctatc attgccaaac atccacgcta attgttgttt   1140
ctgtctagca ttagggtaga tttttagttt gattcctttt aacat                   1185
```

<210> SEQ ID NO 20
<211> LENGTH: 1218
<212> TYPE: DNA
<213> ORGANISM: Lactobacillus agilis

<400> SEQUENCE: 20

```
ttacgcatta gttgttaatt caaatttagg ttgttcttgc ccactaatat attgcgtacc     60
caataattgg atattcattg cacctaagcg gtcatcatta gagcgataat cgcaattagt    120
gcaataatac tcatgtaagt cgtgattccg gtgagatttt ttaatcgttc cgcatttagg    180
acaacgttgc gaagtatatt gagctgaaac ttcaattact tcactattat ttaagtacgc    240
tttgtaggtt aagaattgtg ctaattgata aaaagcccag gatttatttt gattacgtaa    300
ggctttgggt aaatcagtgc gttcaaagga aacacctgtt aagtcttcta aaacaagcaa    360
ggtgttggaa ctaaattttt ggaccagtgt cttagacaaa cgatggttaa catcggtcat    420
ccaacggttc tctcgtctgg ataatttctt taaacgccgt ttagctgatt tagtgccttt    480
agcttgtaat ttggctcgta acttttgata cttagcgcgt ttgcgcatca ctgccttacc    540
gtcaaagaag gcggtttgac cttgttcgtc ataagtagta gctaaaaaac gtaaaccacg    600
gtcaatacca accacgtgtt ttacagtttg gttatcaaaa tcagctaccg ttttagtagc    660
tgaaatgtgt aaataccact taccaccagt tttaagtaat ttagctaagc caaacttcca    720
agtaccatca aagtattggt caaagccgtg acaaataggg ttaactttaa ctcgaccgtt    780
aagggtgtta attgataatt gaccgctact taaataagac cagtcacgat tacgttgcaa    840
gtctacttga ggtcggttaa aggtaattgg tttttgtaac caagttaaat ctcgaatttc    900
acgataccat tcaccagtat taatatcttg atacttataa gggttgcgtt tcatttgagt    960
tttaactgtt ttataacgag caattacagt tctgattaca gattgagcca tttgtgattt   1020
aagcataaat agactacgta aattagtata caaaactttg tttaatcggc tttgttgcat   1080
atcaaaatca tgattaaaaa tgtattcaga aacataatta caagctaagc gatattgttc   1140
catcgtatta gtaaaactcg aagcaatctc tgcgttagca agatttaatt tcactttgat   1200
agtaatttgt atttccat                                                 1218
```

<210> SEQ ID NO 21
<211> LENGTH: 1146
<212> TYPE: DNA
<213> ORGANISM: Cyanothece sp.

<400> SEQUENCE: 21
tcaccccttg aaacagattt cttgagcggc ggacacgtcc ctatcgacaa aattatcaac 60
cccataaccg cattcatgac agacgtgaaa cctatcagat agagtttttc tgacttgtgc 120
ccgacaattg gggcaagttt ggctagttcc tcgatggtca accaaaccga aatacttacc 180
ccttaccttg cagacatatt tcaggatgtc cctaaattgc ccaaacccgg catctaaaga 240
atgtttaccc aaaaatccct tagccattat gcggaaatca atatcttcca taaagatact 300
atcccccata tcacagcatt tgtgggctaa tttaaactgg taatctttac gcttaaaagc 360
aatatgatta tgttgttttt ctactttcag tcgggctttt tcgtagttct tagaacgttt 420
ttgctttctg gctaaccgac gttgtagcac tttcagccga cggtgttcgg ttttgaagaa 480
tttacgtcct ttttctacat ggttatcgga tgtagccaag taactagaaa gtcccacatc 540
aataccaaga aaatgcccaa atggtgtctc aatttcaggt aagttcaaat ctgattggat 600
attgattaca gcaaaccagc cggaggcttt tttgataact cttacctgtt tgatgacaaa 660
accattagga attggacgat gaagatttat ctgcacattc cccaacttag gtaatttaat 720
ttgccacccg gtcaaaggat tgcttctaaa ttgaggaaac aataaagact tcatttgtcc 780
atatttcttg aaccgaggaa aaccaaatcc tctattgcga aaaaagtccc aagcatcatg 840
aagtcttctg atgttagtct gtaagacttg acttggaatt ttggataagg aaggaaatac 900
tttcttagct ttgggtaatt gattttgttg aaagtgataa cttgggaaag gataatcagc 960
agacattatg tattctgact ctaaagaaca ccgatctatt ggacacttcc ttgaagcaat 1020
ccagtctttg agttcacgca aagcatagtt ataagaacga cgacaaattt caagccattc 1080
agataacatt tcttcttgct tactatcagg gtagattctg taggtgtaat ttagtgttag 1140
agtcat 1146

<210> SEQ ID NO 22
<211> LENGTH: 2037
<212> TYPE: DNA
<213> ORGANISM: Tolypothrix sp.

<400> SEQUENCE: 22
atgagccgcg atcgccagaa gaaatccacg agtccaatcc atagaactat acgatgccat 60
ctccatgcta gtgaagatgt actgcgtaaa gtatgggaag aaatgaccca aaaaaatact 120
cctctgattg ttcaattatt gaagagtgta agtgagcaac cagaatttga aaccaatcaa 180
gagaagggaa caataagtaa aaaagaaatc acaaaattac gcaaagctct aacaaacgat 240
tctgatcttc aacaacagtc aggtcgtctt ggctcatcag cagactcttt agtaacagag 300
gtttatacat catggcttac attatctcaa aaaataaaaa agcagaaaga aggtaaagaa 360
tattttctaa ataatattct caaaagtgat gttgaacttg tacaagaaag taattgtgat 420
ttacagacaa tccgttgtaa agcacaagat atactgagcc agccaaaaga atttctagaa 480
cagattacta atcatgatgc cgttctaaat caaacaaagt cagcgaggaa aaaagttcaa 540
aacagtagta atgaaattaa cgcctccaaa caaagggaaa attctgatta ccaagaaaac 600
gtagataaaa atatcccaga aacattgact gaaattttat ataaaatcca taaaataact 660
caggatattc taacgcagtg tgccgtcgcc tacctgataa aaaaccataa tcaagttagt 720

-continued

```
gatctagagg aagatatcaa aaagcttaaa aagcgtcgca ctgaaaaaca agtccagatt    780
aaacgtctag aagaacaaat acagaagaat aaattaccta atggtagaga tataacagga    840
gaaagatata atcatgcatt tgataattta atcaatcaag tacctcaaaa caatgaagag    900
ttcgcagaat ggatagctag cttattaaat aaagtctcag atttaccgta tcctatcgat    960
tatttgtata gcgatttaac ttggtataaa aatgaacaaa gaaaaatttg tgtttacttc   1020
aatggctggg ctaaatttca ctttcaaatt tgttgtaata aacgccaact tcatttcttt   1080
aaacgctttc tagaagacta taaagctctt aaagaaagtg agaaaggaga aataaaactt   1140
tcaggtagct tggttacact acgttctgta cagttgttgt ggcaacaagg tgaaggcgct   1200
ggtgagccgt ggaaagttaa taaattagct ttgcattgta cctatgatgc tcgtttattg   1260
acagcagagg gtactgaaga agtaagacaa gaaaagactg atactacaca aaaacaagta   1320
actaaagcag aaggtaatga aaatatcgat agcgatgaac aaaaaaacct gaatagaaat   1380
atatcttcat tgtctcggct taataattca tttgctcgtc ccagtaagcc aatttatcga   1440
ggtcagtcta atataattgt tggtgttagt ttccatcctg ttgaattagc aacacttgtt   1500
gtagttgata taattactaa agaaaaaatc atctgcaaaa cagtcaaaca gttactaggt   1560
gatgcttttt ctctgttaag tcgtagacga cgacaacaag tgcattttcg taaagaaaga   1620
gaaaaagctc agaaaaaaga ctctccttgt aatatgggcg aatcgcaact aggagaatac   1680
gttgataaat tgctagccaa gagaatagta gaagtcacta aggaatataa ggctagctgc   1740
attgttttac caagattaaa agacacgagg gaaatccgta ccagtgtcat tcaagcaaaa   1800
gcggaagcca aattccctgg tgatgtaaat gctcaaaaaa tatatgtgaa ggagtataat   1860
cgccagatac acaattggag ctacggcagg cttcaagaat ccataaagtc aaaagctgcc   1920
gagtttaaaa ttagtattga atttggtatg cagccatctt atgacaatct gcaagaacaa   1980
gcgataaatc tagcattgtc tgcttaccaa tgcagaatta atactattgg tagataa      2037
```

<210> SEQ ID NO 23
<211> LENGTH: 1188
<212> TYPE: DNA
<213> ORGANISM: Lyngbya sp.

<400> SEQUENCE: 23

```
atgcaacgag cctttaagac aaaactgaaa ctgaacaaca aacagaaaac tttaatggct     60
caacacgcag ggtattctag gtggatttgg aattgggcgt taaacctttg gaacgaggct    120
tatgctgcgg atttaaaacc ctctgttaat aagctcaaaa agttctacac ccatcatgtt    180
aagcctgttt atccctggat gaaaaccttg tcctcaagag tttatcagtt tgccttcatg    240
cacctgggag aagcatttag tcggtttttc aaaggtttgg ctaaatatcc taaattcaag    300
aagaaaggca gaaatgatag ctttactctt gataactgcg gtaaggttat gcagttttca    360
gggactcggt taaagatccc cttcattgga tgggttagta cctatgagcc gttacctgaa    420
atcaacacaa agcgaattac aatcagtcgt actgccgaga attggtactt atccgtcgcc    480
tatgaatttg aacccgaacg cacggagaag tcaagagaat acctgggtgt tgatgttggg    540
ataaaggttt tggcgacttg ctcagacggc actgtttttg ctaatcccag agcgtacaag    600
aaggcaactc aaaaattggc gcgacttcaa cgcgaactct ctagaaagca aaaaggttca    660
aataacagga ataaggctag actgaaactg acaaaagtac atgaaagagt ggctgacatc    720
cgaaaaaata caattcataa attaacctca tggctatgca aaaatcacgc ggtcattggg    780
```

```
ttagaggact tgaatgtttc tgggatgtta aagaaccata atttagcagg tgctattgct    840

gattcggctt tgtatgaaat tcgccgccaa gttgagtata aggctaattg gtatggctca    900

atcgtagttt ttgctgacag attttatccg tcgtctaaaa cttgttcaaa ttgtgggcat    960

attcaagaaa tgcctctaaa agaaagggtt ttcaactgca aagtttgcgg cgaagtcaaa   1020

gatcgtgatt tcaacgccag cctcaatgcg cgaacatcgt ggccgttggc tattcggttt   1080

gagcctgtgg atcgggtact gccgacagtc cgagatgaag cagcgcaaag tccgatctcg   1140

gcggtttccg tcgagaagga actttgcaag acaggaacga aactttga                1188
```

<210> SEQ ID NO 24
<211> LENGTH: 1257
<212> TYPE: DNA
<213> ORGANISM: Unknown
<220> FEATURE:
<223> OTHER INFORMATION: Uncultured archaeon sequence

<400> SEQUENCE: 24

```
atgcactacg cctacaggta tcgactccat ccgactgaag cccagcgaga gacgctgaat     60

tttcatcgtg atacctgcag gcaactctat aaccacgcgc tcaccgaatt cgagcagatt    120

ccccagtcgg cggggacgct cacccagcga gtgcgacaag tccgtgacca acttcccgat    180

ctcaaagact ggtgggacga cctcaccgag ttgtactcga cggtcgccca agccgctgtg    240

atgcggattg aggatgccat tgaagctctg tctgaactga aacgaagggc ctacgatgtg    300

ggaagtctca attggaagtc gccacgcgag tatcggagtt ttacgtacgt acagaaaggc    360

ttcgagttcg acaagaagaa cggccagact gtcctctcac tcaaaacact cgctgacatc    420

ccactcagct accaccgtga aatccccgat gatctcacgg tcaaagaggt gagtatcaaa    480

caggaacgga ctggtgagtg ggacgcctcc ttcgcggtgg atgacaagga agagccagcc    540

aagccagaga atccagcccg ttgtgtcggt atcgacgtag gaattctcaa gtatgctcac    600

gacacagacg gatgtgctgt cgggtcactt gacttgcaac atgaacagga gcgtctcaag    660

cgtgaacagc ggtccctctc gcgaaaacaa cacggctcga acaactggga gaaacaacgg    720

ctgaaagtag ctaagcgtca tcaaaaggtc cgccgaaaac gccacgactt cctgcacaaa    780

ctctcgaact actacgccac cgagtacgac atggtagccg ttgaggactt ggacgtgaag    840

ccgatgttgg agtcaactgg caacagtcaa aacaccgcct cggcagcgtg ggacacgttc    900

accacactgc tcgagtacaa gtgcaagcgg gaagggacgc actttgttga ggttgaccca    960

gctgggacaa cgaaacagtg cgcttcgtgt ggtgtcgggt cagataagcc actgtgggtt   1020

cgagaacact cgtgtccagc gtgtggattc gagatggata gagatgcgaa cgcggccatt   1080

aatattctgt ttcgcgggtt cgagaagcta ggactgggac agtccgaaga gacaacgcct   1140

gtggagaccg cgctccctct gttcacctcg tcggacggtg ccgacgttgt ggatggaaag   1200

cgtgtcgtgg aaacaggaag ccccaccctc aaggaagccg cgacagcggc tgagtag      1257
```

<210> SEQ ID NO 25
<211> LENGTH: 2049
<212> TYPE: DNA
<213> ORGANISM: Cyanothece sp.

<400> SEQUENCE: 25

```
atgaccctca aaacccttga atgccgtctt tatgcgccat cagacaccct ccgttatctc     60

tggttattaa tggcggagaa aaatacacct ctcattaacg aaatcattaa ccaccttagt    120

gagcatcctg actttgatca atggtttaaa gccaagcaaa ttcctaaatc agccattagt    180
```

```
gacatttgta atgacctgaa aagtcaagaa aactatcaaa atcaacctgg acgcttttat    240

tcatcagcaa tcagtcttac ccactatatg tttaaatcgt ggtttgctgt ccacaaacaa    300

ctacaaagac gaatcgaagg gaagcggcga tggttaaacc tattaaaaag tgatcaagaa    360

ttagaacaaa attgtggtca atccttagag ataatcattc aaaaagccga agaaatttta    420

aaattaatgg actctgagaa gagtcaatct tcatcaaaac ccaaaaagcc taaaaaaccc    480

aagaaaaaga aaaaatcatc ttcagaagaa accattacct tatttgaccg ccttttttaaa    540

gcctataatc aaggaaacga ttctctagaa agttatgcct tagcttatct actcaaaaat    600

aatggtcaaa ttcctgaaga tgacgaagat ttagacaaat ttgccctaag aaaacgcaaa    660

aaagaaattg aaatcgaacg acttcagcaa caattagaaa atcgtattcc attaggacga    720

gatttgacag gagaactttg gcaagagatg ttaaccatcg ttaacgaaag tattccccaa    780

gacgaaaatg aagcctcagc atggcaagcg aaattactca aaaaatccca taatattccc    840

tatcctgttg cctatgaaac caatactgac ctcaaatggt caaaagacag ccgaggacat    900

cttctcgtta cctttaacgg cttagtagaa tcattaaaga aactgaacct taacccagaa    960

tttgaaatta gatgcgatcg ccgtcattta ccttggtttc aacgtttttg caaagatcag   1020

gaaattaaag cgaataacga tcaacactct agcgcattat tcgttctacg ttctgctcga   1080

ctgatttggc gtgaaggaca gggaaaagaa gatccttgga agattcatca actttatctt   1140

caatgttcag tagaaaccca attatggacg gaagcaggaa caaaacaagt tcaaagtgaa   1200

aaaatggttg aatttcaact aaatcagcta cggatgaagc cagaattaac ctttcctatc   1260

ttttttcgtt ctcagtcact tcctacttac tttaaccttt ggaaagtcat caccagttac   1320

cgtatcctca aattcttgga aaaaggagac ttcaccaaag cacagaaaaa ctttcaagat   1380

gccattaaac ggacagaatc ttgtttagaa aatcttcaaa gctcttactt aacctctcaa   1440

aagtctcttt atcaaggaaa tccagagatt atcatggggg tagcaatggg tttatctcaa   1500

cctgccacta tagcagtggt taatgtcgta acacaggaag ttttaaccta tcgtagcctt   1560

aagcaactat tgggcaaaaa ctataacctt cttaatcgcc agcgtcaaca aaaacagaaa   1620

ctctcccatc aacgccataa agcccagaaa aaagacgctt ttaaccagta tggagagtca   1680

gaattagggc aatatgtaga tcggttaatt gcgaaagcga ttgttcaagt cgccaaggaa   1740

tatcaagctg atagcatcgc tgttcctaaa atacgacaga tgcgagaaat tattcaatct   1800

gaagttcaag caagagcaga acgtaaaatt caaggctata aagagggaca aaaaaagtat   1860

gctcaacagt atcgagaaaa tgttcatcaa tggagctatg gtcgcttaat tgagtcgatt   1920

catcaagcat ctgccaaatt tggtatcaga gttgaaattg cctctcaatc ctatcaagga   1980

agtttccaag agcaagccca aaatttagcg atcgctgctt atacaaatcg tcttgaagca   2040

gttggctag                                                          2049


<210> SEQ ID NO 26
<211> LENGTH: 1851
<212> TYPE: DNA
<213> ORGANISM: Geminocystis sp.

<400> SEQUENCE: 26

ctatttcttc ttgagatttt tttcagtagc actcaaaaca agttgtaagg ctttttccgt     60

caatgtgcct tgttttggtt gtttagcttc taccacgaca ataccaactt tttcgcagat    120

taacttcacg ttttcaatca atctgccata actccattga tggacttgga ctcgataatc    180
```

-continued

```
ttgagcatat ttcttttgcc cttccttgta ttcgggaatt ttcttctccg ccctgagttg    240

aatttctgct tcagtaatcg atcgcatatc ccttaatcga ggaataagaa tcgttgatac    300

ttgatattct tgagcgacag taagaatagc tttagcaatc agtcgatcga ggtattctcc    360

caaattagac tctccttttt gttgaaagtt aaatcttttt ctggctttgt ggttttgatg    420

gctcagtttt tgtttttcta tcctccgtct tctcaatagc cgataatctt ctcttagcag    480

ttgtttcgta tttcgataag tgattacttt atctgtctct atatcaacaa tggcgatggt    540

gacaggttgt tctaatccca tagctattcc taaatgaaca ttaggttttc cttgataaac    600

aggtttacta ggtcgaggaa aagtattatt gagtttcgct agagtagaat ttttacgacg    660

aataaaagcc tgttgagaat cgcttaattc ctcttttgct ttcatcaaat cgattatctt    720

ggtaacttct ttttgctttt cttctacgat cgtactcgta ccttctgccg tcaaacaacg    780

agtttcaaaa gtacaatgta aatagagttt atgtctatcc cataattcac cttttccctc    840

atcttccttc caaaggatca tagctgaacg gagggtaaat aaagcactcg acaattgatc    900

tttactagct ttttttaatt cctgatcctc ataaaacctc tgaaaataag gtaattgacg    960

atgatcgcag cagagttgaa aagaatgctc tcctaagcca ctaaaacgaa tggaaagacg   1020

atttttctca ttgagactcc attttaaatc ctcgttggtt tcgtaaagaa tcggataggg   1080

aattgatgac tgattttgtt tgagaatgga aaaccaagta tttgcttccg tttgatcaat   1140

aggggcagta gtagaagcag taatgagagt atcaagccac tttttatctt ctaaatccct   1200

tcctaaaggt attcgacttt caatttgtct gtgtaatttg gtaattttaa tctcaacttt   1260

acgctttaaa tcttgatatt tttccgttgt ttctggtttc ttagggatag tacaaccatt   1320

cttgagtaga taaataatcg cactttttat ctcaggcttt tttgttttgc cacacttctc   1380

aaaaagaatt gttgaaattc gatcgtgact gactgttgaa tctatagagt caagaatcaa   1440

agtagcttgt tgttgtaagg attccaaaga attatcaaaa tgtttaatta attccgtgtc   1500

aggcaatagc atttctaccc aacgaagatt accttgtaat ttccaatcta aggctttttg   1560

aacttcaaac catgacttgt aaatatagtc gatgactttg ttaacagagg cataaaaacg   1620

ggatggttgt tcttcaaaag ggtaattatt cttgagttcg gctatttgtc gggctaagaa   1680

atctttaggt aatcttttct ttgttctcca gtgggggaag tcaggatgtt gctttatcct   1740

taacaaaatt tcgttgataa gaggagtatt cttttgtgcc atcaactgcc aaagaaattg   1800

acgggtatca cgagaagcga tcaaacgaca ttggatagtg acgtgagcca t            1851
```

<210> SEQ ID NO 27
<211> LENGTH: 1125
<212> TYPE: DNA
<213> ORGANISM: Leptolyngbya sp.

<400> SEQUENCE: 27

```
tcagacagcg attgcaggca aagcctgtct cacatcgcct accttagcgg tcgatgcccc     60

aaccgcacaa atattcttgg ctgcgttttc atcccgtccg ttcactgact gacaggacgg    120

acaccgccat tctcttgtgt tcaaatccaa ctctttcaag acgtgcccac aatggctgca    180

agtcttagag gatggatacc attgatcaat gaagatcgct tgcttatctt tcttcttggc    240

aacccactca agaatctgaa tgaactcacc aaacgcgaga tctgaaatct tgcgtcccca    300

gagtcgctgc attcctttga ggttcaacgt ctcgaaacac agcacatcga acttatcggt    360

cagtttatgc gccaacttcc aaaaccaatc agaacgacga ttgcaaacat cttcatgctt    420

gcgtaccaga ttgagtcttg cttgttcccg attagctgaa catgaccgtt tcttggaatg    480
```

```
ctgacgactg gctttcttga tggcattgag cgattgtttc agaaattgag gcgactcaat    540
cgtggttcca tctgaaccgg tgaggaacgt tttcaaaccg aaatcaaatc cagcgattcg    600
actcgtctcg aatttgcttt ctgattcttc cacgctgtct accacgatga ccataaacaa    660
ctctcctaat ggagtccgct taatggtcag agtcttgaca gtgccctcaa tggctctaga    720
gttccaatac tgaaataccc gattcccgat tttgattcgg tttccgccta agaatttgta    780
gccagcttgc ttcagggtga atgatttgta tcgtctgact ttcttgaatc ccggtggtct    840
aactcctttc ttgtgatgct taaaaaacag ttgataggct ttctcgattc gttgacagat    900
atcctgcaca gcttgagacc caaccgtttg ccagaatgct ttacgctttc tcaacttggc    960
aatatgactt tgaagtttgc tgcaattcaa gtgtttaccc catatccggt agtaccgttt   1020
gtggagtgca atgcaatggt tgtagatcac cccggcagcg ttgatactgc gcttgaggtg   1080
tcgattccgc ttgctctgat atagcttgaa cttcaatgtc ttcat                   1125
```

<210> SEQ ID NO 28
<211> LENGTH: 1839
<212> TYPE: DNA
<213> ORGANISM: Cyanothece sp.

<400> SEQUENCE: 28

```
ttaagcggac aaacgtgatc ggtaagcctt aaaagctaat tccgcagctt tttgtagcgg     60
agttccctgt aatggttgtt gactttcttc aataaatatt cctaatttag aagcctgtgc    120
ttggatatta tcaattaatc taccgtaact ccattcatgg acttgcatcc gatattttt     180
agcatattca gcttgtgctt caatacaatt agggatttta gcttcagctt tagcttggat    240
ttcactttga gtcgcttctc ttatatcctc tagtttcgga acaacaatac ttcctgcttg    300
atatttttga gctattgata tgattgcttt agccaataaa cggtcaatat gttgccctaa    360
ttcagaatca ccaaactggt taaaagcctc ttttcgttgt gcaatatttc tttgatgaga    420
ttgacgttgt ttttgtcttt gttgacggtt aagtaaagga taatttttttc caagtaattg    480
tttaatgttt cggtaagtta acacttttct tgttactcca tcaataacgg caatggtagc    540
aggtttttttg agttccattg aaacaccaac taaaatatta gattttcctt gatataaagg    600
ttgactggga cgaggaaagg gtttttcgag tctatttaag gttgattgtt ttcgcctaac    660
aaaagctttt tgatttttag ttaagtcacc tttttcattc atccgtgtta aaattcctgc    720
aatttcatca gctttttctt gcttaacttg ttcggttcct tcgtgtgtcc agcaacgagt    780
ctctaatgta cattgaaggg ttaaacggtg aatatcccaa agttcccctt tccctttgcc    840
ttcttgccac agaatacgcc ctgagcgtaa agtaaacaaa ccactagaat gttgatcttt    900
accgtctttc tttacttgtt gatcttcgta aaagcgttga atccatttaa gttgtctttg    960
gtcacagtaa atttcaaatt ttaggtcgct tataccatta aattgtacac aaaaacgacc   1020
tttttcattt tttgaccaag ttaaatcttc gttggtttcg taattaatag gaaaaggaat   1080
tgattgagat tttttcaaca atttgtcttg ccatgttctt gattgttcta catctttggg   1140
atcagtatca caagcaagat ttaatgtttc taaccaatta tcattggtta aatctcgtcc   1200
ttgaggaaga cgaccattaa tttgtttttg cagtcgttta attgtaattt ctactttacg   1260
acgacgttta gcaaatttct tagcatcttc tggtttttta gggagttgac agcgattttt   1320
aagtaagtaa ttaagggctg tttgagttaa aatattttgc tcatctctat aggcttgaaa   1380
tagactgtta aataggcgtt ctgttccttc ataagattga agtatttcgg ttgcttttg    1440
```

-continued

```
gcgaattgtt tctaaatctg tttgactgtc tttgattaat tgctcatcac tttttaagac   1500

ttctaaccag cgtctttttc cgtcaagttt tcgctgtagt cgttgttgaa gtttgagcca   1560

agatttaaag atatattcga ctaagctgat accagaggtg taaaaccttg cgggttgtcc   1620

taaaaaacga ggatctttct ttaattcatt acctaattgt tcgataacct ttgctgttag   1680

tcttcctcgc tgtctccact gttcaaagtc aggatattgt gcgacttgtt gcagtaattc   1740

attgataaat ggcgtgttta actcagccat tagttgccaa agagtttgac gggtggcttc   1800

tttagcgacg agacgacatt ggatggtgat ttgactcat                          1839
```

<210> SEQ ID NO 29
<211> LENGTH: 1092
<212> TYPE: DNA
<213> ORGANISM: Lyngbya sp.

<400> SEQUENCE: 29

```
ctatttgggt tcctgtttct tagcacctgg cttaacagat ttactctgtt cagctcttac     60

agtcgctccg caggctgaca cggcaagtcc tgccgccaaa atgtttatac tggcgttgag    120

atctcggtca tggtgagagt tacatttagg gcaatcccac tcccggatat tcagcggcat    180

tttttctgcg atgtatccac aattagaaca tcgttttgaa ctgggaaacc atctatctat    240

tttgattaac tcccgtccgt accactccgc tttataggtg agttgtcgaa caagttctcc    300

ccagtttgca tcgctgatta ctctggcgaa cccgtaaggg tgatttttaa ccatgttctt    360

cacagccaaa tcctcaacaa ctatcgtttg attttcacga attagttggg tggttagctt    420

atgagtatgg tcgcgacgag tatcagcaat tttagcttgg atacgagcaa ctttaactcg    480

ggctttctct ctattctttg aacctttagt tttccggtta aaagactttt gagcgagtcg    540

gagtttttta tatagctgat taaaatgttt gggattggaa actttaaccc cgtcagatgt    600

ggtgaacaga ctggtgattc ccagatcgat tcctatctgt tttttgacag gctctaactt    660

ctgattcatt ggatcatcaa tcctcaaaga aacaaaccat ctcccactcg gatctaattt    720

gaccgtaatg gtagatggtt cgcaattttt agggagttga cgactccacc gaatcggtaa    780

aggttctttg cactttgcaa tgtaaacttg accctcttta aacttaaatg ctgacttcgt    840

aaactctgca ctgccaccat tgcgtttttt cttgaagttc gggtattttc cccgacccgc    900

aaagaagttg gtaaaagcag tttgcagatg tcttaatcct tgctggagtg gaacacagct    960

cacctcattt aagaagtcta attcttcctt tttcttccag tttgtcagca ttgaagaagt   1020

ttgagaatag ccaacccgtt cttttttttc ataccacgcc tcagtgcgtg ttgctagtgc   1080

tttgttgtac ac                                                       1092
```

<210> SEQ ID NO 30
<211> LENGTH: 1380
<212> TYPE: DNA
<213> ORGANISM: Mycobacterium tuberculosis

<400> SEQUENCE: 30

```
tcacgcgact tgcaccccgt ctcggggttg ttcggcagcc ttggggctgc ttcccttccg     60

cgcttcacag ccacctgccg ggcgaggccc ggtcttacgg tcggctccac gcttgacggc    120

ggccccaact gggccgacga tgctggatgt ttcctcgtag cgtgcgaggt tgatggcagc    180

gcagtcatca cgctgatgga ccactgagca tcggtcgcat tgccattgtt cgtcccagcc    240

gatgtcttgc acatgccggc aggcgtggca ggttttcgac gacgggaacc agcggtcggc    300

gaccaccagc gccgacccgt accagactgt cttgtaggac aagtgccgac gcggagtgcc    360
```

```
cagggccgca tccgacagtc cgcgccgacg agcgcgggca cccggcaacc ctttttgccg    420
caacatctct gtcgcgtcca agccttcgac aacaatgcgg ccgtgggttt gagccaaccg    480
tgtcgtcagg acgtgcaggt gatgggtgcg gacatcgttg acccggcgat gcaaccggga    540
aatctgagtg gtgcgctcac ggtagcgccg tgaacctttc gtgcaacgcg aacgggcccg    600
gcacacgtgg cgtagctcgc gcagcgcggc gccgagcggt cgtgggttct caacctgctc    660
gatcgccgtg ccgtcagcgg tggcgaccgt cgccaggcgc cggaccccga catcgacacc    720
aacccgcgaa ccggggtgca ccaccttcgg ctgctgcgga cgctggacaa gcacccgcac    780
actggcatcc agacgagtgc cgttgcggcg caccgagatc gccaatactc gcgcccgacc    840
ggccttgatc aggcgttcga tacggcgggt gttctcgtgc gtgcggacgg tcccgatgac    900
cggcagggtg aggtgacggc ggtcgggttc cacacgcatc gctccggtcg tgaacgacac    960
tcgatcctgg tcgcggcctt tgcgtttgaa acggggaaac ccgacccgtt taccggcgcg   1020
tttgccggcg cgggaggtct gccagttcca gtacgcctcg accgcacccg cgatgccatc   1080
ggcgtaggcc tcttttgagc attcaggcca ccacgcgaca ccggtctcgg tgttgacgca   1140
cacgtcgtcc ttgacggtgt tccagcgttt gcgcagcacg cgcagcgacg gtttcgctgt   1200
cacggtcccg ctggcatgcc acgcctggat gtcggctttc agggtggcca cggtccagtt   1260
gtatgccttg cgacgagcac cgaaatgccg tgccagcgcc ttggcctggt cctcggtcgg   1320
gtccagcgtg aaccgaaacg cttggaccgt ccagccatcg ggaacctcga acttgggcat   1380
```

<210> SEQ ID NO 31
<211> LENGTH: 1122
<212> TYPE: DNA
<213> ORGANISM: Tolypothrix sp.

<400> SEQUENCE: 31

```
tcagacagcg attgctggcg tagccagtct gacatcacct aagccaacag tcgatgcccc     60
gactgcacaa atattgcgac tagcgttttc gtctcttcca ttaactgact gacaggaagg    120
acaacgccac tctctaactg acaaatcaag actttctaga atatgtttac aattagagca    180
tgtcttgcta cttggatacc actggtcgat aaagacaacc agtttattct tcttcttggc    240
aacccattct aggatttgca gaaactcacc aaacgctaag tctgatattt gcctgcccca    300
aagacgttgc attcctttga gatttaaagt ctcaaaacag agaatatcga acctatctgt    360
tagctcatga gctaatttcc agaaccaatc acgccgacgg ttggaaatat cttcatgctt    420
gcgtactaaa ttctttctgg ctcgttctct gttagatgag ccttttagct ttttggaatg    480
ccgcgaactt gctttttttaa tggcgcttag ggattgcttg aaaaattggg gcgattcaat    540
tttagtgccg tctgagcaag tgaggaatgt ctttaaccca aaatcaaagc cagcgatttt    600
acccgtctta acttcaactt ctgagctacc ctcatcaaca accaaaacca taaataactc    660
acctaacggg gtgcgtttaa tagttagggt tttgactgtt ccctcaattt ctctggactt    720
ccaaaactgg taaactcgac taccaatttt taccctattt ccacccaaaa acttataacc    780
tgcctgctta agggtgaacg atttgtattt cttgaccttc ttaaatcctg gtggtcttac    840
tcctttgtta ttgtgtttga aaaacaattg gtaagctttc tcaatgcgtt gacaaatatc    900
ttgtgctgct tgagaaccta ctgattgcca aaaagaatta cgctttctta atttggcgat    960
atgagcctga agttttgcac agtttaaatg cttgccaaac atccggtaat accttttatg   1020
tagagcaatg caatggttat aaatcactcc agcagcgttg attgtgcgct tgaggtgtct   1080
```

-continued

```
attccttttg tgttcgtaca atttaaactt cagtgttttc at                        1122


<210> SEQ ID NO 32
<211> LENGTH: 1908
<212> TYPE: DNA
<213> ORGANISM: Nostoc sp.

<400> SEQUENCE: 32

ttaaattaaa gcggcttggc gttcctgata tgcgaagacg gctaaatctc gcgctttttc      60

ttggggactg cctctgattg gctgtgtacc aatttcagta aaaattccgg cttttgcagc     120

ttgggattta atactctcaa ttaatcggcc gtaaccccag cgatgaacac tcatccggta     180

ttctttggcg tatttttgtt gaacttcctt gtaacctggg catttcttct ctgctctgga     240

ttggatttca ctactgattt gctcacgcat atcgcggagt tttggaataa ctatactgcc     300

tgcttgatag gttttagcga tcgcaataat tgcatctgcc aataatctat ctacatattg     360

tcctaactct gattcaccaa aagagtttgg cgcatttcgt ttctgaactt tgtggcgttc     420

gtgagatagg cgttgctgtt gttgtcgctg gcggttgaga aggttgtagt ttttgccaag     480

tagttgtttg acagtgcgat aagctagaac ttcattttta ataacatcca ctacagctag     540

tgttactggc ttttctagac caaaactaac accaactagg attgagggtt gtccttgata     600

attaggcttg ctgggacgag ggaagggatt attaattcga tctagcgtgg attgctgacg     660

agtgacaaaa gcttgttgtt tatcgttgag gacatctttc cgttttgctt gatttagcgt     720

ttcggtaatt tttgtagttt tctcgcttac gacctgttga gttccttcaa tagtccacat     780

tcgagtatct aaagtacagt aaagatgcag tttatttact ttccagggtt cacctttttc     840

ttctcctagc gaccaagcaa tccttcctga acgcagagta aacaaactgc ttgagtgttg     900

gtttttacta ttgcgtttaa gttcttgatc ttctaggaag cgtttaaagt agtgcagatg     960

acgcttatca cagtaaatct caaaggttag ttttcccaag ccattgaatc gaacaaagag    1020

acgacctttg tcattttgca accatgtcat atcttcgtta gattcgtaag ccacaggaaa    1080

agggacatca gcaggttttc ttaatagtgc tgcttgccaa gcttttgcct cattttcatt    1140

ttgaggtaca ttggttgtag caatttctaa agtttttaac cactcttctc ctgttaaatc    1200

tctaccttta ggtatgcgac tttgcagttg gtcttttaat cgctcaattt ctatttcctt    1260

tttgcgtcta tttctattaa attcttctgg gtcttcgtcg cgttcgctga tttgacagtt    1320

atttttgagt agatatgcga tcgcacaacg agtaagagtc tcttgtgttt gttcgtaagt    1380

gtttaaaaga ttttgaaaaa gtgaaggtgt ttgtaacttt gcagattttc tagttctttt    1440

gctctttctc tggtttttat tctggtcaga ctggggggta aatttggcaa gaatttcgtt    1500

agcttcagta cgaattacgt ttaagctaca ttggctttct tgttcgagtt gtagatcact    1560

tttgaggatt atgagccaac gttctttacc ttctatttgc cgctttcttc gtttttgtaa    1620

agcgaaccag gatttatata cataatctac tagagcgatc gctgaggtgt aaaagcgccc    1680

aggttgatca gaaaaacgct cttgattttt gagggagtta acaagagttt tgaggaattc    1740

ggtagggatt ttaccttttt ctagccaagt ttcaaattct gggtgttttc ctacctgtgc    1800

cagtagttca ttgacaagtg gtgtattttt gtcagtcatc agttcccaca cttgtcggag    1860

ggtgtcttct tcagcaacca agcgacattg aattgtaata acgctcat                 1908


<210> SEQ ID NO 33
<211> LENGTH: 1125
<212> TYPE: DNA
<213> ORGANISM: Desmospora sp.
```

<400> SEQUENCE: 33
ctaagacgct aatttagcta agttcatcgc ggcattgaag tcccgatcca tatggagtcc 60
acagtcacat ttcatccaac ggtcggataa cttcagttct ttatggattt gaccacaact 120
ggagcatgtt ttgcttgagg gataccaccg atcagcaata attagctcaa cgttgtacca 180
cttgcattta tactccaatt gccgtctgat ctcatagaag ttgcactgtt ggatgtgctt 240
ggcaaggtgc tgattcttca tcatcccttt tacattcaaa tcctcaatga ccacatgaga 300
aggcttggtt ttcacgatct ccgttgtcat ttggtgaatg taatcttttc ggatgtgatg 360
gatacgactt cttaacttag ctatgctctt ttcgagtttt ataaggttgc gtgttttccg 420
gtaacggttt ccctccttgt tcagttggta tttacgagaa gccctccttt gcaaccgttt 480
gaaacgcttc tccagtcgtt tcatcttgcc tgacttattg atgttcttat agattgttcc 540
attgctcaag gtagctaatg tttttatccc caagtcgatc ccaacgggct gattagtggg 600
cttggaatga tccacgtaat caggaatttc tactgtgatg gaaacaaacc aatggattcc 660
ttctttgctg atccgatagg ataacggctt aaactcttct ggcaagtaac ctgtttctgc 720
taaccgtatc catccaatct tttcaagtcg gattcggtca ggctccagtt tcactttgtg 780
tggatcattg tagaaactcc acttggatcg tcgacgactc ttaaaccttg ggaacttcga 840
tagcccctta aaaaagcgtt taaatgcttc atcacaatcc ttgattgcct gcttggtgat 900
gttattgctg aagttgtaca accacttgta ttcatccgtc tgtttcaatt gcgtaagatg 960
tttccgcaaa tctccttggc tatagctctt cttcgtctcc tcgtaatgat ctttttctg 1020 attcaatgcc cagttgtatg cccatcttgc cacatgtgcc gattgttcta actgtgtacg 1080
ctgtttatgg ttcggagata gacggatttt gaaagcctta atcat 1125

<210> SEQ ID NO 34
<211> LENGTH: 1194
<212> TYPE: DNA
<213> ORGANISM: Synechococcus sp.

<400> SEQUENCE: 34
atgacccaag tcctgaccgt ctcctgcaag ctcaaggtgt cccagtcgca agccgccaaa 60
ttggacgcga cgatggaggc ttttggccaa gccttgaact gggtcaacca gaacacgccg 120
gagaaagtcg ccaacgccgt taagctccag tctctgtgct accgcgaaat ccgggcccgg 180
ttcggcttgt ccagtaactt ggcccagcag gtctgcagac ggctggccgg cgcccgtaaa 240
gttgcccgac agaaaaaccg ccccgtcaaa gtgttcaagg gtggcttcgc tacctacgat 300
gcacgtatct tttcgttccg cgagaaagac tggacggtgt cgctgaccac ggtggagggt 360
cgagagcgct ttgagctggc gattggccgt taccagagag aacagctgac aggctccaat 420
ccaaaatccg ccactctggt caaacgcaaa gatggctcct acttcattca aatctgtgtg 480
gaagcggagc catccccacc gcaacgcacg ggcagagtgt tgggggtgga tttgggcagg 540
acggatattg ctcatacatc ggaaggagat aactggaatg gacagcagct gaacaaagtc 600
cgagaccatt actcgcggtt gagggcggta ctccaacgca aagccagtaa gggcacacgc 660
agttcgcgac gcagatgccg tcaactgctg caacggctgt ctggcaagga gaggcgcttt 720
caggcgtggg tcaatcatcg catctccaaa gctattgtct ctagggcaaa gaccacaaac 780
agcgctattg ccctggaaga cctgacaggg atccgggaaa gggtcaatca acagccacga 840
ggtaagacag agtgcaggcg ggccaatagt tgggcattct accagctcag gatgttcgtg 900
gcctacaagg ctgccatcgc cggagtacct gtggtactgg tgtcgcccgc ctacacgtcg 960
cagacctgcc accggtgttt gcacatccat cccgatccta cgcaatccta tcgcagtggt 1020
aagtcgttca agtgtgggca ctgtggatgg gaaggggatg cggatttgaa tggtgcgaat 1080
gtgattgcgc tcttgggggc tgtcgtaaac cagcctagag gtccgggctt gttttgttct 1140
ctggtagagc agaacaggct cagggctact gaaagcccgc tccgtaccgc ttag 1194

<210> SEQ ID NO 35
<211> LENGTH: 1647
<212> TYPE: DNA
<213> ORGANISM: Corynebacterium maris

<400> SEQUENCE: 35
ttatctgacc tgtaacgggt gtttctgctc gctttgtatc cgcacgttat aagggacgag 60
cagccgatta ctcgactgct gtgaccacgc gggccttgcc gcttctaccc ctgctccgtc 120
cccgacacct ggccgggtgc ggtgtgctgt gggtgtccac ggccatttac cctctgcccc 180
ctccggggcg gagctatcgc caaggctgaa ctgcgctaga cgagctgcct cgcgcaggac 240
gttgatcgcg gcgttgacgt ctcggtcgat cagtatcccg cactgctggc agtcgtagac 300
tcgcttggct agtggcattt tggttttcga gccacacgct gagcagattt gcgacgacgg 360
gaaaaactgg tcgaccgcaa taagggcgac gccgcgttcg gtgcacttgt agtcgagctg 420
gcgacgaaac tccccgggcg agacatccag gatggcccgg ttgaggcccg ccttctgctt 480
cacattctta cccgggttgt ccacagtgcc gcgcgccgag gaggtcatac ccgccacgtt 540
gaggtcttcg accccaatcg cggcgaaccc acccgctagg gcggtggtca cctcgtggag 600
aaatccgtga cgtcggagcg cgaccgtgtg gtggtggcgg gccagacgct gagcaagttt 660
tcttctcctg ttggatcctt tctgggtgcg ggccagcttg cgctgggtgc gcttgatctt 720
cttctccgcc cgggccaagt gacgggggtt ggggatgctc tccccggtgg agagggtaac 780
cggtcggctg acaccgaagt cgagaccgac agcgccagcg gcctgctggc ggcgggtggg 840
gtgcggtgga ttctgcgggg cggggcgttc caccaggaag gagacatacc atcggtcggc 900
ggcgcgagag acggtgtaag attttatctt tccgccctgt cgcagtgccc ttaccaggcg 960
ttttgtgcta tcgactgtcc ggaaagtacc catatgtgac agacggacgt gccggtagtc 1020
ggtaatctcc cccgaccgtg cttcgccacg cttgtaggtc gcgaagcctt tcgggcccat 1080
cgcctcaggg gcggggatag taaatgactc gcgcgaatgg tgttttcttt taaactgtgg 1140
cggccccatc gctgggcctt tacgttttcc tgactgagac gtcagccaat tggagaggga 1200
atttccacac atttgcagcc cagagaccag cacccgccgg tgcgcggtgt gcaaccaggg 1260
ggtggcatac cgttcctcct caccccagac agcggcggga tccgccccg cttcgatagc 1320 tgcagcagcg tggcgatgac gggccacctg ctgggtgaga atcttggaaa actgctggta 1380
accgggatat tgcagggcaa aattagcctt ggcttctttc tttacctggt cccacgcaac 1440
cgagaaatta acaccagtgc tgacgagctc tttccatcgt ccatcccgtg cggcctggat 1500
gtcgtgggta taggcgcaca tcatgttgta ggcgacacga gccgtcccca cctgctgtcg 1560
cagcacctct agctgagcaa ggttgggatc caagcgcagt ttatacccac ggtgcacgac 1620
aggtggtctc ggggacgtgt cggtcat 1647

<210> SEQ ID NO 36
<211> LENGTH: 1488
<212> TYPE: DNA
<213> ORGANISM: Mycobacterium sp.

<400> SEQUENCE: 36
ctagctgacc agtgttaatg gacgctgatc cgcagtcttc ggatgatcag tcgattgctc 60
ggctgaggtg gccgcaccgt ggtggtgcgg tcttcccgcg tcagtgacct ggcgtcgccg 120
gcccactgat gtgggggcgg gcgctcggcc tcggcgggcg ttttgcgtct cctcggtgtc 180
gggggtgacg gccaccgcgt aggtggcgat gttgatggcc gcgttgacgt ctcgatcgag 240
gtcgaggcca cattcggcgc accgatatgc acgctgagac aaacggagct tggttctcgc 300
tccgcaggtc gagcatgtct ggctggacgg gtaccacctg tcgcagaccg cgatggtgga 360
ggcgtaccag cgagccttgt agttgagttg gtggcgaagt tcgccggggg cggcgtcgag 420
aatggcgcgg ttgagccctg ctttggcgcg cacgttggtg ccgggctggt cgatggtgcc 480
gcgcgcggag cgcgtcatgc cgaggacgtt gaggtcctcg atggccacgg tcgcccagcc 540
ggtggcgagt cgtttggtga gggtgtgcag agtggtggcg cgttgctcgg cgacttcgtg 600
gtgccggcga ccaacgacgg ctgccgcgcg tcgccggcgc gttgatcccc tctgggtgcg 660
ggagagcttg cgttgagctt tgttgaggcg ggcccgtgcg cggtcgaggt ggcgagggtt 720
gtcgatgatg tcgccggtcg agagtgccgc gaggtggtgg actccgacgt cgacgccgac 780
cgtgccagcc ttgcgctgcc ggcgggtcgg cgctgcagtg atcgctgcgg gggttttggt 840
gaggatgctg gcgtaccagc gatgtccacc gcggctgatg gtgacggact ggatgatggc 900
gccacggtcg agtgctcggc agagcttctt ggtggagtcg tggacgcgca gcgatccgag 960
gcgcggcacg atgatgcgtc ggtatccggt gtcggggcgg atcgacgggt tcttgacgtc 1020
gtggtggatg cgaaacgagt cgcgtgagcg gtgcttggtt ttgaaccgcg gccggctgac 1080
tcgctggccg cggcgtttcc cggtgatcga gtcgagccag ttcttccaag cggtgtcgac 1140
gtcgatcatt gcggattgga aggcgtaggt ggagacggtg tgccaccacg ggcagtcacc 1200
gtcgaggtcg gtccggttgt cgcctttggt ggcgttgagg gccttctgga ttgccggctt 1260
ggtcgggatc ttcggtgcct gtgtggcagc gactttcgga tctacgcctt gctcgacgag 1320
cgtggtgatc gtggcctggc gcgcgtcgag tgcggcgaac ttggcggcga gcgcgtggtt 1380
gtaggcccag cgggcggcgc cggcgtgttg gcggcactgc tgttcctggg tcggcgtgag 1440
gtcgagcgcg aaccggtacg cgcgcatttc gacgtcgccg gtggtcat 1488

<210> SEQ ID NO 37
<211> LENGTH: 1542
<212> TYPE: DNA
<213> ORGANISM: Mycobacterium yongonense

<400> SEQUENCE: 37
gtgacgaccg cgcgggcgaa tgaaatccct acgtgtcaga cccaacacct aaggtccacc 60
cacatgaccg atgtcgagct cagcgcctac cggttcgcgc tcgacaccac tcctgcccaa 120
ctcacgatgc tgcgccagca cgccggcgcc gcccgatggg cctacaacca cgcattgggt 180
gtgaagttcg ccgcactgga cgaacgcaaa accgtgatcg ctgggctggt ggaacagggc 240
cttgacccga aaacctctgc ggcccaagct ccgaagattc cgacgaagcc agcaattcag 300
aaagcactca acaccaccaa gggtgatgac cggatcagcg cggccgggga ctgcccgtgg 360
tggcacaccg tcagcaccta cgcattccag tccgcgttcg ccgacgctga caccgcgtgg 420
aagaactggc tagcgtcact gactgggaaa cgctccggcc ccataggggc accgcgcttc 480
aaatccaaac atcgctcccg tgattcgttc cgcatccacc acgacgtcaa caatccgacc 540

-continued

```
atccgcccgg atgacgggta tcgccgaatc atcgtgcccc gcttaggatc actgcgggtt    600
cacgactcga ccaaacgcct taaacgagcc atcgaccgcg gcgctgtcat ccagtccgtc    660
acgatcagcc gcggtggtca tcgctggtac gccagcatcc ttgtcaaagc tccagccgca    720
catgcggccc ccactcggcg tcagcgccag gccggcactg tcggcgttga cctgggcgtg    780
catcacctcg ccgccctgtc caccggcgac atcatcgaca acccccgcca cttggctgcc    840
ggtcaaaagc gcctcaccaa ggcgcagcgc gcactgtccc gcaccgagaa aggctcgaac    900
cgccggcggc gagctgccgc ccgcgtcggc cgacgccacc acgaaatcac cgaacggcgc    960
gcgaccaccc tgcacaccct gaccaagcac ctggccacca attgggccac cgtcgcgatc   1020
gaagacctca acgttgcggg catgacccga tccgcccgcg gcaccatcga caaccccggc   1080
acgaacgtgc gcgccaaagc cggactttcg cgcgccatcc tcgacacctc accgggcgag   1140
ctgcgccgcc agctcaccta caaaaccggc tggtatggct ccactctcgc gatctgcgat   1200
aggtggttcc cgtccagcca gcagtgttgc gaatgcaaag tgagaaccaa gcttcggctt   1260
tcgcaacgcg tgttcacctg cccagcgtgt gggtacggac cgatcgatcg ggacgtgcac   1320
gctgcgcgga acatcgccgc ctatgcggcc gtcgcctccg acaccgggga gacgttaacc   1380
gcccgccgag ataccgcgga agcccccaca cgtgtgggtc gccgccgcgg tgccgttgac   1440
gcgggaagac cacaccggga aaccggtgcg gccaccccag cagagcaacc tgctggtcac   1500
ccaaagcacg cagatcagcg cacattaccg ctggtcagct ag                      1542
```

```
<210> SEQ ID NO 38
<211> LENGTH: 1335
<212> TYPE: DNA
<213> ORGANISM: Thermincola ferriacetica

<400> SEQUENCE: 38

atggaggagc gcgagggggc agtaattccc cttaattcat tgaggggata cacggacccc     60
ctcgtttttc tgaaaaaagg gggtgaccag atattgtttc taacggtgaa ggcacaggta    120
catgccgata gagaaaccga agccgttctg aaagacgcga tgttttgtgc caccaaagtt    180
tacaacggcc tgctgtggca tctgcgggaa ggatcgaaag agaccggcaa ggtaaacctg    240
agttggtcga acatcaaccg aataatcaaa gaacttcccc aggcgaaagg ctactattcc    300
ctgtccgtgc ggatgacctg tctcgaagtg atggaggcgt acaggtcctt tttcgccttg    360
aagaaaaacg gacgtgttaa gcacaacgct cccggcttcc ggcgaaaaac cgcattgtca    420
ccgctaaaat acgtccaaag cgggtttaaa gtagtcggtg accgggtaac cgtaagcctg    480
ggcacatccc gcccggacgg cgtgcgtcgg gtttcctttc gcgtttcccg ccgatccggg    540
ataagcctaa gtaacctgcg cgaactttcc atcatctacg ataagctaac cgggcggctg    600
gaagcccgtc tggtggtgga agttcagtta tgcgaaaatg ccggtaccgg cagggcggca    660
gtggacctgg gcgagacagt gctgttggcg gcggcatttg acgacggcgg gtctattctc    720
tattccggca gactgatcaa gtcaatccgg cggtattggc agaaagtgcg tgcgaaagtc    780
aaacccccgt ccaaagaaca gccgcgcatg tcccggcatt accgccagat tgcccgcaag    840
gagcgccggc aggtagaaca cctgctgcat atagtctcca agcactttgt ggaagagtgt    900
gtgatgcgcg gggtgggcga gatcgtattc ggcgacctga ccggcagggt ggaaggcagg    960
aggtttggcc ggatgaacca gcggctgcac gcatgggcgt tccacaaact gacagacatg   1020
gttgtgtaca aagcggcgct ggtcgggatc gcggtgcgga agcacgacga aaacggcacg   1080
tctataacct gccacgcctg cggtgtagaa aaaccgtcga accggaaaag ccgcggcttg   1140
```

tacctgtgca ggtgcggctg gacggcgcac gccgacatca atgcagccct aaatatctac 1200
gagagggcgt acaacgtatc tcccgtcaag gggagtagtg gcctggtggc gaggcccgtg 1260
gtcttgtcgt tccggatgga tcggcatacg gtccacgaac cgaagcgcag gataaccctg 1320
cgcccatccg cttaa 1335

<210> SEQ ID NO 39
<211> LENGTH: 1413
<212> TYPE: DNA
<213> ORGANISM: Clostridium botulinum

<400> SEQUENCE: 39
ttaagctata tttactctaa ttggatgtaa ccctacaccc tctatctcgt cagctttcac 60
attcgagagt acttttctca ttatttgata tgctccattt acatcagcat tgattttaac 120
accattgttg cttacaaata atcctctata tactcttctc ttcttattat agttttcttt 180
attaggtaat tcgttgtcta aaaagctagt tccacttgta taagattctt cagttataat 240
tatatttaat cctacatttt cacatttata aattagctta tttataaatt cttgatgtgg 300
tattcctaca aatgattgat taactacttt agacatattg ctttctcttt tccaatcctt 360
attattacct acaataatag tattgatatt atttgctaaa gcataatcta ttactttttt 420
actagcttta tgaacaaagt ctattatttt attatttctt tttatagtta atctgttcat 480
tctatttgta taatccaaat tattcattct cttagctatt tctttataat agcttaattt 540
cttgttatag tatttgttta ttgattttag acctttacca ttgattatta taggttttaa 600
tcctatatta ttaacaacag ttgcaaagtt atctaaacca atatcaatac ttatatattt 660
accattgtca tttaactttt ctttctttc tattttataa actacctcaa taacataatg 720
cttatttcta ggcaatattc taacttgctg aagattacca tttatattag ttttcaattc 780
atacttatta aaacatttag gaaattgaat atatcctttt ttttgtttac aattttgatt 840
ggtgaatact aaaatatttt taccattttt cttcttatac ttaggtaatt taggtcttcc 900
attatacttt tctttatgtt tagaccaatc ttttatactt tcaaaaaaac tgatccaatt 960
cttatctaat aattttaagg tttgttgaga tacctgtgac ataagagatt tataatctat 1020
accatcttta agtaaaaatt ctaagaaatc atatcctaaa tacttattat cttcattaaa 1080
gtaatttatt aattttaatt tcttgtttaa ttctttgcct tgtttaattg ctctttgttt 1140
ggctttttca aaattaactt ttctaagttc attaaactca ttaactttag cattaatact 1200
atttaagtac tcatgttgtt cagtagttaa ttcttcatct tcttttaatt ttgatgttaa 1260
tatgaatact tgtctaagtt gataattagc ataattatat agatttttag ataaaaaagt 1320
ataatgattt aacaattcat ataattcatg attttgattt atcatatgtt tttcaactct 1380
ctgaacagta ttatcatctt ttttcgttgt cat 1413

<210> SEQ ID NO 40
<211> LENGTH: 1239
<212> TYPE: DNA
<213> ORGANISM: Coprothermobacter platensis

<400> SEQUENCE: 40
tcactgagtg aagcttacac agatgtaggg attactccct aggatccgtg cagcggtttc 60
cctctccaga ggcttaagtt cgggccgatc caaccctacg gcttgcttag gctccaagcc 120
taaccccttc cttagtatca ccaacgctgc atttacgtct ctgtcacttt cccatccaca 180

-continued

```
ctcgcattcc atcatcctct ctgataagct caatctgtgt actttcccgc actggaagca    240
ctcttgggta gtacgttcat acctcgctac ttcaataggt gtctcaaggc tgttcctcaa    300
ccttgacttc aatccaccta tccctgaggc atgtatctgc ctaccaaaca atgcttccca    360
tccctttatg aaatcgtctt ggtacactac taccttgtac tgcttcaagt atgctaatac    420
cttgttctgt acatccttgc gtctattgtt tatcttttcg tattcttttc ttagctttgc    480
ccttaatttc tctctattgc ttgatccgtt cttgcatctg gatatatccc tctgaagtct    540
cttcagcctc tttgtctcat gtagctcaaa ccttatctgc aaaccgttgg ataatgtgag    600
cttcttattc actccaaagt ctatccctac ggcttcacct atatgcttac gcactgaatc    660
ttctcttgga atgtagcatg ttacatgcaa ataataccca ctaggcttcc tcaccagcac    720
gccgtttgct atctctgcct tttctggaat ctgttgcaat cctaatacac gaaacgtgcc    780
taagttctgt atcctcactc tattacgtgc aaagtcaagt ttgtacgtta ctccatattg    840
cttcaatggt atggagttta taaacttctt tggttttaat gctcctactt tgtgcccgtt    900
cttctttagt ttccctaaag ctctaaggtt atctcttagc ctgtctgcta tctcttgctt    960
tacttgtgag cctagaacag ttaacactct ctctttaaat gtcttactaa cttttacatc   1020
tactgcatct atcttgttta ctgctaggct caaccgttct gtgtcagaaa caagccagtt   1080
atacaaccac tttgcttctg cgaaggctct acttagaagg ccctctttat gctgtgacaa   1140
gttctgcagc ttcaattggt acactgttgc tctttgtgtt ttacgtcttt ccttggtctc   1200
ttggagtgta ctttttatct tctctgcctt gcttatcac                          1239
```

<210> SEQ ID NO 41
<211> LENGTH: 1494
<212> TYPE: DNA
<213> ORGANISM: Syntrophomonas palmitatica

<400> SEQUENCE: 41

```
ttattttgct tttctaattt tctttggttt caaaatatta gtacttccgc aaacctcgca     60
ggtatttcct gaagcctgta tgtgaccaca ttctttacag gttatactgc ggtaaggaat    120
acctagttct aaacacttct ccattattat ctggtcgatg tacggtgtgg atatgttttt    180
tgccgcattg tagtctgcgt ttacgttttc ttttttttact atgccgccac attcctcaca    240
aacatccccg gatacttgga cgtgcctgca gttaatacat atagtcctac tgccgtaacc    300
gcattgttta cattcaaata ctgcctgtga tgaacggttg gtttttttcaa tatacccgca    360
catcgaacac ctttgggatg tatattgggg gtttattgca acaacggtaa tgccatgttc    420
cttggcttta ttaacaattt ttgtctgcag gtcgtaataa ggccagttct tgagaaattt    480
actgcctgtt gtgtcagcta taccttcaag gttttcgatt tggattgtcc cacagccttg    540
cttaatagca gcttctacaa ttcgatttgc atagcggtgg tttattgtat ccctaaaatt    600
cttttccttc tcgctcaatg tttctatggg ttttaacgcc cttttgcgcc catgtccttt    660
acgggcgtcc cctgaatgtt tgatttgatt ttggatggac accctgcgag ctcgtatcat    720
tttgcggaaa tgttctattt ccccaccgtc gatacagcct cttttataag aactattaaa    780
cgcccagtaa acagcttttg caacgccaag gtctactccc atgactttat cagggtcgag    840
gactgtctca tgtgtaggga atgtataggg tatgatgcaa taccatttcc cctggtggtc    900
tttcttgatt tggagttgtc cttgcgtgta tgatttacta ctgtcaatat ggtccttact    960
cataatacgg tcgaatatca tacgggttga tgagtctcta actgctacca gaaaatacct   1020
atgagtgcct ttaccactat ccttggagta ttccttggag tataactgta cgtctattat   1080
```

```
gtatttgttc ttatttttta ttaatttata aatgttattt tgcagccgga ttggtgctgt   1140

tgttatctta tatgtaggca ttgagatttg gttccgataa atgagtttag cgttgcgttt   1200

ccaaacatct ttagcgtggt ttactatttg gttcgctacc ttacctggta attcaggatg   1260

gagaagttta gttttatgat acatagcgtt atataagtct tttgaggaaa tacggtcttc   1320

cttgggcatt gaaaagtaat tatacaggtc gcgcagacac atattccccg cttcagcgca   1380

gaatctggac atagtagaca aatctttgcg ccagttatca tcctgctttg tgcattcggg   1440

gtctaaaaac atatccagta tctttaattt tattgctttt accgattcgc ccat         1494
```

<210> SEQ ID NO 42
<211> LENGTH: 1179
<212> TYPE: DNA
<213> ORGANISM: Thermus scotoductus

<400> SEQUENCE: 42

```
atgttttgcg ccactaaggt ctacaacggc ctcatgtggc acctgcgcca ggagctgaag     60

gagaagggca aggtggacct acgccggtcc accctcaatc ggaccctaaa gacgctgcca    120

cgagccaagg ggtactactc cctatcggta cagctcaccc gggatgaggt catccaggcc    180

tataggtctt tcttcgccct gaagaaaaat ggggggacgg aacatcatgc tcctcggttc    240

cggcccaagt ttaccctttc ccccctcaag tacgtccaaa gcgggttcaa gctggagggg    300

gaccggttga ccctttcctt gggtaagggt agggaggacg gtgtccgcca agtcagcttt    360

cggattcacc accgccccgg cgtggagtac gaacgggtac gggaggtctc catcatctac    420

gacaaggggt ccgggcagtt tgaagcccgt ctggtggtgg aggtcaaggc ccgtgggaac    480

cacggccaag ggcgggtggc ggtggatctg ggggaaaccg tactcctggc ggccgctttt    540

gaagacggga cggtccttct ctactctggc cgtttcatca aggcggcccg tcggtactgg    600

cagaaggtgc gggcaagggt gaaacccca tcccaggaga atccccgcat gtcccgtcgt    660

ttcaggcaga ttgcccgcaa ggaaagccga caggtggggc acttccttca cctggctacc    720

tcccacttca tccgcgagtg tgtccaacgc ggggtgaagg agatcgtcat cgggaatctc    780

acgggcatcc gggaagggat ggattacggt ccccgggtaa accagcgctt acacgcttgg    840

ccctaccgca agatccttca catgctccgg tacaaggcgg cccttgtggg gatcaccgta    900

cggaacgacg tggaggagcg gggtacctcc cgcacctgcc atgcttgtgg ccaggtgagg    960

aaggccaacc gggttcaccg gggactctac cgttgctcct gtgggtggac ggcccaggcg   1020

gatgtgaatg ctgcgctcaa tatctacgag cgggcattcc acgtatctcc cgtgaagggg   1080

agtagtggcc gagtggcgcg gcccgtggtc ttgtcattcc ggttgggatg gcatacggtc   1140

cacgaaccga agcgcaagga gtgcttgcgt gcatcctaa                           1179
```

<210> SEQ ID NO 43
<211> LENGTH: 1281
<212> TYPE: DNA
<213> ORGANISM: Thermincola ferriacetica

<400> SEQUENCE: 43

```
atgttgcagg tgaccaaagc tgtgcgcttt cagattatca agcctttaaa tttttcgtgg     60

gatgagtttg gcaggatact gaacgacctg tcatatcaca caactctaat gtgcaacgca    120

gcggtccaga tgtactggga gcacaatgtc atgcggaacc ggtacaaagc cgagcacggc    180

aggtacccgc aggacaaaga gatatacggc cagagcttcc ggaacgtggt ataccaccgg    240
```

-continued

```
ctgcgggaga tgtacccgct gatggcatct tccaacgtca gccagacaaa ccagtttgcc    300
ttgaaacgat ggcagacaga cttgcgtgag gtcatgcgcc tgcagaagtc tgtaccctcc    360
ttccgcctgg ggactcctgt tcaggtagct aaccagaact atagtttgta tatcgcgaaa    420
ggcgaaccgc cggaatattg cgcggaaatc acgctgttgg gaaaggatgc cgcctgtcgc    480
cggttcactg ttctgctcga tgctggtgac gcgccgaaaa aggctgtatt ccggcgcatc    540
gtggaaggaa agtataagca gggagttatg cagatcatca aacatcccag aaaaaagaaa    600
tggttctgca tagtctcata cacaataacc aaagaccctg ctcccggttt ggaccaggaa    660
cgtgtcatgg gtgtgaacct tgccaccggc gaggcggtat actgggcttt ttcctttcg     720
ccgaaacggg gaagcatccc cgccggcgag atcgaggccg cggagaaaaa gattcgggcc    780
atcactgccc ggcgcagaga gatgcagcgg actgcaggcg tgaccggcca cggcaggaaa    840
cgcaggctca aggccaccag ggtattggcc gggaaaactg caaacatccg cgatgccatc    900
aaccacaaat acagcaggcg gatagtccgg atcgccgctg ccaaccggtg cggcaaaata    960
aggctggccg acatgtccgc gctggggatg tcaggcgcgc ttaaagcatg gccctggtcc   1020
gacctggtgc agaaaatagg gtataaggcc gcagaacagg gcattgacgt agaaatagta   1080
gaaaagcccg gagaccgggc caaagcgtgg cacacctgtt ccgagtgcgg gtattccgcc   1140
ccggaaaacg tgggagacaa caccgaattc ctggcctgca aggagtgcgg ggccagaata   1200
agcctggagt ataacgccgc gctgaacata gcggtattgg cccgggacag catcccggaa   1260
cagcagacat cggcaagctg a                                             1281
```

```
<210> SEQ ID NO 44
<211> LENGTH: 1206
<212> TYPE: DNA
<213> ORGANISM: Clostridioides difficile

<400> SEQUENCE: 44

ttattttaca aatttatcac tttttgctat atttctagca gcattatagt ctgcattagc     60
ttcaaatcca cattctaaac atttaaattt agcctgtgtt tccctgtttt ctttgtctac    120
atgaccacac tctgaacatg tttgagaagt ataagcagga tttacatgtt taacttttat    180
cccaactcta tctgctttat attttatcat ttcttgaagt tcatagtaag accaatttct    240
aagaagtcta tctccaaatc catctttagt taatttttct aaatgtatat actcgcattt    300
atttttttta gcaaattcaa ctactctttt acttaatgcg tgattgtagg tcttaaccca    360
actttttttct ttttctctta aagattctaa tccctttaat ttatcttttc tacctttacc    420
accatttaca tttttaagct gctgttgaag ccttcttctc cttgattgga attgaagtct    480
ttgtttcata aattcatcta tagttcccat tccttctcgt acatatgaaa catcatttaa    540
agctacatat actggaatgg ctatacccat atctactcca caaactctac cttttactat    600
ttcatctact tgcttatatg gtatatctat tgtaagatta agtattagct tattattttt    660
atcaaattgt aacgaacttt ggcttacttt atattcttta tttaggactt tatttaaagt    720
atgtattaat tcaactttgt ttttatcttt tctaccaatt agaatcttaa aaactatttt    780
atttacccac tttatataaa actccttatc ttcttcatag aactttaaat ctctacctct    840
agtcattaaa ggaaaatctc ttttataatt agtaaaaccc ctctctcctt tagcaagacc    900
attttttaat gatgtagaaa aatccttttt aactttttgg gtaatagaac ttttagtatc    960
aataccttta ccaaagttta ttccattaaa tatctcattt gagttggtta aactttttttg   1020
agaatcttta aataagtctg attttatatc tctgccactt gctagatatg cacttgttaa   1080
```

tattcccatt gctagattaa gtccttgata ttgtgcatat tggctatctc ttataaattt 1140
atattgttct tttcttttt cttcttcttc aactatagtt aattttagtt ttttaactgc 1200
aatcat 1206

<210> SEQ ID NO 45
<211> LENGTH: 1812
<212> TYPE: DNA
<213> ORGANISM: Mycobacterium conceptionense

<400> SEQUENCE: 45
tcaggccgcg gactggaccg ctcgcgtcag catgtgcgtc agcgccgact cgtcctggtc 60
gtacttctcc ccgcacccgt cgcacgccac caccaccgac atgaaccggc cgtccgacgg 120
gttctcgtgt ccgcacttcg cgtgcaccac ggacactccg gtgtgcgaaa ccgtgtccac 180
cggaacagcg tcccggtccg cggcggcgac cagggtctgc cgcagctccc ccggcgcagc 240
atgcgcgcgg cggcggttga tcctcgccgc ggtttcgttc ggcaactcct ccgtcttcgt 300
cgtggcgctg cgctgtgcga tgtccgcgta gctcgtgtcg tcgagcacca ggcgcccggc 360
ctggctcacc agtaccgccg ccacctgccg gtacacgtcc agccgctgcg ccgccgaacg 420
gcgacggccg ccctcctggt ggtgccagga aatccagtcc tggtgtcgcc actgcgcgag 480
ggcctcacgg atgtcggtgg agaccgattc gtcgtcggcc cacacacgcg ccagccacgc 540
gaagcggttc ggcgacttcc acatccgcac gttccccgcg cccagctcct cgccctcgcg 600
gcttgggtga gggcgcgggc ccgtctccgc caggtagtcg accagccgtg cgcgcagctc 660
gttcatgcgg tcggcacggt ggctggcgat gaggtgcgcc cgctcaacgc ggcgcgggac 720
cgcctcgggc acgaagatct ctccactgcg gccaccgggg tcgaccgtga gggtgtcccg 780
gaagtcgaac ggaacctcga tcggctcggt ggagcgccac cgcgcgacac ggacgccggt 840
gtcggtgttg cgccagccca ggtgcaccgc gacgtccggt ccgtccgtga cgggctcggg 900
gtcggggatc ttcgcggtga cactgatctg cgcgcggagg gtgccggcgg tccgggtgac 960
cgtgagccgg gcgccggtga tgtccgcgtc cagcggcagc atgcggtgct gctggaccgg 1020
gatgtccagc cactgcggtt cgccgctgag ctggcccgcc cgcatccgca cggtgactcg 1080
gccgatcatg cggcgctcgc ggcgtgggat gcgttcccag cggtccggct ggacccaggg 1140
cacggacagt acgcggccgt acttcccgtc cacgtcggcg atcagttccg gagtgcgctg 1200
cggctgcccg gcctgccgct gcagctgcac ggcgatggat ccagtgccgt cgaagcggtg 1260
gtgccgcagc tgcgcgggct ggccggcggc gcgcatctgg ccgatccgct tcaccgcggc 1320
cttgtggtga tcgagtacgt cgttgaacgt cgcccagaac aggtcaccgt cctggcagta 1380
ggtcttgtag agcgccttct gctgagcctt gagcgcgtcg gaggcatcta ccaggcgccc 1440
cttcgcctcc tcgtgcacct cggagatcgc ggctcggcgc gtgctcctgg cctcgcgcac 1500
ccgcttccgc gccgctgtga gcttctgcgc gagaggtcca gtgatgcgct tggtgcgcag 1560
cttcgtccgc tcttcggata cggccgcagc ggcctgctcc gcagccgact cagcatccgc 1620
cagctccgtc tcagcggcgg cgaccgctgg gtacgaggac cagatgccgg ccttcgccgt 1680
ctcgtagtcc agctgcaagg tgacgaggtc ctcgcgcagg tcatgcgcca gccggagctg 1740
ccgcatcagc tgctccggag ggttgtccgt ccagcggtag tggacgccgg cggtgtgcac 1800
tgtgatcgcc at 1812

<210> SEQ ID NO 46

<211> LENGTH: 1674
<212> TYPE: DNA
<213> ORGANISM: Rothia mucilaginosa

<400> SEQUENCE: 46
ctacggtgac ccgccgcccg tggcggctgg ccttgacgca tccaacgcca catcccccaa 60
caccaccgaa ccggcagcat cagagtcagc gactccgcgt ccgtttagac tctcccccgt 120
gccgggggcg agttgcgctt catacatccg tacagcctcc gcacggatat tacgtgccgc 180
attcacgtca cgatcaatcc gcacaccgca ggctgcgcac tcaaagacac gcacgcgaag 240
gtcgagcttg gttttcgctc gtgctccgca ggcgctacac gtctgagagg atgcaaagaa 300
gcggtcaata atctgtacct gtgagccgta ccagctggcc ttatactcca gctgacggcg 360
caacgtacta aaagcggcat ccagaataga ccggttgagt ccggctttct ggcgcacgtt 420
tttgcccggt gcctcgatgg taccggcagc tgaagcggtc atacccgcta tagccaagtc 480
ttcaagcccg atgagggtat acccggtgct caggcgctta gaaacctggt gcaagcccga 540
ttcacggcgc aaggctacca ggtggtggtg ccgtgcaatc tgctgcacaa tacgggcacg 600
acggttagag cccttctgag cacgcgagag ggcacgttgc agacgcacca ggcgcttctc 660
agcggcacgt gcccagcgag ggttcgccaa ggtaggcgca ccatcaccgg tgaactccag 720
ggaagggtac cgcgcgaagc gctgcggggc ctgctcgtca gagagcgcgg cgaggtatcg 780
cacgcccagg tctacaccga cggcgccagc ggcacactgg gcacgggtgg gggtcgcaga 840
cgggcgggtg agttccacga ggatggagac ataccagcgg tcagcggcac gagataccgt 900
gtaagagcga acctgagcgc cagcacgcac cgccttgacg aggtgacgag tagtgtcatg 960
ggtgcggata acacccaggt gcgagaggcg cacgtggcgg taatcctcaa tggtcggggt 1020
ggtcttgatg ccgcggcgct tcagttgcgc tttacggcgc gcatattcgg gctcgccgcg 1080
taggtatgcg gtgccgtagg cgccgatagt ctccggggcg gggatggtga aagaatcacg 1140
gctagcgccc ttgcgcttga atcggggtgt gccaacgagt cggccactac gggcaccggt 1200
acgggagtcg aagaaattct tccatgcctt atcggcagat tgcagacctg aaacgaggac 1260
tcggcggggg atggtgtgca tccacggctc ggaagagcgt tcagtctcgg gccatacggc 1320
ggtagggtcg gcaccgtcgg tgattgcgtt gctagcagcg cggtggcgat taatttcagg 1380
ggtcaggtac tgggttccgt atgccgcata accaatggac ttatacgttg catcgctttt 1440
ggctaatgcc ttgagctcag ccttaacggt ggtctcttca gcgcctgcgt cgatgcgggt 1500
gtgccagtag tctgctcgga cgcgggagac ctcaaggttg tgggcggtga ggaggttata 1560
ggcgtagcgt gctgcgcctg cacactgtgc caaggcgatt ttctgtgcct gagtgggatc 1620
gaggcggaac ttataggcgc ggagcatggt gtcagcgtca gtgctgattt tcat 1674

<210> SEQ ID NO 47
<211> LENGTH: 1503
<212> TYPE: DNA
<213> ORGANISM: Cyanothece sp.

<400> SEQUENCE: 47
tcataacgta tcgcttgcgc gatagttatt ttcttgttca aacaaattca attgttttcc 60
caggttccca ggcacattct gtttgccatt tctggcagaa tgttttctcc ttttaccccc 120
tgttaattca gaggtggacg tttgaaacag atttaactgt ttcggttcgg gcaagtccct 180
ccctacctta atcaattcgc attttttctg agaaaaagtg cgttttttta tttttaactg 240
atactgatta attgctttat ttttaatatt taaacaggct tgaaaatttg cgtcatcaac 300
atggccacac cgaacacaga gaaatttttc tccttttctg ttagatgaat caatatgatg 360
acacttgcta cattcttggc tggtatgctt tggattaact ttcaaaacaa tctttcctga 420
ctttgcagcc agatactcaa tttttgaat taaagaatac caagaagcat caagaattag 480
tctattaaga gcgcgtttag cactctgccc atttttgaga aatcgtcctt tctctttatc 540
atatttcggc ttgcaccgct taaccatatt ggatattttt aaatcctcta cagcaatagc 600
gtccgatgag ttgactattt tttgggcagc ttgccactga taagcttctc gtttctgtgc 660
tattttatgc tgaaaaagac ttaatttctt ttgtgctttt ttgcggttat tagaacgttt 720
ctttttccta gaaactctcc tttgtataat tcgttgtaat cttttagttt taggattggt 780
ggcaaattta gggttattta ttgctgaatt atcactacaa taaatcaact tgcctaaccc 840
catatccagg ccaatcactg ttttaatttc ttcaacaggt ttaattggaa aactagggac 900
tgaaacgtct tctattcgga tggaaacata atatccatca cttttttttcc gaaccgttac 960 ggatttaatt ttaaatccat cgggtagggg acgggaatta taatatttta tccatcctaa 1020
tttggggaga tatattttat taccttttaa tttaactcct acagtgtatg taaaagacct 1080
aaatgtgcta cagtttttga attttggaaa ttttctatta gaagaaaaga aatttttgta 1140
ggctacctct aatcttttca agttttgttg taaaacagtg gaatcaattt ctttatacca 1200
aggacgagct ttcttcagtt ctggcaaaga agtcatctgc atttcacaga cacttctttt 1260
tttaccatta tctttccaag gctctcctgt cgccccaccc ttaacaatac aacaagttaa 1320
gggtgatgct actgccttac tccttaaatc acaatattct ccttgaatga aagattgatg 1380
atagctgttt attcggtcag ctaaactcca gttatacgtg cttctaagca agtctagcca 1440
gctatctatt ttagctgact gctcttgatt tggacgtagt ttgtagaggt agccgagcag 1500
cat 1503

<210> SEQ ID NO 48
<211> LENGTH: 2040
<212> TYPE: DNA
<213> ORGANISM: Lyngbya sp.

<400> SEQUENCE: 48
atgacagtca aagtttttga atttaaaatt tatcccaaaa aggagtttca agaacagttt 60
aaccgttggg cttatgggct gaagaaattc tacaattttt gtctagaaca atttgaactt 120
ttagacgaat acacttactg ggataaactc agcaaaaccc gtgttccctg ttgtccgatt 180
ccctggaatt taaagttaat tgaaactgag gaacccaacc cctacttacc ggaattaaaa 240
aataagcatt atgtgagtta tagcaatctg atcgccccca aagatattcc tgtaattcgt 300
aacgccccag aagctagaca gtatacctta aaggaaggtg aaacggctaa agatgttttt 360
aaacgggtaa aaaatcctga taaaattgtt gtaacaatgg ctaaacccga atcaagtgga 420
ctggataaat ggcctagagg ttggttgggt ggagttggat attctcaacc tgttaaacaa 480
gattacaaac cctctttaat taagaacttt ccaaacagtg aaaaaacgag agatgcggga 540
attttagtca aaaaggaaac tctagaaaac tcagatttac ccgatgagat taaaaaggcg 600
attttagatg ttccctacaa gtttcgtaca ggcacacttt catcactctg taccagttgg 660
caagaataca tgaagtcacg aacgggtcag aatgatttaa agcgaggtaa acctaaatat 720
aaacgatatc gcgatcgcat tgaaacgatt attcacccta acccaaatgc gggttctagc 780
aagcctgcca gtaaagatgc ttgtcggtta gagggagata atattttagt tttaccctca 840

```
tttggtaaga taaaaataaa aggattagat cgaagatttc gcgataatga tggctcgata    900

cccagagtaa aagttgttaa agttctaaaa cgtccgagcg cttggtatgt tcagctaacg    960

gccgatatta accgcagtaa taagctcttt aaaaagccat tgggagcgat tgggattgat   1020

accggattaa aagaggagaa ctggattacg acagatagat tttcggtgac aaaacctcgt   1080

tggtatcgag agtctgaaga aaaattggct cgtttgcagc gagaattaga tgcaaaaaag   1140

ttacagcgtg ttatcctttg gctgaatcat cctgaaaatt caacagaacg aatcaaagag   1200

gtttttcccg gtatttctaa agagtctata gaaaaagtaa aaggctgtaa acgcccccaa   1260

gatttacagg atttggtttc caataacgaa ctgagtacat cggggttaaa tcagcttaag   1320

cattttaatt ttagagattg tgaaaaggtt gaaagttgtt atttatttga caaactcctc   1380

tcggtttcta ataaagaaat tgaattggca gaacgcatcg gtaaattaca cgaaaggaac   1440

aagcgacgca ggcgatcgca caaccaaaaa caaagcactt ggttaacgcg aaaatatagt   1500

ataatccgca tagaggatgg tttacaaaaa aatgtcggta agtctaaagc gaaaatatcg   1560

gaggataatc gctcctttga acgcaatgct caaaattcaa gagcagggat gaataagtct   1620

gttttagatg cggcgattgg tggttttatt tcgttggttg aggataagtc taaagaatgg   1680

gggcgggatt ttaaacgcat gaaaccgggt aaggggaaag cctacagcca gcgttgtccg   1740

gtttgtcatc acgagaataa agaacagaaa gacattacca accatcaaga ttataattgc   1800

tcaaattgtg ggtttactca ccgaagtcgt gatattgtcc caggcgttaa catgattttg   1860

gatgagtttg aagcaggaga tattcaatgg gatgatctca gtaaagaagc ccgacaagct   1920

tggcgactgc gagaaaaatg gctttctgaa aatgcgcctg ggagtggctg tcaagatgaa   1980

gtgactacgg ataagccctc aaacgcccgc agaaagagga atcggaagaa aaagacttga   2040
```

<210> SEQ ID NO 49
<211> LENGTH: 1530
<212> TYPE: DNA
<213> ORGANISM: Streptomyces sp.

<400> SEQUENCE: 49

```
tcaggacgac tttgcttgtc cgttatacgt gggaggggat gtcggtggat tgctccgccg     60

aggtggcgcc gggctgggcc gggcgtcttc ccgtttcact gggtcctgct tctccgcccg    120

ggggcgggga agtcttacgg actctccacg ggcgttttga gtctccccct taccggaggc    180

gacttgttgt ggcgtgggtc gcgccgcggt gtgccgttcg atgttgcggg ccgcgttgag    240

gtcgcggtcg agcaccaggc cgcagtgggc gcagtggaac acccgctcgt tcagcgtgag    300

gcttgggttt cgccatccgc agtcggagca ggtcttgctg gagggccacc aacggtccag    360

gaccgcgagt tgggagccgt accaggaagt cttgtaggtg agctggcggc gggtctccgc    420

catggcggtg tcgaggatgg ccctgttgag gccggccttc tgtcggacgc tccggccggg    480

gcgcttcagg gtgccgcgcg ccgtcgcggt catgcccgcg acgtgcaggt cctcgatgtg    540

gatcgtggcg taacgggtgg cgagcttctt ggtcacctgg tgcagggcgg cacgccgacg    600

gaccgtcacc tcgtggtgga ggcgtgcgac gcggcgacgg gccttgtccc ggcgcgcgga    660

gcccttctgc ttgcgggaca gggcgcgttg cgcctgccgc agtcgcttcg cgacccgggc    720

caggtggcgg gggttggtga cgaagtgacc ctctcggtcc gggctcttcg ggtccagggg    780

gcgggacagg gccgcgagca tcttgacccc gaggtcgacg ccgacggttc ccgccgtctg    840

ctgtgcgcgc gtcggcttct ccggaagatc cacctgcacc ttgcacagca cggacgcgta    900

ccagcggtgc ccggaccggg acaccgtcac cgactggatg cgagcctctt cacggctgat    960
```

-continued gagccgccca agacggcggg cgttgtcgtg aagacggatc tccccgaacg cgggcaagcg 1020
cagtctgcgg tacgtggtca gccggatgcc tggcttcttg acgtcgtggt ggagacggaa 1080
gctgtcgcgg gccagtccgc gcttcttgaa gcgggggtag ccgacacggc gtccggcccg 1140
cttgcccttg aaggagtcca gccagttctt ccacgccgcg tccgcgtcga ggaacgccga 1200
ctggaagacg taggtgttca tctcgtgcca ccacggtgcg atgccctcaa cacctcggcg 1260
gtcatccccg cgctcggcga cgaaccgctt gtagaccgtc ggcttggtcg gagtgggcac 1320
cttcacgcgc ttgcgtgccg tcgcctcctc gacgcccgcg tcgaccagcg cgacgacctg 1380
agtgcgccag tcctcgtggg cggccttctt ggccgccagg gcgtagttga aggcgagacg 1440
cgagttgccg caccagcgca gcaggcgctg ttcctgagcg gggtgggag cgagcgtaaa 1500 gcggaaggcc cgcaagattt ccgtcttcat 1530

<210> SEQ ID NO 50
<211> LENGTH: 1188
<212> TYPE: DNA
<213> ORGANISM: Limnoraphis robusta

<400> SEQUENCE: 50
tcacgactta ggtttctgtt tgcttccctt acgggttttt cgcagttgcc ctttaacact 60
atggttatca ggtcttacac tcgcttcaca gactgtaacg gtgtgtccca ccgccaaaat 120
atttcgactg gcgttgatat ctctatcgtg gtgtgttccg cagtcgggac agtcccactc 180
tctaacattc aacggcagtt tatcaagaat atgcccacag ttgccacagc gtttagaact 240
gggaaaccat cggtcaactt ttaccaagtt tcgaccatac cacttggctt tatattccag 300
ttgcctcacc aactccgacc atgcagcatc actgatagca cgggcaagct tgggattttt 360
gaccatattt ttaactgcca aatcctcaac cactatcgtt tggttttcac gaatcagtcg 420
agttgtcagt ttgtgcaaat ggtcttttct ggaatcagag attttagctt gaatccgagc 480
aactttgagc ctagctttat cccgatttcg agaagctttt tgtttgcgac tcaaagattt 540
ttgtgctttt ctcaactttt gatagtgcgc ctcatacgct ttaggattag caatcttttc 600
acctgtactc agggtaacga gactgctaat gccaacatcc agtcccacag cactatcaac 660
tggttgcatg gtttggtcag tcggagcatt gattcgcaaa ctaacaaacc aacgtccaga 720
aggttcaagt ctaactgtga tggtactagg ttcacatccc ttgggcagtt gcctagacca 780
tttaattggc aatgggtcag aacactttgc caagtatact tgtcgatctt tccaccggaa 840
agcagacttg gtaaactctg cgctaccacc actacgcttc tttttgaagt tgggatattt 900
cgccctgcca gcaaagaaat tagtgaaagc agtttgcaga tgtctcaagc cttgttgcag 960
tggcacacaa ctaacttcat tcaaaaactg aagttcttcc agttttttcc actgcgtcaa 1020
cattgcagaa gactgaacgt aatcaacctt ctgttgtctg tcataccaag cttcggttct 1080
cgctgccaaa gctttgttaa ataccaaccg cacacaacca attgtccggc gcaatatttg 1140
ttcttgctcg gtagttggat acactctgta acggtaggct ttttccat 1188

<210> SEQ ID NO 51
<211> LENGTH: 1164
<212> TYPE: DNA
<213> ORGANISM: Clostridioides difficile

<400> SEQUENCE: 51
ttgaaaagag catacaaaat agaaattaat cctactactg aacaaaaatc taaaatacat 60

-continued

```
caaacgattg gtgttagtag atttatatat aacttctata ttgctcacaa taaagaagtt    120
tatgagagta aaggtaaatt tataagcggt atggattttt ctaaatggtt aaataatgaa    180
tatattccta ataatcaaga tatgaaatgg attagagatg tatcttctaa ggctacaaaa    240
caagctatta tgaatggaga taaagctttt aaagatttct ttaaaaaaac taaaggtttt    300
cctaagttca aaaaaaagaa aaatcaagat gttaaagcat attttccaaa gaataacaaa    360
actgattgga ctattgaaag gcatagagtc aaaataccta ctcttggttg ggtaagacta    420
aaagaatttg gatatatacc aataaattca atagttaaaa gtgatacagt aagtcaaaaa    480
tctgatagat actatgtatc tatattagtt ggggaagatg atattcaagt atctaaatgt    540
actattgaag gaataggtat tgacttagga attaaagatt ttgcaatatg ttcaaatgga    600
agtaaattta aaaatataaa taagacttcg actgtcaaaa aagttgaaaa gaaattaaaa    660
agagagcaaa gaaaactttc aagaaaatat gagagtttaa aagtaagaaa taaaaatata    720
aaagaaggag tagctactcg tcaaaatatc caaaaacaga tagtcaaagt acaaaaaatt    780
catcaaagat tagctaatat aagaactgat tatattaata aaacagtatt tcaggtaata    840
gagcaaaagc caagttatat aaccattgaa gatttaaatg ttactggaat gatgaaaaat    900
aagcatttat caaaggcaat atcaagtcaa aagtttttg aatttagaac taaactaact    960
gctaagtgta agcaaaataa tatagaactt agagtagttg acagatggta tccatcatca   1020
aagacttgta gccaatgtgg agaggttaat aacggtttaa aacttaaaga tagagtgtac   1080
aaatgtgaat gtggattatc tattgataga gatttaaatg caagtattaa tcttaaaaat   1140
gctaaaaaat ataagatagc ttaa                                          1164
```

<210> SEQ ID NO 52
<211> LENGTH: 1599
<212> TYPE: DNA
<213> ORGANISM: Propionimicrobium lymphophilum

<400> SEQUENCE: 52

```
atgtcttacc tgtgcgcgcg tggaaggttc aacttgtcgg gattctcgac aggttcgatg     60
ggtgtcttac ccgtgcgtgc gtcactgttt gcgcttcttt tcacgacttt gcacggtgcc    120
cgaatctccg cacactggta tggcatgagc aaagaaaacg atcacacagt cacatgcata    180
aaaatctgtt tagagccgaa caaggctcag cgcgcccagt ttgcgtcctt cgcgggcagc    240
gccagatggg catacaactt cgcgttagca atcaaaattg gttaccagaa acgctggttt    300
gaagcccgca aacaattcat cgagtcaggc ttagacgaga aagcagcagg caagaaagcc    360
agcgaacaag tagggcggat gcctaactat atgtctattg ccacaaatga gtggacacag    420
cttcgtgacg aagtttgccc ctggtatcca gaagtgccta ggagagtgtt tgttggcgga    480
ttccagcgcg cagatgccgc attcaaaaac tggttcgact ccaagtctgg ccgcagaagc    540
ggggcagcga tgggttggcc aaagttcaag tcgaaaagca agtcccgcga atctttcgta    600
atcgctaacg atgttcagcc ggctttcgtt gctaacttga atcgctacat taaaaccggc    660
gagctagccg acatggacta ccgccacata aaggtgccca agtgcgggga ggttcgctta    720
acccctggat cggcaggaca actacgccaa ctcggtagga cgatgcttgc tgaggcgaaa    780
actggtgagc taatcacccg tattacttct ggcaccatat ctcgcctagg tgacagatgg    840
tatgtaagcc tggtcatatc tggcccattc gttccagacg ctatctccac taagcgtcag    900
cgccgcaacg gggtggtagg tgtcgacctc ggttcgggac gtttctacgc cactacatcg    960
gaggggctaa gcatcattaa ccccaaattt gtctctaagt atgagcagga gctagctaga   1020
```

```
gcaaaccggg cactagccaa gaccgctaag ggttcagccg ctaggaagaa ggctctggct   1080

aggttgcgca gggttcatgc ccgctcagct ttagctaggg atggtttcag ccatcaggtc   1140

tcggcatggc taactagcca gttcgccggt gttgcggtag aaaaatttga tttagcctcc   1200

atgcttgcct ctgctaaagg aacggtcgaa aagcctggca agaatgtgga tgttaaggcc   1260

cgctttaatg cccatcttgc tgatgtgggt attgcttcga ccatagacaa gctgctctat   1320

aagggtaagc gtgacggttg cagagtgcag gtagtcaata ctttggataa ttcgtctacc   1380

acttgcgcca aatgtggcca tacatgcgtt tgcggcccgg agcagaaaac gtttacttgc   1440

cccgattgcg gttacaatgc tcccagacag ttgaactctg ctcaatatat taggcagcta   1500

gccacggtag ggttcgacga gctggggcta gacatgacag ccagcctgac acctgatacg   1560

ggtaagcgcc ctatcgcctt catgacttcc gcacactag                          1599
```

<210> SEQ ID NO 53
<211> LENGTH: 1254
<212> TYPE: DNA
<213> ORGANISM: Lactobacillus helveticus

<400> SEQUENCE: 53

```
ttgttccgcc tctttcttaa acatatgttt gatataatct taaaaagaaa ggagggaaca     60

aatgtgctaa aagggatcaa attaagactc tatcctaata gaacacaaca aaaccagctt    120

gagcagatgt ttggcaatga tcgttttgtt tggaatcaaa tgctggccat gatgaatgag    180

cgctatcaga ataataaagc tttgcctttt ttaggcaagt tcaagctgaa ttatctgctt    240

aagccgctta aaaaagaata tcctttttttg aaaaccagcg attcttcaag cttgcaggta    300

gttaatgaat tcctaactca atcttggaag aacttctttc aagataaaac tggccaagta    360

ggcaagcctc gttttcattc acgcaagtat ctgaaaaagt cttatacagg caagtcaatc    420

ataaaaactg caggtaaaag gtacttgaag attcctaaat taggctatgt caaaaccagc    480

aagactggag ttttgcaaaa cactaagatt aagcgctaca ctgttctgct tgaaccaaca    540

ggaaaatatt atttgtctct acaggtagaa atatctgaac cagaaaagta cagcttaact    600

ggcaaacgag ttgggattga tgttggcgtg gctgatttag cgattctgtc taatgggcta    660

aaatatccta gttttaatag ctattatttt gaaaagaaag ctaaaatttg gcagaaaaag    720

tattctcgtc gcagacattt agttaaattg ctagttttac aaaataagaa taaaagggtg    780

ctttgtccta gaagtttaga aagctttact aattggcaaa aagcgcaaaa gtcaaaagct    840

aagtgccaag ctaaagcagc taatcagcgc agagattacc tgcataaact aactacgcat    900

ttagttaagc aatatgatgt aattgcgatt gaagatttga aaaccaagaa tcttcagaaa    960

aatcatcatt tggctaagtc aattgccaat gcttcatggc gaatgtttag acaaatgcta   1020

gaatacaaat gcgaatggta tggcaagaaa ctaattgcag ttgatcccaa gaacacttcc   1080

agaatttgtt caaaatgtgg ctataatagt ggcgctaagc cattagagat tcgtgaatgg   1140

acctgttcta agtgtcaaac caagcatgat cgagatatta atgcggcaat taatatcttg   1200

cataaaggaa gtacaaagcc aactggtcag ggactgacca tggtaacaag ctga         1254
```

<210> SEQ ID NO 54
<211> LENGTH: 1203
<212> TYPE: DNA
<213> ORGANISM: Scytonema hofmanni

<400> SEQUENCE: 54

-continued

```
tcactctttg ggcttcctct ttccgcgact caacttactt gaaggaattt cttccgacat     60
gcagaggctg atgtctccag aggcgtttaa cgttcccgtg tgccccacgg tacgaagtgc    120
aagttccagt atgtttcgag cggcattcca gtctgtgtct aaaactaacc cacactgatg    180
acatttatga gttctttgac tcaaagactt cttaataact tccccacact tggaacagtt    240
ttggctggtg tagtgcggtg ggacggcaac cgttgccacc ccaaaaacct taccgaaata    300
ctccaaccag tttcggaaag ccgaccaagc cgcgtccgat atcgacttag acagtttcct    360
gtttttaacc atattccgca cctgcaagtc ttcgtaggca accaagtcgt tagactggat    420
gacgcatctt gccaacttca cggcaaaatc tttacgctgc ctacttactt tgaggtgctt    480
tctgctcaat cggtttctgc tcttggctct gtttttcgag cctttggtag tgcgagaaag    540
cctgcgacca agacggttga gagctttttc agactttctc aaatgacgtg ggttttcaac    600
cgtctttcca tccgagtcag tataaaagtg agccaacccc acatccaatc caatagtttt    660
acctgttggc tctctttttt caacccgttc aacatcaagg caaaactgaa cgtagtaccc    720
gtcagcacga cgaacagccc gaactcgctt aatctgcttc aactggtaga aatgcaggtc    780
gcgagttccc cacatcttga aacttccagc tttaaaacca tcggtgaaag taatggttct    840
tctatcttcc gaaagcttcc agccacaggt cttgtactct acagaaccat gcgtttgatg    900
cttcttaaaa cgtggaaaac ccttcttcgc agctttcttc ttacaattgt cgtagaaccg    960
agcaatagcc gaccaagcac gttcagcaga agcttgacgt gccatagaat tgagtttgtt   1020
agcgaacgga aattcacgtt ggagaacgac gcagtaggca ctcaattcat agcgcccaat   1080
ataagggtta tccatccagt atctaatgca agaattgcgg ataaaacgcg cagtacgaat   1140
ggcttcatca agctgttcat actgttgttt tgttccctca agctttgctt caaataccaa   1200
cat                                                                  1203
```

<210> SEQ ID NO 55
<211> LENGTH: 1479
<212> TYPE: DNA
<213> ORGANISM: Kitasatospora cheerisanensis

<400> SEQUENCE: 55

```
gtgacacagg tggagacgct gcgcgcgtac aagttcgccc tggacccgac cgctgcgcag     60
ctcgccgacc tcgcccggca cgcaggcgcg gccaggtggg cgttcaacca cgccctcggc    120
tcgaaggtcg ccgcgcaccg ccagtggcgc gccgccgtcg atgccctggt cgccggcggc    180
atgccggagc cgcaggcccg caaggccgtg aaggtcccgg tgccgggcaa tcaggcgatc    240
aagaagacgc tgaacgggtt gaagggcgac tcccgctccg acccggcact cccggacggc    300
ttccacggac ctccccggcc ctgcccctgg tggcacgagg tgtcgacgta cgccttccag    360
tccgcgttca tcgacgcgga ccgggcgtgg ggcaactggc tggactccct gaccggccga    420
cgcgccggcg gcccggtcgg ctacccccgc ttcaagcgca agggccgcgc ccgcgactcc    480
ttccgtctgc accacgacgt gaagaagccg acgatccgcc tcgacggcta ccggcggctc    540
cagctcccgc gcctcgggtc gatccgcgtc cacgactccg gcaagcgcct ggcccgcctg    600
atcgccaagg gccacgccgt gatccagtcc gtcaccgtct tccgcggcgg caaccgctgg    660
tacgccagcg tcctcgccaa ggtgcagcag gacatccccg acaagccgac ccgcgcccag    720
accggccggg gcaccgtcgg cgttgactgg ggcatcaagc acctcgccac gctctcccag    780
cccctcgacc ccgccgaccc ggccaccctc cacgtcgcca acccgcgcca cctcgacgcc    840
tggaaccggc aactcgccac ggcgcagcgc gcgctgtccc gcaccgagcg cgggtcgaag    900
```

```
cgccgcgcga aggcggcccg cagggtcggc gccatccagc accggatcgc acaacggcgc    960
gccaccacgg tgcacctgct caccaagcgg ctcgccaccg ggttcgccac cgtcgccgtc   1020
gaagacctga acgtccgcgg catgagcgcc tccgcacgcg gcaccgtcga acaacccggc   1080
agccgcgtcc gacagaaagc cggcctcaac cgtggcatcc tcgatgccgc ccccggcgaa   1140
ctccgacgcc aactcaccta caagacttcc tggtacggct ccaccctcgc ggtcctcgac   1200
cgctggcacc cgtccagcaa gacctgctcc tcctgcggaa cagcgaaacc caagctgacc   1260
ctgagcgagc gggtgttcac ctgcaccacc tgcggcctga cgatcgaccg cgaccacaac   1320
gcggccgtca acatcgccag acacgccgtc gtccccctgg tagaggggga cgctaacgcc   1380
cgcagaagtc cacgcccggc cgatgcaggc cgggacggac acgccgaaag gcagaagcgg   1440
gaaggcccac cacccggtgg gtcacctcgg cgggagtaa                          1479
```

<210> SEQ ID NO 56
<211> LENGTH: 1209
<212> TYPE: DNA
<213> ORGANISM: Spirulina subsalsa

<400> SEQUENCE: 56

```
ctaccccacc ctgccgttgg cgaggatggg gcttcctgat tcaacaggaa cagcatctag     60
caaaaccgaa atcttgccag gttgtcttac gttccctccc caggccgtat cgctggttcc    120
caacgacaat atccgcaagg cttcattttt aatgttttgt gctgcattaa tatcacggtc    180
atggtgagtg ccacaatgtt gacattccca ttgccgaact tctaacggta agctatccac    240
tcgattcagg caaacgtgac aggtttttga agacgcaaaa tagcggtcaa cttcaatata    300
ggttttgcct tcccactcgg ctttatattt aagcattgtg gtaaacattc cccaacccac    360
atcactaatt gccttggcta gtttagggtt ttttaccatc cctttgacgt tcagattctc    420
tacagcaatc acttggtttt cgttaactat cttgcgggat agtttgtgta gaaagtcctc    480
acgacatcgg gctatcttac tatgaacttt ggcgactttt tgtttcgcct tagctcgatt    540
tttactccct ttttgtttac ggcatagctt ttgtcgctta cgctttaggt ttttctgatg    600
cttggcaaaa tggcgaggat tatcgtactt agacccatcg ctagtaatgg caaaatgagt    660
tagtccaaca tcaatgccaa tagctttacc ctcaactgat gggctaatgg catctttccc    720
gtcatctact aacactgaag catagtattt gccatccgga tttttagaga gagtaacggt    780
tttgattttc ccttcaaatt cccgatgacg acggcaatac actaacccaa tcttccccgg    840
tattttgaga tagtcccctt caaacttaac gttggcagga taactcagag actgccgacc    900
atgcttggac ttgaaacggg gtaactgcgc ccgcttgtca aagaagtttt tgtaggcagt    960
agaaagatta agggcaacca cttgtaagga ttgggagtaa gcatctgtta gccaaggata   1020
ttcctttttt agtcctggta ataggccttg gatatatccc ctagacaatc ccttacccgt   1080
ctcgatatag gtttttcggc acaagtctaa ggcaaaattc caataccaac gacagcatcc   1140
gaacgcctta gctagggatg ctttttgctc gtcagtagga tagatacgat acttgtacgc   1200
tttatacat                                                           1209
```

<210> SEQ ID NO 57
<211> LENGTH: 1929
<212> TYPE: DNA
<213> ORGANISM: Anabaena cylindrica

<400> SEQUENCE: 57

-continued

```
atgagcgtta tcacaattca atgtcgcttg gttgctgaag aagacagcct ccgtcaacta     60
tgggaattga tgagtgaaaa aaatacacca ttcatcaatg aaattttgct acagatagga    120
aaacacccag aatttgaaac ctggctagaa aaaggtagaa taccggctga attactcaaa    180
acactgggta actccctgaa aactcaagaa ccttttactg gacaacctgg acgtttttac    240
acctcagcga ttactttagt ggattatctg tataaatcct ggtttgcttt acagaaacgc    300
agaaagcagc aaatagaagg gaaacagcgt tggctaaaaa tgctcaaaag tgatcaagaa    360
cttgagcaag aaagtcaatc tagcttagaa gtaatccgta ataaagccac tgaacttttt    420
agcaaattta cccctcagtc cgatagcgaa gcgctccgta ggaatcaaaa tgacaaacag    480
aaaaaggtaa aaaagactaa aaaatccaca aaaccgaaaa catcttcaat tttcaaaatt    540
tttttaagca cttacgaaga agcggaagaa cctcttactc gttgcgctct tgcatatcta    600
ctcaaaaata actgtcaaat tagtgaactg gatgaaaacc cagaagaatt taccagaaat    660
aagcgcagaa aagaaataga aattgagcga ttaaaagatc aactccaaag tcgcatcccc    720
aaaggtagag atttgacagg agaagaatgg ttagaaacct tagaaattgc caccttcaat    780
gttccgcaaa atgaaaatga agcaaaagca tggcaagcag cacttttaag aaaaactgct    840
aatgttccct ttcctgtagc ttatgaatct aacgaggata tgacatggtt aaagaatgat    900
aaaaatcgtc tctttgtacg gttcaatggc ttgggaaaac ttacttttga gatttactgc    960
gataagcgtc atttgcacta cttccaacgc tttttagagg atcaagaaat tctacgcaat   1020
agtaaaaggc agcactcaag cagtttgttt actctacgct caggaagaat agcttggttg   1080
ccaggtgaag aaaaaggtga acattggaaa gtaaatcaac taaattttta ttgttcttta   1140
gatactcgaa tgctgactac cgaaggaact caacaggtag ttgaggagaa agttacagca   1200
attaccgaaa ttttaaataa aacaaaacag aaagatgatc tcaacgataa acaacaagct   1260
tttattactc gtcagcaatc aacactagct cgaattaata accctttcc tcgtcccagt   1320
aaacctaatt atcaaggtaa atcttctatc ctcataggtg ttagttttgg actagaaaaa   1380
ccagtcacag tagcagtcgt agatgttgtt aaaaataaag ttatagctta tcgcagtgtc   1440
aaacaactac ttggtgaaaa ctataatctt ctgaatcgtc agcgacaaca acagcaacgc   1500
ctatctcacg aacgccacaa agcccaaaaa caaaatgcac ccaactcttt tggtgaatct   1560
gaattaggac aatatgtgga tagattgtta gcagatgcaa ttattgcgat cgctaaaaaa   1620
tatcaagctg gcagtatagt tttacccaaa ctccgcgata tgcgagagca aatcagcagt   1680
gaaattcaat ccagagcaga aaatcaatgc cctggttaca aagaaggcca acaaaaatac   1740
gccaaagaat atcgaataaa cgttcatcgc tggagttatg gacgattaat cgagagtatc   1800
aaatcccaag cagcacaagc tggaattgca attgaaactg gaaaacagtc aatcagaggc   1860
agtccacaag aaaaagcacg agatttagcc gtctttactt accaagaacg tcaagctgcg   1920
ctaatttag                                                           1929
```

<210> SEQ ID NO 58
<211> LENGTH: 2136
<212> TYPE: DNA
<213> ORGANISM: Crinalium epipsammum

<400> SEQUENCE: 58

```
atgtctgacc aaacatccca aaataacgaa attaccatcc aatctctcct cgaagcccca     60
gaagaaaccc tatgcttcct ctggcaacta atggtcaacg tcactgaact catcaacagc    120
cttcttcacc acatcaacac gcacccagac ttcgacattt ggttgaccca atgtgcaatt    180
```

cctgcctccg ttatcaattc ctttataaaa acggctaaaa ctcagtctcc ctatcgagaa 240
atgcccactc gctttatcac ttcagcccaa aacctcgtta atgagatgtt caagtcatgg 300
tttgaaatcc aacgactcaa acgactatcc ctcaagggaa aacggcattt ttttacaatt 360
ctcaaaagcg acgaagaact acaaagagaa agcgattgta cctttgacac cctctgccaa 420
gaagcagcta tcatccttca acaaactcaa ctccaaatcg aacaaaaacg ccttgacgct 480
aatcagcccc ctcctaccct ggataagcag gcattttggg aagtagccca cgtcctctac 540
aaagcctatg accaagccga tacacccctg gttcgctctg gcattgcctt actcctcaaa 600
aaccagaacc aagtaccaga acaatttgaa gaccccaaaa aataccagca acgccgacaa 660
gctaaacaag aggaaatcga acgtttagaa catcaacttc aatcaaaagc ccccaaaggt 720
cggctaaccg accaacaaga atggctcaga atccttgaaa aagcctcgca acctatcact 780
gaagtcgcag aatttagaga catccaagct caactgctca ggaaattctt cgcactcgtt 840
tatcctgtaa cctttagtac taataccgac ttgcaatggt ctactaacca acaaggacgt 900
atttgtgttc aattttacgg tatgagtaaa tacacatttg aaattgcctg tgatagacgg 960
caactcaact ggttcaaacg gttcctagct gattatcaac tttacaaaca gcacaaaaca 1020
caaattccga caggtttgat gcctttacgc tgcgcccgtc tagtttggac agaaggacaa 1080
gatgattttg cccttattgt cgctacttgg ttattgattg ctgtaataca gcataagttt 1140
taccatattg cttggttact gctgaagaat caccgtatca ttaaatcacc tccttggaga 1200
gttcatcacc ttcatctcca ctgcatcgta gaccatcgac tctggacaca ggaaggcaaa 1260
gaaattgtta aagccgaaaa aatcccccaa actgaaaagt taatcaacga ttttcaacag 1320
aaagaacgaa ttcaggaaaa tggattaacg actgggcaac aacaaagact caaagcgagt 1380
gaaacctccc tccgtcttct ccaaaattgc gaccactttg ccgcttctaa gcgtatctct 1440
taccgaggtc aacccaatcg aatactagga gttagtattg gactgcatga acccgtaaca 1500
atcatgattg ttaacacgac tacaggtaaa acccttgcct ctcgtaatac taagcagcta 1560
ctagacaaaa aaaggcgggt acgagatcaa caacccgaac tgccaaaata cgaagaacgc 1620
cagcatttca ctaacatcta taaagaaata tcagactacg aattatttct gttttatcgc 1680
caacagaagc aacagcatca acaccaacgt cacaaagctc aaattaaagc gactccagat 1740
cattcaaaag aagctaactt agggctatat attaatcgac ttctagccaa agccattatc 1800
gaatttgccc aacaacatca ggtcagcacc atcatccttc ccgacctgaa gaacaaacga 1860
gagagtatcg aaagtgaggc gaaagcactt gctaaattaa aaattcctaa agataaaagc 1920
aggcaacagc aatatactag aaacatcctg tccgaagtca gccaatggag ctacaagcaa 1980
ctaagcgact gtatcatcaa caaagcctca cagtcaggta ttgctataga aatcattcaa 2040
caaatttctc aaggtaaccc ctaccaaaaa gctagaaact tgattactac ttttacaaaa 2100
aacagtggaa ataaatgttc tgccaaaata gaatga 2136

<210> SEQ ID NO 59
<211> LENGTH: 1845
<212> TYPE: DNA
<213> ORGANISM: Crinalium epipsammum

<400> SEQUENCE: 59
atgagtcaga ttaccgttca gtgtcgtttg gttgcaagtg aatcaacccg ccatcatctc 60
tggaaactaa tggcagacct gaacacgccc ttaattaacg aattactggc gcgaatggct 120

-continued

```
caacatcaag actttgaaac ctggagaaaa aagggcaagc tcccggatgg aatagtcaag    180
cagctatacc aacctcttaa aactgaccct cgcttcacaa atcaacctgg acggttttat    240
acaagtgcaa ttaccgtcgt tgactacatc tataaatctt ggtttaaaat tcaacaacgc    300
ctagaacaaa agctaaaagg gcaaattcgt tggttaggaa tgctcaaaag tgatgaagaa    360
ttagctgccg aaagtaacac atctatagaa gtaattcgca ctaacgcagc cgaacttatt    420
acttccctgt cctctgaaga tggtagtgtt tctactagac tttggaaaac atacgacgaa    480
acagacgaca tccttaccca ctgcgtcatc tgctatttac tcaaaaatgg tagtaaagtc    540
ccaaaaaaac ctgaagaaaa cttagaaaaa tttgctaaac gccgtcgcaa agttgaaatt    600
aagattgaac gcttaagacg gcaactagaa agtcgcatcc caaaaggtcg agatttaaca    660
gggaaaaact ggttagaaac attagcgatc gcatctacca ccgcccccgc agatgaacca    720
gaagctcaat cctggcaaga tacactgcta actgaatcaa aacttgttcc tttccccgta    780
gcctacgaga ctaacgaaaa tttaacttgg agtaaaaacg aaaaaggtcg tctttgtgtt    840
caaatcagtg gcttgagtaa gcatattttc caaatctatt gcgaccaacg ccaactcaaa    900
tggtttcaac gcttttatga agatcaagaa atcaaaaaag ctaataaaga tcaatattct    960
agcggtcttt tcaccctgcg ctcaggaaga attgcttggc aagaaggcac agataagggt   1020
gaaccttgga atattcatca cctcatcctc tactgcaccg tagacacccg tttatggacg   1080
gctgaaggca cagaacaagt ttgccaggaa aaagcagaag atatcgccaa aaccccttacc   1140
agaatgaaga aaaaaggcga tctcaatgac cgacagcaag cctttattcg tcgtcaacaa   1200
tcaacactag ctcgacttaa caacccatat ccccgtccta gtcagcccct ttatcaaggt   1260
cagcctcata ttcttgtagg tttggcattt ggactagata aacctgccac cgcagcagtt   1320
gttgatggga caacaggcaa agcaattact tatcgtagtc ttaaacaact gcttggagat   1380
aattacgaac tactaaataa gcagcgcaaa cgtaaacaac aacaatctca tcaacgccat   1440
aaagctcaaa gtaatggaag atccaatcaa tttggtgatt ctgacttagg tgaatatgta   1500
gatcgtttac tcgcaaaagc tctcgtcaca cttgcccaaa gctatcaagc aggtagtatt   1560
gttctaccaa aactaggcga tatacgtgaa ttaatccaaa gtgaaattca agccaaagca   1620
gagcaaaaga ttccaggtta tatcgcagga caggaaaaat acgccaagca gtacaaaatt   1680
agtgtccatc agtggagcta tggacgattg attgacaata tcaaagctca agctgccaaa   1740
ataagtattg tcatagaaga aggacaacaa cccattcgtg gtagccctca agaaaaagct   1800
aaagaaatgg caattagtgc ctatgacgat cgcactaaat cttga                   1845
```

<210> SEQ ID NO 60
<211> LENGTH: 1932
<212> TYPE: DNA
<213> ORGANISM: Cyanothece sp.

<400> SEQUENCE: 60

```
atgagcatgt acacgattca ctgtcacctg actgcctccg agccagttcg ccgccatctc     60
tggtacctca tggctggcag taatactccc ctggtcaaca atctattgaa gctagtcagc    120
cagcatcctg actttgaaac ttggcagcgc aaaggtgaca tctcgaaaag ttccgttgaa    180
gcgctttgtg agccgctcaa agaaacttat cctggtcaac ccggacgatt ctacagctct    240
gcgatcctca gggtgaccta cacctataag tcgtggctgg cacttcagaa gaaccgtcga    300
tatcgactag aaggaaaaca acgatggctt catgtagttg aaagtgacag tgaattactt    360
caccgcagcg gctcctccat tgaaactctt aagtatcggg cgcaggatat tcttgttcaa    420
```

ctcaacgtag aacaacaaac acaaaagact tctgtaaccg acatcagcac cattacccca 480
gaagaaactc catcttccaa aaacgaaagc cttttcccaa gcctgtttag agcctacgat 540
tctgaagatg acatcttgag ccgatgtgcg atcgcgtact taatcaaaaa cggtggcaaa 600
attcctgaaa cagaagagga tcaagagaaa tttacccagc gagtcaatag caagcgcgag 660
gaaatagaac agcttgaaat agaactgagt gcccgctacc ccaaaggtcg agatttgacg 720
ggtgaggagt ttctggagac cttggcgatc gccacccaac aactttctga aaccgttgct 780
caggcgaggg agtggaacga caaaatattg acacagccca aatttatgcc ctatcccatc 840
atttacggta gttccactga tgtgcgttgg agaaaaactt ccaaaagtag aattaccgtc 900
agctttaatg ggatcgataa atatctcaag gcggctgatc ccgaaatcaa ggcatggttt 960
aaagaccatc aggaataccc gttccggttg cactgtgatg aacgccaact gcccttcttt 1020
cagagatttt tagaggattg gcaattttat caagcaaaca aagagaccta cccagcaggt 1080
ttactcacac tcagttcgac tctactaggt tggagagagg gtgagggtaa aggtgatccc 1140
tggaacgtga accgccttgc cctttactgc accttcgata cacgattgat gacggcagaa 1200
ggtactctag acgttcaaaa agagaaatct gaaaaagccc tcaaaaattt ggcaaaggca 1260
aaacctgatc ctcgcaacca ctcaacgctc gatcgcctca agaatttgcc tgtaagacct 1320
agccggactc cctaccaggg taacccagaa attttggttg gactcagagt cgggcttacc 1380
aaccctataa cagcagcagt tgttaatggc aggacagggg aagttttaac ctatcgcaca 1440
ccctcaacct tactgggcga tcgctatgac ctttttaacc gtcatcgcca ccagcaggag 1500
caaaatgcct tggaacgcca caagtatcag aagcgaggtg taacgtacca accttcagag 1560
tcagagcttg gcaagtatgt cgatcgcctt ctggcaaaag ctatcattga actggctcaa 1620
acctataaag caggaagcat tgttatcccc tgtctgaccc atcttcggga aattcttgct 1680
agtgagattg cagcacgggc cgaagagaag tgcccagggt cagtggaagc tcaagataat 1740
tatgctaaag agtatcgccg gaaaattcat aattggagct acaacagact catttcagcg 1800
atctgtagca aagctgagca actggggatc atcgtcgaat cgggatttca gccgtacgaa 1860
ggtgattcct atcaacaggc aaaagacttg gcgatcgctg tctatcactc tcgccagctt 1920
gctttaaagt aa 1932

<210> SEQ ID NO 61
<211> LENGTH: 2004
<212> TYPE: DNA
<213> ORGANISM: Cyanothece sp.

<400> SEQUENCE: 61
atgagtacca tcacgattca atgtcgcctt gtcgccccag aagcaacccg tcaagccctt 60
tggcagttga tggcgcaaaa aaatacgccc cttgtcagtg aactcttaag acaagtagcg 120
caacatcctg attttgaaac gtggagacag caaggaaaac tcgaagcagg aattatcaaa 180
aaactctgcg aacccctcaa aaaagatccc cgttttaacg agcaacctgc acgattttat 240
accagtgcga tcgccctggt agattacatt tacaaatctt ggttaaaact tcaacaacgg 300
ttacagcgca agctagaagg acaaaatcgc tggttagcca tgcttaaaag cgatgacgaa 360
ttaatccaaa ttagtcaaac aaacatagaa ataatccaag caaaagccac tgaaatctta 420
tccactcttc aaccacaaga tagagaacaa tcatcaaaaa agaaagctaa aaagtgtaaa 480
aaatcaacca ataagaatag cctcttcagc caacttgata aactttacaa tgaaatcaat 540

```
aataatttaa ctcattgtgc tattcgttac ttacttaaaa atggtggtaa aattcctcaa    600
agacctgaag atactgaaaa atttgctcaa cgtcgtcgta aagtagaaat caagatagaa    660
cgtatcattg aacagataga aagctcaatt cctcaaggca gagacttaac aggagatagt    720
tggctagaaa cgttaattat cgccgctaac actgccactg tagaagctga ggacgttaaa    780
tcgtggcagg ataaactttt aagtcaatcc aaatctattc cctatcccgt tgcttacgaa    840
accaatgaag acttaacatg gagtattaat gagaaaggtc gtctctgtgt tcgattcaat    900
ggcttaggta aacacacttt tcagatttac tgtgatcaaa gacaattaaa atggtttcaa    960
cgcttttatg aggatcaaca aatcaaaaaa gacggcaagg atcaccattc cagtgcttta   1020
tttagcttac gatctggtcg aattgtctgg caagaaggcc taggaaaagg aaaaccttgg   1080
aatattcatc gtttaacatt acattgttct ttagatactc gtttttggac agaagaagga   1140
acacagcaag tacagcaaga gaaatctaag aaatttcaga caaatcgcct acggatgaaa   1200
cctgaattaa cttttagtat tttcttccgt tcccagacgc ttgaaaccta cttacaggta   1260
tggttagtca ttacagccta tcgccttcaa tctttcttag acaagggcaa tgttgctaag   1320
gctcatcaag agtttcaaaa agccatcaaa agaaacgaat cttccctaca aaaaattacc   1380
agttcttata atcgtcccca taagacctta tatcaaggaa aatctcatat ttttgtgggt   1440
gtggcaatgg gactcgaaaa acctgctacc gttgcggttg ttgatgggac aacaggaaaa   1500
gcgatcgctt accgtagtct caaacaactt ttagggaata attatcacct gtttaaccgt   1560
caaggtaaac aaaaacaaaa tacttctcac caacgccata aatctcaaaa acactttgct   1620
gataatcaat ttggtgaatc acaattaggg caatacattg attgcttact cgctaaagct   1680
attatttctg tggctcaaac ctattgtgca ggaagtattg ttgttcctaa actcaaagat   1740
atgcgtgaac taattcaatc agaaattcag gctaaagcag aagcaaaaat tcctggttat   1800
gtagaaggac aggcaaaata cgctaaaagc taccgtgttc aagttcatca atggagtcat   1860
ggcagactta ttgataacat tacctctcaa gcttctaaat tcaatatcac cgttgaagaa   1920
ggagaacaac cacatcaagg aaatccacaa gacaaagcga aattgttagc gatcgcagct   1980
tatcattccc gtttatgtgc ttga                                          2004
```

<210> SEQ ID NO 62
<211> LENGTH: 1968
<212> TYPE: DNA
<213> ORGANISM: Halothece sp.

<400> SEQUENCE: 62

```
atgagtcaaa taacgattca atgccgtctt gttgccagcg cagaaactcg ccagcacgta     60
tgggaattga tggcggaaca aaacacaccg ttagttaacg aactgctcaa acaagtagcg    120
gaacatcctg aatttgaaac ttggcaacag aaaggaaaac tccctgcggg aatcgttagc    180
aaactctgta agccattgaa agaggactct cgcttcagtg gtcaacctgg acgattttat    240
acgagcgcga ctaagttggt ggaatatatt tatcaatctt ggctggctct acaaaaacgc    300
ttgcaatgga ggctcaacgg tcaaaaacgc tggttagaga ttcttaaaag tgatcaagaa    360
ctctgtcaac aagcagactg ctcgttagaa acactttgcc ataaagccag cgaaatcctt    420
gcctcttttc agtcttctac aactaagagc aaaaagaaat cgaaaaagca aaaaaatagt    480
tctcggaaaa gtctgtttga tgcttatgat agtgctgaag atagtttaac tcggagcgcg    540
atcgcgtacc tccttaaaaa caattgtaaa attcccgaac agcaagaaga ccctgaaaaa    600
ttcactcaac gacgacgtaa agcagaaatc aaagttgaac gattaactcg gcaaattgat    660
```

agcagtttac ccaaaggacg agacttgact ggagaacggt ggttagaaac cttaatcacc 720
gcagctaata aagttcctca aaatatagag gagttcaaat cttggcaaaa tatcttactc 780
actaaaccca aatctgttcc ctttcccatt agttacgaaa ccaatgagga tttaacttgg 840
agtaaaaacg aaaaaggtcg tctttgtgtt cgctttagtg gcttaagtga ccatactctc 900
caaatttatt gtgaccaaag acaactcaag tggtttcaaa gattttacga agatcaggag 960
acaaaacgag ccagcaaaaa ccagcattct agtagtttat ttactcttcg ttctgcacgt 1020
attttatggc aagaaggcac agctaaaggt caggcttggc ataggaatta tcttagtctt 1080
tactgtaccg ttgatactcg cttatggaca gcagaaggaa ccgaacaagt cagacaggaa 1140
aaaactgatg aaattactaa aattctcacg aatatggagg agaaaggcga tttaagtcaa 1200
acccaagaag cctttattaa gcgtaaacaa acaacgcttg atagattgaa taattcttat 1260
cctcgtccta gtaaacctct ttatcaaggt caatctcatc ttcttcttgg gattgcattt 1320
ggattagaga aacctgctac gatcgcgatt gtggatggta ccacaggaaa agcaatcact 1380
tatcgcagta tcaaacaact ccttggggaa aactataaac tgctcaaccg tcatcgaaaa 1440
cagaaacaag ttcaatccca tcaacggcat aaaaaccaga aaagtttgc ccctaatcag 1500 ttaagaaatt ctgagctagg agaatatatt gatcatttaa ttgcaaaagc aattgttaac 1560
attgctcaaa agtataaagt gggaagtatt gttctgccta aacttgacaa tatccgtgaa 1620
gttattcaaa gcgaagttca aatgcgagca gaacaaaaaa ttcctggtgt tgtagagaaa 1680
caaaaggaat atgctaaaca gcatagaatc caagttcatc aatggagtta taaccgacta 1740
attgaaagta tcaaagctaa agctaatcaa aaagaaatcg tcatcgaaca agccaagcaa 1800
ccaaatagaa tccaagttca tcaatggagt tataaccgac taattgaaag tatcaaagct 1860
aaagctaatc aaaaagaaat cgtcatcgaa caagccaagc aaccaattcg tgatagctct 1920
caagaagagg caaaagaatt agctacaata gcttataagt ctcgttaa 1968

<210> SEQ ID NO 63
<211> LENGTH: 1914
<212> TYPE: DNA
<213> ORGANISM: Microcoleus sp.

<400> SEQUENCE: 63
atgagcatca ttacagttca atgccagctc aaagcgacta aagactccct gcgccatctc 60
tggagcctaa tggtggaaaa aaatacactt ttggtcaacg aacttctgaa gcagattaat 120
actcacccgg atttagagaa ttggttgaaa gtaggaaaca tcaaagccga agttattgaa 180
ggactctgcg acaatctcag aactgaatct cgcttccagg atatgcctgg tcgtttcgcc 240
aacgctgctg agaaattagt caaagacatt tacaagtctt ggttcgctct acaagaagaa 300
cggaggtttc gtctctggag aaaacaacgc tggttttctc tgttaagaag cgatttggaa 360
ctagaacaag aaagcggttt gagcttggag aagttgcgta ctgaagcgac gaaaatcctg 420
atcaaggctc agttggagtg tagccgagaa gcagaaccag accaagccac tacagacaac 480
tccagcgctc tatgggataa cctctttaca gcctacgata aattcaaatc tccccgccta 540
cgctgtgtta ttgcttattt attgaaaaat ggctgccagg ttaacaaagt agaagaagac 600
cccgaagctt atcaacggcg gcggcgcaag aaggaaatcc aaatcgaacg cctcaaagaa 660
caacttaaga gtcgtcttcc caagggaaga aatttatctg agcaagagtg gctggaagcc 720
ctggaacaag cgcagggact aatcattgat gacgaacact tgagacaagt gcaagccagt 780

-continued

```
ctgactagaa aacaaagccc tgttcccttc tcgatatcct atgaaaccag caccgacttg    840
cgatggtcga gcaatgaaca ggggcgcatc tgcgttagct tcaatggcaa aggcatcagc    900
aagcatacct ttgaggtctt ttgcgaccag cgccaactac actggtttga acgcttttat    960
gaagactaca aaatttttac gcagaacaag gatcaggttc ctgctggatt gttgactcta   1020
cgttctgctc gattagtttg gcaagaaggt gaaggtgagg gcgaaccttg gcaagtgcat   1080
cggctgctgc ttcactgctc tgttgagact cgtttgtgga cggcacaggg aactgaggag   1140
gtacgtgcag aaaagattgc tcaaacgcaa gcagctatcg accgccagaa agcaaaaggc   1200
actcaaagta aaaaactgaa tacttctcta gagcggctta aaacgtttca gggcttctcc   1260
cgtcccagca gagcaagcta caagggcaat tgctcaattg tcattggggt aagcttcgga   1320
cgagctaaac cagcaacggt tgcagttgtc aacgtcgaaa ctggcgaagt tctagcatat   1380
cgtgatgtta agcaattact gaataagcca atcaaggaag ggaaaactaa gaagaaaaag   1440
actcagtatg aatatctcaa gcgtaggcaa gagcaacaac gcctcaatag ccaccaacgt   1500
cacaacgctc aaaaaaatgg tgctccttgt aactttggag aatcgaaaca aggggagtat   1560
gtggatagac tgctggcaaa agcgattgtc gaagtggctt cacagtatcg agctagcagt   1620
attgtcctac ctgacttgag aaatatcgag gaagcggctg agagtgaagt ccgggctaga   1680
gccgaacaaa aatttccggg caatcaaaag cttcaagata gctacgccaa ggattatcgt   1740
gccagcattc actgttggag ttacagtcga ttagcccagt gtattgagct taaagccgga   1800
aaagccggga ttgccacaga aaaagtacac caaccgcatg ggacacccc tcaagagaaa   1860
gcaagggatt tagtgctagc tgcctatgca aaccgtaaag tatcagttag ctag         1914
```

<210> SEQ ID NO 64
<211> LENGTH: 1908
<212> TYPE: DNA
<213> ORGANISM: Microcoleus sp.

<400> SEQUENCE: 64

```
ttaggggttg agacgggagt gataagctgc gatcgccatt tcttttgcct tttcctgggg      60
gctgcctcgg acaggctgtt gtccttgttc gattgagatg cctatctttg ctgcctgaac    120
ctgaatgttc tcaatcaatc tgccgtaact ccattgatga acattaaccc gatactgttt    180
ggcgtacttt tgctgtcctt cgacataact gggaattttt tgctcagctc tagtttgaat    240
ctcgctgtgc actagctctc gcatatctcc cagcttggga aggacaatgc tgcctgcctg    300
gtaggtttga gctaaggtga caatttcttt agccaacagt cggtctacat attcccctag    360
ctcggattcc ccaaattgat tagaggtagc atttttctgt gctttgtggc gttggtgaga    420
ctggcgttgt ttttcttgtc gttgacggtt gaaaagtttg tagttatctc cgagtagttg    480
tcggatgctg cggtaggcga tcgcttcgcc tgtagtgcca tctacgatcg ctgctgtagc    540
gggtttccca aggcccaagc taatacccac agcaatgtgc gaccgcccct gatacagagg    600
ttggctagga cgagggaagg ggttattgag acgggcgagg gtggagtttt tgcgcttaat    660
gaaagcttgt tgtttgtcgt taaggtcgcc tttctctttc attctggcaa gggttttggc    720
gatatcatcg gctttctctt gacgcacttg ctcagtgcct tcagccgtcc aaaggcgagt    780
gtctagagtg cagtagagag tcaggtgatg gatgttccaa gcgtcgcctt ttcccttccc    840
taatgcccaa gcaatctgtc ctgagcgcag ggtaaacaag ctactggagt gctggtcttt    900
gctctctcgc ttgatttgtt ggtcttccag gaagcgttga aaccacttga gctggcgttg    960
gtcacagtag atttgaaagg tgtgttcgct caagccgttg aattttacgc agaggcgacc   1020
```

```
tttggaattt ttgctccagg tcaggtcttc gttactttca taagtaactg gaaaggggac   1080

agactggggt ttggttaaga gcctgtcttg ccaagaacga gcttgagact cattttcagg   1140

gacggtgcta gtggcagcga tcaatgtctc taaccacttt tccccggtta agtttcgacc   1200

tttgggaata cggctggcta gttgttcttc taaccttgaa atcttgattt cagttttgcg   1260

gcggcgcttg gcaaattttt ctttgtcttc ctcttggtca ggaattttgc agccattttt   1320

gagcaagtag cagatggcgt tcttggtcag gaggtcttct atatcgtcgt aaacctggaa   1380

gagagtttta gagatactgc gattagagcc taagtcttgg ggtttcttgc tctttttgcc   1440

tttggtttga gtgggttgag gcgactcgtt cttagaggtc aggggaacca ggatttcact   1500

ggctttggtg cgaatgacct ctagagtaca accgctctgg ttgactaatt cctcgtcgct   1560

tttgagcatt cctaaccagc gcatctgtcc ctctagtttg cgctgtaacc gttgctgcac   1620

cttcaaccaa gatttgtaga tgtagtctac cagcgcgctc gcagaagcat aaaaacgacc   1680

aggctgaccg atgaagcgag aatcagtcct gaggggttca cacagttgtt tgatgatgcc   1740

agcaggaatt ttgcgttttt gtcgccaagt ctcgaaatca ggatgctgac cgatttgttc   1800

gaggagttcg ttaattagag gcgtatttcg ttctgccatc aatgtccaga tctggtggcg   1860

agttgaaacg tttgcaacta ggcggcattg aatggtgatt tggctcat               1908
```

<210> SEQ ID NO 65
<211> LENGTH: 2025
<212> TYPE: DNA
<213> ORGANISM: Nostoc sp.

<400> SEQUENCE: 65

```
atgagccgcg atcgtaaaaa gggttccaag agtccaagcc taagaactat acgatgtcat     60

ctgcatacca aagaagatgt acttcgtaaa gtatgggaag aaatgactca aaaaaatact    120

cctttaattg ttgaattgct gaagagtgtg agcgaacaac cagaatttga aactaataaa    180

gaaaacggaa aaataacgaa gaaagaaatc acaaacttac gtaaatctct gactcaagat    240

tcaggtcgcc tttactcatc ggtggacaac ttagtgcaag aagtttattc agcatggctg    300

actttatacc aaaaaagaaa aaagcagaaa gaaggcaaag agtattttct caacaatata    360

ctcaaaagtg acatcgagct tgtagaagag agtaattgtg atttacaaat tctacgggct    420

aaagcacagg aaatcatttc taatccacaa gatattctca ggcaaattac tattgataat    480

cccaaggata aacctactaa atctattcaa aaacgagtta gaaaaaacat taatgcttca    540

aatagtgata cagcaaaaaa taatatttta aattctcaag aaaaaactac agaagaaaac    600

atatcaaaaa gcgtaataga gattttatac gaaattcaca aaacaacaca ggatacaata    660

atacgctgtg ctgttactta cctgataaag aactatacta aaattagtga tacagaagaa    720

gatttaaaca aattaaaaga gcgtcgtgcc gagaaagaaa tagaaattaa acgcttggag    780

aagcagattc aagatagtcg attacctaat ggtagagata tcactggagc cagatatctt    840

gaggcatttg ataagttaat aaatcaagtg cctaaaaata atgaagagtt tgcaaattgg    900

atagctgacg catcgagaaa aatatcaaat ttgccatatc caatagatta tttatacagt    960

gatttaactt ggtataaaaa tcaagatgga aagatttttg tatactttaa tggttggtct   1020

aagtatcact ttcaaatttg ttgtaataaa cgccagcgtc atttttttga aaggttccta   1080

gaagaccata aggcttggaa agagagcgag aaaggagaag taaaactctc aggaagcctg   1140

gtgacactac gctgtgtaca gttgttatgg caacaaggtg aaggcaaggg tgaaccttgg   1200
```

aaagttaaca aattatcttt acattgtaca tatgatactc gtttatggac agcagaaggt 1260
actgaagagg cgagaaaaga aaagataaat aaaatacaaa gacaagttga acaagcagaa 1320
gagactgaaa atctagatga acagcaacaa aaacaattga agaaaaataa atcttcattg 1380
tctcgactga ataattcttt caatcgtcct attcagccaa tttaccaagg tctatctaac 1440
atgattgttg gcgttagttt tcatccagtg gaattagcaa cagttgctgt agttgataca 1500
accactcaaa aagtcatagc ctataagaca atcaacgagt tactagataa tgcttttcat 1560
ctattaagcc gtatgcgacg acaacaaata catttccgta aagagaggaa aaaagctcag 1620
aaaaaagatt cgccttgtaa tctaggggaa tcaaaactag gggaatatgt ggataaatta 1680
ctagcaaaga gaatagtgga agtcgctaag gaatatcagg ctatttgcat tgtcctaccc 1740
aaattaaaag atatgaagga aattcgcacc agtgtaattc aagcaaaagc tgaaaccaag 1800
tttccaggta atgtcaatgc acaaaaatta tatgtcaagg aatataatcg ccaggtacat 1860
aattggagtt acaacagact tcaagaatcc ataaagtcaa aagctgctga attgaaaatt 1920
agtattgaat ttggtattca gctatcttat gacactctgc aagcacaagc gagggattta 1980
gcattgtctg cctatcaatg caggattcat actattgata gataa 2025

<210> SEQ ID NO 66
<211> LENGTH: 1614
<212> TYPE: DNA
<213> ORGANISM: Dermacoccus sp.

<400> SEQUENCE: 66
tcatctccgc gtgcgcgggg ccgacccttg cggggtgctg tgtttccgcg ctttgcagtt 60
ggtgggggaa gcatttgccc tcactttcgc ttccccgtcg gggggagatg accggacgcg 120
attacacggc cggggtggcc cacctcgcgg tgggtcttcc cgcttcgcag aacgtcgcgc 180
gacagatgtc tcaccgcgcc ctccacgggc gttttgcgac tcctccatgc cgggggcgtc 240
gtgggatgcg agagcggtgc gaaggacgtt cttcgccgcg ttgacgtcac ggtcaagcac 300
cgtggcgcag ttctcgcagt ggtacacgcg ttccgaccgg ggcagattgg ctttctccgc 360
cccgcacgtc gaacacgtcc tgctcgtggg aacgaagcac cctgagggca ggagctgcga 420
tcggtaccac gaagtcttgt aggtgagttg tcgccgcatc tcggcgaagc tcgcgtcgag 480
gatggaacgg ttgaggcccg ctttcgcggc gacgttgcgg ccaggcttgt cgatgctgcc 540
tcgtgcgctg cgcgtcatga cggcgacgtt gaggtcgtcg acagcgacga cggcgtgcga 600
ggtcgcgagc tgcttcgtga tggcgtgcag tgtgctcgcg cggtgctggg cgacagcggc 660
gtgctctcgc gcgagacggg ctcgagcctt gacgcggccc gtcgtgggtg tgacgcgttg 720
gccacgcttg gggggtgtcga tgaggtcgcc gttgggtagg cgccacttgc tgcgcgacaa 780
ggcgcgctgg gcgcgggtca gccgcttctg cgccgcgcgc aggtggcgcg ggttgtcgat 840
gatggtggcg tcgctgaaag ccatcaggtg gtgcacaccc acgtcgaccc cgaccgcgcc 900
tgcggcttgc tggcgcgggg tggggtggtc ggggatgtcg agtgtttcca gcgcgaggat 960
gctcactgac cagccgttgc ccgcgcggga gatcgtggct gactggatgc gtgccacgcc 1020
gcgacggatg cgtcgggcga ggtggcggat gttgcccttg agccggatgg agccggtgac 1080
ggagatcttc ttcggcagcg tcagtcggcg gtagccgtcc gggcggatgc tgggacgctt 1140
cacgtcgtgg gccagggtga agctatcgcg gcagcgcccc ttggacttga agcgggggta 1200
tccgacacgc cgcccggcgc gtcgacctgt cagggagtcg agccagttct gccacgccgt 1260
gtcagcttgg cgcatccccg agacccagct gcggcggttg acctcggtgc gccaggcgta 1320
atccgggtcg cggtcgaacg ccttctcgtt ggtttgggat gtggggatgc ggtagtagcg 1380
cgaggcgtcc ttcttcgcgg cggcgagggc ctgatctgcg tcgaggtggc cgtagcgggt 1440
gtaggtcaga tcggcgacgc acgcgctcca catgcggtgg gcgtgcacct tggcgccgag 1500
ggcccagttg aaagcggcgc gggaggcgcc cgcatgagag gccagtgctg cggtctgtgc 1560
gtcggtcggg tccaggggga cgcggtatgc gcgcaagatt tcacgagtgg tcat 1614

<210> SEQ ID NO 67
<211> LENGTH: 1509
<212> TYPE: DNA
<213> ORGANISM: Nocardiopsis synnemataformans

<400> SEQUENCE: 67
gtggaggtcg tggctgaagt actgcgcacg ttcaagttcg cgctcgaccc cacctcgacc 60
caactgcaga ctctgggtcg ctactcaggc aacgcccgac tcgcgtacaa cttcgcgctc 120
gcgatgaaga aggaagccca ccagcagtgg cgtgatcggg tagacacact cgtcgccacc 180
ggtgtggacg aaaaagcggc ccgtgaccgg ctcaagggca ctgtcaaggt ccctaaaaag 240
ccgcaggtgt acaaggcctt ccagctactg cgcggcgacg ccgccaaggg catcgaaggt 300 ctcgcccccct ggcacgccga gatccccacg cacgtcttcc agtccgcctg gatcaacgct 360
gaccgtgcct ggcagaactg gatcgactcc taccgcggta cgcgagccgg gcgccgggtg 420
ggctacccca agttcaagaa gaagttccgc agccgcgact ccttccgtct ccatcaaagt 480
tctggacgcc ccgtcctgcg cctggagggc tacaggcgcc tgcacctgtc cggtcaactc 540
gggacggtac gcctgcatgg ttcagccaaa cgcttgcacc gcctggtctc ctctagccag 600
gccaaggtgc agtcggtgac catctcccgt ggcggatccc gctggtacgc caacgtgctg 660
tgcaaggtcg attccaacct ccccggcccc acccgacgcc agcgcgctaa caacagagtt 720
gggctcgact ggggtgtgca ccacctggcc gccttgtcca caccgattga gggcaccact 780
ctcgtggaca accccaaaca cctggccaag gccaccacgc ggttacgcaa ggcacagcgt 840
gccctgtcac gaacgcaaaa gggatcgaag cgacggcaca cggcagcctc cagagtgggc 900
aagcttcacc accaggtagc tgagcaacgc gccacgttcc tgcacgcctt gaccaagcgt 960
ctgtgcacca cattcgcctt cgtggcggtc gaggacttga acgtagcagg catgacccac 1020
tcggctcgcg gcaccaagga caagccggga acgaacgtac gggccaaggc cgggctgaac 1080
cggtctatct tggacgcagc ccctggagag ctacgccgtc agttggaata caagacttcc 1140
tggtacgggt ctcagctcgc gctctgcgat cgctggttcc cctccagcaa gacctgctcg 1200
gcatgtgggt ggcaaaaccc aagcctctct ctgtccgagc gggtgttcgt ctgtgccgag 1260
tgcgggttgc gggtcgaccg tgatctgaac gcggcacgca acatcgccgc tcacgcggaa 1320
gtgccgtctg gcaccggtgc ccctggtaga ggggagtccg tgaacgcccg tggaggtcgt 1380
gtcagtcccc cgctctctcg ggagcgtggg cagcgtccat cgaagcggga agacgctggt 1440
ctcaaagggc cagcgccacc tcggcggagc aatccgccga catccctaac gcgtgtctca 1500
agaacataa 1509

<210> SEQ ID NO 68
<211> LENGTH: 1548
<212> TYPE: DNA
<213> ORGANISM: Streptomyces sp.

<400> SEQUENCE: 68

-continued

```
tcagaacaga gttacttgct cgtaaccggt gggtgggggt gggagcgcca gcggattgct      60
ccgctggggt ggcaccgccg gggcggtgtc ttctcgcttc gtcgcgggat gccttccggc     120
ccgtgggccg gtgggtcttg ttcctgctcg gcgagcgttt tgcgtctccc ctctatcagg     180
ggcgacgggt ggtgcggtgt ctgcgagggc tgcgtgggtg gcgatgttgc gggaggcgtt     240
gaggtcccgg tcgatgcgta gtccgcagcc tgtgcagtgg aaggtcctgt cggcgagtgt     300
gaggcgtgga ttttgccgtc cacacgctga gcaggtcttg ctggagggcc accagcggtc     360
gaggaccgcg aggcgggagc cgtaccagca ggtcttgtag gtgagctggc ggcgcagctc     420
gccgggggcg gtgtcgagga tggagcggtt caggccggct ttggcgcgca cgttgcggct     480
cggggcgtcg atggtgccct tggcgctgcg ggtcatgcca gcgacgtgca ggtcctcgac     540
ggcaacctcg gcgaacccgg tcgcgagtcg cttggtcagc tgatgcagcg tgctttcgcg     600
ccggacggcg acttcgtgat ggagacggcc gacgcgccgg acggccttcg cccttcgctt     660
cgaccccttc tgcgtgcgcg ccagtgcccg ctgcgccttg gccaggcgct gggcagcgcg     720
tcgcaggtgg cgggggttct cgacatacag cgaggcccgg tcataggggt ggaggggttg     780
ggagagggca gcgaggtgct tgacgccgag gtcgacaccg acccgtcccc gtctgcgctg     840
cgcgcgggtg gagcgttgcg gtactgactg gtcgaccttg cacaggacgg aggcgtacca     900
gcggtgcccg cagcgggcca cggtcacgga ctgcacgacg gcccggccgc ggtcgatgag     960
gcgtgcgagg cgtttcccga agtcgtggag gcggacttcg ccgatggtcg gcaggcgcag    1020
ccggcggtag ccagccagcc ggatgccggg cttcttcacg tcgtggtgaa ggcgaaagga    1080
gtcgcgggcg cggcccttct tcttgaaccg cgggtacccg acccgctgcc cggcacgtgc    1140
acctgtgagg gaggagagcc agttcttcca cgcggtgtcc gcgtcggcca tcgccgcctg    1200
gaagcagtag gttttgacct cccaccacca cggacaaggc cggcgcggtc ccagaacgcc    1260
gtcgggaagg tcttgaacgc gggagtcacc cttgaacgag ttcagccgct tctgaatcgt    1320
gggcttcgtc ggcaccggca cccgcacctg cttgcgggcc tgctcctcgg ctactccttc    1380
ggcgaggagg gcgccgacct ggcggcgcca ctcccggtgc gcggcgacct tctcgcccag    1440
ggcccaattg aacgcccacc gcgccgcacc tgcgtgctgc tgcagagccc cgacctgggc    1500
gcgtgtcggg tcgagggtga acttgaaggc gcgcaggacc tccgccat                 1548
```

<210> SEQ ID NO 69
<211> LENGTH: 1215
<212> TYPE: DNA
<213> ORGANISM: Clostridioides difficile

<400> SEQUENCE: 69

```
atggttgcta tgattgcagt taaaaaacta aaattaacta tagttgaaga agaagaaaaa      60
agaaaagaac aatataaatt tataagagat agccaatatg cacaatatca aggacttaat     120
ctagcaatgg gaatattaac aagtgcatat ctagtaagtg gcagagatat aaaatcagac     180
ttatttaaag attctcaaaa aagtttaact aactcaaatg agatatttaa tggaataaac     240
tttggtaaag gtattgatac taaaagttct attacccaaa aagttaaaaa agatttttct     300
acatcattaa aaaatggcct ggctaaagga gagaggggtt ttactaatta taaaagagat     360
tttcctttaa tgactagagg tagagattta aagttctatg aagaagataa ggagttttat     420
ataaagtggg taaataaaat agtttttaag attctaattg gtagaaaaga taaaaacaaa     480
gttgaattaa tacatacttt aaataaagtc ctaaataaag aatataaagt aagccaaagt     540
tcgttacaat ttgataaaaa taataaacta atacttaatc ttacaataga tataccatac     600
```

aaaaaagttg atgaaatagt aaaggataga gtatgtggag ttgatatggg tatagccatt 660
ccaatttatg tagctttaaa tgatgtttca tatgtacgag aaggaatggg aactatagat 720
gaatttatga aacaaagact tcaattccaa tcaagaagaa gaaggcttca acagcaactt 780
aaaaatgtaa atggtggtaa aggtagaaaa gataaattaa agggattaga atctttaaga 840
gaaaaagaaa aaagttgggt taagacctac aatcatgcat taagtaaaag agtagttgaa 900
tttgctaaaa aaaataaatg tgagtatata catttagaaa agttaactaa agatgggttt 960
ggagatagac ttcttagaaa ttggtcttac tatgaacttc aagaaatgat aaaatataaa 1020
gcagatagag ttgggataaa agttaaacat gtaaatcctg cttatacttc tcaaacatgt 1080
tcagagtgtg gtcatgcaga taaagaaaac agggaaacac aggctaaatt taaatgttta 1140
gaatgtggat ttgaagctaa tgcagattat aatgctgcta gaaatatagc aaaaagtgat 1200
aaatttgtaa aataa 1215

<210> SEQ ID NO 70
<211> LENGTH: 1530
<212> TYPE: DNA
<213> ORGANISM: Chloroflexi bacterium

<400> SEQUENCE: 70
atgctgcgcg cctaccgtct tgagctcgaa attgcttctg agagaaaaag gcgcttcctg 60
catcagcatt tcggcgcggc gcgcttcatc tacaactggg cgctacgtct ggtgcgagaa 120
aagggatttg agtttttcaa gcagggaaag ggaggaatcg gcaagcgcat cctctactac 180
tggcgtgagg aacgcgataa agtcgcgccc tggcaccatg aaatcaatgc gcatacattc 240
aacggggccg tactggacct ggggcgtgac ctgaaacatc atagtccgag ccaactgaga 300
ggacgcagcc gaaaccgaca cagaagcgct cacttctatg gcatcaagtt gcagcatatc 360
ggtcggcgca gcataaagct accgggcagc agggcggggg aatttcgtgg gggcgtgtac 420
ctgaaggtca aaaagggtac cgggaagctt tacgaagaca ttcagcaggg tcgcatccgc 480
accattaaac ggataacggt gtcggagaga gccgggcgct attttgcctc ggtgctatgc 540
gaagtgcagg agccggagcc gttgccctgc acgggtcggg tctgtggcct cgacgtagga 600
atttcctcga tcgttacggt agcgttgagc gacggccgta tcataaaaca gggcaatccg 660
cagtggcttg caaaaaagct aagacggcta cgtcgcatac aaaggtcact ggctcgatgc 720
aagacgcatt tcccgcgcga cccagggttc aaaagcctgc acatactgcg ccgtgatggc 780
gaggtgctag ccgtattccc gctgatgtgg cgcaggcaga acggcgaact ggtgccggag 840
gttggcgacg acgtgcgcat actcgccgaa ggcgtggctt cctatgcgct gctttcgcgc 900
gcgcccgatc gcctcgaaaa gccttatcgt ctgaccgtcg gcgggcaggg cagtggcgcc 960
aacattgagc tttcgaccat gcgcatacga caggggcacc ccgtacgcgt cgtgcattta 1020
agcgtcgatc gaagccatac catggagcgc cggcgcaaga cgctcgcccg cgcccactat 1080
cgtgtgtctg tcgcacgaga agatttctgg caccggctgt ccacatggct tgtgcgcaac 1140
tgtgacgtga tcgttgtaga atcgctcagt atcaaaggaa tgctcagaag cggtcgtttt 1200
tcgcgtcaca ttgccgatgc ggcatgggga actttttttcc agatgctcca gtacaagtgt 1260
gagcggtatg ggcgcaccct gctcagggta gagcgttctt atccgagcag caagaagtgc 1320
agccgttgcg gtaagattcg aaaggcattg tcactatcgg aacgcacgta tcggtgtgat 1380
cagtgcggac tgaagataga tcgtgacgag aacgctgcgt tgaacttgat gaaactcggg 1440
ttggctcacc ttacgagccc taccgccaga ctggcgggaa gtgacgccgg aggagatacg 1500
atcgcgggtg gtgccgccgc ctgcacgtag 1530

<210> SEQ ID NO 71
<211> LENGTH: 1530
<212> TYPE: DNA
<213> ORGANISM: Pseudomonas sp.

<400> SEQUENCE: 71
ctacgtgcag gcggcggcac cacccgcgat cgtatctcct ccggcgtcac ttcccgccag 60
tctggcggta gggctcgtaa ggtgagccaa cccgagtttc atcaagttca acgcagcgtt 120
ctcgtcacga tctatcttca gtccgcactg atcacaccga tacgtgcgtt ccgatagtga 180
caatgccttt cgaatcttac cgcaacggct gcacttcttg ctgctcggat aagaacgctc 240
taccctgagc agggtgcgcc cataccgctc acacttgtac tggagcatct ggaaaaaagt 300
tccccatgcc gcatcggcaa tgtgacgcga aaaacgaccg cttctgagca ttcctttgat 360
actgagcgat tctacaacga tcacgtcaca gttgcgcaca agccatgtgg acagccggtg 420
ccagaaatct tctcgtgcga cagacacacg atagtgggcg cgggcgagcg tcttgcgccg 480
gcgctccatg gtatggcttc gatcgacgct taaatgcacg acgcgtacgg ggtgcccctg 540
tcgtatgcgc atggtcgaaa gctcaatgtt ggcgccactg ccctgcccgc cgacggtcag 600
acgataaggc ttttcgaggc gatcgggcgc gcgcgaaagc agcgcatagg aagccacgcc 660
ttcggcgagt atgcgcacgt cgtcgccaac ctccggcacc agttcgccgt tctgcctgcg 720
ccacatcagc gggaatacgg ctagcacctc gccatcacgg cgcagtatgt gcaggctttt 780
gaaccctggg tcgcgcggga aatgcgtctt gcatcgagcc agtgaccttt gtatgcgacg 840
tagccgtctt agcttttttg caagccactg cggattgccc tgttttatga tacggccgtc 900
gctcaacgct accgtaacga tcgaggaaat tcctacgtcg aggccacaga cccgacccgt 960
gcagggcaac ggctccggct cctgcacttc gcatagcacc gaggcaaaat agcgcccggc 1020
tctctccgac accgttatcc gtttaatggt gcggatgcga ccctgctgaa tgtcttcgta 1080
aagcttcccg gtaccctttt tgaccttcag gtacacgccc ccacgaaatt cccccgccct 1140
gctgcccggt agctttatgc tgcgccgacc gatatgctgc aacttgatgc catagaagtg 1200
agcgcttctg tgtcggtttc ggctgcgtcc tctcagttgg ctcggactat gatgtttcag 1260
gtcacgcccc aggtccagta cggccccgtt gaatgtatgc gcattgattt catggtgcca 1320
gggcgcgact ttatcgcgtt cctcacgcca gtagtagagg atgcgcttgc cgattcctcc 1380
ctttccctgc ttgaaaaact caaatccctt ttctcgcacc agacgtagcg cccagttgta 1440
gatgaagcgc gccgcgccga aatgctgatg caggaagcgc ctttttctct cagaagcaat 1500
ttcgagctca agacggtagg cgcgcagcat 1530

<210> SEQ ID NO 72
<211> LENGTH: 1125
<212> TYPE: DNA
<213> ORGANISM: Anoxybacillus flavithermus

<400> SEQUENCE: 72
atgatcgtat ataaagcgta tcggtttcgt atctacccaa atcagaaaca aaaaatactg 60
ataaataaaa cgttcggatg cgcacgtttt gtgtttaatc attttcttgc caaatggaac 120
aacgcataca aagaaacagg aaaaggactt tcttatcagt cttgttctgc acaattgacc 180
aagttgaaaa aagaatacac ttggctaaaa gaagtggaca gtatcgcact tcaaacctcg 240

```
ttgaaacatt tgtcggatgc ttacacacgc tttttccaaa aacaaaacga cagacctcgc    300

tttaagtcaa aaaagaacaa ggtacaatct tatacaacaa agtacacgaa cggaaatatt    360

gcgattgtag gtaacaaaat caaacttccg aaactagggt tcgttcgttt tgccaaaagt    420

cgtgaagtcg aaggacgtat cttatccacg accattcgac gtaatccaag cggaaaatat    480

tttgtatcta ttcttgcaga aacagatgtg caaccactcc ctaaaacaca tacaactgtt    540

ggtatcgaca tgggactaaa gcactttgct attctctcag acggcaccaa gtacgctaat    600

ccgatattct ttcggaagct tgaagaaaaa ttagcaaaag cacaacgtat cctatctagg    660

cgccaaaggg ggagttccaa ttggcataaa cagcgtatga aggtcgctcg tattcatgag    720

agtatcgtga atgccagaaa cgactatttg cataaaatct ccaccgagat cgtcaaaaac    780

cacgacatca tcgggatgga agatttgtca gtcagcaaca tgctcaaaaa cgacaaacta    840

gccaaggcga ttagcgaagc gtcatgggca acgttcgaag cgatgatcgc gtacaaagcc    900

aaatggtatg ggaaacaatt gattgtggtg gcgaaaaact ttccatccag tcagttatgt    960

tcctgctgcg gatatcaaaa caaggatgtg aaacatcttg ctttacgtga gtgggaatgt   1020

ccaaattgtc acactcatca tgaccgagat gtaaatgcaa gtataaatat taaaaacgaa   1080

gccgttcggc ttctaaccgc aggaactgcg gggctagcct actaa                   1125
```

<210> SEQ ID NO 73
<211> LENGTH: 1197
<212> TYPE: DNA
<213> ORGANISM: Cellulosilyticum ruminicola

<400> SEQUENCE: 73

```
atgatagcag tacgtaaatt gaagattatg gttttgtgtg atgatgaaag caagaaaaat     60

gagcaatata agtttttaag agatagccaa tatgctcaat atttagggtt aaatagagca    120

atgtcatttt tagcaaaaga atatttgagt ggagataaag agcgatttaa agaggccaag    180

aaaaagttaa ctaatacgtg tgagtgttat caaaatataa attttgggac aggtattgac    240

agtaaatcac agattactca aaaagtaaaa aaggatttgc aagcagatat aaaaaaatgga    300

ttagctagag gagaacgaag tattcgtaat tatagaagga catttccatt aattactaga    360

ggtagagatt taaagttttc ttacaatggt gatgagatta ttattaaatg ggtaaataaa    420

atctatttta aagtgctaat aggaagaaag gataaaaact atttagagct gatgcataca    480

ctagaaaaaa ttattaatgg tgagtataag gtatgtacat cttcaattca aattgataag    540

aaactcatat taaatttaac tttagagatt ccagataaag ttaagaaaga atttcaggag    600

aatagagtgc tcggcgtaga tttggggatt aaatttccag catatgcttg tgttagtgat    660

aatacttatg taagacgtag ttttggtagc attgatgaat ttttaaaggt aagaatacaa    720

tttgataaaa gaagaaaacg tatacaacaa cagcttcaaa atgtaaaagg aggaaaagga    780

agaaaggaca aattacaagc attagataga atgagagatt gtgaaagaaa atgggtaaga    840

aattataatc atgccttatc aaaaagaatt atcgactttg cttttagaaa taaatgtgga    900

attattcact tagaaaaact tgaaaaagat ggatttaaaa ataagctatt aagaaattgg    960

agttattatg aactacaaga tatgataggt tataaggctg aaagagaagg catagtggtt   1020

aagtatgtag aaccagcata tacatcacag acatgtagta aatgtggata tgttgataga   1080

gaaaatagac cttctcaaga gcatttctta tgtaaggagt gtgggtttga aattaatgca   1140

gatcataatg ccgctattaa tattgcaaga agtaataaag tgattgtaga taaataa      1197
```

<210> SEQ ID NO 74
<211> LENGTH: 1932
<212> TYPE: DNA
<213> ORGANISM: Anabaena variabilis

<400> SEQUENCE: 74
atgagtgtta ttactatcca atgtcgatta atagccagcg aagctacccg cagctatctg 60
tggcaattga tggcacagaa aaatacacct ttgattaacg aactaattga acagctagga 120
atacatcctg agatagagca gtggttgaaa aagggcaagc taccagatgg agtagtcaaa 180
ccactgtgcg actcactcat tacgcaagaa tcttttgcta atcaacccaa acgttttaat 240
aaatctgcta ttgaggtagt tgagtatatt tacaagtcat ggctagcttt acagaaagag 300
cgacaacaaa caatagatag aaaagaacat tggctcaaga tgctcaaaag cgatgtggaa 360
ttggagcaag agagtaaatg tactttagat gctattcgct ctcaagctac taaaattctg 420
ccgaaatatc ttgctcaatc cgaacaaaat aataatcaga ctcagagtca aaacaagaaa 480
aagagtaaaa aaagtaaaac taaaaacgag aactctacat tatttgatat tttattcaaa 540
gcttatgaca aagcgaaaaa tccccttaat cgatgcactc ttgcgtattt gctcaaaaat 600
aactgtcagg ttagccaaaa agacgaagac ccaaatcagt atgctctacg ccgcagtaag 660
aaagagaaag aaattgaacg tctcaaaaaa caactacaat ctaggaaacc caatggtcgt 720
gatttgacag gaagagagtg gcaacaaact ctcataatgg caacttcatc tgttcctgaa 780
agtaacgatg aagctaatat ttggcagaaa cgtcttttaa aaaaagatat ttcactccca 840
ttcccaattc gattcagaac taacgaagac ctaatttggt caaaaaatga agaaggacgt 900
atttgtgtta gcttctcagg tgaaggattg aatgatcaca tctttgaaat atactgcggc 960
aatagacaaa ttcactggtt tcaaagattt ttagaagatc agaacatcaa aaacgataat 1020
aatgaccagc attcatctgc tctgttcact ttacgttcgg caattttagc gtggcaagaa 1080
aataaacaac ataaagaaaa tagcctccct tggaatactc gtcgtttaac tctttattgc 1140
acccttgata cacgcttgtg gacaactgac ggtactgaga aggtaaagca agagaaagta 1200
gacgaattta ctcaacaatt ggccaacatg gaacagaaag aaaacctcaa tcagaatcag 1260
caaaattatg tcaaacgcct gcaatcaaca ttaaataaac tcaacaatgc ttacccacgt 1320
cataatcatg atttgtatca gggtaaacca tcaattctag ttggtgtgag tttaggttta 1380
gaaaagcctg caacattagc tattgtggac agttccacaa atatagttct tgcatatcgt 1440
agtatcaaac agctacttgg cgataattac aagttgctga accgccagcg acagcagcag 1500
caacgtaact ctcatgaacg ccacaaagct caaaaaagca atatgccaaa taagttatca 1560
gaatctgatt taggaaagta cattgataac ttactagcac aagcaattat cgcattagct 1620
aaaaattacc aagctggcag tattgttcta ccgacaatga aaaatgtacg ggagagcatt 1680
caaagtgaaa tagaagctag ggcagttaaa agatgtccta attacaagga aggtcagcaa 1740
cagtatgcta aacagtaccg ccagagcatt catcgttgga gttacaacag attgatgcag 1800
tttattcaga gtcaagcagt taaggcaaac atttctatag agcaagggcc acaaccgatt 1860
cgaggtagtt ctcaagaaaa agcgcgagat ttagcgatcg cagcttacta tttacgccaa 1920
aataaatctt aa 1932

<210> SEQ ID NO 75
<211> LENGTH: 1920
<212> TYPE: DNA
<213> ORGANISM: Nostoc punctiforme

<400> SEQUENCE: 75
tcaacttcgc ctagctagcc gatcatggta agcagaaagt gctaattcct ttgcttgttc 60
atgagggcta cctctaacag gttgttttcc ctcttcaatc acaattcctg cctgactacc 120
tttactttga atactctgta ttaatctgcc atagctccac ttgtgaacat taactcggta 180
ttgtttggcg tatttttgct gaacttctac ggagcctgga cattttgctt cggctatagc 240
ttgaatttca ctttgaacaa tctctcgcat atcccctagc ttaggcaaaa ctatattgcc 300
agctttatag gtttgtgcga tcgcaataat ttctttagcc aataatctgt ctacatactg 360
ccctaactca gatgtaccaa attgattggg agagaagctt ttttgtgctt tgtggcgttc 420
gtgggatgat gatcgctgtt gtcgtctttg ccgattcaga agttcgtaat tgtcgccaag 480
taactggcgg atactccggt aagctagaac tttacctgcg atcgcatcta ctacagctac 540
ggtggcaggt tttctagtc ccaggcttac tccaaccaaa atgtgtgatt gaccttggta 600
aaggggttga ctaggacgct caaagctatt attcattcga ttaagcgttg attctttacg 660
ttgaataaaa gctttctgtg tatcctttag gtcacttttt tctttcatct tcgtgatgag 720
tttgctaatt tcttctgctt tctcttggcg aacctgttct gttccgtcag cagtccatag 780
gcgattgtca acacagcagt agaggttcaa tcggttaagg ttccaaggtt cgctcttacc 840
ctctccttct tgccaaacta ggtgaccatt tctgagagtg aataagccac tagaatactg 900
gcttttactt tggcgtttag tttgttgatc ttctaggaaa cgttgaaacc agtgaagttg 960
gcgattgtcg cagtatacct caaagctaag atcgctcaat ccattgaagt gaacacacag 1020
cctacctttt tgattctttg accaaaccat atcctcgttc gtttcaaaaa caaggggaa 1080 tggaagagaa cttggtcgag ttaatagaat atcctgccag cgcttggctt cggcgttatc 1140
ttcaggaaag gtggttgtag cagtgaagag tgtctctaac catttacgat tggtcaaatc 1200
tcgaccttta ggcatccgac ttattaactt ttcggtaagc ctttgaattt ggatttcaac 1260
ttgacgacga cgtttagcaa atttttctga atcttcttct ttatcgctaa gtttgcagcc 1320
atttttcaat aagtagctga tggcgctgcg gctaaggatg tcttctgtct cttggtaagc 1380
ttcaaataat ttattggata aactgcggtc agaactagat gacgaggatt ttttagcctc 1440
cttgcccttt tttgttttgg gttgagagct atctgagtca gatgttggca tagcttttgc 1500
caaaatttca gaggctttgg tacgaatagc cccatacta gaaccgctag tttccacaag 1560
ttcaacatca ctgttgagca tttctagcca gcgcattttg ccgtctagct gttgctgtag 1620
acgtttttgt atagccagcc aagacttgta gatgtagtcc acaatatgaa tcgccgacat 1680
atataaacgg ctaggttgac ctacaaagcg agggtcagtc ttgagaggtt ggcacagttg 1740
actaacaaca gttgttggaa gcttaccttg ttgtcgccaa ttctcgaagt ctgggtgttt 1800
accaagttgt tcaattagtt cattaattaa gggtgtgttt aaagttgcca tcaatttcca 1860
cagtttttgg cgggttgatt cactggcaat aagacggcac tggatagtaa tctgactcat 1920

<210> SEQ ID NO 76
<211> LENGTH: 1296
<212> TYPE: DNA
<213> ORGANISM: Sulfolobus islandicus

<400> SEQUENCE: 76
gtgtcgaaga acttaaggct taatgacttt caaccacaag aggaatacgt ttacctaact 60
tactccctga agaataataa gaaggtgaag agcaagatat tactagagaa ctataaacac 120

```
ctactacaga aggctttaga ctggttatgg gagaggacta agatagagag gaaggaggtc    180
aagaagggca agaaaatttt cgctaaggtt aaagtaacct tgccaaagaa aaaggaagtt    240
tacaaggtgt tgagggatga gttagagaag gttaacaatc tagcttcaca ttacgttgac    300
aaagcaataa atgatgctta ctcaatcttg gatagttgga ggaggagggc tgaaaaagga    360
caagcgtcat taaggaaacc tagattgaag aaggtttacg ttagggtaaa gtcgacactt    420
agaaaggttg agggtgagag tgtaagggtt acagtaagac tttacgaata cgtcaccttc    480
tcatggtctc acaaatggtt ttcaaggagg gttgaagggc ttgagttggg tgagccaata    540
attaaggagg atagagttca cctaccattc cgttacagat tgccttggtt ttcaccccta    600
gatttcctag caattgatag caacctttac acattggacg cttatgatgg ggagaagttt    660
gttacatttt ccttgaagga gttgtacagt ctaaaattcg gtatggagtt gaagaggagt    720
aaaatacaat cttttgcttc taaacacggt aggaagggaa aggtattgtt gaggaggtac    780
tcccaccgtg aaaggaaccg tgtgctggat tatgttcaca agttcgtgaa taagttgctg    840
gagacgtatc ctctcactat gtttgctgtt gagaagttga ataagcagtc aatgttccaa    900
gacgctgatg acaagctgtc taagaggatt tcaaggactg tgtggaggac tatacaccgt    960
gtggtaaagt acaaggctcc cctttatggt tctttcgtta aggaggtgag cccacatctc   1020
acttccaagt cctgccccag atgtggatgg gtttcccgaa aggtcggcag gacttttcac   1080
tgcgagaggt gcgggttcac tctggatagg caattgaacg catttctcaa tatttacctc   1140
aagatgtgcg ggttccccta catccgtgat attccgcggg tgtgggtcgg ggttatcccg   1200
ctaaaggggc ggaggggtat gaacggggca atgccccgtg actctgttga agcccaaggg   1260
ctgaggattg gatacaaatt catgaaaatt caatga                             1296
```

<210> SEQ ID NO 77
<211> LENGTH: 1296
<212> TYPE: DNA
<213> ORGANISM: Ammonifex degensii

<400> SEQUENCE: 77

```
atgaagcaca ccaacgtcgt ccgggttctt ccagataaac agcagaagca aatcctggaa     60
atcatcgggg accgctgcgc cgccctctac aacgccgtcc agtacaggtg caggcaggcg    120
ttcttcaagg gagaacctgt gccttcctac gccgccttgt gctccgagtt cgaggagcac    180
ccggcctaca aagccctgcc gtcagacatc gggcaggagg tcatcaagaa ggcgaggaag    240
gcgtgggact cctacttcgc gtgcctgaga ctgtaccgga aaggcaagct gaaggagcca    300
ccgcgcgtgc ccgggtactg gaaggaccgc cgcacgggga agaggctggt cgggccgatc    360
ccggtcaagt ccccgcggtc ctactccctg gacgccagga cgctttccct gaccctgccc    420
gcagacctgc gggaaaagcg tggagatcgc ctggttctgc gcacaaaggg tctcttacgc    480
ttccacggcc aacctaagac cctggagctc aggtacgacc ctgtgagaaa gcgctggtat    540
gcccaccagg tggtggaggt gcctgagccg gctcgacctg cccggcctga aaagcacgcc    600
gccgtcgacc tgggcgcgag ggtcctggtc gccctggccg tagagggact cggccgccag    660
ctcctcttct ccgcccggga agtcatcaag gacttcctct actggaccaa tcagatcgca    720
ggggagcagt caaagctcaa ccggacggga agaaagacct ccaggaagct gaggaggttt    780
tatcagcttc gcgcccgcag gctcaggcac gcctttgtcg ctttggccgc ggaagttgcc    840
cgcattctca agcggcaccg ggtgaccacg cttttcctcg aagacctgac gggcgtccgg    900
gaggacatgg acttcgggcc gaaaaacgtc ctggtgcaca acttctgggc cttcaggatg    960
```

ttgaggaacc tcatcgaggc tgcctgtgcc cgggccggga taaaggtcgt ccccgtggag 1020
ccgcgcggca cctcttcccg gtgcgccgtc tgcgggcatc ccgtcaggcg gcccgtgcgg 1080
cataaagcgg tgtgcgagaa gtgcggtaag ctctggcacg cagacgccaa cgcggcgtta 1140
aacatactcc tccagggctc ctcgaagggg cacggggcgg aggccacgcc ccagaagccg 1200
cttgcctacc ggtggaacag acaccggtgg gtgagccgct tcgaacctgc cgccggtacg 1260
cttaaagcgg cgagcggcag ccggacggcg gcttaa 1296

<210> SEQ ID NO 78
<211> LENGTH: 1611
<212> TYPE: DNA
<213> ORGANISM: Meiothermus silvanus

<400> SEQUENCE: 78
ctagacctgc gcctgcacct cttgcgcgcg gcggagcagg ttgcgagcgg cgttctcgtc 60
ctggtcgtag aagcgctcac aggtggggca gtacagccgc aattccttgg ccgggtcgcc 120
caccagagcg cccccacaag cgtggcaatc ggtggtggtg tgcgccggat tgagcttcct 180
gacgggtttt ccgcgctggg cgaaggcgtt gactagcgcg tcccggagcg tcgagggcga 240
ggcgatggtg cggtagcggc gggccgcgtc gggcaggtcc gagccgccct ggtcgagttc 300
ggctgccgcg cggaggttga agtcctccac gatgagtgcg tcgtactgcc gggccagcgt 360
cgctgccagc acccgatact gctccctgcg gcgcaggatc atctgctcgc gcaggttggc 420
ctcgtactgc cagaggtggc ggtcgcgctt gtgccagccc tccaggaggc cataagcggc 480
ctcgtcggca tggacacgct cggactgcca ccggcggaag agcgcggcga aacgggcagg 540
gctgcgccac tggggcaggg ttttggtctc ctccgcgagc cagtcgggca ggggcgcggg 600
cggtgcttcg agccaggccg cgagggcctc cttgagcgcg ttgaggtgct ggtcgcggat 660
cgagcgcaaa tcctcaacct tgctgaattg cttgaggtcg ccctcgctaa gggcgatctc 720
gccccccgcc ccgtcctccc cgacccagaa gcccgccctc aggccgcctt ccaccctgcg 780
ccagccgagg tccaccgcta ccgctccccg gcccgtgggc gaggccaccg gagggccctc 840
tacctccacg acgacgctca ccgtccagcg cagccggtca gctactcggt gccagtgcag 900
gctcacttcc cggcaaaccc cgtccggcag ctcccggtgc aggtagaccg gcaccgtgat 960
ccacagcggt tgccgctcca ccgagcgcac cctgaatttc atcagcaccc gctgatgctt 1020
gcgccgcgta gcccggtcgc ggtagatgat tggatcgggc agcgggagct gcacccgcgt 1080
gtcgctgccg atctcgcgca tcggcagccc ctcggtgtac agcacggcca gccgcccttc 1140
gtgggggctg tagcggcgaa agcggagctc gggagactgc cgggccttgt cgaaggcccg 1200
ctccacgtcc aggtagttgc tggaatacag ccccttcgcc ccgaagctcc gccgcagggc 1260
gttgcgctcc tcgcgctggc gggattgcag ttccagcagg cgcggatggc cgtacagggc 1320
cttttgccgc tctcgggccg cgacgtactc gggatgtttt cttatcccct tctcccccgc 1380
agccttcagc cgctcgtaga cctggttcgg gctctcgagg cccgactccg ccgccaggtt 1440
agcgagcaag gcggtccgct cctcgcgctg gcgcaactcc atctccacca gggcgttgta 1500
gtagtccgtc cgcaagcggt gctgttccag caccgcttcc atcccctcct gcggggcgtc 1560
cgcgccgaac tggtaggctt ttacgtgtcg ggcttttttg ccaaaaggca t 1611

<210> SEQ ID NO 79
<211> LENGTH: 1143
<212> TYPE: DNA

<213> ORGANISM: Candidatus Nitrososphaera gargensis

<400> SEQUENCE: 79

```
gtgtacaaaa aaatgctcaa ctacaagttc cgtctctatc caacaacgaa agagcaggag     60
cttctgttag agcagacact tgattgctgc aggtgggtgt acaactactt tcttgacaaa    120
aacatgtcag aatatgacat gaactatatt ctgactgaat taaaagagca gcacccttgg    180
cttcacaaat actaccactc taaaatgttg cagatggtag caaagcaggt tgcagcagct    240
agaaaggtcg ctgttggcag gctttcgtac agaaaggatg aagatttcaa cgcttttaca    300
tacaaccagt ctggctttcg gattgagaaa gacaagctcg tgctttcgaa gataggtagt    360
ataaagattg tactccatcg tcaacctgtc aatgtcaagc aggtcactgt atgtcgcagt    420
aagacgggaa agaagtggta cgcagttgta gcctgcgatg tactgcgcag gctgtattca    480
acgataatca aatacacaaa accagcagta ggcattgatg taggtataac aaagttctgc    540
cacgactctg acaaccatgc agtggaaaat ccgcagtttc tgaccaagat gctaaaacca    600
ttgagaaaag ctcacagaag agtatcaaga aggcagatag gcagcaacaa ccgagagaaa    660
gcaaagcata tgttagccag attgtacgaa cgcatccata ataaacgcca cgatttccta    720
cacaagaaat cggcgtacta tgccagccac tacgacctga tattcctaga gcgcttgaaa    780
gtattgaacc tgaccaagaa ccacaggctt gcacgcaaaa tcctggacgc aagctggtct    840
gcttttaaaa atatgctgca gtacaaggct aacagagtga tagaggtaga gcctgcatat    900
tcctcggttg actgctcaag atgtggacac cctgttccaa agtcacttgc agtacgtacc    960
catgcatgtc aaaaatgtgg agcagtactt gacagggact acaacgcttc tcttaacatc   1020
ctccagcgag ggttagaatc gctgatgatg ttgctaccgg tggaacgccg ggaagtcacg   1080
cctgtagaga tcgcacagca acggtcgctg aagcaggaag cccacgaatt tattcgtggg   1140
tag                                                                 1143
```

<210> SEQ ID NO 80
<211> LENGTH: 1101
<212> TYPE: DNA
<213> ORGANISM: Campylobacter fetus

<400> SEQUENCE: 80

```
ctagcctact tttgtaggtc ttacaaattc tccactaaga gttgatgccc caactctaaa     60
aatatttaaa ctagcattat aatctctgtc tatttttgtg ttgcatttag gacaatcaaa    120
tactctatct tttaggctta aatctttttt gacatatcca caacaactac aagttttaga    180
actaggatag aatttatcaa tcttaacaac atttgttttt gttgctaaga tatttataaa    240
ttcactatat gctaaatcat ttatttttct accccaaatt ttagccatag cctttaaatt    300
caagtcttca ataaaaacat tatcatattt cttagctaaa atatttgcaa gtttaaaaaa    360
ataatccttt ctttgattag ctagttttat atgaaatttt gctaattcta atttagcctt    420
ttttctatta tttgagccaa ttttttttga gctaagtttt ctttgtttgg cttttaattc    480
ttttaaagat ttgagataaa ttaaaggcga ttttatagtc atattatcac taagtgttag    540
aaatgtttta agtccaaagt ctatacccac gcttttacct gttgtgatat tttctttatc    600
ctttgttttt aagctaacac agatataaaa agagcctaaa ttatctctct taatggttat    660
agtttttatt ttatcatcag catttattgt ttgatttttg ctaaatttaa agctataacc    720
attaaaagag ataacattat cttttagttt ataacccaca cttcctttta gagtgaaaga    780
tttgtattta atacgctttt taaagctagg tagtcctcca agtcttttaa agaatttttt    840
```

atacgcattg tctatccttt cagtgatttg ttggattgct tgtgagccta atttattcca 900
atgtttatat ttatcaagtt ttttaagttt agtgagatgt ttttgaagtc tagctttatt 960
aaggcttttg tggtagagtt tataatacct tttatgcaaa gctatacaat gattatagac 1020
gctacaagct atgtttataa gctcatctat atgttttgtt tttttggttt tataaagctt 1080
atatttgtag gttagcaaca t 1101

<210> SEQ ID NO 81
<211> LENGTH: 1254
<212> TYPE: DNA
<213> ORGANISM: Methanosarcina vacuolata

<400> SEQUENCE: 81
tcaggaacag ggcaaaaatt ccctcttttc gttcatctga gctattttag aactggattg 60
tttgaaagac agtatttcat gccttttttgg atgtaacccg acatcctcta tcccgtctgc 120
aaaagcttcc gggattgcct ttttgattat attgagcgcc ccgttcaaat ctgcgtttat 180
gatagttccg ctggcagacc tgaactgtcc tctgtttatc cgttttccta cgtatgactc 240
gtggtgtttc acaggttcgt tatccaggaa actgcatttc gaggtatgac tttcctcatt 300
gactatgacg tcaattccga cttcttcggc cttgtacttg atcatctgaa tcagcgtggc 360
aaacgggatg ttcacgaagt tctggttatt tcgcttcccg tggttgattt tctgtttcca 420
gtcgggattg tttccgatca cgatcgtttt gacctcgttt gatctggcat actcgataac 480
gtccctgctc aacttatgga agtagtcttt gatcttgtta ttccgtttcc agtcaagttt 540
agcaagcttc ttgccgtatt tgagaccgga cttatcgtaa acgctctgga cccttgcctt 600
ctccttattg tagaactggt tcatgctttt cacaacgccg cccttaacga caatcgggtc 660
tgccccgaag ttgtttccga tagttacgac gttagataca cctaaatcaa ttccgattac 720
ccgcgtggaa tccagctcac agggcgtgac ttccttctcg taaacgatct cacagacgta 780
gttgaaccgc ctcgggatta ttcgtacctg gcacagcttt acgtccttca gccttgtttt 840
aaattccagg tcgatctttc cggggaattt caggacacca tctttgattt tgcactgctg 900
attcgtgaag accaaaatgt tctccccgtc tttcggcttg tactttggtg ggttcggctc 960
accctgaaac ttcgaatgat cctttttcca ttccttgatg gccctgaaaa aagacttcca 1020
attcttatcg aggagtttta agatctgctg agatgtttgt gcagggagct gtttgtactc 1080
atctgtgttt ttcaacgttg agcataactc agagtaccta atccatttct ggctacgttt 1140
gagttcctgc tggatccgat aattcgctgc gttgtacagg ttttttgaag cgtggcacgt 1200
agctgatatg gactctgatt tgaattgtat ctgctcagtc cgtgtgactg tcat 1254

<210> SEQ ID NO 82
<211> LENGTH: 1248
<212> TYPE: DNA
<213> ORGANISM: Geobacillus sp.

<400> SEQUENCE: 82
tcaagcaatc cttattcttt gaggcgtgtc cacttcgccg ctagagcata agacactcag 60
gtctacagct ttacttttct ttaagatgtt taatgcgcca ttgacatcag cattaattag 120
tttgccagac tttgttcgat acaagccgcg cttaatacgt ttgccgctga acttatattc 180
ttttggattg tcggcattat attcaggaat ctcatcgccg tcaaaaaagc tggcttgaga 240
cgtataggat tcttcctgtt tcaagaattc aatgccgtaa aattcacaaa gatattctag 300

-continued

```
tttttctttt atgttaccga gaggaatatt gacaaagttt tgatttgtct tttttcctag    360

attcatattg cgttgccatg tttccgcata gccaatgaca agtttgccaa tttgattttc    420

aatacagtag ttaatgatgt aacggcaagt cttgttgata taatcattca ctttattatt    480

gcgattcata gcaagcaaag cctgtttacg agtggtgcct ttgatttttt gcttatcttt    540

tatgctttga agtctggcat tttctttgtt aaaccattga tttatacttt ttaatctccg    600

cccatcaatg ataaatgatc tgccgtctga tgtgacacaa gtggcaagat tgtttaatcc    660

taaatcaatt gccagtgctt tttggtcgtt taattctctt tgatcttcag gcatttcata    720

tttgtactga atctcaaaga acctggcatg atgcttagga atgatttcaa tctgcttaat    780

ctttttgtcc agtaacacag gcggaatcgt tatcgtgata ggcttgtgag tctttttaaa    840

taggcgagaa tacggtatcg tgaatttgtt gccgtctata cgaatctggc caatgatcag    900

tgaatgaaag ccatcttttt taagatattt tggaatactg atagccttgt ggtcatattt    960

tccttgtttg gcaagactga tcaaaccaaa gaaagatgta aaggcttcat tgaccttttt   1020

taaaatttgc tgtgccatgt tgctgtttaa cagcttatag ttttcgttag ttttggcaag   1080

atgataattt ttctcataat taagaaattc cttgtgttca aaatagtatt gtctgacatt   1140

gtacaatccg acgttgtaca tgttcttggc aatatggcac agttctcgaa gagtcaagta   1200

ttcttctttg gtcaaaccat ttagctgttg tttgatacaa aaatacat                1248
```

<210> SEQ ID NO 83
<211> LENGTH: 1428
<212> TYPE: DNA
<213> ORGANISM: Clostridium ultunense

<400> SEQUENCE: 83

```
gtgcaacaga cggtcaagca gaaaagtctg ccgctgaaca aggataagtg gatcaaaatc     60

gcacaaacaa tagaagccta cgcccgccag aaggacacgt ttctggttaa atacgggcac    120

gtccaatacc tgcatcactt aggtgcaaag cgcagactgc gggacgagct ggttgcagcc    180

ggtttcacca gccctttcgg gctacaggcc cgccagtgga agctggcttt ggacgacgcc    240

ctgttcaccc tggagaggca gtgggaggcc gccatcgtcg gggtcaaaga gcggctttac    300

cgtcatgaag gcctgtctga cgaagaaaag cactacgcct tctggctttt atatagagat    360

gaaaagcgcg gccgggattg gaagaggctc caggcgattt tcactcatga agacgtggtt    420

aatcaaaaaa taagtttgga ctcagggggc cgtgccaagg tgagaaatta tctgaagcgc    480

gcctttcgcc gcatcttagg cacaaggcct tgcgtcaaaa aagcacgcag tttcgtggta    540

gaccagcaaa tgtaccgggt atttaacacg ggaaagcggc agtatatcgc cgtagcgaca    600

ttaacccccg gcgaaagggc ggtcataccc ttgactggga tacacgccat gcgaggcaac    660

ttgcgggtag tcctcttgcc ggacgaacaa gcggtggaaa tccacctgag cagggaaccg    720

cgaatccgcc cgtccggcga ggaagaagcc ggcatcgacc tgggcgtgac ggaagtattt    780

accgatgata ctggcaaaaa gtaccggccc gagtacggcg aagccctgca ggagatgtcc    840

gaccatattt tggacaagag ccggaaacgc ggaaaactct gggccttgcg ccggaaattc    900

ctggagcaag atcccaacaa agcccggcgg attctcaggc acaacctcgg cctgatcaag    960

cagacgaaaa ggaataaaag ataccggacc aggtgcgaaa acgaaatcaa ccgggcgttt   1020

aacgaactct acaaagaacg ctggccgcag atcatcgctt acgaagacct cgcccacctg   1080

cgcggcaaag ccaaaagcaa aggcctctcc cgcaaggtga gcggctggca gcgaaacatc   1140

attaaggagc gccgggaata caagaactac gtctactccg tcaccgaccc cggaccgcaa   1200
```

aacgcggcct attccagcca ggagtgcccg cagtgcgggt gggttgacgc caagaatcgc 1260
aatggagaca ttttcaaatg ccgccaatgc ggttttactg ccgatgctga ccaggtagca 1320
gccatgaacc tgaaaaaaag gctgcacgac gaagagataa cccgttacac cccgtataaa 1380
agagtgaaag aaatattgct ccagcgttat tatcaacaag ccaattaa 1428

<210> SEQ ID NO 84
<211> LENGTH: 1494
<212> TYPE: DNA
<213> ORGANISM: Clostridium novyi

<400> SEQUENCE: 84
atgattacag ttaggaaaat aaagttaaca ataatgggag ataaagatac aagaaatagt 60
caatacaaat ggattagaga tgaacaatac aatcagtaca gagctttaaa tatgggtatg 120
acttatttag ctgtaaatga tattttatat atgaatgaaa gcggattaga aattcgaact 180
attaaagatt taaaagattg tgaaaaagat attgataaaa ataaaaaaga aattgaaaag 240
ttaactgcaa ggctagagaa ggaacaaaat aagaaaaatt cctcatcaga aaaattagat 300
gagattaaat ataaaataag tttagtagaa aacaaaattg aagattataa attaaaaata 360
gttgagttaa ataaaattat tgaagaaaca caaaaagaaa gaatggatat acaaaaagaa 420
tttaaagaaa aatatgtaga tgatctttat caagttttag ataaaatacc ctttaagcat 480
ttagacaata aaagtctagt tactcaaaga ataaaagctg atataaagtc agataaaagt 540
aatggactat taaaaggtga aagaagtatt aggaactaca agagaaactt tcctttaatg 600
actagaggac gagatttaaa atttaaatat gatgataatg atgatattga aataaagtgg 660
atggaaggaa ttaaatttaa agttattttg ggaaatagaa taaaaaattc cttagagctt 720
agacacactt tacataaagt tatagaggga aaatataaaa tatgtgatag tagtttgcaa 780
tttgataaaa ataataatct tatacttaat ttaactctag acattcctat tgatattgta 840
aataaaaaag tttcaggaag agttgtagga gtagatttag gattaaagat accagcatat 900
tgtgcattaa atgatgttga atatattaaa aaatctatag gacgtataga tgatttcttg 960
aaagttagaa ctcaaatgca gagtagaaga agaagacttc aaattgcaat acaaagtgct 1020
aaaggtggaa aaggtagggt gaataaactt caagccttgg agagatttgc tgaaaaggag 1080
aagaattttg caaagacata taatcatttt ttaagttcta atatagttaa atttgcagtt 1140
agcaatcagg ccgaacaaat taatatggag ttattaagtt taaaagaaac tcaaaataag 1200
tcaatactaa gaaattggag ttattatcaa cttcaaacaa tgattgagta taaagcccaa 1260
cgtgaaggga ttaaagttaa gtacatagat ccttatcata catcacaaac atgtagtaaa 1320
tgtggtaatt atgaagaagg acaaagagaa tctcaagctg attttatatg caaaaaatgt 1380
ggttataaag ttaatgctga ttataatgca gctagaaata tcgctatgag taataaatat 1440
ataacaaaaa aagaagaaag taagtattac aaaattaaag aaagtatggt ataa 1494

<210> SEQ ID NO 85
<211> LENGTH: 1491
<212> TYPE: DNA
<213> ORGANISM: Bacillus cereus

<400> SEQUENCE: 85
atgattttaa ctagaaaaat taagttggtt attgtatcag agaatcggga agagggatat 60
aatttaatcc gtactgagat aagagaacag cataaagcac ttaatttagc ctataatcat 120

```
ttgtattttg aacataatgc tatacaaaaa ttgaagcaga atgacgagga ctacaaacag    180

aaaagaaata agctacaaga attaattaac aagaaatatg aggaacatca aaaggcaaaa    240

aacttagaga agaaagaagc actacgagaa gcgtacaata acaagaaaca ggaactatat    300

aattttgaaa aggaatataa tgagaaagca cgtcaaactt atcaacaggt agttgggttt    360

acacaacaaa cgagagtacg aaatttaatt aaccgtgagt gtaatttaat gagtgataca    420

aaggatggca ttacaagtaa ggtaacacaa gactataaaa atgattgtaa agcgggcttg    480

ttaattggga agcgttcgct acggaattat aagaaagata atcctttact tgttagaggc    540

agaagcttga agttttacaa ggaggatggg gattatttta ttaagtggaa caagggaacg    600

atctttaaat gtattttgca tattaggaaa aagaatgtag tggaattaca aagcgtccta    660

gaaaatgtcc ttctgggtgc ttataaggtt tgtgatagta gtatcggttt caacaacaag    720

gatatgatat tgaatctatc attaaatatc ccagataaag aaacacaagg ctatatccca    780

ggtcgagttg ttggagttga tttaggatta aaaattccag cttacttatc attaagtgat    840

aaggtgtacg tcagaaaagg gataggaagt atagatgact tcttgcgtgt gagaacacaa    900

atgcaaaagc gtagacgccg attacaaaaa tctttagcag ctgtaaaagg tggaaaagga    960

agagaaaaga aattaaaagc gttagaccat ctaaaaggga aagaagctaa ctttgctaaa   1020

acctataacc atttcttgag tacacaaatt gtaacatttg cagtcaaaaa tcaagctggt   1080

cagattaata tggagttcct agaatttgat aagatgaaaa ataagtcttt attaagaaat   1140

tggtcttatt atcaactgca aatcatggtt gaatataaag caaaacgaga gggaataata   1200

ataaaatacg ttgatgctta ccttacaagc caaacttgta gtaaatgtga tcattacgaa   1260

gacggacaac gagaaaaaca ggaaaatttt atgtgtaaaa attgtggttt agaagtaaac   1320

gctgattaca acgcttcaca gaatatagcg aaaagcacga gttatatatc agatagtaca   1380

gagagtgagt atcataagaa aaagcaacaa gtgttaaagg aaatattagg agagaacgac   1440

ataatgaatg aacagctatc attgtttaat aattgcgatg atattgctta g            1491
```

<210> SEQ ID NO 86
<211> LENGTH: 1224
<212> TYPE: DNA
<213> ORGANISM: Methylobacter whittenburyi

<400> SEQUENCE: 86

```
tcatgtccac gtccgtaaat tccggcctat atcgccgtac tgtttaaaac gcccttttt      60

caggatgttt ttggctgcat tgatgtcagc attttcaata tgcccacact caacacaggc    120

aaaaatagcc tgagtctttc tattttcctt gcttacataa ccacaagccg agcaagtttg    180

cgaggtataa gcaggattta tcagcgtcaa cacgctacca tgacgcactg ttttatattc    240

gagctgtcgt ctaaactcaa acaatccttg attcaataac gacctgttca agcctgattt    300

ttgctttacc tgcttaccgg gctcttcagc tgttcctttt gctgatttag tcatgttcct    360

tagcttcaag tcttccagtg caatcattcc atatttttta gatagctcgg atgaaacctg    420

gtgggcatga ctcactctta tgtcagcaat acgcttgtgc agctttgcga tccgctcctt    480

ttgcttttga cgacggttac tgccttttc catcttggcc aattgtcttt gtaatttggt     540

taattttgct tggttctgtt caagagcttt cgcgctatcg taaacaatac cattcgacaa    600

gctggcgaac ttggcaaccc ccatatcgat gccgacaatt ttatcgccac aggattcata    660

ttcataatcg ccttcaatca gaaatgagac ccaccattta ccggccctgt atgaaatggt    720

ggtcgatttt atttttcctt caggaatgct atcgccaaga gtggcagtcc cccaccctt     780
```

```
cggcaatata agtttatttc cgctcacgtg attattgtta acgaccacgc tagttagggt    840

aaagctttcg cccatgccac gttttttgaa ttttggatac ccgggtgttt cgccattttt    900

aacccggcga aagaaattat tgaacgcgct ttttatgtcg gcttttatgg cttcttggcc    960

gacgcaggaa ggcactatta atttgctttt agcgtcatac atccaaggat acaggtttgc   1020

tttatcggca ttgaacagct tgtcgatcaa aaaagctgaa ggttgaggtt tggtgttgtc   1080

ctctttccac gcatcgtaca tttgttgcca tttgcccaac gcatagttga aggccacgcg   1140

acggacatta atacattgga acaacatagc agcttgcttg ttgttgactc tcaatctagt   1200

tttagatgct gtcaatattg ccat                                          1224


<210> SEQ ID NO 87
<211> LENGTH: 1689
<212> TYPE: DNA
<213> ORGANISM: Streptococcus parasanguinis

<400> SEQUENCE: 87

ctacggtgac ccgccgccag tagcggctgg ccttgacgca tacaacgccg catcccccaa     60

caccaccgaa ccggtagcat cagagcctgc gactccgcgt ccgtttagac tctcccccgt    120

gccgggggcg agttgcgcct catacatccg tacagcctcc gcacgaatat tacgtgccgc    180

gttcacgtca cggtcaatcc gcacaccaca ggccgtgcac tcaaagacac gcacgtggag    240

tccgagcttg gttttcgctc gtgctccgca ggcgctacac gtctgagagg atgcaaagaa    300

gcggtcaata atctgtacct gcgagccgta ccagctggcc ttgtattcca gctgacggcg    360

cagcgtacta aaagcggcat ccagaatgga ctggttgagc ccggccttct ggcgcacatt    420

cttgcccggt gcctcaacag taccggcagc tgaggcggtc atacccgcta cagccaagtc    480

ttcaagcccg atgagggtgt acccggtgct caggcgctta gagacctgat gcaaccccga    540

ttcacggcgc aaggctacca ggtggtggtg ccgtgcaatc tgctgcacaa gacgggcacg    600

acgattagag cccttctgag cacgtgagag agcacgctgc agacgcacca ggcggcgctc    660

ggcggtacgt gcccagcggg ggttagccag ggtaggggca ccgtcaccgg tgaactccaa    720

ggacgggtac tgtgcgaagc gctgcggtgc ctgctcgtca gagagcgcgg cgaggtagcg    780

tacacccagg tctacaccga cggcgccagc ggtacgctga gcacgagtag ggtcatcgg     840

ggtacgggac agcttaacaa ggatggagac gtaccaccgg tcagcggcac gggagacagt    900

gaatgatttg acatcagcac cagctcgcac ggccttcacc agcggcttcg tagtgttatg    960

agtacgaata acgcccaagg atgccaggcg cacgtggcgg tagtcctcaa tggtcgggat   1020

ggtcttgatg ccgcggcgct tcagctgtac cgtgcggcgt gcatattcag gtgtgcccct   1080

cttgtagggg gtgccgtagc ctccaagctc gtcattacgt gggtcgcggt cgacagtaaa   1140

agattcgtgg ctaatgccct tactcttgaa ccgggggaca cccattcggg ggccagcacg   1200

caggcctttg agggatgcaa aatagttgtc ccacgctgca tgggcgttct ttatcccgga   1260

gactagaaca cgtcggtcga tggtgtgcat ccaaggctca gaagaccgtt cagtttcggg   1320

ccagacaaca gcggggtcag caccgtcagc aatagcctga gcagcagcct tatgacgctg   1380

tttctcaggg gttaggtatc gctttccgta ttcataatga ccaatgtact tataagcagg   1440

gttctcttct tttaagtcct caagctcagc attgaccgta gtctcgtcgg cacctgagtc   1500

aatacgggtg tgccaatagt ctgctcgggt gcgaaaaacc ttacggttat ggtcagtgaa   1560

gaggttgtac gtatagcgtg ctgcacctac acactgcatc agcttagctt tttgtgcctg   1620
```

-continued attggggtcg aggcggaatt tataggcacg gtacaggaca ccatcgtcgg tgctggtttt 1680
ctcagccat 1689

<210> SEQ ID NO 88
<211> LENGTH: 1950
<212> TYPE: DNA
<213> ORGANISM: Calothrix sp.

<400> SEQUENCE: 88
atgagcatta tcacgattca atgtcgcttg gttgcaaatg accgaaccct tcagcatctc 60
tgggaactga tggcggagaa aaacacgccc ttaatatctg agttgctcga acaactagga 120
aagcatcctg actttgagac atggttaaaa aacggtaaag tgccaaaaga cacaataaaa 180
atactatgcg actctctcaa aactcaaagt cgtttcgctg gtcaaccagg tcgtttttat 240
acctctgcga ttagtcaggt gaaagaaatc tataaatcct ggcttacttt gcagaagcgg 300
cgccaacgac aaatagaagg aaagcaacgc tggttgggaa tgctaaaaag tgatgtggag 360
ttacaagagg aaagtaattg cagtttagaa aaaattcgcg ctaaagggac tgaaattcta 420
gctgaatttg tctcaaaatt taccaaagat acgactaaaa agtctaagac aaaaataaaa 480
tctaccaaaa agtctaataa aaaaacaaaa aaagatacag aagaatcaaa ttctacactc 540
ttccaagcat tatgtgatat ctatgataaa acagaagata ctttgtcaaa atgtgctatt 600
atatacttgc taaaaaataa ttgtcaagta attgacacag aggaaaaccc agacacattt 660
ttaaaacgga agcgagctaa agaaatagaa attaagcgac tacaagacca gattgtaggc 720
agaataccaa aaggtcgtga tttaacagat aaaaagtggt tggatacaat caaacttgct 780
tcttctcaag ttcctcaaga tgaaaacgaa gcaaaatcat ggcagaatca gctacttaaa 840
acatctagtt ctgttccgta ctcagtagac tatgagacta acacagatat aaaatgggta 900
aaacataata atggaagtat tttcgttaac tttaatggtt taggcgaaca tcaatttgaa 960
gtatattgtg attctagaca gcttccctat tttcaacgtt tttgtgaaga tatgcagatt 1020
tggcataatg acgaagaaaa atattcttcc gcactgttta tgctgcgttc agcgcgtcta 1080
gtttggttag aaaaaaaagg gaggggtaaa ccttggaatg tgaattacct ttatctccac 1140
tgctccttgg atacatcact atggacagca gaaggaacag agcagattcg cataaacaaa 1200
atcaatgaaa ctgatgaagc aatagccaaa gcaaaaacta aagacaagca ggaacttact 1260
gaaaatcaac ttgcctatct tcaaagacaa caatctacac gcaataaact aaacaactct 1320
tttcctggtc gccctagtaa acctatatac aagggtaatt cgcatattct tgtcggggtt 1380
agtttaggat tagaaaaacc agtcactgta gcagcagtag acgtagtgag caataaagtt 1440
ttagcttatc gcagtgtgaa acaactactt ggtcaaaact ataaactctt aaaccgtcag 1500
cgacagcaac aaaaacatct tgctcagaaa cgtcacgaat ctcaaaagaa acaggcgccg 1560
aatcaatttg gtgaatcaga gctagggcta tatgtagaca gattattagc aaagtcaata 1620
attaactttg caaaaactta ccaagctagt agtatcgctc taccaaaact tcgtgatatg 1680
cgagaaatca ttcagagcga gattcaagcg aaagcagaaa gtaagattcc aggatacaaa 1740
gaaggtcagg aaaagtacgc aaaagagtac cgtatgagtg ttcaccgttg gagctatgga 1800
agattaattg ggaatattca agctcaagcc gctcaagccg gaattttaat agaaacatca 1860
tctgggcaaa taaggggtag tcctcaagaa caagcaaaac atttagcgat ttccgcttat 1920
atagaacgcc aaacaatttt aaataagtaa 1950

<210> SEQ ID NO 89
<211> LENGTH: 1122
<212> TYPE: DNA
<213> ORGANISM: Bacillus cereus

<400> SEQUENCE: 89
atgatgatca ataaaacata taaattccgt atctatccaa ataaatcaca agcggcacta 60
atcaataaaa cgattggttg ttctcgtttt gtattcaatc acttcctatc tttatgggat 120
catgcatata aagaaacagg aaaaggtttg acatatggta catgctctgc caaacttcct 180
gccttgaaga aagagtttgt ttggctaaaa gaagtggata gtattgcgat tcagtcgtct 240
gttcgcaacc ttgcggatgc ttatatacgc tttttcaaaa aacaaaacag tgccccgcgt 300
ttcaaatcta agaagaacaa cgtacaatct tacaccacaa aacaaacaaa tgaaaacatt 360
gccattgtag ggaacaaaat aaagttaccg aaactaggcc ttgttcgatt tgccaaaagt 420
cgtgaagtag agggacgtat tgtaaatgtg accgttagac ggaacccttc tggtagatac 480
tttgtgtcat tgttaattga aacagaagtg caagaacttc cgaaaacaaa ctcttacatt 540
ggaatggatg tgggactaaa agagttcgcc attttatcaa atggaaaaac ctataaaaac 600
ccaaagtttt ttcgatcatt agaagagaag ttggcaaaag cacagcgtgt tctttctagg 660
agaatgaaag gatcttctcg atggaataaa caacgattaa aagtagctag aatttatgaa 720
tacatgacga atgctagaaa agattacttg gacaaaatct cgactgaaat catcaaaaac 780
cacgatgtta tcggtataga ggatttgcaa gtatcggata tgttaaagaa tcataagtta 840
gcaaaagcaa ttagtgaggt atcatggtca caatttcgaa ctatgttgga atataaagca 900
aaatggtatg gcaaacaagt cattgtcgta tccaaaacat ttccttccag ccaattatgt 960
tcatgttgtg ggtatcaaaa taaagacgtt aaaaatctaa acctacgtaa atgggattgc 1020
ccttcttgtc atacacatca tgatagggat attaacgcaa gtatcaatct aaagaatgaa 1080
gcgataaggc ttctaaccgc aaggactgcg gggttagcct aa 1122

<210> SEQ ID NO 90
<211> LENGTH: 1107
<212> TYPE: DNA
<213> ORGANISM: Pseudonocardia asaccharolytica

<400> SEQUENCE: 90
gtggtgttca acgacgcgat cgccgcccgc cgggccgcac acgagaacgg cgagccgtac 60
cccacggacg gcgcgctgtc caaggcgctc accgcggcca agcgcacccc ggagagggcg 120
tggctcggcg aggtgtcggc cgtggtgctg caacaggcac tggcggacgc gaacaccgcc 180
taccggaact tcttcgcctc gatcaagggc gcccgcaagg gccgcaagct gggtgtgccc 240
cggttccggt cccgcaagga ccgggcgcag tcgatccggt tcaccatggc tgcccggttc 300
cgggtcaccc tggcgggccg gttgcggctg cccgggatcg gcgacgtccc ggtgcgctgg 360
tcgcgcgagc tgccgggcga gccgtcgagc gtgaccgtca ccgtggacgc ggccgggcgg 420
taccacgcct cgttcgtcgt cgacgtcccc gaccagccgt tgcccctcgt gcagcacgag 480
gtgggcatcg acctggggct gacgcacttc gcggtgctgt cggacggggc gaaggtcgac 540
gccccgcgga ttgcgcggaa ggcgcaggcc aagctggcgc gggcgcagaa ggaactcgcc 600
cgacggcagc gcgggtcgaa gaatcgggag aagtcacgcc gcaaggtcgc ccgcgcgcac 660
gtgcgggtgg cggacacgcg gcgggactgg ttgcacaagc tgtcgaccac cgtggttcgg 720
gagaaccaac tgatcgcggt ggaagacctg gccgtgtccg gtctggcccg gacccggctg 780

-continued

```
gcccgcagcg tgcacgacgc gggctggtcc acgttcgtcg cgatgctgac gtacaaggcg    840

cagcgggccg gacggacgct ggtgaaggtg gaccggtggt tcccctccac tcgggcgtgc    900

tcggcgtgtg gggcgatcgg cgaggccaag cccctgcacg tgcgggagtg gacctgcggg    960

tgcggcaccg tgcacgaccg ggacgtcaac gcggcccgga acatcctcgc ggctggacga   1020

gccgtgatgc ctgtggagac ggcgtcagac ctcgggaaac cggggcagtt gtccgcgaag   1080

caggaaccca ccgggagcgc ggcctaa                                       1107
```

<210> SEQ ID NO 91
<211> LENGTH: 1095
<212> TYPE: DNA
<213> ORGANISM: Clostridium perfringens

<400> SEQUENCE: 91

```
ttatgctatc aaattttcta agtttatact tgcatttaag tctctatcgt gttctgttcc     60

acagttcgga caagtccatt ttctaagacc tagatttttt acatcactat ttttatatct    120

acagcaagaa catagttgag aactagcgta attactagga gcaacaataa tatttcttcc    180

ataccattta gccttatact ctaacattac tctaaattca taccaactag cctctgatat    240

tacttttgct aatttatgat ttttcatcat attacttact ttcaaatctt ctattgctat    300

tgattggttt tctctaatta gctttgtaga taatttgtgt aagaaatctt ttctttgatc    360

tgctattttt tgatgtaatt tagctacttt taacctaatt ttatttctat tagaactccc    420

cttttgtttc cttgataaat ctttttgtaa tttccttaat ctttttttctg attttctaag    480

atgtttagga ttaggtactc tatatccatc tgaacatatt gcaaactctt taagtcctac    540

gtctacacct atttttttat caactttagg taattttata ttttcagtat caactaatac    600

agaaacaaag tattgtccca ttggattttt agaaacagta aaacttttaa tttcaccttt    660

gaataatcta tgttgtttta tttttaccat agattttaat ttaggtaatt ttatatatcc    720

attttcaata tatatagtac ctttttgatt attagtttta taacttattc tattagtttt    780

ctttttgaat tttgggaaac caatagattt atctctaaag aaatttttat aagcagtatc    840

taaatttaat tgagcgtttg ctaaggcaag cgaatctact tcttttaacc attcatattc    900

tttttgaat ttagctggtg ttaagtataa tttagccatt tctttaggtg ttaatatgtc    960

tttattagct tcataaactt caattctatt agctaacatt tgattgtata taaacctact   1020

acaaccacaa gctttagcaa tatatatttg ttgttctata ttgggatata ttctgtattt   1080

ataagccttt aacat                                                    1095
```

<210> SEQ ID NO 92
<211> LENGTH: 1095
<212> TYPE: DNA
<213> ORGANISM: Anoxybacillus suryakundensis

<400> SEQUENCE: 92

```
ttagtaggct agccccgcag ttcctgcggt tagaagccga acggcttcat tcttaatatt     60

gatacttgcg ttcacatctc ggtcatgacg ggtatggcaa tttgggcatt gccattcacg    120

caaagtgaga tgtttcacgt ctttattttg atatccgcaa tgggagcata actggctcga    180

tgggaagttt ttcgccacca caaccaattg cttcccatac cacttggcct tgtatgcgat    240

catcgctttg aacgtttccc atgacgcctc gcagatcgct ttggagagtt tgttgttttt    300

gagcatgcta gcaactgaca aatcttccat cccgatgatg tcgtggtttt tgacgatctc    360

ggtggagatt ttgtgcaagt agtcgtttcg ggaatttgtg attttctcgt gtatgcgcgc    420
```

```
aaccttgatt cgttgcttat gccaattcga actcccgatt ttgcgcctag aaagaatgcg    480

ttgagctttg actaattttt tttcaagttt ccgaagaaat tttggattcg catacgttgt    540

tccgtctgaa agaatgacaa agttctttaa acccatgtcg ataccaacag cagtatgtgt    600

ttttgggagt ggttgcacat ctgtttttac aagaatggat acgaaatatt ttccgcttgg    660

attgcgtcga atggtgacgg ataacatacg tccttctacc tcacgacttt tggcaaaacg    720

aacgaatcct agtttcggaa gcttgatttt gttacctaca atcgctatat ttcctttcgt    780

gtatttcgtt gtatacgatt gcaccttgtt cttctttgac ttaaaacgag gtttgtcgtt    840

ttgtttttgg aaaaatcgtg tgaatgcatc cgacaaatgt ttcagcgagg tttgaagtgc    900

gatgctgtcc acttctttga gccaagtgta ttcttttttc aacttggtca attgcgaaga    960

acacgcctga taagacagtc ctttccctgt ttttttgtat gtgtcgttcc atctgacgag   1020

aaaatggtta aacacaaaac gtgagcatcc gaacgtttta ttaattagca cctcttgttt   1080

tttgttcggg tacat                                                    1095
```

<210> SEQ ID NO 93
<211> LENGTH: 7
<212> TYPE: PRT
<213> ORGANISM: Simian virus 40

<400> SEQUENCE: 93

```
Pro Lys Lys Lys Arg Lys Val
1               5
```

<210> SEQ ID NO 94
<211> LENGTH: 16
<212> TYPE: PRT
<213> ORGANISM: Artificial Sequence
<220> FEATURE:
<223> OTHER INFORMATION: Synthetic nucleoplasmin bipartite NLS

<400> SEQUENCE: 94

```
Lys Arg Pro Ala Ala Thr Lys Lys Ala Gly Gln Ala Lys Lys Lys Lys
1               5                   10                  15
```

<210> SEQ ID NO 95
<211> LENGTH: 9
<212> TYPE: PRT
<213> ORGANISM: Homo sapiens

<400> SEQUENCE: 95

```
Pro Ala Ala Lys Arg Val Lys Leu Asp
1               5
```

<210> SEQ ID NO 96
<211> LENGTH: 11
<212> TYPE: PRT
<213> ORGANISM: Homo sapiens

<400> SEQUENCE: 96

```
Arg Gln Arg Arg Asn Glu Leu Lys Arg Ser Pro
1               5                   10
```

<210> SEQ ID NO 97
<211> LENGTH: 38
<212> TYPE: PRT
<213> ORGANISM: Homo sapiens

<400> SEQUENCE: 97

-continued

```
Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35
```

<210> SEQ ID NO 98
<211> LENGTH: 42
<212> TYPE: PRT
<213> ORGANISM: Homo sapiens

<400> SEQUENCE: 98

```
Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40
```

<210> SEQ ID NO 99
<211> LENGTH: 8
<212> TYPE: PRT
<213> ORGANISM: Homo sapiens

<400> SEQUENCE: 99

```
Val Ser Arg Lys Arg Pro Arg Pro
1               5
```

<210> SEQ ID NO 100
<211> LENGTH: 8
<212> TYPE: PRT
<213> ORGANISM: Homo sapiens

<400> SEQUENCE: 100

```
Pro Pro Lys Lys Ala Arg Glu Asp
1               5
```

<210> SEQ ID NO 101
<211> LENGTH: 8
<212> TYPE: PRT
<213> ORGANISM: Homo sapiens

<400> SEQUENCE: 101

```
Pro Gln Pro Lys Lys Lys Pro Leu
1               5
```

<210> SEQ ID NO 102
<211> LENGTH: 12
<212> TYPE: PRT
<213> ORGANISM: Mus sp.

<400> SEQUENCE: 102

```
Ser Ala Leu Ile Lys Lys Lys Lys Lys Met Ala Pro
1               5                   10
```

<210> SEQ ID NO 103
<211> LENGTH: 5
<212> TYPE: PRT
<213> ORGANISM: Influenza virus

<400> SEQUENCE: 103

```
Asp Arg Leu Arg Arg
```

1 5

<210> SEQ ID NO 104
<211> LENGTH: 7
<212> TYPE: PRT
<213> ORGANISM: Influenza virus

<400> SEQUENCE: 104

Pro Lys Gln Lys Lys Arg Lys
1 5

<210> SEQ ID NO 105
<211> LENGTH: 10
<212> TYPE: PRT
<213> ORGANISM: Hepatitis D virus

<400> SEQUENCE: 105

Arg Lys Leu Lys Lys Lys Ile Lys Lys Leu
1 5 10

<210> SEQ ID NO 106
<211> LENGTH: 10
<212> TYPE: PRT
<213> ORGANISM: Mus sp.

<400> SEQUENCE: 106

Arg Glu Lys Lys Lys Phe Leu Lys Arg Arg
1 5 10

<210> SEQ ID NO 107
<211> LENGTH: 20
<212> TYPE: PRT
<213> ORGANISM: Homo sapiens

<400> SEQUENCE: 107

Lys Arg Lys Gly Asp Glu Val Asp Gly Val Asp Glu Val Ala Lys Lys
1 5 10 15

Lys Ser Lys Lys
20

<210> SEQ ID NO 108
<211> LENGTH: 17
<212> TYPE: PRT
<213> ORGANISM: Homo sapiens

<400> SEQUENCE: 108

Arg Lys Cys Leu Gln Ala Gly Met Asn Leu Glu Ala Arg Lys Thr Lys
1 5 10 15

Lys

<210> SEQ ID NO 109
<211> LENGTH: 596
<212> TYPE: PRT
<213> ORGANISM: Candidatus Desulfofervidus auxilii

<400> SEQUENCE: 109

Met Thr Thr Met Thr Val His Thr Met Gly Val His Tyr Lys Trp Gln
1 5 10 15

Ile Pro Glu Val Leu Arg Gln Gln Leu Trp Leu Ala His Asn Leu Arg
20 25 30

Glu Asp Leu Val Ser Leu Gln Leu Ala Tyr Asp Asp Asp Leu Lys Ala
35 40 45

-continued

```
Ile Trp Ser Ser Tyr Pro Asp Val Ala Gln Ala Glu Asp Thr Met Ala
    50                  55                  60

Ala Ala Glu Ala Asp Ala Val Ala Leu Ser Glu Arg Val Lys Gln Ala
65                  70                  75                  80

Arg Ile Glu Ala Arg Ser Lys Lys Ile Ser Thr Glu Leu Thr Gln Gln
                85                  90                  95

Leu Arg Asp Ala Lys Lys Arg Leu Lys Asp Ala Arg Gln Ala Arg Arg
            100                 105                 110

Asp Ala Ile Ala Val Val Lys Asp Asp Ala Ala Glu Arg Arg Lys Ala
        115                 120                 125

Arg Ser Asp Gln Leu Ala Ala Asp Gln Lys Ala Leu Tyr Gly Gln Tyr
    130                 135                 140

Cys Arg Asp Gly Asp Leu Tyr Trp Ala Ser Phe Asn Thr Val Leu Asp
145                 150                 155                 160

His His Lys Thr Ala Val Lys Arg Ile Ala Ala Gln Arg Ala Ser Gly
                165                 170                 175

Lys Pro Ala Thr Leu Arg His His Arg Phe Asp Gly Ser Gly Thr Ile
            180                 185                 190

Ala Val Gln Leu Gln Arg Gln Ala Gly Ala Pro Pro Arg Thr Pro Met
        195                 200                 205

Val Leu Ala Asp Glu Ala Gly Lys Tyr Arg Asn Val Leu His Ile Pro
    210                 215                 220

Gly Trp Thr Asp Pro Asp Val Trp Glu Gln Met Thr Arg Ser Gln Cys
225                 230                 235                 240

Arg Gln Ser Gly Arg Val Thr Val Arg Met Arg Cys Gly Ser Thr Asp
                245                 250                 255

Gly Gln Pro Gln Trp Ile Asp Leu Pro Val Gln Val His Arg Trp Leu
            260                 265                 270

Pro Ala Asp Ala Asp Ile Thr Gly Ala Glu Leu Val Val Thr Arg Val
        275                 280                 285

Ala Gly Ile Tyr Arg Ala Lys Leu Cys Val Thr Ala Arg Ile Gly Asp
    290                 295                 300

Thr Glu Pro Val Thr Ser Gly Pro Thr Val Ala Leu His Leu Gly Trp
305                 310                 315                 320

Arg Ser Thr Glu Glu Gly Thr Ala Val Ala Thr Trp Arg Ser Asp Ala
                325                 330                 335

Pro Leu Asp Ile Pro Phe Gly Leu Arg Thr Val Met Arg Val Asp Ala
            340                 345                 350

Ala Gly Thr Ser Gly Ile Ile Val Val Pro Ala Thr Ile Glu Arg Arg
        355                 360                 365

Leu Thr Arg Thr Glu Asn Ile Ala Ser Ser Arg Ser Leu Ala Leu Asp
    370                 375                 380

Ala Leu Arg Asp Lys Val Val Gly Trp Leu Ser Asp Asn Asp Ala Pro
385                 390                 395                 400

Thr Tyr Arg Asp Ala Pro Leu Glu Ala Ala Thr Val Lys Gln Trp Lys
                405                 410                 415

Ser Pro Gln Arg Phe Ala Ser Leu Ala His Ala Trp Lys Asp Asn Gly
            420                 425                 430

Thr Glu Ile Ser Asp Ile Leu Trp Ala Trp Phe Ser Leu Asp Arg Lys
        435                 440                 445

Gln Trp Ala Gln Gln Glu Asn Gly Arg Arg Lys Ala Leu Gly His Arg
    450                 455                 460

Asp Asp Leu Tyr Arg Gln Ile Ala Ala Val Ile Ser Asp Gln Ala Gly
```

```
465                 470                 475                 480

His Val Leu Val Asp Asp Thr Ser Val Ala Glu Leu Ser Ala Arg Ala
                485                 490                 495

Met Glu Arg Thr Glu Leu Pro Thr Glu Val Gln Gln Lys Ile Asp Arg
            500                 505                 510

Arg Arg Asp His Ala Ala Pro Gly Gly Leu Arg Ala Ser Val Val Ala
        515                 520                 525

Ala Met Thr Arg Asp Gly Val Pro Val Thr Ile Val Ala Ala Ala Asp
    530                 535                 540

Phe Thr Arg Thr His Ser Arg Cys Gly His Val Asn Pro Ala Asp Asp
545                 550                 555                 560

Arg Tyr Leu Ser Asn Pro Val Arg Cys Asp Gly Cys Gly Ala Met Tyr
                565                 570                 575

Asp Gln Asp Arg Ser Phe Val Thr Leu Met Leu Arg Ala Ala Thr Ala
            580                 585                 590

Pro Ser Asn Pro
        595


<210> SEQ ID NO 110
<211> LENGTH: 607
<212> TYPE: PRT
<213> ORGANISM: Geitlerinema sp.

<400> SEQUENCE: 110

Met Thr Arg Val Thr Val Gln Thr Ala Gly Val His Tyr Lys Trp Gln
1               5                   10                  15

Met Pro Asp Gln Leu Thr Gln Gln Leu Arg Leu Ala His Asp Leu Arg
            20                  25                  30

Glu Asp Leu Val Thr Leu Glu Tyr Glu Tyr Glu Asp Ala Val Lys Ala
        35                  40                  45

Val Trp Ser Ser Tyr Pro Ala Val Ala Ala Leu Glu Ala Gln Val Ala
    50                  55                  60

Glu Leu Asp Glu Arg Ala Ser Glu Leu Ala Ser Thr Val Lys Glu Glu
65                  70                  75                  80

Lys Ser Arg Gln Arg Thr Lys Arg Pro Ser His Pro Ala Val Ala Gln
                85                  90                  95

Leu Ala Glu Thr Arg Ala Gln Leu Lys Ala Ala Lys Ala Ser Arg Arg
            100                 105                 110

Glu Ala Ile Ala Ser Val Arg Asp Glu Ala Thr Glu Arg Leu Arg Thr
        115                 120                 125

Ile Ser Asp Glu Arg Tyr Ala Ala Gln Lys Gln Leu Tyr Arg Asp Tyr
    130                 135                 140

Cys Thr Asp Gly Leu Leu Tyr Trp Ala Thr Phe Asn Ala Val Leu Asp
145                 150                 155                 160

His His Lys Thr Ala Val Lys Arg Ile Ala Ala His Arg Lys Gln Gly
                165                 170                 175

Arg Ala Ala Gln Leu Arg His His Arg Trp Asp Gly Thr Gly Thr Ile
            180                 185                 190

Ser Val Gln Leu Gln Arg Gln Ala Thr Asp Pro Ala Arg Thr Pro Ala
        195                 200                 205

Ile Ile Ala Asp Ala Asp Thr Gly Lys Trp Arg Ser Ser Leu Ile Val
    210                 215                 220

Pro Trp Val Asn Pro Asp Val Trp Asp Thr Met Asp Arg Ala Ser Arg
225                 230                 235                 240
```

-continued

```
Arg Lys Ala Gly Arg Val Val Ile Arg Met Arg Cys Gly Ser Ser Arg
                245                 250                 255

Asn Pro Asp Gly Thr Lys Thr Ser Glu Trp Ile Asp Val Pro Val Gln
            260                 265                 270

Gln His Arg Met Leu Pro Ala Asp Ala Asp Ile Thr Ala Ala Gln Leu
        275                 280                 285

Thr Val Arg Arg Glu Gly Ala Asp Leu Arg Ala Thr Ile Gly Ile Thr
    290                 295                 300

Ala Lys Ile Pro Asp Gln Gly Glu Val Asp Glu Gly Pro Thr Ile Ala
305                 310                 315                 320

Val His Leu Gly Trp Arg Ser Ser Asp His Gly Thr Val Val Ala Thr
                325                 330                 335

Trp Arg Ser Thr Glu Pro Leu Asp Ile Pro Glu Thr Leu Arg Gly Val
            340                 345                 350

Ile Thr Thr Gln Ser Ala Glu Arg Thr Val Gly Ser Ile Val Val Pro
        355                 360                 365

His Arg Ile Glu Gln Arg Val His His His Ala Thr Val Ala Ser His
    370                 375                 380

Arg Asp Leu Ala Val Asp Ser Ile Arg Asp Thr Leu Val Ala Trp Leu
385                 390                 395                 400

Thr Glu His Gly Pro Gln Pro His Pro Tyr Asp Gly Asp Pro Ile Thr
                405                 410                 415

Ala Ala Ser Val Gln Arg Trp Lys Ala Pro Arg Arg Phe Ala Trp Leu
            420                 425                 430

Ala Leu Gln Trp Arg Asp Thr Pro Pro Pro Glu Gly Ala Asp Ile Ala
        435                 440                 445

Glu Thr Leu Glu Ala Trp Arg Arg Ala Asp Lys Lys Leu Trp Leu Glu
    450                 455                 460

Ser Glu His Gly Arg Gly Arg Ala Leu Arg His Arg Thr Asp Leu His
465                 470                 475                 480

Arg Gln Val Ala Ala Tyr Phe Ala Gly Val Ala Gly Arg Ile Val Val
                485                 490                 495

Asp Asp Ser Asp Ile Ala Gln Ile Ala Gly Thr Ala Lys His Ser Glu
            500                 505                 510

Leu Leu Thr Asp Val Asp Arg Gln Ile Ala Arg Arg Arg Ala Ile Ala
        515                 520                 525

Ala Pro Gly Met Leu Arg Ala Ala Ile Val Ala Ala Ala Thr Arg Asp
    530                 535                 540

Glu Val Pro Thr Thr Thr Val Ser His Thr Gly Leu Ser Arg Val His
545                 550                 555                 560

Ala Ala Cys Gly His Glu Asn Pro Ala Asp Asp Arg Tyr Leu Met Gln
                565                 570                 575

Pro Val Leu Cys Asp Gly Cys Gly Arg Thr Tyr Asp Thr Asp Leu Ser
            580                 585                 590

Ala Thr Ile Leu Met Leu Gln Arg Ala Ser Ala Ala Thr Ser Asn
        595                 600                 605
```

<210> SEQ ID NO 111
<211> LENGTH: 603
<212> TYPE: PRT
<213> ORGANISM: Mycobacterium mucogenicum

<400> SEQUENCE: 111

```
Met Ala Ile Thr Val His Thr Ala Gly Val His Tyr Arg Trp Thr Asp
1               5                   10                  15
```

-continued

```
Asn Pro Pro Glu Gln Leu Met Arg Gln Leu Arg Leu Ala His Asp Leu
            20                  25                  30

Arg Glu Asp Leu Val Thr Leu Gln Leu Asp Tyr Glu Thr Ala Lys Ala
        35                  40                  45

Gly Ile Trp Ser Ser Tyr Pro Ala Val Ala Ala Ala Glu Thr Glu Leu
    50                  55                  60

Ala Asp Ala Glu Ser Ala Ala Glu Gln Ala Ala Ala Ala Val Ser Glu
65                  70                  75                  80

Glu Arg Thr Lys Leu Arg Thr Lys Arg Ile Thr Gly Pro Leu Ala Gln
                85                  90                  95

Lys Leu Thr Ala Ala Arg Lys Arg Val Arg Glu Ala Arg Ser Thr Arg
            100                 105                 110

Arg Ala Ala Ile Ser Glu Val His Glu Glu Ala Lys Gly Arg Leu Val
        115                 120                 125

Asp Ala Ser Asp Ala Leu Lys Ala Gln Gln Lys Ala Leu Tyr Lys Thr
    130                 135                 140

Tyr Cys Gln Asp Gly Asp Leu Phe Trp Ala Thr Phe Asn Asp Val Leu
145                 150                 155                 160

Asp His His Lys Ala Ala Val Lys Arg Ile Gly Gln Met Arg Ala Ala
                165                 170                 175

Gly Gln Pro Ala Gln Leu Arg His His Arg Phe Asp Gly Thr Gly Ser
            180                 185                 190

Ile Ala Val Gln Leu Gln Arg Gln Ala Gly Gln Pro Gln Arg Thr Pro
        195                 200                 205

Glu Leu Ile Ala Asp Val Asp Gly Lys Tyr Gly Arg Val Leu Ser Val
    210                 215                 220

Pro Trp Val Gln Pro Asp Arg Trp Glu Arg Ile Pro Arg Arg Glu Arg
225                 230                 235                 240

Arg Met Ile Gly Arg Val Thr Val Arg Met Arg Ala Gly Gln Leu Ser
                245                 250                 255

Gly Glu Pro Gln Trp Leu Asp Ile Pro Val Gln Gln His Arg Met Leu
            260                 265                 270

Pro Leu Asp Ala Asp Ile Thr Gly Ala Arg Leu Thr Val Thr Arg Thr
        275                 280                 285

Ala Gly Thr Leu Arg Ala Gln Ile Ser Val Thr Ala Lys Ile Pro Asp
    290                 295                 300

Pro Glu Pro Val Thr Asp Gly Pro Asp Val Ala Val His Leu Gly Trp
305                 310                 315                 320

Arg Asn Thr Asp Thr Gly Val Arg Val Ala Arg Trp Arg Ser Thr Glu
                325                 330                 335

Pro Ile Glu Val Pro Phe Asp Phe Arg Asp Thr Leu Thr Val Asp Pro
            340                 345                 350

Gly Gly Arg Ser Gly Glu Ile Phe Val Pro Glu Ala Val Pro Arg Arg
        355                 360                 365

Val Glu Arg Ala His Leu Ile Ala Ser His Arg Ala Asp Arg Met Asn
    370                 375                 380

Glu Leu Arg Ala Arg Leu Val Asp Tyr Leu Ala Glu Thr Gly Pro Arg
385                 390                 395                 400

Pro His Pro Ser Arg Glu Gly Glu Glu Leu Gly Ala Gly Asn Val Arg
                405                 410                 415

Met Trp Lys Ser Pro Asn Arg Phe Ala Trp Leu Ala Arg Val Trp Ala
            420                 425                 430
```

-continued

```
Asp Asp Glu Ser Val Ser Thr Asp Ile Arg Glu Ala Leu Ala Gln Trp
        435                 440                 445

Arg His Gln Asp Trp Ile Ser Trp His His Gln Glu Gly Gly Arg Arg
    450                 455                 460

Arg Ser Ala Ala Gln Arg Leu Asp Val Tyr Arg Gln Val Ala Ala Val
465                 470                 475                 480

Leu Val Ser Gln Ala Gly Arg Leu Val Leu Asp Asp Thr Ser Tyr Ala
                485                 490                 495

Asp Ile Ala Gln Arg Ser Ala Thr Thr Lys Thr Glu Glu Leu Pro Asn
            500                 505                 510

Glu Thr Ala Ala Arg Ile Asn Arg Arg Arg Ala His Ala Ala Pro Gly
        515                 520                 525

Glu Leu Arg Gln Thr Leu Val Ala Ala Ala Asp Arg Asp Ala Val Pro
    530                 535                 540

Val Asp Thr Val Ser His Thr Gly Val Ser Val Val His Ala Lys Cys
545                 550                 555                 560

Gly His Glu Asn Pro Ser Asp Gly Arg Phe Met Ser Val Val Val Ala
                565                 570                 575

Cys Asp Gly Cys Gly Glu Lys Tyr Asp Gln Asp Glu Ser Ala Leu Thr
            580                 585                 590

His Met Leu Thr Arg Ala Val Gln Ser Ala Ala
        595                 600


<210> SEQ ID NO 112
<211> LENGTH: 664
<212> TYPE: PRT
<213> ORGANISM: Pelobacter propionicus

<400> SEQUENCE: 112

Met Lys Arg Val Thr Ile Thr Ile Asp Gly Glu Gln Thr Lys Gly Ile
1               5                   10                  15

Val Ile Gly Thr Ile Ala Ala Asn His Thr Ala Ala Glu Trp Leu Leu
            20                  25                  30

Thr Ala Ser Val Ser Ala Lys Ser Ala Lys Val Arg Phe Asp Pro Glu
        35                  40                  45

Glu Ala Val Ala Glu Thr Ser Ser Leu Val Met Ile Ala Pro Thr Arg
    50                  55                  60

Thr Glu Lys Tyr Leu Tyr Leu Val Pro Asp Glu Gln Val Gln Pro Val
65                  70                  75                  80

Thr Thr Ile Val Arg Lys Tyr Gly Leu Leu Ser Pro Leu Asp Trp Asp
                85                  90                  95

Cys Pro Asp Tyr Pro Ala Gly Asp Ala Phe Glu His Leu Phe Leu Gln
            100                 105                 110

Asn Lys Leu Trp Asn Asp Leu Val Thr Ile Glu Arg Glu His Arg Ala
        115                 120                 125

Lys Tyr Arg Glu Leu Ile Gly Ser Asp Glu Glu Thr Ala Gln Met Asp
    130                 135                 140

Thr Glu Ile Ala Ser Ile Lys Asp Arg Leu Ser Val Leu Asp Glu Gly
145                 150                 155                 160

Arg Lys Lys Leu Arg Val Glu His Arg Lys Lys Lys Cys Pro Glu Ile
                165                 170                 175

Asp Cys Leu Asp Glu Asn Ile Lys Lys Leu Lys Ser Glu Leu Lys Ala
            180                 185                 190

Val Ala Ser Lys Ala Lys Glu Thr Arg Ala Ala Ala Lys Asp Arg Ile
        195                 200                 205
```

-continued

```
Arg Ala Ala Gly Asn Asp Ile Glu Asn Leu Glu Lys Asp Arg Gln Ala
    210                 215                 220

Ala Val Ile Lys Ala Tyr Asn Asn Ser Gly Leu Trp Trp Gly Asn Tyr
225                 230                 235                 240

Asn Ala Val Leu Glu Ser Tyr Lys Lys Ala Arg Ile Lys Ala Leu Lys
                245                 250                 255

Asp Gly Ala Glu Leu Lys Tyr His Arg Phe Asp Gly Ser Gly Arg Phe
            260                 265                 270

Thr Asn Gln Ile Gln Gly Gly Met Ser Val Gln Asp Leu Leu Glu Gly
        275                 280                 285

Asn Arg Asn Val Ala Ser Leu Arg Leu Val Ser Ser Gly Glu Leu Gly
    290                 295                 300

Asp Ile Ser Gly Lys Lys Pro Pro Ser Leu Asp Leu Gln Ser Val Gly
305                 310                 315                 320

Ser Arg Arg Asp Ser Arg Glu Tyr Gly Ile Leu Ala Ile Thr Leu Tyr
                325                 330                 335

Thr Gly Thr Asp Glu Gln Ser Lys Lys Phe Arg Arg Thr Leu Ser Phe
            340                 345                 350

Pro Val Ile Leu His Arg Pro Leu Pro Glu Gly Ala Thr Leu Lys Ser
        355                 360                 365

Leu Ser Val His Arg Lys Arg Val Gly Thr Asp Phe Val Trp Ser Val
    370                 375                 380

Val Phe Thr Phe Thr Thr Asp Cys Pro Thr Tyr Asp Gln Arg Ser Ser
385                 390                 395                 400

Thr Gly Asn Arg Cys Gly Leu Asn Leu Gly Trp Lys Lys Gln Ala Gly
                405                 410                 415

Gly Gly Leu Arg Val Ala Thr Ile Tyr Asp Gly Ser Asp Ala Arg His
            420                 425                 430

Ile Thr Leu Pro Gln Ala Ile Ile Asp Gly Leu Asp Tyr Val Asn Gly
        435                 440                 445

Asp Leu Gln Gly Arg Ile Asp Ser Ala Ala Asn Glu Asn His Ala Trp
    450                 455                 460

Leu Leu Glu Gln Trp Gly Gly Asp Glu Leu Pro Glu Ser Leu Gln Glu
465                 470                 475                 480

Leu Arg Ser Met Leu Arg Arg Ser Lys Arg Pro His Pro Ala Lys Phe
                485                 490                 495

Ala Lys Ala Val Ile Ala Trp Arg Asn Tyr Pro Glu Tyr Leu Gly Asp
            500                 505                 510

Ala Arg Asp Glu Ala Glu Gln Arg Arg Lys Ala Thr Lys Arg Leu Thr
        515                 520                 525

Ile Glu Met Ala His Lys Arg Glu Lys Leu Leu Arg Arg Arg Met Asp
    530                 535                 540

Phe Tyr Arg Asn Thr Ala Lys Gln Leu Thr Ser Val Tyr Asp Val Ile
545                 550                 555                 560

Cys Leu Asp Lys Met Asp Leu Arg Arg Leu Ala Leu Leu Glu Lys Gly
                565                 570                 575

Asp Gly Thr Pro Asn Glu Leu Thr Lys Ile Ala Arg Lys Gln Arg Gln
            580                 585                 590

Gln Ala Ala Ile Ser Glu Leu Arg Glu Cys Leu Ser Lys Ala Ala Ala
        595                 600                 605

Lys Asn Gly Thr Gln Ile Glu Gln Val Ser Thr Ala Ser Ser Ala Thr
    610                 615                 620
```

```
Cys Ser Ala Cys Lys Gly Lys Met Glu Gln Val Asp Gly Ile Met Trp
625                 630                 635                 640

Arg Cys Arg Glu Cys Arg Ala Leu Val Asp Gln Asp Ile Asn Ala Ala
                645                 650                 655

Ala Asn Leu Phe Arg Glu Val Leu
            660


<210> SEQ ID NO 113
<211> LENGTH: 536
<212> TYPE: PRT
<213> ORGANISM: Borrelia crocidurae

<400> SEQUENCE: 113

Met Pro Phe Gly Lys Lys Ala Arg His Val Lys Ala Tyr Gln Phe Gly
1               5                   10                  15

Ala Asp Ala Pro Gln Glu Gly Met Glu Ala Val Leu Glu Gln His Arg
            20                  25                  30

Leu Arg Thr Asp Tyr Tyr Asn Ala Leu Val Glu Met Glu Leu Arg Gln
        35                  40                  45

Arg Glu Glu Arg Thr Ala Leu Leu Ala Asn Leu Ala Ala Glu Ser Gly
    50                  55                  60

Leu Glu Ser Pro Asn Gln Val Tyr Glu Arg Leu Lys Ala Ala Gly Glu
65                  70                  75                  80

Lys Gly Ile Arg Lys His Pro Glu Tyr Val Ala Ala Arg Glu Arg Gln
                85                  90                  95

Lys Ala Leu Tyr Gly His Pro Arg Leu Leu Glu Leu Gln Ser Arg Gln
            100                 105                 110

Arg Glu Glu Arg Asn Ala Leu Arg Arg Ser Phe Gly Ala Lys Gly Leu
        115                 120                 125

Tyr Ser Ser Asn Tyr Leu Asp Val Glu Arg Ala Phe Asp Lys Ala Arg
    130                 135                 140

Gln Ser Pro Glu Leu Arg Phe Arg Arg Tyr Ser Pro His Glu Gly Arg
145                 150                 155                 160

Leu Ala Val Leu Tyr Thr Glu Gly Leu Pro Met Arg Glu Ile Gly Ser
                165                 170                 175

Asp Thr Arg Val Gln Leu Pro Leu Pro Asp Pro Ile Ile Tyr Arg Asp
            180                 185                 190

Arg Ala Thr Arg Arg Lys His Gln Arg Val Leu Met Lys Phe Arg Val
        195                 200                 205

Arg Ser Val Glu Arg Gln Pro Leu Trp Ile Thr Val Pro Val Tyr Leu
    210                 215                 220

His Arg Glu Leu Pro Asp Gly Val Cys Arg Glu Val Ser Leu His Trp
225                 230                 235                 240

His Arg Val Ala Asp Arg Leu Arg Trp Thr Val Ser Val Val Val Glu
                245                 250                 255

Val Glu Gly Pro Pro Val Ala Ser Pro Thr Gly Arg Gly Ala Val Ala
            260                 265                 270

Val Asp Leu Gly Trp Arg Arg Val Glu Gly Gly Leu Arg Ala Gly Phe
        275                 280                 285

Trp Val Gly Glu Asp Gly Ala Gly Gly Glu Ile Ala Leu Ser Glu Gly
    290                 295                 300

Asp Leu Lys Gln Phe Ser Lys Val Glu Asp Leu Arg Ser Ile Arg Asp
305                 310                 315                 320

Gln His Leu Asn Ala Leu Lys Glu Ala Leu Ala Ala Trp Leu Glu Ala
                325                 330                 335
```

```
Pro Pro Ala Pro Leu Pro Asp Trp Leu Ala Glu Glu Thr Lys Thr Leu
            340                 345                 350

Pro Gln Trp Arg Ser Pro Ala Arg Phe Ala Ala Leu Phe Arg Arg Trp
        355                 360                 365

Gln Ser Glu Arg Val His Ala Asp Glu Ala Ala Tyr Gly Leu Leu Glu
    370                 375                 380

Gly Trp His Lys Arg Asp Arg His Leu Trp Gln Tyr Glu Ala Asn Leu
385                 390                 395                 400

Arg Glu Gln Met Ile Leu Arg Arg Arg Glu Gln Tyr Arg Val Leu Ala
                405                 410                 415

Ala Thr Leu Ala Arg Gln Tyr Asp Ala Leu Ile Val Glu Asp Phe Asn
            420                 425                 430

Leu Arg Ala Ala Ala Glu Leu Asp Gln Gly Gly Ser Asp Leu Pro Asp
        435                 440                 445

Ala Ala Arg Arg Tyr Arg Thr Ile Ala Ser Pro Ser Thr Leu Arg Asp
    450                 455                 460

Ala Leu Val Asn Ala Phe Ala Gln Arg Gly Lys Pro Val Arg Lys Leu
465                 470                 475                 480

Asn Pro Ala His Thr Thr Thr Asp Cys His Ala Cys Gly Gly Ala Leu
                485                 490                 495

Val Gly Asp Pro Ala Lys Glu Leu Arg Leu Tyr Cys Pro Thr Cys Glu
            500                 505                 510

Arg Phe Tyr Asp Gln Asp Glu Asn Ala Ala Arg Asn Leu Leu Arg Arg
        515                 520                 525

Ala Gln Glu Val Gln Ala Gln Val
    530                 535
```

<210> SEQ ID NO 114
<211> LENGTH: 567
<212> TYPE: PRT
<213> ORGANISM: Streptomyces wadayamensis

<400> SEQUENCE: 114

```
Met Glu Thr Ala Ala Thr Lys Asn Tyr Leu Ala Leu Ser Phe Gly Cys
1               5                   10                  15

Leu Ser Pro Thr Arg Gly Glu Glu Tyr Leu Leu Asp Gln Ile Lys Lys
            20                  25                  30

Lys His Asp Leu Trp Asn Lys Leu Val Glu Lys Asp Arg Glu His Arg
        35                  40                  45

Glu Lys Val Arg Gln Val Met Val Phe Glu Ser Glu Thr Thr Lys Lys
    50                  55                  60

Ile Lys Glu Leu Glu Glu Glu Leu Asn Ser Leu Arg Glu Glu Ile Lys
65                  70                  75                  80

Asn Gln Arg Lys Thr Lys Arg Thr Gly Lys Val Asp Leu Thr Asp Gln
                85                  90                  95

Lys Ala Arg Ile Glu Glu Ile Lys Pro Gln Leu Lys Gln Leu Lys Glu
            100                 105                 110

Lys Phe Lys Glu Glu Arg Ser Phe Ile Phe Glu Ala Arg Lys Gln Glu
        115                 120                 125

Leu Ala Gln Leu Glu Lys Glu Arg Trp Ala Val Val Lys Glu Leu Gly
    130                 135                 140

Lys Gly Ser Gly Leu Tyr Trp Cys Asn Leu Glu Asp Val Val Asn Ser
145                 150                 155                 160

Tyr Asp Ile Gly Arg Lys Lys Ala Lys Ala Ala Gly Gly Glu Met Arg
```

-continued

```
                165                 170                 175

Phe His Arg Trp Asp Gly Thr Gly Lys Val Thr Val Arg Phe Gln Lys
            180                 185                 190

Gly Leu Pro Val Asn Glu Met Phe Ser Cys Thr Asn Asn Leu Leu Gln
        195                 200                 205

Ile Asp Pro Val Asp Lys Asp Ala Trp Tyr Asn Pro Val Arg Ala Ile
    210                 215                 220

Arg Arg Lys Lys Ser Arg Thr Arg Val Arg Leu Arg Ala Cys Ser Glu
225                 230                 235                 240

Asn Lys Lys Pro Leu Phe Ile Glu Leu Pro Val Val Leu His Arg Glu
                245                 250                 255

Ile Pro Glu Asp Ala Leu Ile Arg Thr Ala Ser Val Ile Arg Glu Lys
            260                 265                 270

Val Gly Met Arg Tyr Arg Tyr Lys Leu Asn Leu Val Leu Glu Ile Leu
        275                 280                 285

Gly Glu Asn Thr Asn Arg Ile Leu Pro Ala Leu Glu Gly Thr Ala Ala
    290                 295                 300

Ile Asp Leu Gly Trp Arg Thr Val Lys Asp Gly Leu Arg Val Ala Cys
305                 310                 315                 320

Leu Val Asp Asp Lys Gly His Ser Glu Glu Leu Ile Leu Asp Asn Asp
                325                 330                 335

Val Leu His Glu Phe Asn Lys Ile Lys Asp Leu Gln Ser Ile Arg Asp
            340                 345                 350

Asn Leu Phe Asn Glu Thr Lys Ala Lys Leu Met Glu Leu Leu Lys Thr
        355                 360                 365

Leu Glu Leu Pro Asp Glu Ala Lys Glu Arg Thr Ser His Met Ala Asn
    370                 375                 380

Trp Arg Ser Gln Gln Lys Met Leu Arg Leu His Gln Tyr Trp Arg Glu
385                 390                 395                 400

Asn Arg Leu Pro Gly Asp Asp Glu Val Trp Glu Val Leu Glu Tyr Trp
                405                 410                 415

Arg Lys Arg Glu Ile His Leu Tyr Glu Trp Gln Glu Asn Leu Arg Asp
            420                 425                 430

Gln Val Leu Arg Arg Arg Lys Glu Ile Tyr Arg Ile Phe Ala Ala Lys
        435                 440                 445

Ile Thr Arg Lys Tyr Lys Thr Ile Val Leu Glu Glu Phe Thr Leu Asn
    450                 455                 460

Lys Thr Val Gln Lys Pro Asn Pro Glu Glu Gly Pro Ala Gly Thr Leu
465                 470                 475                 480

Pro Ala Asn Arg Asn Arg Phe Ile Ala Ala Ile Ser Glu Phe Arg Asn
                485                 490                 495

Glu Leu Ala Asn Ala Cys Arg Lys Asn His Val Glu Phe Thr Tyr Val
            500                 505                 510

Pro Ala Glu Asn Thr Thr Ile Thr Cys His Lys Cys Gly His Lys Glu
        515                 520                 525

Lys Phe Asp Ala Ala Ala Gln Ile Ile His Thr Cys Ser Thr Cys Gly
    530                 535                 540

Glu Leu Trp Asp Gln Asp Tyr Asn Ala Ala Lys Asn Leu Leu Ala Phe
545                 550                 555                 560

Ser Gln Lys Gly Gly Val Lys
                565
```

<210> SEQ ID NO 115

-continued

<211> LENGTH: 405
<212> TYPE: PRT
<213> ORGANISM: Unknown
<220> FEATURE:
<223> OTHER INFORMATION: TnpB protein sequence

<400> SEQUENCE: 115

Met Leu Ile Ser Tyr Arg Phe Arg Ile Tyr Pro Ser Lys Thr Val Gln
1 5 10 15

Ala Lys Leu Asn Glu Gln Leu Glu Leu Cys Arg Trp Leu Tyr Asn Arg
20 25 30

Leu Leu Ser Glu Val Asn Lys Ala Arg Lys Glu Gly Arg Arg Ile Arg
35 40 45

Arg Glu Asp Thr Gln Ser Leu Ile Val Arg Ile Lys Arg Glu Glu Lys
50 55 60

Pro Glu Leu Ser Lys Val Tyr Ser Lys Val Leu Gln Met Val Asn Tyr
65 70 75 80

Gln Leu Arg Ser Asn Ile Ser Ser Leu Asn Glu Leu Arg Lys Lys Gly
85 90 95

Val Lys Val Gly Trp Leu Arg Tyr Lys Thr Ser Pro Asn Ser Phe Lys
100 105 110

Thr Leu Asn Phe Asn Gln Ser Gly Phe Lys Ile Asp Phe Asp Arg Lys
115 120 125

Lys Leu Ser Leu Ser Lys Val Gly Asp Ile Pro Ile Arg Leu His Arg
130 135 140

Ser Ile Gly Gly Lys Ile Lys Gly Val Ile Ile Lys Arg Thr Lys Ser
145 150 155 160

Gly Lys Trp Tyr Ala Ile Val Gln Ala Glu Val Asp Lys Gln Pro Leu
165 170 175

Pro Pro Thr Gly Arg Ala Ile Gly Ile Asp Val Gly Ile Thr His Phe
180 185 190

Cys Val Asp Ser Asp Gly Asn Tyr Phe Glu His Pro Lys Tyr Leu Asp
195 200 205

Arg Thr Leu Glu Lys Ile Lys Lys Val Gln Lys Gln Leu Ser Arg Lys
210 215 220

Gln Lys Gly Ser Lys Asn Arg Glu Lys Val Arg Ile Gly Leu Ala Lys
225 230 235 240

Leu Tyr Glu Lys Leu Glu Asn Gln Arg Asn Asp Phe Leu His Lys Leu
245 250 255

Ser Arg Tyr Tyr Val Asn Asn Tyr Asp Ile Met Val Val Glu Asp Leu
260 265 270

Asn Val Lys Glu Met Ala Glu Asn Gly Ser Ser Thr Thr Leu Asn Arg
275 280 285

His Ile Thr Asp Ser Ala Trp Ser Lys Phe Val Arg Leu Leu Cys Glu
290 295 300

Lys Ala Glu Arg Ala Ala Arg Thr Val Val Lys Val Asn Pro Lys Asn
305 310 315 320

Thr Ser Lys Arg Cys Ala Met Cys Gly Tyr Ile Val Asn Asn Leu Lys
325 330 335

Leu His Asp Arg Thr Phe Thr Cys Pro Ile Cys Gly Trp Glu Ala Asp
340 345 350

Arg Asp Tyr Asn Ala Ser Leu Asn Ile Leu Asp Val Gly Met Gly Arg
355 360 365

Ser Arg Thr Pro Val Glu Gly Glu Pro Leu Pro Cys Val Ile Ser Tyr
370 375 380

Arg Glu Val Ile Ala Gly Gln Val Leu Ser Met Lys Gln Glu Val Pro
385 390 395 400

Ser Val Arg Ala Glu
405

<210> SEQ ID NO 116
<211> LENGTH: 375
<212> TYPE: PRT
<213> ORGANISM: Unknown
<220> FEATURE:
<223> OTHER INFORMATION: TnpB protein sequence

<400> SEQUENCE: 116

Met Ser Leu Leu Ser Val Lys Cys Lys Leu Ile Pro Asp Ala Ser Thr
1 5 10 15

Ala Glu Lys Leu Ser Arg Thr Val Asn Gln Phe Ala Asn Ala Cys Asn
20 25 30

Tyr Ala Leu Gln Val Ala Arg Arg Asp Asn Ile Trp Asn Lys Phe Ala
35 40 45

Leu Gln Arg Ala Val Tyr Ala Asp Leu Arg Ala Glu Tyr Gly Leu Ser
50 55 60

Ala Asn Leu Ala Ile Arg Ala Ile Ala Arg Val Gly Lys Arg Lys Gly
65 70 75 80

His Lys Ala Gly Gly Phe Lys Ala Thr Ser Val Asp Tyr Asp Gln Arg
85 90 95

Ile Leu Ser Val Asn Val Asp Thr Glu Thr Val Ser Leu Ser Thr Val
100 105 110

Asp Gly Arg Val Lys Val Pro Met Arg Ile Ala Gly Tyr Gln Arg His
115 120 125

Leu Leu Arg Thr Ala Lys Ser Ile Gln Gly Gly Gln Leu Val Arg Gly
130 135 140

Arg Asp Ser Ser Trp Tyr Ile His Leu Trp Cys Glu Tyr Asp Asp Pro
145 150 155 160

Pro Val Leu Asp Pro Gln Gly Met Leu Gly Val Asp Leu Gly Ile Val
165 170 175

Asn Ile Ala Thr Asp Ser Asp Gly Glu Thr Tyr Ser Gly Lys His Leu
180 185 190

Asn Ser Val Arg His Arg His Arg Arg Leu Arg Lys Lys Leu Gln Lys
195 200 205

Lys Gly Thr Lys Gly Ala Lys Arg Arg Leu Lys Lys Leu Ser Gly Lys
210 215 220

Glu Thr Arg Phe Ser Asn His Val Asn His Thr Leu Ser Lys Arg Ile
225 230 235 240

Val Ala Lys Ala Gln Arg Thr Glu Arg Ala Leu Ala Leu Glu Asp Leu
245 250 255

Gln Gly Ile Arg Glu Arg Val Arg Leu Arg Arg Pro Gln Arg Ala Thr
260 265 270

Leu His Ser Trp Ala Phe Phe Asp Leu Gly Gln Lys Leu Arg Tyr Lys
275 280 285

Ala Glu Arg Ala Gly Val Pro Leu Val Phe Val Asp Pro Arg Asn Thr
290 295 300

Ser Arg Gln Cys Pro Ala Cys Gly His Ala Glu Arg Ala Asn Arg Pro
305 310 315 320

Thr Gln Ala Leu Phe Arg Cys Val Ala Cys Gly Tyr Ser Gly Ala Ala
325 330 335

Asp Tyr Val Ala Ala Val Asn Ile Ala Val Arg Gly Trp Ala Ala Val
340 345 350

Asn Arg Pro Tyr Leu Gly Glu Ala Ser Arg Val Ser Leu His Gly Ser
355 360 365

Val Pro Gly Ser Pro Arg Leu
370 375

<210> SEQ ID NO 117
<211> LENGTH: 401
<212> TYPE: PRT
<213> ORGANISM: Unknown
<220> FEATURE:
<223> OTHER INFORMATION: TnpB protein sequence

<400> SEQUENCE: 117

Met Leu Glu Ser Gln Pro Ile Thr Val Ala Cys Lys Leu Gln Val Ala
1 5 10 15

Asn Thr Leu Ala Lys Glu Ile Asp Glu Thr Met Met Val Phe Ala Cys
20 25 30

Ala Cys Asp Trp Val Asn Gln Asn Thr Pro Glu Lys Met Thr Asn Lys
35 40 45

Thr Ala Met Gln Ser Leu Val Tyr Gln Asp Val Arg Val Asn Phe Gly
50 55 60

Leu Ser Ser Asn Leu Ala Ile Gln Ala Ile Arg Arg Val Cys Ala Asn
65 70 75 80

Arg Lys Thr Ala Lys Gln Lys Gly Lys Lys Val Lys Glu Phe Lys Pro
85 90 95

Thr Ser Ile Ser Tyr Asp Ala Arg Ile Phe Ser Phe Arg Glu Ser Asp
100 105 110

Trp Thr Val Ser Val Lys Leu Leu Asn Ser Arg Gln Arg Ile Lys Leu
115 120 125

Leu Ile Gly Asn Tyr Gln Ile Gly Leu Leu Lys Ser Lys Asn Pro Thr
130 135 140

Ser Ala Thr Leu Val Lys Arg Lys Ser Gly Asn Tyr Tyr Ile His Ile
145 150 155 160

Thr Leu Asp Glu Pro Thr Gln Pro Glu Ala Lys Thr Asp Lys Val Leu
165 170 175

Gly Val Asp Leu Gly Arg Thr Asp Ile Ala Thr Thr Ser Glu Gly Glu
180 185 190

Ser Trp Ser Gly Lys Gln Ile Thr Ala Lys Arg Asn His Tyr Ala Lys
195 200 205

Leu Arg Thr Thr Ile Gln Lys Lys Ala Ser Lys Gly Thr Arg Ser Ser
210 215 220

Arg Arg Arg Cys Arg Gln Leu Leu Ala Arg Leu Ser Gly Lys Glu Arg
225 230 235 240

Arg Phe Gln Lys His Ile Asn His Glu Ile Ser Arg Gln Leu Val Asn
245 250 255

Asn Ala Val Thr Asn Lys Gln Ala Ile Ala Ile Glu Asp Leu Thr Gly
260 265 270

Ile Arg Glu Arg Thr Asn Arg Lys Pro Arg Ser Lys Lys Asp Lys Arg
275 280 285

Leu Gly Asn Asn Trp Ala Phe Tyr Gln Leu Arg Gln Phe Leu Thr Tyr
290 295 300

Lys Cys Ile Leu Ala Gly Val Lys Leu Ile Leu Val Asn Pro Ala Tyr
305 310 315 320

```
Thr Ser Leu Ser Cys His Lys Cys Leu Val Ile Gly Asp Arg Lys Gly
                325                 330                 335

Lys Gly Phe Ser Cys Asn Asn Cys Gly Asn Lys Cys Asp Ala Asp Tyr
            340                 345                 350

Asn Gly Ala Gln Asn Ile Lys Ala Leu Gly Ala Ile Ile Asn Arg Pro
        355                 360                 365

Gly Gly Ser Gly Leu Ser Cys Lys Leu Lys Thr Asn Val Gln Tyr Ile
    370                 375                 380

Gln Leu Ser Leu Phe Glu Gly Leu Gly Leu Leu Lys Thr Ser Thr Ser
385                 390                 395                 400

Ala


<210> SEQ ID NO 118
<211> LENGTH: 690
<212> TYPE: PRT
<213> ORGANISM: Lactobacillus fermentum

<400> SEQUENCE: 118

Met Ala Val Lys Val Phe Glu Phe Lys Ile Tyr Pro His Lys Asp Phe
1               5                   10                  15

Gln Glu Gln Phe Asn Arg Trp Ala Tyr Gly Leu Lys Lys Phe Tyr Asn
            20                  25                  30

Phe Cys Leu Gln Gln Phe Glu Leu Leu Asp Glu Tyr Thr Tyr Trp Asp
        35                  40                  45

Lys Leu Ser Lys Thr Arg Val Pro Cys Cys Pro Val Pro Trp Ser Leu
    50                  55                  60

Lys Leu Ile Glu Thr Leu Asp Pro Asn Pro Tyr Leu Pro Glu Leu Lys
65                  70                  75                  80

Asn Lys His Tyr Val Ser Tyr Ser Asn Leu Ile Ala Pro Gln Asp Ile
                85                  90                  95

Pro Val Ile Arg Asn Ala Pro Glu Ala Arg Gln Tyr Thr Leu Lys Lys
            100                 105                 110

Gly Glu Thr Ala Lys Asp Val Phe Lys Arg Val Lys Asn Pro Asp Gln
        115                 120                 125

Ile Val Val Thr Thr Ala Lys Pro Glu Ser Ser Gly Leu Asp Lys Trp
    130                 135                 140

Pro Arg Gly Trp Leu Gly Gly Val Gly Tyr Ser Gln Pro Pro Lys Gln
145                 150                 155                 160

Asp Tyr Gln Pro Ser Leu Ile Lys Asn Phe Pro Asn Ser Glu Lys Thr
                165                 170                 175

Lys Asp Ala Gly Ile Leu Val Lys Lys Glu Thr Leu Glu Asn Ser Asn
            180                 185                 190

Leu Pro Asp Glu Ile Lys Lys Val Ile Leu Asp Val Pro Tyr Lys Phe
        195                 200                 205

Arg Ser Gly Thr Leu Ala Met Leu Cys Thr Ser Trp Gln Glu Tyr Leu
    210                 215                 220

Lys Ser Arg Ser Gly Gln Lys Asp Leu Lys Arg Gly Lys Pro Lys Tyr
225                 230                 235                 240

Lys Arg Tyr Arg Asp Arg Ile Glu Thr Ile Ile His Pro Asn Pro Asn
                245                 250                 255

Ala Gly Ser Ser Lys Pro Ala Ser Lys Asp Ala Cys Arg Leu Glu Gly
            260                 265                 270

Asp Asn Ile Leu Val Leu Pro Ser Phe Gly Lys Val Lys Ile Lys Gly
        275                 280                 285
```

-continued

Leu Asp Lys Arg Phe Arg Asp Asn Asp Gly Ser Ile Pro Arg Val Lys
290 295 300

Val Val Lys Val Leu Lys Arg Pro Ser Gly Trp Tyr Ile Gln Leu Thr
305 310 315 320

Ala Asp Ile Asn Arg Ser Asn Lys Leu Phe Lys Lys Pro Leu Gly Ala
325 330 335

Ile Gly Ile Asp Thr Gly Leu Lys Glu Asp Asn Trp Ile Thr Thr Asp
340 345 350

Arg Phe Ala Val Thr Lys Pro Arg Trp Tyr Arg Glu Ser Glu Glu Lys
355 360 365

Leu Ala Arg Leu Gln Lys Glu Leu Asp Ala Lys Lys Leu Gln Arg Val
370 375 380

Ile Leu Trp Leu Asn His Pro Asp Asn Ser Ile Glu Arg Ile Lys Thr
385 390 395 400

Ile Phe Pro Ser Ile Ala Lys Glu Ala Leu Glu Lys Val Lys Ala Cys
405 410 415

Lys Arg Pro Gln Tyr Leu His Glu Leu Val Lys Asn Asn Glu Leu Ser
420 425 430

Thr Ser Gly Leu Asn Gln Leu Lys His Phe Asn Phe Arg Asp Cys Glu
435 440 445

Lys Val Glu Ser Cys Tyr Leu Phe Asp Lys Leu Leu Ser Ala Ser Asn
450 455 460

Lys Glu Ile Glu Leu Ala Gln Arg Ile Arg Lys Leu His Glu Lys Leu
465 470 475 480

Lys Arg Arg Arg Arg Ser His Asn Gln Lys Gln Ser Thr Trp Leu Thr
485 490 495

Arg Lys Tyr Ser Ile Ile Arg Ile Glu Asp Gly Leu Gln Lys Asn Val
500 505 510

Gly Lys Ser Lys Ala Lys Val Ser Glu Asp Asn Arg Ser Phe Glu Arg
515 520 525

Asn Ala Gln Asn Ser Arg Thr Gly Met Asn Lys Ser Val Leu Asp Ala
530 535 540

Ala Ile Gly Gly Phe Ile Ser Leu Val Glu Ser Lys Ser Lys Glu Trp
545 550 555 560

Gly Arg Asp Phe Lys Arg Met Lys Pro Gly Lys Gly Lys Ala Tyr Ser
565 570 575

Gln Arg Cys Pro Val Cys His His Glu Asn Lys Glu Gln Lys Asp Ile
580 585 590

Thr Asn His Gln Asp Tyr Asn Cys Ser Asn Cys Gly Phe Thr His Arg
595 600 605

Ser Arg Asp Val Ile Pro Gly Ile Asn Met Ile Leu Asp Glu Phe Glu
610 615 620

Glu Gln Gln Gln Lys Asn Leu Leu Gly Ile Glu Thr Glu Glu Gln Lys
625 630 635 640

Ile Ile Trp Asp Asp Leu Ser Lys Glu Cys Arg Gln Ala Trp Arg Leu
645 650 655

Arg Glu Lys Trp Leu Ser Glu Asn Ala Pro Gly Gly Gly Cys Gln Asp
660 665 670

Glu Val Asn Ser Asp Lys Pro Ser Asn Thr Arg Lys Ser Arg Arg Arg
675 680 685

Lys Lys
690

<210> SEQ ID NO 119
<211> LENGTH: 679
<212> TYPE: PRT
<213> ORGANISM: Cyanothece sp.

<400> SEQUENCE: 119

Met Thr Val Lys Val Phe Glu Phe Lys Ile Tyr Pro Lys Lys Glu Phe
1 5 10 15

Gln Glu Gln Phe Asn Arg Trp Ala Tyr Gly Leu Lys Lys Phe Tyr Asn
20 25 30

Phe Cys Leu Glu Gln Phe Glu Leu Leu Asp Glu Tyr Thr Tyr Trp Asp
35 40 45

Lys Leu Ser Lys Thr Arg Val Pro Cys Cys Pro Ile Pro Trp Asn Leu
50 55 60

Lys Leu Ile Glu Thr Glu Glu Pro Asn Pro Tyr Leu Pro Glu Leu Lys
65 70 75 80

Asn Lys His Tyr Val Ser Tyr Ser Asn Leu Ile Ala Pro Lys Asp Ile
85 90 95

Pro Val Ile Arg Asn Ala Pro Glu Ala Arg Gln Tyr Thr Leu Lys Glu
100 105 110

Gly Glu Thr Ala Lys Asp Val Phe Lys Arg Val Lys Asn Pro Asp Lys
115 120 125

Ile Val Val Thr Met Ala Lys Pro Glu Ser Ser Gly Leu Asp Lys Trp
130 135 140

Pro Arg Gly Trp Leu Gly Gly Val Gly Tyr Ser Gln Pro Val Lys Gln
145 150 155 160

Asp Tyr Lys Pro Ser Leu Ile Lys Asn Phe Pro Asn Ser Glu Lys Thr
165 170 175

Arg Asp Ala Gly Ile Leu Val Lys Lys Glu Thr Leu Glu Asn Ser Asp
180 185 190

Leu Pro Asp Glu Ile Lys Lys Ala Ile Leu Asp Val Pro Tyr Lys Phe
195 200 205

Arg Thr Gly Thr Leu Ser Ser Leu Cys Thr Ser Trp Gln Glu Tyr Met
210 215 220

Lys Ser Arg Thr Gly Gln Asn Asp Leu Lys Arg Gly Lys Pro Lys Tyr
225 230 235 240

Lys Arg Tyr Arg Asp Arg Ile Glu Thr Ile Ile His Pro Asn Pro Asn
245 250 255

Ala Gly Ser Ser Lys Pro Ala Ser Lys Asp Ala Cys Arg Leu Glu Gly
260 265 270

Asp Asn Ile Leu Val Leu Pro Ser Phe Gly Lys Ile Lys Ile Lys Gly
275 280 285

Leu Asp Arg Arg Phe Arg Asp Asn Asp Gly Ser Ile Pro Arg Val Lys
290 295 300

Val Val Lys Val Leu Lys Arg Pro Ser Ala Trp Tyr Val Gln Leu Thr
305 310 315 320

Ala Asp Ile Asn Arg Ser Asn Lys Leu Phe Lys Lys Pro Leu Gly Ala
325 330 335

Ile Gly Ile Asp Thr Gly Leu Lys Glu Glu Asn Trp Ile Thr Thr Asp
340 345 350

Arg Phe Ser Val Thr Lys Pro Arg Trp Tyr Arg Glu Ser Glu Glu Lys
355 360 365

Leu Ala Arg Leu Gln Arg Glu Leu Asp Ala Lys Lys Leu Gln Arg Val
370 375 380

Ile Leu Trp Leu Asn His Pro Glu Asn Ser Thr Glu Arg Ile Lys Glu
385 390 395 400

Val Phe Pro Gly Ile Ser Lys Glu Ser Ile Glu Lys Val Lys Gly Cys
405 410 415

Lys Arg Pro Gln Asp Leu Gln Asp Leu Val Ser Asn Asn Glu Leu Ser
420 425 430

Thr Ser Gly Leu Asn Gln Leu Lys His Phe Asn Phe Arg Asp Cys Glu
435 440 445

Lys Val Glu Ser Cys Tyr Leu Phe Asp Lys Leu Leu Ser Val Ser Asn
450 455 460

Lys Glu Ile Glu Leu Ala Glu Arg Ile Gly Lys Leu His Glu Arg Asn
465 470 475 480

Lys Arg Arg Arg Arg Ser His Asn Gln Lys Gln Ser Thr Trp Leu Thr
485 490 495

Arg Lys Tyr Ser Ile Ile Arg Ile Glu Asp Gly Leu Gln Lys Asn Val
500 505 510

Gly Lys Ser Lys Ala Lys Ile Ser Glu Asp Asn Arg Ser Phe Glu Arg
515 520 525

Asn Ala Gln Asn Ser Arg Ala Gly Met Asn Lys Ser Val Leu Asp Ala
530 535 540

Ala Ile Gly Gly Phe Ile Ser Leu Val Glu Asp Lys Ser Lys Glu Trp
545 550 555 560

Gly Arg Asp Phe Lys Arg Met Lys Pro Gly Lys Gly Lys Ala Tyr Ser
565 570 575

Gln Arg Cys Pro Val Cys His His Glu Asn Lys Glu Gln Lys Asp Ile
580 585 590

Thr Asn His Gln Asp Tyr Asn Cys Ser Asn Cys Gly Phe Thr His Arg
595 600 605

Ser Arg Asp Ile Val Pro Gly Val Asn Met Ile Leu Asp Glu Phe Glu
610 615 620

Ala Gly Asp Ile Gln Trp Asp Asp Leu Ser Lys Glu Ala Arg Gln Ala
625 630 635 640

Trp Arg Leu Arg Glu Lys Trp Leu Ser Glu Asn Ala Pro Gly Ser Gly
645 650 655

Cys Gln Asp Glu Val Thr Thr Asp Lys Pro Ser Asn Ala Arg Arg Lys
660 665 670

Arg Asn Arg Lys Lys Lys Thr
675

<210> SEQ ID NO 120
<211> LENGTH: 631
<212> TYPE: PRT
<213> ORGANISM: Microcoleus sp.

<400> SEQUENCE: 120

Met Leu Thr Leu Glu Phe Lys Ala Asp Phe Ser Leu Glu Gln Gln Ala
1 5 10 15

Lys Ile Asp Arg Trp Leu Glu Ile Asn Arg Ser Leu Trp Asn Met Gly
20 25 30

Leu Ala Ala Leu Glu Asp Phe Asp Asp Phe Tyr Ser Tyr Val Lys Gly
35 40 45

Gln Lys Glu Tyr Ala Pro Cys Cys Pro Ile Gln Tyr Glu Tyr Arg Pro
50 55 60

Leu Ser Glu Glu Glu Lys Ala Cys Ile Pro Thr His Glu Lys Thr Ser

-continued

```
65                  70                  75                  80

Asp Arg Lys Tyr Leu Ala Pro Phe Cys Arg Ile Ile Ser Glu Lys Ser
                85                  90                  95

Arg Trp Tyr Val Lys Lys Leu Pro Ile Tyr Lys Val Pro Thr Pro Ala
            100                 105                 110

Glu Lys Lys Asp Ser Trp Gly Trp Leu Pro Ser Asn His Asp Glu Asp
        115                 120                 125

Arg Lys Tyr Ser Asn Cys Thr Gly Tyr Ser Cys Pro Ile Pro Arg Tyr
    130                 135                 140

Gly Ser Val Glu Asn Pro Ser Trp Tyr Glu Pro Met Ile Arg Asn Pro
145                 150                 155                 160

Thr Tyr Lys Gly Ser Gly Gly Leu Ser Leu Val Ser Lys Thr Glu Asn
                165                 170                 175

Leu Pro Gln Trp Met Lys Asp Ser Asp Ile Pro Gln Arg Phe Arg Ala
            180                 185                 190

Gly Glu Met Gly Gln Leu Asp Thr Ala Trp Gln Glu Tyr Leu Lys Ser
        195                 200                 205

Arg Tyr Gly Gln Ser Glu Val Lys Arg Gly Lys Pro Gln Tyr Lys Arg
    210                 215                 220

Lys Arg Asp Lys Leu Gln Thr Leu Ile Asn Thr Asn Pro Ser Ala Asn
225                 230                 235                 240

Glu Arg Leu Val Gly Asn Asn Ile Phe Ala Gly Ile Pro Lys Leu Gly
                245                 250                 255

Lys Val Arg Cys Lys Gly Ile Asp Lys Arg Trp Arg Asn Pro Asp Gly
            260                 265                 270

Ser Ile Pro Arg Val Ala Thr Tyr Lys Ile Cys Lys Arg Pro Asp Ala
        275                 280                 285

Tyr Tyr Ile Gln Leu Ser Gly Glu Val Gln Arg Ser Phe Ser Val Lys
    290                 295                 300

Ala Thr Asn Ala Ser Ile Gly Ile Asp Pro Gly Leu Gln Tyr Glu Leu
305                 310                 315                 320

Ser Leu Ser Asp Gly Thr Arg Ile Gln Pro Gln Lys Phe Tyr Arg Lys
                325                 330                 335

Ser Glu Glu Arg Arg Ala Lys Leu Gln Gln Lys Leu Ala Lys Lys Leu
            340                 345                 350

Thr Glu Arg Leu Ile Leu Trp Ile His His Pro Asp Arg Thr Ile Gln
        355                 360                 365

Glu Ile Arg Lys Asn Phe Phe Pro Ile Ser Asn Glu Ser Tyr Glu Ala
    370                 375                 380

Leu Arg Ala Ala Lys Thr Glu Ala Glu Val Ile Lys Ala Ile Gly Ala
385                 390                 395                 400

Ser Arg Leu Asn Thr Leu Lys Tyr Asn Ile Val Pro Asp Ala Pro Pro
                405                 410                 415

Thr Met Lys Asp Lys Ser Pro Phe Ser Gly Ala Lys Gln Lys Ala Leu
            420                 425                 430

Glu Lys Ala Ile Arg Lys Leu Asp Arg Lys Ile Ser Leu Gln Arg Arg
        435                 440                 445

Asn His Asp His Lys Ile Thr Thr Met Ile Val Arg Asn Tyr Gly Phe
    450                 455                 460

Ile Ala Val Glu Asp Gly Leu Gln Asp Glu Lys Leu Arg Lys Arg Thr
465                 470                 475                 480

Lys Pro Lys Glu Arg Glu Asp Gly Gln Gly Tyr Glu Gln Thr Gly Ala
                485                 490                 495
```

```
Lys Arg Lys Ser Gly Leu Ser Lys Ser Leu Ala Asp Ala Ser Pro Gly
            500                 505                 510

Arg Lys Ile Ala Phe Leu Lys Gln Lys Ala Asp Arg Ala Gly Arg Val
        515                 520                 525

Phe Ser Gln His Pro Ala Pro Tyr Thr Thr Lys Glu Cys Pro Val Cys
    530                 535                 540

Gly Ser Met Asn Glu Ala Ser Tyr Asn Val Asp Asp Glu Gly Asn Arg
545                 550                 555                 560

Leu Tyr Leu Cys Ile Ile Cys Gly Trp Glu Cys Asp Arg Asp Val Asn
                565                 570                 575

Ser Gly Val Asn Ile Glu Leu Ala Gln Phe Gly Asn Asn Pro His Thr
            580                 585                 590

Val Leu Ser Ala Asn Ala Gln Arg Ala Arg Phe Ala Asn Ser Val Trp
        595                 600                 605

Glu Ile Ala His Pro Glu Ala Ser Thr Lys Pro Arg Trp Lys Lys Thr
    610                 615                 620

Glu Lys Arg Lys Lys Arg Lys
625                 630


<210> SEQ ID NO 121
<211> LENGTH: 494
<212> TYPE: PRT
<213> ORGANISM: Cyanothece sp.

<400> SEQUENCE: 121

Met Phe Ala Ile Lys Ser Met Ser Glu Leu Val Gln His His Ile Thr
1               5                   10                  15

Ile Gln Leu Lys Ala Tyr Leu Ser Thr Thr Gln Thr Ala Leu Phe Glu
            20                  25                  30

Asn Trp Thr Asp Ser Leu Arg Pro Leu Tyr Asn Leu Ala Leu Gly Leu
        35                  40                  45

Leu Tyr Glu Glu Gln Gln Arg Arg Trp Arg Thr Asn Gln Lys Phe Leu
    50                  55                  60

Lys Asn Tyr Leu Asp Lys Ser Ser Leu Gln Thr Tyr Leu Asn Glu Ile
65                  70                  75                  80

Glu Asn Lys Pro Asp Ile Tyr Pro Val Glu Trp His Ile Thr Lys Ala
                85                  90                  95

Leu Pro Glu Cys Asp Trp Leu Thr Lys Glu Glu Asn Glu Val Arg Lys
            100                 105                 110

Lys Asp Asn Thr Lys Ser Leu Ala Cys Arg Thr Ile Asn Arg Asp Gly
        115                 120                 125

Asn Phe Phe Thr Pro Ile Arg Pro Tyr Trp His Leu Glu Glu Pro Gln
    130                 135                 140

Lys Leu Ala Lys Phe Lys Cys Phe Thr Asn Gln Trp Leu Ile Ser Cys
145                 150                 155                 160

Asn Leu Leu Thr Asn Tyr His Leu Gln Lys Leu Leu Asn Val Asn Met
                165                 170                 175

Lys Val Arg Gln Ser Phe Ile Ser Met Asn Leu Met Glu Ala Trp Lys
            180                 185                 190

Arg Tyr Gln Lys Gly Asp Phe Arg Lys Leu Lys Phe Lys Ser Lys Arg
        195                 200                 205

Asn Pro Val Ile Ser Leu Cys Asn Lys Gln Thr Asn Arg Ile Lys Phe
    210                 215                 220

Asp Pro Glu Ala Asn Asn Cys Gln Leu Leu Gly Lys Glu Phe Gly Leu
```

225 230 235 240

Ile Glu Phe Arg Gly Leu His Asn Arg His Gln Gly Gln Ile Gln Pro
245 250 255

Arg Asn Gly Ser Leu Thr Lys Lys Ala Asp Gly Tyr Tyr Leu Asn Leu
260 265 270

Val Phe Gln Val Glu His Lys Pro Ile Pro Asp Ser Asp Leu Gln Val
275 280 285

Gly Ile Asp Pro Gly Leu Val Thr Leu Leu Thr Leu Ser Asp Gly Lys
290 295 300

Cys Ile Ser Asn Gln Arg Phe Leu Lys Glu Asn Glu Arg His Leu Thr
305 310 315 320

Val Leu Gln Lys Lys Leu Ser Arg Gln Thr Pro Gly Ser Lys Asn Trp
325 330 335

Glu Lys Thr Lys Lys Ala Leu Ala Lys Ile His Lys Gln Thr Ala Asp
340 345 350

His Arg Lys Tyr Tyr Asn His Lys Val Ser Thr His Leu Val Asn Lys
355 360 365

Tyr Gly Ala Ile Ala Ile Glu Asp Thr Lys Leu Thr Asn Met Asn Lys
370 375 380

Arg Pro Lys Ala Glu Lys Arg Glu Asp Gly Lys Gly Tyr Glu His Asn
385 390 395 400

Gly Ala Lys Ala Lys Ala Gly Leu Asn Gln Ser Phe His Asp Ala Gly
405 410 415

Leu Gly Gln Leu Arg Ala Phe Leu Glu Ser Lys Ala Asn Ser Tyr Glu
420 425 430

Asn Arg His Ile Glu Arg Val Arg Ala Asn Tyr Thr Ser Gln Lys Cys
435 440 445

Ser Arg Cys Gly His Thr Asp Ser Glu Asn Arg Leu Thr Gln Ala Ser
450 455 460

Phe His Cys Leu Lys Cys Gly Leu Glu Met Pro Ala Asp Leu Asn Ala
465 470 475 480

Ala Ile Asn Ile Glu Gln Thr Ala Phe Gly Leu Asp Lys Ser
485 490

<210> SEQ ID NO 122
<211> LENGTH: 582
<212> TYPE: PRT
<213> ORGANISM: Haloarcula amylolytica

<400> SEQUENCE: 122

Met Lys Val Leu Glu Phe Lys Ile His Pro Thr Glu Glu Gln Val Ser
1 5 10 15

Lys Ile Asp Gln Ser Leu Ala Ala Cys Lys Leu Leu Trp Asn Leu Ser
20 25 30

Ile Ala Leu Lys Glu Glu Ser Lys Gln Arg Tyr Tyr Arg Lys Lys His
35 40 45

Lys Phe Asp Glu Phe Ser Pro Glu Ile Trp Gly Leu Ser Tyr Ser Gly
50 55 60

His Tyr Asp Glu Lys Glu Phe Lys Thr Leu Lys Asp Lys Glu Lys Lys
65 70 75 80

Leu Leu Ile Gly Asn Pro Cys Cys Lys Ile Ala Tyr Phe Lys Lys Thr
85 90 95

Ser Asn Gly Lys Glu Tyr Thr Pro Leu Asn Ser Ile Pro Ile Arg Arg
100 105 110

```
Phe Met Asn Ala Glu Asn Ile Asp Lys Asp Ala Val Asn Tyr Leu Asn
        115                 120                 125

Arg Lys Lys Leu Ala Phe Tyr Phe Arg Glu Asn Thr Ala Lys Phe Ile
    130                 135                 140

Gly Glu Ile Glu Thr Glu Phe Lys Lys Gly Phe Phe Lys Ser Val Ile
145                 150                 155                 160

Lys Thr Ala Tyr Asp Ala Ala Lys Lys Gly Ile Arg Gly Ile Pro Arg
                165                 170                 175

Phe Lys Gly Arg Arg Asp Lys Val Glu Thr Leu Val Asn Gly Gln Pro
            180                 185                 190

Asp Thr Ile Lys Ile Lys Ser Asn Gly Val Ile Val Ser Ser Lys Ile
        195                 200                 205

Gly Leu Leu Lys Val Arg Gly Leu Asp Arg Leu Gln Gly Lys Ala Pro
    210                 215                 220

Arg Met Ala Lys Ile Thr Arg Lys Ala Thr Gly Tyr Tyr Leu Gln Leu
225                 230                 235                 240

Thr Val Glu Thr Asp Asp Thr Ile Tyr Lys Glu Ser Asp Lys Cys Val
                245                 250                 255

Gly Leu Asp Met Gly Ala Val Ala Ile Phe Thr Asp Asp Leu Gly Arg
            260                 265                 270

Gln Ser Glu Ala Lys Arg Tyr Ala Lys Ile Gln Lys Lys Arg Leu Asn
        275                 280                 285

Arg Leu Gln Arg Gln Ala Ser Arg Gln Lys Asp Gly Ser Asn Asn Gln
    290                 295                 300

Arg Lys Thr Tyr Ala Lys Leu Ala Arg Val His Glu Lys Ile Ala Arg
305                 310                 315                 320

Gln Arg Lys Gly Arg Asn Ala Gln Leu Ala His Lys Ile Thr Ser Glu
                325                 330                 335

Tyr Gln Ser Val Ile Leu Glu Asp Leu Lys Leu Lys Asn Met Thr Ala
            340                 345                 350

Ala Ala Lys Pro Lys Glu Arg Glu Asp Gly Asp Gly Tyr Lys Gln Asn
        355                 360                 365

Gly Lys Lys Arg Lys Ser Gly Leu Asn Lys Ala Leu Leu Asp Asn Ala
    370                 375                 380

Ile Gly Gln Leu Arg Thr Phe Ile Glu Asn Lys Ala Asn Glu Arg Gly
385                 390                 395                 400

Arg Lys Ile Ile Arg Val Asn Pro Lys His Thr Ser Gln Thr Cys Pro
                405                 410                 415

Asn Cys Gly Asn Ile Asp Lys Ala Asn Arg Val Ser Gln Ser Lys Phe
            420                 425                 430

Lys Cys Val Ser Cys Gly Tyr Glu Ala His Ala Asp Gln Asn Ala Ala
        435                 440                 445

Ala Asn Ile Leu Ile Arg Gly Leu Arg Asp Glu Phe Leu Arg Ala Ile
    450                 455                 460

Gly Ser Leu Tyr Lys Phe Pro Val Ser Met Ile Gly Lys Tyr Pro Gly
465                 470                 475                 480

Leu Ala Gly Glu Phe Thr Pro Asp Leu Asp Ala Asn Gln Glu Ser Ile
                485                 490                 495

Gly Asp Ala Pro Ile Glu Asn Ala Asp Arg Ser Thr Ser Lys Gln Met
            500                 505                 510

Lys Gln Glu Gly Asn Arg Ile Pro Thr Gln Ser Glu Asn Asp Ser Gln
        515                 520                 525

Ser Leu Ile Phe Leu Ser Ala Pro Pro Gln Pro Cys Glu Asp Ser His
```

-continued

```
    530                 535                 540

Gly Thr Asn Asn Pro Lys Ala Leu Ser Asp Lys Ala Ser Lys Arg Lys
545                 550                 555                 560

Ser Lys Lys Ser Arg Gly Ala Ile Pro Glu Asn Pro Asp Gln Leu Thr
                565                 570                 575

Ile Trp Asp Leu Leu Asp
            580


<210> SEQ ID NO 123
<211> LENGTH: 588
<212> TYPE: PRT
<213> ORGANISM: Rothia mucilaginosa

<400> SEQUENCE: 123

Met Lys Thr Leu Glu Phe Lys Ile Tyr Pro Thr Leu Ala Gln Ser Gln
1               5                   10                  15

Thr Ile Asp Lys Trp Leu Asp Lys Leu Lys Trp Val Trp Asn Thr Gly
            20                  25                  30

Leu Ser Leu Lys Leu Ala Gly Arg Gln Lys Tyr Tyr Arg Glu Lys Glu
        35                  40                  45

Ile Gly Asp Gln Val Ile Pro Asp Gly Val Val Leu Gln Trp Lys Trp
    50                  55                  60

Arg Lys Val Val Thr Glu Asp Lys Lys Gly Lys Ser Thr Glu Lys Trp
65                  70                  75                  80

Glu Lys Val Arg Leu Val Gly Thr Gly Val Ile Arg Pro Lys Asn Gly
                85                  90                  95

Tyr Pro Tyr Cys Glu Ile Arg Gln His Leu Asn Ile Glu Asp Pro Asp
            100                 105                 110

Lys Tyr Gly Gln Cys Glu Phe Tyr Arg Ser Asp Lys Ile Pro Asp Phe
        115                 120                 125

Met Ala Asp Val Pro Thr Lys Phe Lys Ala Gly Val Ile Asp Ser Leu
    130                 135                 140

Lys Lys Ser Trp Lys Ala Tyr Val Thr Pro Lys His Pro Gly Arg Lys
145                 150                 155                 160

Pro Lys Phe Lys Gly Arg Asn Asp Lys Ile Lys Ser Leu Val Asn Leu
                165                 170                 175

Asn Ala Gly Gly Lys Ser Lys Glu Leu Lys Pro Glu Lys Ile Pro Gly
            180                 185                 190

Ser Asn Asn Gly Tyr Val Gln Phe Pro Lys Leu Gly Lys Ile Arg Val
        195                 200                 205

Lys Gly Leu Phe Asp Arg Tyr Asp Trp Gln Glu Trp Gly Ala Ala Arg
    210                 215                 220

Ile Val Ile Glu Pro Ser Gly Tyr Tyr Leu His Val Cys Val Asp Val
225                 230                 235                 240

Pro Asp Glu Pro Leu Pro Lys Ser Asp Lys Ser Val Gly Ile Asp Pro
                245                 250                 255

Gly Leu Leu Ser Val Ile Thr Thr Asp Gln Gly Arg Glu Val Glu Pro
            260                 265                 270

Pro Arg Leu Phe Arg Lys Gln Gln Ala Lys Leu Arg Arg Leu Gln Arg
        275                 280                 285

Lys Ala Ser Arg Gln Val Lys Gly Gly Cys Asn Gln Lys Lys Thr Tyr
    290                 295                 300

Arg Lys Ile Ala Leu His His Glu Lys Ile Arg Arg Ser Arg Asn Ala
305                 310                 315                 320
```

-continued

```
Phe Asn His Lys Leu Ser Thr Lys Ile Val Arg Glu Tyr Ser Gly Ile
                325                 330                 335

Val Met Glu Asp Ile Lys Ile Gln Asn Leu Asn Arg Lys Pro Lys Ala
            340                 345                 350

Lys Lys Arg Glu Asp Gly Asn Gly Tyr Glu Gln Asn Gly Ala Lys Arg
        355                 360                 365

Lys Ala Gly Leu Asn Lys Ser Phe Ala Asp Ser Ala Leu Gly Asp Leu
    370                 375                 380

Ile Ser Lys Ile Glu Thr Lys Cys Gln Asp Thr Asp Arg Glu Phe Val
385                 390                 395                 400

Lys Val Ala Ala His Tyr Thr Thr Val Asp Cys Ser Asn Cys Gly Ala
                405                 410                 415

Lys Ile Lys Lys Ala Leu Ser Gln Arg Thr His Arg Cys Thr Glu Cys
            420                 425                 430

Gly His Thr Glu Gly Arg Asp Ser Asn Ala Ala Lys Asn Ile Leu Leu
        435                 440                 445

Lys Gly Lys Lys Gln Leu Gln Thr Val Tyr Arg Ala Trp Ala Trp Glu
    450                 455                 460

His Gly Glu Thr Arg Lys Pro Asp Ser Glu Cys Glu Thr His Cys His
465                 470                 475                 480

Gln Glu Gly Val Gln Ala Pro Pro Glu Asp Glu His Ser Ser Gln Leu
                485                 490                 495

Thr Leu Val Arg Thr Pro Ala Lys Gly Thr Gln Arg Gly Arg Gly Asp
            500                 505                 510

Val Lys Thr Ser Thr Pro Ala Lys Thr Thr Ser Lys Leu Asp Thr Val
        515                 520                 525

Ser Asp Pro Asn Leu Asp Asn Lys Pro Asp Thr Arg Ala Pro Cys Thr
    530                 535                 540

Ser Ser Ile Ser Pro Asn Ser Val Glu Asn Lys Ile Pro Lys Thr Lys
545                 550                 555                 560

Lys Asn Lys Arg Ser Ala Gln Ser Ser Ser Glu Ser Phe Thr Gln Leu
                565                 570                 575

Thr Ile Trp Asp Thr Ala Gly Glu Ile Ser Phe Glu
            580                 585


<210> SEQ ID NO 124
<211> LENGTH: 477
<212> TYPE: PRT
<213> ORGANISM: Synechococcus sp.

<400> SEQUENCE: 124

Met Pro Phe Ile Leu Lys Gln Arg Gly Val Arg Met Ile Thr Val Arg
1               5                   10                  15

Lys Leu Lys Ile Val Cys Lys Asp Lys Glu Phe Tyr Asp Phe Phe Lys
            20                  25                  30

Trp Glu Gln Arg Glu Gln Asn Lys Ala Leu Asn Ile Ala Ile Gly Leu
        35                  40                  45

Ile His Ser Ser Thr Val Leu Arg Ser Ile Asp Ser Gly Ala Glu Ala
    50                  55                  60

Gln Leu Lys Lys Ser Ile Gly Lys Leu Thr Gln Asn Ile Glu Lys Leu
65                  70                  75                  80

Gly Lys Glu Leu Glu Lys Glu Lys Ile Thr Asp Lys Lys Lys Glu Gln
                85                  90                  95

Leu Leu Lys Ala Ile Asn Thr Asn Lys Glu Leu Ile Ala Ser Lys Glu
            100                 105                 110
```

-continued

```
Lys Glu Leu Lys Ala Gly Glu Glu Phe Arg Cys Gly Ile Asp Lys Lys
        115                 120                 125

Phe Asn Glu Leu Tyr Met Asn Lys Thr Thr Leu Tyr His Val Leu Asp
    130                 135                 140

Ser Ile Cys Asp Phe Lys Tyr Lys Arg Thr Ile Glu Leu Val Arg Gln
145                 150                 155                 160

Lys Val Lys Gln Asp Tyr Ser Asn Ser Phe Thr Asp Ile Val Thr Gly
                165                 170                 175

Lys Val Ser Leu Gln Asn Tyr Lys Ser Thr Phe Pro Leu Met Ile Asp
            180                 185                 190

Gly Ser Cys Ile Ser Ile Leu Lys Glu Val Asp Glu Leu Asp Ile Val
        195                 200                 205

Asn Gly Tyr Lys Ile Lys Ile Met Leu Gly Tyr Glu Leu Asp Ile Ile
    210                 215                 220

Leu Gly Lys Arg Glu Asn Glu Asn Ser Leu Glu Leu Gln Lys Thr Leu
225                 230                 235                 240

Glu Lys Cys Ile Thr Gly Asp Tyr Lys Ile Cys Ala Ser Ser Ile Gln
                245                 250                 255

Arg Asp Lys Asn Asn Asn Val Ile Phe Asn Leu Thr Leu Asp Ile Pro
            260                 265                 270

Ile Glu Lys Asp Tyr Lys Pro Val Lys Gly Arg Val Cys Gly Val Asp
        275                 280                 285

Leu Gly Ile Lys Tyr Pro Ala Tyr Met Cys Leu Asn Glu Asp Thr Tyr
    290                 295                 300

Lys Lys Glu Ala Val Gly Ser Ile Asn Asn Phe Leu Arg Ile Arg Lys
305                 310                 315                 320

Gln Met Gln Glu Arg Arg Lys Lys Leu Gln Lys Glu Leu Leu Leu Thr
                325                 330                 335

Asn Gly Gly Lys Gly Arg Thr Lys Lys Thr Gln Ala Leu Glu Lys Leu
            340                 345                 350

Arg Glu Asn Glu Lys Asn Phe Ala Lys Thr Tyr Asn His Ala Ile Ser
        355                 360                 365

Lys Arg Ile Val Gly Phe Ala Arg Lys Asn Lys Cys Glu Tyr Ile Asn
    370                 375                 380

Leu Glu Lys Leu Thr Lys Asp Gly Phe Gly Asp Ser Ile Leu Arg Asn
385                 390                 395                 400

Trp Ser Tyr Phe Glu Leu Gln Lys Met Ile Glu Tyr Lys Ala Lys Ser
                405                 410                 415

Lys Gly Ile Glu Val Arg Tyr Ile Asp Pro Cys Phe Thr Ser Gln Lys
            420                 425                 430

Cys Ser Lys Cys Gly Tyr Ile Asp Lys Glu Asn Arg Glu Thr Gln Glu
        435                 440                 445

Asp Phe Ile Cys Lys Lys Cys Gly Phe Lys Leu Asn Ala Asp His Asn
    450                 455                 460

Ala Ser Ile Asn Ile Ala Arg Ser Lys Glu Phe Ile Lys
465                 470                 475


<210> SEQ ID NO 125
<211> LENGTH: 478
<212> TYPE: PRT
<213> ORGANISM: Cyanothece sp.

<400> SEQUENCE: 125

Met Ile Ile Ala Arg Lys Ile Lys Leu Ile Ile Ile Gly Glu Asn Arg
```

-continued

```
1               5                   10                  15

Asp Ala Gln Tyr Lys Phe Ile Arg Glu Glu Arg Tyr Lys Gln Asn Lys
            20                  25                  30

Ala Leu Asn Val Ala Met Asn His Leu Tyr Phe Leu His Val Ala Lys
        35                  40                  45

Glu Lys Ile Arg Leu Leu Asp Asn Lys Phe Leu Gln Asp Glu Lys Lys
    50                  55                  60

Leu Gln Glu Ser Ile Asn Lys Leu Tyr Ala Glu Lys Lys Val Ile Lys
65                  70                  75                  80

Asp Glu Lys Lys Arg Asn Glu Leu Glu Lys Lys Ile Glu Lys Gln Thr
                85                  90                  95

Asn Glu Leu Lys Lys Leu Arg Ser Lys Ser Asn Lys Glu Ala Asp Lys
            100                 105                 110

Val Leu Gln Glu Ala Ile Lys Ile Asn Leu Ser Ser Thr Thr Arg Glu
        115                 120                 125

Val Ile Ser Lys Gln Phe Glu Leu Ile Ser Asp Thr Lys Asp Arg Ile
    130                 135                 140

Thr Gln Lys Val Ser Gln Asp Phe Lys Ser Asp Leu Lys His Gly Leu
145                 150                 155                 160

Leu Ser Gly Glu Arg Val Leu Arg Thr Tyr Lys Lys Asn Asn Pro Leu
                165                 170                 175

Leu Ile Arg Gly Arg Ala Leu Asn Phe Tyr Arg Glu Gly Lys Asp Val
            180                 185                 190

Met Ile Lys Trp Tyr Gly Gly Ile Ile Phe Lys Cys Met Leu Gly Gln
        195                 200                 205

His Lys Asn Asn Ala Pro Glu Leu Lys Ala Thr Leu Ser Lys Val Leu
    210                 215                 220

Glu Gly Ser Tyr Lys Val Cys Asp Ser Ser Ile Ser Val Gly Lys Glu
225                 230                 235                 240

Leu Ile Leu Asn Leu Ser Leu Asp Ile Gly Glu Val Asp Thr Asn Val
                245                 250                 255

Ser Cys Lys Lys Gly Arg Val Leu Gly Val Asp Leu Gly Met Lys Val
            260                 265                 270

Pro Ala Tyr Met Ser Ile Asn Asp Lys Pro Tyr Ile Arg Lys Ala Leu
        275                 280                 285

Gly Ser Leu Asp Asp Phe Leu Lys Ile Arg Val Gln Met Gln Lys Arg
    290                 295                 300

Arg Arg Asn Leu His Lys Thr Leu Val Asn Val Lys Gly Gly Lys Gly
305                 310                 315                 320

Arg Glu Lys Lys Leu Gln Ala Leu Asp Arg Leu Lys Asp Lys Glu Lys
                325                 330                 335

Asn Phe Ala Thr Thr Tyr Asn His Phe Leu Ser Tyr Asn Ile Val Lys
            340                 345                 350

Phe Ala Lys Asp Asn Leu Ala Glu Gln Ile Asn Met Glu Phe Leu Ala
        355                 360                 365

Leu Ala Gly Glu Asp Lys Asn Ile Ile Leu Arg Asn Trp Ser Tyr Tyr
    370                 375                 380

Gln Leu Gln Gln Phe Val Glu Tyr Lys Ala Lys Arg Glu Gly Ile Asp
385                 390                 395                 400

Val Lys Tyr Val Asp Pro Tyr Arg Thr Ser Gln Met Cys Ser Lys Cys
                405                 410                 415

Gly Asn Tyr Glu Pro Gly Gln Arg Glu Ser Gln Glu Lys Phe Ile Cys
            420                 425                 430
```

```
Lys Ser Cys His Leu Glu Ile Asn Ala Asp Tyr Asn Ala Ser Gln Asn
        435                 440                 445

Ile Ala His Ser Thr Lys Tyr Ile Thr Asn Lys Asn Gln Ser Glu Tyr
    450                 455                 460

Leu Lys Lys Leu Gln Gln Thr Thr Lys Leu Glu Lys Tyr Ser
465                 470                 475


<210> SEQ ID NO 126
<211> LENGTH: 497
<212> TYPE: PRT
<213> ORGANISM: Lyngbya sp.

<400> SEQUENCE: 126

Met Ile Thr Val Arg Lys Ile Lys Leu Thr Ile Met Gly Asp Lys Asp
1               5                   10                  15

Thr Arg Asn Ser Gln Tyr Lys Trp Ile Arg Asp Glu Gln Tyr Asn Gln
            20                  25                  30

Tyr Arg Ala Leu Asn Met Gly Met Thr Tyr Leu Ala Val Asn Asp Ile
        35                  40                  45

Leu Tyr Met Asn Glu Ser Gly Leu Glu Ile Arg Thr Ile Lys Asp Leu
    50                  55                  60

Lys Asp Cys Glu Lys Asp Ile Asp Lys Asn Lys Lys Glu Ile Glu Lys
65                  70                  75                  80

Leu Thr Ala Arg Leu Glu Lys Glu Gln Asn Lys Lys Asn Ser Ser Ser
                85                  90                  95

Glu Lys Leu Asp Glu Ile Lys Tyr Lys Ile Ser Leu Val Glu Asn Lys
            100                 105                 110

Ile Glu Asp Tyr Lys Leu Lys Ile Val Glu Leu Asn Lys Ile Ile Glu
        115                 120                 125

Glu Thr Gln Lys Glu Arg Met Asp Ile Gln Lys Glu Phe Lys Glu Lys
    130                 135                 140

Tyr Val Asp Asp Leu Tyr Gln Val Leu Asp Lys Ile Pro Phe Lys His
145                 150                 155                 160

Leu Asp Asn Lys Ser Leu Val Thr Gln Arg Ile Lys Ala Asp Ile Lys
                165                 170                 175

Ser Asp Lys Ser Asn Gly Leu Leu Lys Gly Glu Arg Ser Ile Arg Asn
            180                 185                 190

Tyr Lys Arg Asn Phe Pro Leu Met Thr Arg Gly Arg Asp Leu Lys Phe
        195                 200                 205

Lys Tyr Asp Asp Asn Asp Asp Ile Glu Ile Lys Trp Met Glu Gly Ile
    210                 215                 220

Lys Phe Lys Val Ile Leu Gly Asn Arg Ile Lys Asn Ser Leu Glu Leu
225                 230                 235                 240

Arg His Thr Leu His Lys Val Ile Glu Gly Lys Tyr Lys Ile Cys Asp
                245                 250                 255

Ser Ser Leu Gln Phe Asp Lys Asn Asn Asn Leu Ile Leu Asn Leu Thr
            260                 265                 270

Leu Asp Ile Pro Ile Asp Ile Val Asn Lys Lys Val Ser Gly Arg Val
        275                 280                 285

Val Gly Val Asp Leu Gly Leu Lys Ile Pro Ala Tyr Cys Ala Leu Asn
    290                 295                 300

Asp Val Glu Tyr Ile Lys Lys Ser Ile Gly Arg Ile Asp Asp Phe Leu
305                 310                 315                 320

Lys Val Arg Thr Gln Met Gln Ser Arg Arg Arg Arg Leu Gln Ile Ala
```

```
                325                 330                 335

Ile Gln Ser Ala Lys Gly Gly Lys Gly Arg Val Asn Lys Leu Gln Ala
            340                 345                 350

Leu Glu Arg Phe Ala Glu Lys Glu Lys Asn Phe Ala Lys Thr Tyr Asn
        355                 360                 365

His Phe Leu Ser Ser Asn Ile Val Lys Phe Ala Val Ser Asn Gln Ala
    370                 375                 380

Glu Gln Ile Asn Met Glu Leu Leu Ser Leu Lys Glu Thr Gln Asn Lys
385                 390                 395                 400

Ser Ile Leu Arg Asn Trp Ser Tyr Tyr Gln Leu Gln Thr Met Ile Glu
                405                 410                 415

Tyr Lys Ala Gln Arg Glu Gly Ile Lys Val Lys Tyr Ile Asp Pro Tyr
            420                 425                 430

His Thr Ser Gln Thr Cys Ser Lys Cys Gly Asn Tyr Glu Glu Gly Gln
        435                 440                 445

Arg Glu Ser Gln Ala Asp Phe Ile Cys Lys Lys Cys Gly Tyr Lys Val
    450                 455                 460

Asn Ala Asp Tyr Asn Ala Ala Arg Asn Ile Ala Met Ser Asn Lys Tyr
465                 470                 475                 480

Ile Thr Lys Lys Glu Glu Ser Lys Tyr Tyr Lys Ile Lys Glu Ser Met
                485                 490                 495

Val


<210> SEQ ID NO 127
<211> LENGTH: 430
<212> TYPE: PRT
<213> ORGANISM: Lyngbya sp.

<400> SEQUENCE: 127

Met Asn Lys Cys Ile Lys Val Ala Ile Lys Asn Cys Lys Glu Leu Asp
1               5                   10                  15

Tyr Lys Val Met Ser Glu Lys Leu Arg Asn Ile Gln Tyr Leu Thr Cys
            20                  25                  30

Lys Ala Ser Asn Lys Val Met Gln Met Tyr Tyr Met Trp Glu Asn Gln
        35                  40                  45

Lys Ile Asp Ile Lys Asn Lys Thr Gly Glu Tyr Pro Asp Asp Lys Glu
    50                  55                  60

Leu Phe Gly Lys Thr Tyr Arg Asn Val Val Glu Gly Glu Met Lys Thr
65                  70                  75                  80

Ile Met Asn Thr Ile Asn Thr Ser Asn Val Gly Gln Thr Asn Ala Ile
                85                  90                  95

Ile Met Lys Lys Trp Asn Thr Asp Lys Lys Glu Val Leu Ser Tyr Gln
            100                 105                 110

Lys Ser Leu Pro Asn Phe Lys Leu Asn Met Pro Ile Tyr Ile Lys Asn
        115                 120                 125

Lys Ser Phe Ser Ile Val Lys Gly Thr Ser Gly Tyr Glu Ile Ile Cys
    130                 135                 140

Ser Ile Phe Asn Lys Ser Gln Asp Leu Lys Arg Leu Thr Phe Ile Ile
145                 150                 155                 160

Asp Lys Leu Asp Gly Asn Lys Lys Ala Thr Leu Asn Lys Ile Ile Asp
                165                 170                 175

Leu Thr Tyr Lys Gln Gly Ala Gly Gln Ile Ile Lys Asp Arg Lys Gly
            180                 185                 190

Lys Trp Tyr Phe Ile Ile Ser Phe Gly Phe Glu Asn Lys Lys Arg Glu
```

```
        195                 200                 205

Leu Asp Ile Asn Arg Ile Leu Gly Ile Asp Val Gly Ile Thr Asn Leu
    210                 215                 220

Leu Thr Met Gln Ile Trp Asp Cys Asn Leu Lys Glu Trp Asp Arg Leu
225                 230                 235                 240

Ala Trp Asn Ser Cys Met Val Asp Gly Arg Glu Leu Met His Tyr Arg
                245                 250                 255

Gln Lys Ile Glu Ala Arg Arg Lys Ser Leu Leu Lys Asn Ser Lys Ile
            260                 265                 270

Ser Glu Lys Asn Thr Gly Lys Ala Gly His Gly Ile Ser Lys Arg Ile
        275                 280                 285

Gln Ala Ile Asp Val Val Arg Asn Lys Glu Lys Asn Phe Arg Asp Thr
    290                 295                 300

Phe Asn His Lys Tyr Ser Arg Tyr Ala Val Asp Phe Ala Ile Arg Asn
305                 310                 315                 320

Asn Cys Gly Ile Ile Gln Met Glu Asn Leu Ala Lys Phe Thr Glu Glu
                325                 330                 335

Val Lys Glu Lys Met Leu Lys Asn Trp Ser Tyr Tyr Asp Leu Gln Ser
            340                 345                 350

Lys Ile Lys Tyr Lys Ala Glu Glu Gln Gly Ile Lys Val Asn Phe Ile
        355                 360                 365

Lys Pro Ser Tyr Thr Ser Lys Arg Cys Ser Leu Cys Gly Ala Ile Asp
    370                 375                 380

Asp Arg Asn Arg Asp Cys Lys Asn Asn Gln Ser Lys Phe Gln Cys Val
385                 390                 395                 400

Val Cys Asp His Lys Glu His Ala Asp Ile Asn Ala Ala Lys Asn Ile
                405                 410                 415

Ala Leu Pro Asp Ile Glu Glu Leu Ile Glu Ser Lys Ile Gly
            420                 425                 430


<210> SEQ ID NO 128
<211> LENGTH: 393
<212> TYPE: PRT
<213> ORGANISM: Desmospora sp.

<400> SEQUENCE: 128

Met Ser Ile Ala Val Lys Val Met Lys Tyr Gln Ile Val Cys Pro Val
1               5                   10                  15

Asn Val Glu Trp Lys Val Phe Glu Thr Tyr Leu Arg Thr Leu Ala Tyr
            20                  25                  30

Gln Ser Arg Thr Ile Gly Asn Arg Thr Ile Gln Lys Ile Trp Glu Phe
        35                  40                  45

Asp Asn Leu Ser Leu Asn His Phe Lys Glu Thr Gly Glu Tyr Pro Ser
    50                  55                  60

Ala Gln Gln Leu Tyr Gly Cys Thr Gln Lys Thr Ile Ser Gly Tyr Ile
65                  70                  75                  80

Tyr Asp Gln Leu Lys Glu Glu Tyr Gln Asp Ile Asn Lys Ala Asn Met
                85                  90                  95

Ser Thr Thr Ile Gln Lys Thr Leu Lys Asn Trp Asn Ser Arg Arg Lys
            100                 105                 110

Glu Ile Trp Arg Gly Glu Arg Lys Gln Asn Ser Met Lys Val Ile Leu
        115                 120                 125

Asp Arg Ile Ile Asp Ser Thr Tyr Ala Lys Gly Ala Cys Met Leu His
    130                 135                 140
```

Lys His Lys Lys Lys Trp Tyr Leu Ser Ile Thr Tyr Lys Ser Asn Ile
145 150 155 160

Lys Glu Glu Leu Lys Phe Asp Glu Asp Leu Ile Met Gly Ile Asp Met
165 170 175

Gly Lys Ile Asn Val Leu Tyr Phe Ala Phe Asn Lys Gly Leu Val Arg
180 185 190

Gly Ala Ile Ser Gly Glu Glu Ile Glu Ala Phe Arg Lys Lys Ile Glu
195 200 205

His Arg Arg Ile Ser Leu Leu Arg Gln Gly Lys Tyr Cys Ser Gly Asn
210 215 220

Arg Ile Gly Lys Gly Arg Glu Lys Arg Ile Lys Pro Ile Asp Val Leu
225 230 235 240

Asn Asp Lys Val Ala Lys Phe Arg Asn Ala Thr Asn His Lys Tyr Ala
245 250 255

Asn Tyr Ile Val Gln Gln Cys Leu Lys Tyr Asn Cys Gly Thr Ile Gln
260 265 270

Leu Glu Asp Leu Lys Gly Ile Ser Lys Glu Gln Thr Phe Leu Lys Asn
275 280 285

Trp Thr Tyr Phe Asp Leu Gln Glu Lys Ile Lys Asn Gln Ala Asn Gln
290 295 300

Tyr Glu Val Lys Val Val Lys Ile Asp Pro Phe Tyr Thr Ser Gln Arg
305 310 315 320

Cys Ser Glu Cys Gly Tyr Ile His Lys Asn Asn Arg Gln Asp Gln Ser
325 330 335

Thr Phe Glu Cys Gln Gln Cys Ser Phe Lys Val His Ala Asp Tyr Asn
340 345 350

Ala Ala Lys Asn Ile Ser Val Tyr Asn Ile Glu Lys Val Ile Gln Lys
355 360 365

Gln Leu Glu Leu Gln Glu Lys Leu Asn Leu Thr Lys Tyr Lys Glu Arg
370 375 380

Tyr Ile Glu Gln Met Glu Asn Ile Asn
385 390

<210> SEQ ID NO 129
<211> LENGTH: 433
<212> TYPE: PRT
<213> ORGANISM: Cyanothece sp.

<400> SEQUENCE: 129

Met Val Cys Asn Lys Val Val Lys Ile Ala Leu Ile Cys Asp Gln Ile
1 5 10 15

Asp Lys Asp Gly Lys Asp Val Asn Tyr Asn Asp Ile Tyr Lys Leu Leu
20 25 30

Trp Asp Leu Gln Lys Gln Thr Arg Glu Ala Lys Asn Lys Val Ile Arg
35 40 45

Leu Cys Trp Glu Trp Ser Gly Tyr Ser Ser Glu Tyr Phe Lys Thr His
50 55 60

Glu Glu Tyr Pro Lys Asp Lys Glu Ile Phe Gly Ile Ser Leu Arg Gly
65 70 75 80

Tyr Leu Tyr Asp Arg Ile Lys Gly Asp Tyr Asn Leu Tyr Ser Gly Asn
85 90 95

Leu Ser Gln Ser Ala Glu Ile Ala Tyr Lys Glu Tyr Lys Asn Ser Leu
100 105 110

Lys Asp Val Leu Arg Gly Asp Lys Ser Ile Ile Asn Tyr Arg Glu Asn
115 120 125

Gln Pro Leu Asp Ile Lys Asn Lys Ala Ile Gln Leu Leu Tyr Glu Asn
130 135 140

Asp Asn Phe Phe Val Arg Val Ala Leu Ile Asn Lys Asp Lys Gln Lys
145 150 155 160

Glu Leu Asn Phe Lys Asp Cys Ser Val Arg Phe Lys Leu Leu Val Lys
165 170 175

Asp Asp Ser Thr Arg Thr Ile Leu Glu Arg Cys Phe Asp Glu Val Tyr
180 185 190

Thr Ile Thr Ala Ser Lys Ile Met Tyr Asn Lys Lys Lys Lys Gln Trp
195 200 205

Tyr Ile Asn Leu Gly Tyr Lys Phe Thr Lys Glu Ile Asp Lys Thr Leu
210 215 220

Asp Lys Asp Arg Ile Leu Gly Val Asp Leu Gly Val Ile Asn Pro Leu
225 230 235 240

Val Ala Ser Val Tyr Gly Ser Tyr Asp Arg Leu Ile Ile Gly Gly Gly
245 250 255

Glu Ile Asp Lys Phe Arg Lys Arg Val Glu Ala Asn Lys Val Gln Met
260 265 270

Leu Lys Gln Gly Lys Tyr Cys Gly Asp Gly Arg Ile Gly His Gly Val
275 280 285

Asn Thr Arg Asn Lys Pro Ala Tyr Asn Ile Glu Asp Lys Ile Ser Arg
290 295 300

Phe Arg Asp Thr Val Asn His Lys Tyr Ser Lys Ala Val Val Asp Tyr
305 310 315 320

Ala Val Lys Asn Asn Cys Gly Thr Ile Gln Met Glu Asp Leu Lys Gly
325 330 335

Ile Thr Gln Asn Lys Asn Glu Arg Tyr Leu Lys Asn Trp Thr Tyr Phe
340 345 350

Asp Leu Gln Thr Lys Ile Glu Tyr Lys Ala Lys Ala Leu Gly Ile Glu
355 360 365

Val Lys Tyr Lys Asn Pro Lys Tyr Thr Ser Gln Arg Cys Ser Lys Cys
370 375 380

Gly His Ile Ala Glu Glu Asn Arg Pro Glu Gln Lys Thr Phe Lys Cys
385 390 395 400

Val Lys Cys Gly Phe Lys Val Asn Ala Asp Tyr Asn Ala Ser Gln Asn
405 410 415

Leu Ala Ile Lys Asp Ile Asp Lys Ile Ile Glu Gln Tyr Tyr Asn Lys
420 425 430

Gly

<210> SEQ ID NO 130
<211> LENGTH: 453
<212> TYPE: PRT
<213> ORGANISM: Ruminococcus albus

<400> SEQUENCE: 130

Met Thr Lys Val Val Lys Leu Ala Leu Ile Ser Asn Val Thr Asp Lys
1 5 10 15

Asp Gly Asn Lys Val Glu Tyr Asn Glu Leu Asn Arg Cys Leu Trp Asp
20 25 30

Leu Gln Lys Glu Thr Arg Asp Leu Lys Asn Ala Val Val Arg Glu Cys
35 40 45

Trp Glu Trp Tyr Gly Phe Thr Asn Asp Tyr Tyr Lys Leu Asn Glu Glu
50 55 60

Tyr Pro Asn Glu Arg Asp Tyr Leu Lys Lys Ala Lys Ser Asp Gly Thr
65 70 75 80

Ile Lys Asp Tyr Ala Leu Asp Gly Phe Ile Tyr Ala Lys Tyr Ser Lys
85 90 95

Lys Tyr Asn Leu His Ser Gly Asn Tyr Ser Gln Thr Leu Arg Asp Ala
100 105 110

Cys Gly Ser Phe Lys Asn Asn Leu Lys Glu Ile Leu Arg Gly Asp Lys
115 120 125

Ser Ile Leu Ser Tyr Arg Ala Asp Gln Pro Leu Asp Ile Lys Lys Thr
130 135 140

Cys Ile Gly Leu Glu Tyr Asp Lys Asp Thr Asn Thr Tyr Tyr Val Thr
145 150 155 160

Leu Val Leu Leu Asn Lys Asn Gly Val Lys His Tyr Asn Ile Ser Asp
165 170 175

Phe Arg Phe Lys Ile Thr Val Lys Asp Asn Ser Thr Arg Thr Ile Leu
180 185 190

Glu Arg Cys Phe Asp Gly Val Tyr Gly Ile Ser Ala Ser Lys Leu Ile
195 200 205

Trp Asn Arg Lys Lys Ser Gln Trp Phe Leu Asn Leu Cys Tyr Ser Phe
210 215 220

Asp Lys Val Glu Val Lys Glu Leu Asp Lys Lys Lys Ile Leu Gly Val
225 230 235 240

Asn Leu Gly Val Tyr Tyr Pro Leu Tyr Ala Ser Ile Ser Gly Glu Lys
245 250 255

Asp Arg Leu Ala Ile Ser Gly Asp Glu Ile Ile Glu Phe Arg Lys Arg
260 265 270

Ile Glu Ala Arg Arg Thr Ala Leu Lys Lys Gln Ala Ala Val Cys Gly
275 280 285

Asp Gly Arg Ile Gly His Gly Tyr Lys Thr Arg Met Lys Pro Leu Gln
290 295 300

Asn Val Ser Asp Lys Ile Ala Asn Phe Arg Asp Thr Phe Asn His Lys
305 310 315 320

Ala Ser Lys Lys Leu Ile Asp Phe Ala Ile Lys Asn Asp Cys Gly Ile
325 330 335

Ile Gln Leu Glu Asn Leu Lys Gly Val Thr Lys Asn Ser Glu Gly Phe
340 345 350

Leu Lys Asn Trp Ser Phe Tyr Asp Leu Gln Ser Lys Ile Glu Asn Lys
355 360 365

Ala Lys Glu Arg Gly Ile Lys Val Val Tyr Ile Glu Pro Ala Tyr Thr
370 375 380

Ser Leu Arg Cys Ser Lys Cys Gly Cys Ile His Lys Asp Asn His Pro
385 390 395 400

Thr Arg Glu Gln Phe Ile Cys Gln Glu Cys Gly Tyr Arg Val Leu His
405 410 415

Asp Tyr Asn Ala Ser Gln Asn Ile Ala Val Lys Asp Ile Asp Lys Ile
420 425 430

Ile Lys Ala Glu Leu Glu Lys Thr Glu Pro Glu Lys Lys Thr Glu Glu
435 440 445

Glu Lys Pro Glu Lys
450

<210> SEQ ID NO 131
<211> LENGTH: 532

<212> TYPE: PRT
<213> ORGANISM: Kitasatospora cheerisanensis

<400> SEQUENCE: 131

Met Ser Tyr Leu Cys Ala Arg Gly Arg Phe Asn Leu Ser Gly Phe Ser
1 5 10 15

Thr Gly Ser Met Gly Val Leu Pro Val Arg Ala Ser Leu Phe Ala Leu
20 25 30

Leu Phe Thr Thr Leu His Gly Ala Arg Ile Ser Ala His Trp Tyr Gly
35 40 45

Met Ser Lys Glu Asn Asp His Thr Val Thr Cys Ile Lys Ile Cys Leu
50 55 60

Glu Pro Asn Lys Ala Gln Arg Ala Gln Phe Ala Ser Phe Ala Gly Ser
65 70 75 80

Ala Arg Trp Ala Tyr Asn Phe Ala Leu Ala Ile Lys Ile Gly Tyr Gln
85 90 95

Lys Arg Trp Phe Glu Ala Arg Lys Gln Phe Ile Glu Ser Gly Leu Asp
100 105 110

Glu Lys Ala Ala Gly Lys Lys Ala Ser Glu Gln Val Gly Arg Met Pro
115 120 125

Asn Tyr Met Ser Ile Ala Thr Asn Glu Trp Thr Gln Leu Arg Asp Glu
130 135 140

Val Cys Pro Trp Tyr Pro Glu Val Pro Arg Arg Val Phe Val Gly Gly
145 150 155 160

Phe Gln Arg Ala Asp Ala Ala Phe Lys Asn Trp Phe Asp Ser Lys Ser
165 170 175

Gly Arg Arg Ser Gly Ala Ala Met Gly Trp Pro Lys Phe Lys Ser Lys
180 185 190

Ser Lys Ser Arg Glu Ser Phe Val Ile Ala Asn Asp Val Gln Pro Ala
195 200 205

Phe Val Ala Asn Leu Asn Arg Tyr Ile Lys Thr Gly Glu Leu Ala Asp
210 215 220

Met Asp Tyr Arg His Ile Lys Val Pro Lys Cys Gly Glu Val Arg Leu
225 230 235 240

Thr Pro Gly Ser Ala Gly Gln Leu Arg Gln Leu Gly Arg Thr Met Leu
245 250 255

Ala Glu Ala Lys Thr Gly Glu Leu Ile Thr Arg Ile Thr Ser Gly Thr
260 265 270

Ile Ser Arg Leu Gly Asp Arg Trp Tyr Val Ser Leu Val Ile Ser Gly
275 280 285

Pro Phe Val Pro Asp Ala Ile Ser Thr Lys Arg Gln Arg Arg Asn Gly
290 295 300

Val Val Gly Val Asp Leu Gly Ser Gly Arg Phe Tyr Ala Thr Thr Ser
305 310 315 320

Glu Gly Leu Ser Ile Ile Asn Pro Lys Phe Val Ser Lys Tyr Glu Gln
325 330 335

Glu Leu Ala Arg Ala Asn Arg Ala Leu Ala Lys Thr Ala Lys Gly Ser
340 345 350

Ala Ala Arg Lys Lys Ala Leu Ala Arg Leu Arg Arg Val His Ala Arg
355 360 365

Ser Ala Leu Ala Arg Asp Gly Phe Ser His Gln Val Ser Ala Trp Leu
370 375 380

Thr Ser Gln Phe Ala Gly Val Ala Val Glu Lys Phe Asp Leu Ala Ser
385 390 395 400

Met Leu Ala Ser Ala Lys Gly Thr Val Glu Lys Pro Gly Lys Asn Val
405 410 415

Asp Val Lys Ala Arg Phe Asn Ala His Leu Ala Asp Val Gly Ile Ala
420 425 430

Ser Thr Ile Asp Lys Leu Leu Tyr Lys Gly Lys Arg Asp Gly Cys Arg
435 440 445

Val Gln Val Val Asn Thr Leu Asp Asn Ser Ser Thr Thr Cys Ala Lys
450 455 460

Cys Gly His Thr Cys Val Cys Gly Pro Glu Gln Lys Thr Phe Thr Cys
465 470 475 480

Pro Asp Cys Gly Tyr Asn Ala Pro Arg Gln Leu Asn Ser Ala Gln Tyr
485 490 495

Ile Arg Gln Leu Ala Thr Val Gly Phe Asp Glu Leu Gly Leu Asp Met
500 505 510

Thr Ala Ser Leu Thr Pro Asp Thr Gly Lys Arg Pro Ile Ala Phe Met
515 520 525

Thr Ser Ala His
530

<210> SEQ ID NO 132
<211> LENGTH: 513
<212> TYPE: PRT
<213> ORGANISM: Spirulina subsalsa

<400> SEQUENCE: 132

Met Ser Ser Glu Arg Ala Pro Lys Leu Arg Asn Val Val Thr Gln Gln
1 5 10 15

Ala Tyr Lys Tyr Ala Leu Glu Pro Thr Pro Arg Gln Gln Cys Ala Phe
20 25 30

Ser Ser His Ala Gly Ala Ala Arg Phe Ala Tyr Asn Trp Gly Ile Ala
35 40 45

Arg Val Ala Asp Ser Leu Asp Ala Tyr Ala Glu Gln Lys Ala Ala Gly
50 55 60

Ile Asp Glu Pro Asp Val Lys Phe Pro Gly His Phe Asp Leu Cys Lys
65 70 75 80

Met Trp Thr Ala Trp Lys Asn Thr Ala Glu Trp Thr Asp Arg His Thr
85 90 95

Gly Gln Thr Thr Thr Gly Val Pro Trp Val Ala Ser Asn Phe Val Gly
100 105 110

Thr Tyr Gln Ala Ala Leu Arg Asp Ala Ala Gly Ala Trp Gln Arg Phe
115 120 125

Phe Arg Ala Arg Lys Thr Gly Ala Arg Ala Gly Arg Pro Arg Phe Lys
130 135 140

Lys Arg Gly Arg Ala Arg Asp Ser Phe Gln Leu His Gly Asp Gly Leu
145 150 155 160

Arg Ile Val Asp Ala Lys His Val Asn Leu Pro Lys Ile Gly Thr Val
165 170 175

Lys Thr Phe Glu Ala Thr Arg Lys Leu Ala Arg Arg Leu Ala Lys Gly
180 185 190

Ser Val Pro Cys Pro Thr Cys Arg Ala Thr Gly Lys Ile Thr Asp Ser
195 200 205

Ala Ser Gly Lys Val Lys Lys Cys Ser Asp Cys Lys Ala Ala Gly Ser
210 215 220

Arg Pro Ala Ala Arg Ile Val Arg Gly Thr Val Ala Arg Asp Ser Ala

-continued

```
225                 230                 235                 240

Gly Arg Trp Tyr Leu Ala Leu Thr Val Glu Leu Val Arg Glu Val Arg
                245                 250                 255

Thr Ala Pro Thr Pro Arg Gln Leu Ala Gly Gly Pro Val Gly Val Asp
            260                 265                 270

Phe Gly Val Arg Gln Val Ala Thr Leu Ser Thr Gly Gln Leu Val Asp
        275                 280                 285

Asn Pro Arg His Leu Glu Ser His Leu Arg Arg Val Lys Thr Ala Gln
    290                 295                 300

Gln Ala Leu Ser Arg Cys Pro Pro Gly Ser Arg Arg Arg Ala Lys Ala
305                 310                 315                 320

Gln Gln Arg Leu Gly Arg Leu His Ala Arg Val Arg His Leu Arg Glu
                325                 330                 335

Asn Ser Leu Gln Gln Ala Thr Ser Ala Leu Ile His Gln His Ser Val
            340                 345                 350

Ile Ala Val Glu Gly Trp Asp Val Gln Gln Thr Ala Gln His Ala Ser
        355                 360                 365

Pro Lys Asn Leu Pro Lys Gln Ile Arg Arg Asn Arg Asn Arg Ala Leu
    370                 375                 380

Leu Asp Thr Gly Ile Gly Ala Ala Arg Trp Gln Leu Gln Ser Lys Gly
385                 390                 395                 400

Ala Trp Tyr Gly Thr Thr Val Val Val Thr Asp Arg His Ala Pro Thr
                405                 410                 415

Gly Arg Gln Cys Ser Ala Cys Gly Thr Val Lys Ala Thr Pro Ile Pro
            420                 425                 430

Pro Thr Gln Asp Glu Tyr Arg Cys Pro Ala Cys Gly Thr Ser Leu Asp
        435                 440                 445

Arg Arg Thr Asn Thr Ala Arg Val Leu Ala Ala Val Ala Ala Gln His
    450                 455                 460

His Asp Ala Pro Ser Gly Gly Glu Ser Lys Asn Ala Arg Gly Glu Asn
465                 470                 475                 480

Thr Arg Pro Thr Ala Pro Arg Arg Asn Gly Gln Phe Ser Ala Lys Arg
                485                 490                 495

Glu Pro Arg Ser Arg Pro Pro Gly Arg Gly Gln Thr Gly Thr Pro Gly
            500                 505                 510

Thr


<210> SEQ ID NO 133
<211> LENGTH: 544
<212> TYPE: PRT
<213> ORGANISM: Clostridioides difficile

<400> SEQUENCE: 133

Met Gly Thr Glu Gly Ala Leu Thr His Arg Val Val Arg Val Cys Leu
1               5                   10                  15

Asp Asp Ala Ala Leu Thr Pro Asp Gln Arg Thr Leu Leu Asp Arg His
            20                  25                  30

Ala Gly Thr Ala Arg Ala Val Trp Asn Trp Gly Leu Ala Ala Arg Asn
        35                  40                  45

Ala Gln Gln Asp Ala Leu Met Ala His Val Arg Ala Val Ala Leu Glu
    50                  55                  60

Gln Ala Ala Ser Asp Glu Thr Ala Ala Ala Glu Leu Leu Asp Asp Arg
65                  70                  75                  80

Asp Trp Arg Thr Ala Thr Ile Lys Ala Ala Pro Asp Glu Leu Arg Arg
```

-continued

```
                85                  90                  95

Pro Leu Arg Ala Ala Thr Leu Gly Arg Ala Phe Thr Ala Glu Thr Arg
            100                 105                 110

Asp Pro Asp Ser Arg Phe Ala Trp Trp Ala Val Glu Arg His Gly Val
        115                 120                 125

Asn Arg Phe Ala Val Ser Ser Ser Leu Gln Ala Leu Asp Ala Ala Phe
    130                 135                 140

Asp Arg Tyr Tyr Arg Asp Thr Gly Gly His Arg Ser Ala Arg Arg Ala
145                 150                 155                 160

Arg Pro Arg Lys Asp Gly Arg Pro Ala Ala Trp Pro Arg Phe Lys Lys
                165                 170                 175

Arg Gly Arg Ala Thr Asp Ala Phe Ala Leu Phe Asn Leu Val Val Ala
            180                 185                 190

Gly Gln Asp Pro Trp Arg Val Ile Glu Gly Ala His Arg Ile Lys Val
        195                 200                 205

Pro Ser Leu Gly Ser Leu Arg Val His Glu Asn Thr Lys Arg Leu Arg
    210                 215                 220

Arg Leu Ile Ala Arg Gly Gly Arg Pro Thr Ser Ala Arg Phe Thr Arg
225                 230                 235                 240

Thr Gly Gly Arg Trp Tyr Met Ser Val Val Val Ala Leu Pro Ala Thr
                245                 250                 255

Ala Ala Ser Thr Val Leu Ser Pro Ala Gly Ala Pro Arg Ala Ala Ala
            260                 265                 270

Pro Thr Arg Ala Gln Thr Arg Ala Gly Leu Val Gly Val Asp Leu Gly
        275                 280                 285

Ile Lys Thr Leu Ala Thr Met Ser Asp Gly Thr Leu Val Ala Asn Ala
    290                 295                 300

Arg His Gly Arg Ala Ala Ala Arg Arg Leu Ala Arg Leu Gln Arg Arg
305                 310                 315                 320

Ala Ala Arg Gln Gln Gly Pro Arg Lys Gly Ala Ala Pro Ser Lys Gly
                325                 330                 335

Trp Val Ala Thr Gln Arg Thr Ile Thr Arg Leu Gln His Asp Thr Ala
            340                 345                 350

Ala Arg Arg Arg Gly Leu Val Tyr Glu Leu Thr Lys Thr Leu Ala Ala
        355                 360                 365

Gly Tyr Ala Ala Val Ala Ile Glu Asp Leu Asn Val Ala Gly Met Thr
    370                 375                 380

Ala Thr Pro Ala Ala Arg Pro Asp Pro Asp Arg Pro Gly Val Tyr Leu
385                 390                 395                 400

Ala Asn Gly Arg Ala Ala Lys Ser Gly Leu Asn Arg Ala Ile Leu Asp
                405                 410                 415

Val Gly Phe Gly Glu Phe Arg Arg Gln Leu Thr Tyr Lys Thr Pro Met
            420                 425                 430

Tyr Gly Ala Gln Leu Leu Glu Ile Ala Arg Phe Ala Pro Thr Ser Lys
        435                 440                 445

Thr Cys Ser Thr Cys Gly Ala Val Arg Ala Lys Leu Arg Leu Asp Glu
    450                 455                 460

Arg Thr Tyr Arg Cys Glu His Cys Gly Leu Val Ile Asp Arg Asp Leu
465                 470                 475                 480

Asn Ala Ala Arg Asn Ile Ala Ala Leu Gly His Gln Ala Leu Gly Thr
                485                 490                 495

Ser Pro Ala Asp Ala Gly Asp Ala Lys Arg Arg Asp His Lys Glu Gly
            500                 505                 510
```

```
Asp Arg Glu Arg Ser Val Ile Leu Val Ser Gln Asp Leu Gly Pro Pro
        515                 520                 525

Arg Ser Ala Glu Arg Val Thr Asp Ser Ser Pro Pro Thr Arg Ala Ala
    530                 535                 540


<210> SEQ ID NO 134
<211> LENGTH: 537
<212> TYPE: PRT
<213> ORGANISM: Clostridium botulinum

<400> SEQUENCE: 134

Met Thr Ser Thr Thr Leu Ala Pro Glu Glu Pro Leu Met Val Phe Arg
1               5                   10                  15

Gly Ala Arg Phe Arg Leu Asp Pro Thr Gly Glu Gln Gln Gly Ile Leu
            20                  25                  30

Ser Gln Gln Ala Gly Ala Ala Arg Val Ala Tyr Asn Met Met Cys Thr
        35                  40                  45

Leu Asn Lys Asp Ile Leu Glu Ala Arg Ser Gln Leu Tyr Ser Thr Leu
    50                  55                  60

Ile Lys Asp Gly Lys Thr Lys Asp Lys Ala Lys Lys Glu Leu Lys Ala
65                  70                  75                  80

Ala Ala Lys Glu Asp Pro Ser Leu Ala Ile Val Trp Ala Arg Asp Phe
                85                  90                  95

Asp Lys Asn Tyr Ile Thr Pro Glu Arg Asn Arg His Lys His Ala Ala
            100                 105                 110

Gln Arg Ile Ala Ala Gly Glu Asn Pro Val Asp Val Trp Asn Pro Asp
        115                 120                 125

Glu Glu Arg Phe Asn Glu Pro Trp Leu His Thr Ala Asn Arg Arg Val
    130                 135                 140

Leu Arg Ser Gly Gln Lys Gln Tyr Glu Gln Ala Leu Asp Asn Phe Phe
145                 150                 155                 160

Lys Ser Gln Asn Gly Ser Arg Ala Gly Gln Lys Met Gly Lys Pro Arg
                165                 170                 175

Phe Lys Thr Lys Ile Arg Ser Thr Asp Ser Phe Thr Ile Asp Ala Val
            180                 185                 190

Asp Val Ser Ser Ser Thr Thr Leu Ile Arg Asp Ile Gly Pro Lys Asp
        195                 200                 205

His Ala Arg Tyr Lys Thr Gly Glu Ala Ser Thr Gly Ile Ile Ala Asp
    210                 215                 220

Tyr Arg His Val Arg Leu Ser His Leu Gly Thr Phe Arg Val Phe Gly
225                 230                 235                 240

Ser Thr Lys Ala Leu Val Arg Gln Leu Asp Arg Gly Gly Arg Ile Lys
                245                 250                 255

Ser Cys Thr Val Ser Arg Ser Ala Asp Arg Trp Tyr Val Ser Phe Leu
            260                 265                 270

Val Glu Leu Pro Ile Glu Ile Ala Arg Ser Thr Pro Thr Lys Lys Gln
        275                 280                 285

Tyr Lys Ala Gly Ala Val Gly Ile Asp Leu Gly Val Lys Ser Leu Ala
    290                 295                 300

Ala Leu Ser Thr Gly Glu Ile Ile Pro Asn Pro Arg Phe Leu Arg Thr
305                 310                 315                 320

Ala Asp Lys Lys Ile Lys Lys Leu Gln Arg Lys Ile Ala Arg Cys Gln
                325                 330                 335

Lys Gly Ser Lys Asn Ser Ile Arg Leu Lys Arg Arg Leu Ala Arg Cys
```

```
            340                 345                 350

His His Glu Leu Ala Leu Gln Arg Ala Gly Tyr Leu Asn Glu Leu Thr
        355                 360                 365

Ser Met Leu Ala Ser Ser Phe Ser Ala Ile Ala Leu Glu Asp Leu Asn
    370                 375                 380

Val Ala Gly Met Thr Ser Ser Ala Arg Gly Thr Val Glu Asn Pro Gly
385                 390                 395                 400

Lys Asn Val Lys Gln Lys Ala Gly Leu Asn Arg Ser Ile Leu Asp Ile
                405                 410                 415

Ser Pro Gly Arg Ile Arg Thr Leu Leu Glu Tyr Lys Cys Thr Asp Arg
            420                 425                 430

Gly Val Glu Leu Gln Val Ile Asp Arg Phe Phe Pro Ser Ser Gln Leu
        435                 440                 445

Cys Ser Ser Cys Gly Ser Lys Thr Thr Ile Pro Leu Ala Gln Arg Ile
    450                 455                 460

Tyr His Cys Asp Val Cys Gly Gly Val Ile Asp Arg Asp Val Asn Ala
465                 470                 475                 480

Ala Ile Asn Ile Val Tyr Glu Ala Lys Arg Leu Val Glu Gln Lys Cys
                485                 490                 495

Ser Glu His Ser Ala Pro Glu Gly Ala Glu Asp Lys Arg Pro Trp Ser
            500                 505                 510

Val His Leu Pro Ser Thr Gln Tyr Val Asp Gly Leu Tyr Thr Arg Lys
        515                 520                 525

Arg Gln Gly Pro Ser Gly His Ser Ser
    530                 535


<210> SEQ ID NO 135
<211> LENGTH: 513
<212> TYPE: PRT
<213> ORGANISM: Mycobacterium yongonense

<400> SEQUENCE: 135

Met Thr Thr Ala Arg Ala Asn Glu Ile Pro Thr Cys Gln Thr Gln His
1               5                   10                  15

Leu Arg Ser Thr His Met Thr Asp Val Glu Leu Ser Ala Tyr Arg Phe
            20                  25                  30

Ala Leu Asp Thr Thr Pro Ala Gln Leu Thr Met Leu Arg Gln His Ala
        35                  40                  45

Gly Ala Ala Arg Trp Ala Tyr Asn His Ala Leu Gly Val Lys Phe Ala
    50                  55                  60

Ala Leu Asp Glu Arg Lys Thr Val Ile Ala Gly Leu Val Glu Gln Gly
65                  70                  75                  80

Leu Asp Pro Lys Thr Ser Ala Ala Gln Ala Pro Lys Ile Pro Thr Lys
                85                  90                  95

Pro Ala Ile Gln Lys Ala Leu Asn Thr Thr Lys Gly Asp Asp Arg Ile
            100                 105                 110

Ser Ala Ala Gly Asp Cys Pro Trp Trp His Thr Val Ser Thr Tyr Ala
        115                 120                 125

Phe Gln Ser Ala Phe Ala Asp Ala Asp Thr Ala Trp Lys Asn Trp Leu
    130                 135                 140

Ala Ser Leu Thr Gly Lys Arg Ser Gly Pro Ile Gly Ala Pro Arg Phe
145                 150                 155                 160

Lys Ser Lys His Arg Ser Arg Asp Ser Phe Arg Ile His His Asp Val
                165                 170                 175
```

-continued

```
Asn Asn Pro Thr Ile Arg Pro Asp Asp Gly Tyr Arg Arg Ile Ile Val
            180                 185                 190

Pro Arg Leu Gly Ser Leu Arg Val His Asp Ser Thr Lys Arg Leu Lys
        195                 200                 205

Arg Ala Ile Asp Arg Gly Ala Val Ile Gln Ser Val Thr Ile Ser Arg
    210                 215                 220

Gly Gly His Arg Trp Tyr Ala Ser Ile Leu Val Lys Ala Pro Ala Ala
225                 230                 235                 240

His Ala Ala Pro Thr Arg Arg Gln Arg Gln Ala Gly Thr Val Gly Val
                245                 250                 255

Asp Leu Gly Val His His Leu Ala Ala Leu Ser Thr Gly Asp Ile Ile
            260                 265                 270

Asp Asn Pro Arg His Leu Ala Ala Gly Gln Lys Arg Leu Thr Lys Ala
        275                 280                 285

Gln Arg Ala Leu Ser Arg Thr Glu Lys Gly Ser Asn Arg Arg Arg Arg
    290                 295                 300

Ala Ala Ala Arg Val Gly Arg Arg His His Glu Ile Thr Glu Arg Arg
305                 310                 315                 320

Ala Thr Thr Leu His Thr Leu Thr Lys His Leu Ala Thr Asn Trp Ala
                325                 330                 335

Thr Val Ala Ile Glu Asp Leu Asn Val Ala Gly Met Thr Arg Ser Ala
            340                 345                 350

Arg Gly Thr Ile Asp Asn Pro Gly Thr Asn Val Arg Ala Lys Ala Gly
        355                 360                 365

Leu Ser Arg Ala Ile Leu Asp Thr Ser Pro Gly Glu Leu Arg Arg Gln
    370                 375                 380

Leu Thr Tyr Lys Thr Gly Trp Tyr Gly Ser Thr Leu Ala Ile Cys Asp
385                 390                 395                 400

Arg Trp Phe Pro Ser Ser Gln Gln Cys Cys Glu Cys Lys Val Arg Thr
                405                 410                 415

Lys Leu Arg Leu Ser Gln Arg Val Phe Thr Cys Pro Ala Cys Gly Tyr
            420                 425                 430

Gly Pro Ile Asp Arg Asp Val His Ala Ala Arg Asn Ile Ala Ala Tyr
        435                 440                 445

Ala Ala Val Ala Ser Asp Thr Gly Glu Thr Leu Thr Ala Arg Arg Asp
    450                 455                 460

Thr Ala Glu Ala Pro Thr Arg Val Gly Arg Arg Arg Gly Ala Val Asp
465                 470                 475                 480

Ala Gly Arg Pro His Arg Glu Thr Gly Ala Ala Thr Pro Ala Glu Gln
                485                 490                 495

Pro Ala Gly His Pro Lys His Ala Asp Gln Arg Thr Leu Pro Leu Val
            500                 505                 510

Ser


<210> SEQ ID NO 136
<211> LENGTH: 515
<212> TYPE: PRT
<213> ORGANISM: Rothia mucilaginosa

<400> SEQUENCE: 136

Met Ala Glu Val Leu Arg Ala Phe Lys Phe Thr Leu Asp Pro Thr Arg
1               5                   10                  15

Ala Gln Val Gly Ala Leu Gln Gln His Ala Gly Ala Ala Arg Trp Ala
            20                  25                  30
```

-continued

```
Phe Asn Trp Ala Leu Gly Glu Lys Val Ala Ala His Arg Glu Trp Arg
        35                  40                  45

Arg Gln Val Gly Ala Leu Leu Ala Glu Gly Val Ala Glu Glu Gln Ala
    50                  55                  60

Arg Lys Gln Val Arg Val Pro Val Pro Thr Lys Pro Thr Ile Gln Lys
65                  70                  75                  80

Arg Leu Asn Ser Phe Lys Gly Asp Ser Arg Val Gln Asp Leu Pro Asp
                85                  90                  95

Gly Val Leu Gly Pro Arg Arg Pro Cys Pro Trp Trp Trp Glu Val Lys
            100                 105                 110

Thr Tyr Cys Phe Gln Ala Ala Met Ala Asp Ala Asp Thr Ala Trp Lys
        115                 120                 125

Asn Trp Leu Ser Ser Leu Thr Gly Ala Arg Ala Gly Gln Arg Val Gly
    130                 135                 140

Tyr Pro Arg Phe Lys Lys Lys Gly Arg Ala Arg Asp Ser Phe Arg Leu
145                 150                 155                 160

His His Asp Val Lys Lys Pro Gly Ile Arg Leu Ala Gly Tyr Arg Arg
                165                 170                 175

Leu Arg Leu Pro Thr Ile Gly Glu Val Arg Leu His Asp Phe Gly Lys
            180                 185                 190

Arg Leu Ala Arg Leu Ile Asp Arg Gly Arg Ala Val Val Gln Ser Val
        195                 200                 205

Thr Val Ala Arg Cys Gly His Arg Trp Tyr Ala Ser Val Leu Cys Lys
    210                 215                 220

Val Asp Gln Ser Val Pro Gln Arg Ser Thr Arg Ala Gln Arg Arg Arg
225                 230                 235                 240

Gly Arg Val Gly Val Asp Leu Gly Val Lys His Leu Ala Ala Leu Ser
                245                 250                 255

Gln Pro Leu His Pro Tyr Asp Arg Ala Ser Leu Tyr Val Glu Asn Pro
            260                 265                 270

Arg His Leu Arg Arg Ala Ala Gln Arg Leu Ala Lys Ala Gln Arg Ala
        275                 280                 285

Leu Ala Arg Thr Gln Lys Gly Ser Lys Arg Arg Ala Lys Ala Val Arg
    290                 295                 300

Arg Val Gly Arg Leu His His Glu Val Ala Val Arg Arg Glu Ser Thr
305                 310                 315                 320

Leu His Gln Leu Thr Lys Arg Leu Ala Thr Gly Phe Ala Glu Val Ala
                325                 330                 335

Val Glu Asp Leu His Val Ala Gly Met Thr Arg Ser Ala Lys Gly Thr
            340                 345                 350

Ile Asp Ala Pro Ser Arg Asn Val Arg Ala Lys Ala Gly Leu Asn Arg
        355                 360                 365

Ser Ile Leu Asp Thr Ala Pro Gly Glu Leu Arg Arg Gln Leu Thr Tyr
    370                 375                 380

Lys Thr Cys Trp Tyr Gly Ser Arg Leu Ala Val Leu Asp Arg Trp Trp
385                 390                 395                 400

Pro Ser Ser Lys Thr Cys Ser Ala Cys Gly Arg Gln Asn Pro Arg Leu
                405                 410                 415

Thr Leu Ala Asp Arg Thr Phe His Cys Thr Gly Cys Gly Leu Arg Ile
            420                 425                 430

Asp Arg Asp Leu Asn Ala Ser Arg Asn Ile Ala Thr His Ala Ala Leu
        435                 440                 445

Ala Asp Thr Ala Pro Pro Val Ala Pro Asp Arg Gly Glu Thr Gln Asn
```

```
    450                 455                 460

Ala Arg Arg Ala Gly Thr Arg Pro Thr Gly Pro Arg Ala Gly Arg His
465                 470                 475                 480

Pro Ala Thr Lys Arg Glu Asp Thr Ala Pro Ala Val Pro Pro Gln Arg
                485                 490                 495

Ser Asn Pro Leu Ala Leu Pro Pro Pro Pro Thr Gly Tyr Glu Gln Val
            500                 505                 510

Thr Leu Phe
        515


<210> SEQ ID NO 137
<211> LENGTH: 558
<212> TYPE: PRT
<213> ORGANISM: Thermincola ferriacetica

<400> SEQUENCE: 137

Met Ala Glu Lys Thr Gly Thr Asp Ala Gly Thr Met Asn Arg Ala Tyr
1               5                   10                  15

Lys Phe Arg Leu Asp Pro Asn Gln Ala Gln Lys Ala Glu Leu Met Arg
            20                  25                  30

Cys Val Gly Ala Ala Arg Tyr Thr Tyr Asn Leu Leu Asn Ala Tyr Asn
        35                  40                  45

Leu Gln Ile Leu Arg Asn Glu Gln Glu Tyr Arg Asn Thr Arg Asn Ala
    50                  55                  60

Glu Gly Ala Asp Tyr Glu Thr Ile Asn Gly Glu Ile Arg Lys Leu Arg
65                  70                  75                  80

Lys Lys Asp Pro Ala Tyr Lys Phe Leu Gly His Ala Glu Tyr Glu Lys
                85                  90                  95

Arg Tyr Leu Thr Pro Glu Lys Gln Arg His Glu Ala Ile Ala Gln Ala
            100                 105                 110

Ile Thr Asp Gly Ala Asp Pro Ala Val Val Trp Ser Glu Thr Glu Arg
        115                 120                 125

Phe Ala Glu Pro Trp Leu His Thr Ile Ala Arg Arg Val Leu Val Ser
    130                 135                 140

Gly Ile Lys Asn Ala Asp Lys Ala Trp Asp Asn Tyr Asn Lys Ser Arg
145                 150                 155                 160

Met Lys Gln Arg Ala Gly Ala Arg Met Gly Ile Pro Arg Phe Lys Arg
                165                 170                 175

Lys Gly Val Ser Arg Asp Ser Phe Thr Val Pro His Glu Thr Thr Gly
            180                 185                 190

Ala Tyr Gly Ala Tyr Tyr His Lys Lys Asp Pro Glu Tyr Ala Arg Arg
        195                 200                 205

Lys Val Gln Leu Lys Arg Arg Gly Ile Ser Ala Lys Pro Thr Ile Thr
    210                 215                 220

Asp Tyr Arg His Val Arg Leu Ala Ser Leu Gly Val Ile Arg Thr His
225                 230                 235                 240

Asn Thr Thr Lys Pro Leu Val Lys Ala Val Arg Ala Gly Ala Glu Ile
                245                 250                 255

Lys Ser Phe Thr Val Ser Arg Ala Ala Asp His Trp Tyr Val Ser Ile
            260                 265                 270

Leu Val Glu Leu Thr Arg Pro Ser Thr Ala Pro Thr Arg Ala Gln Arg
        275                 280                 285

Ser Ala Gly Ala Val Gly Val Asp Leu Gly Val Arg Tyr Leu Ala Ala
    290                 295                 300
```

```
Leu Ser Asp Glu Gln Ala Pro Gln Arg Phe Ala Gln Tyr Pro Ser Leu
305                 310                 315                 320

Glu Phe Thr Ser Asp Gly Ala Pro Thr Leu Ala Asn Pro Arg Trp Ala
                325                 330                 335

Arg Ala Ala Glu Lys Arg Leu Val Arg Leu Gln Arg Ala Leu Ser Arg
            340                 345                 350

Ala Gln Lys Gly Ser Lys Arg Arg Ala Arg Ile Val Gln Gln Ile Ala
        355                 360                 365

Arg His His His Leu Val Ala Leu Arg Arg Glu Ser Gly Leu His Gln
    370                 375                 380

Val Ser Lys Arg Leu Ala Thr Gly Tyr Thr Leu Ile Gly Leu Glu Asp
385                 390                 395                 400

Leu Ala Val Ala Gly Met Thr Ala Ser Ala Ala Gly Thr Ile Glu Ala
                405                 410                 415

Pro Gly Lys Asn Val Arg Gln Lys Ala Gly Leu Asn Arg Ser Ile Leu
            420                 425                 430

Asp Ala Ala Phe Ser Thr Leu Arg Arg Gln Leu Glu Tyr Lys Ala Ser
        435                 440                 445

Trp Tyr Gly Ser Gln Val Gln Ile Ile Asp Arg Phe Phe Ala Ser Ser
    450                 455                 460

Gln Thr Cys Ser Ala Cys Gly Ala Arg Ala Lys Thr Lys Leu Asp Leu
465                 470                 475                 480

Arg Val Arg Val Phe Glu Cys Ala Ala Cys Gly Val Arg Ile Asp Arg
                485                 490                 495

Asp Val Asn Ala Ala Arg Asn Ile Arg Ala Glu Ala Val Arg Met Tyr
            500                 505                 510

Glu Ala Gln Leu Ala Pro Gly Met Gly Glu Ser Leu Asn Gly Arg Gly
        515                 520                 525

Val Thr Asp Ser Asp Ala Ala Val Ser Val Val Leu Gly Asp Ala Ala
    530                 535                 540

Leu Asp Ala Ser Arg Pro Ala Ala Met Gly Gly Gly Ser Pro
545                 550                 555


<210> SEQ ID NO 138
<211> LENGTH: 569
<212> TYPE: PRT
<213> ORGANISM: Thermincola ferriacetica

<400> SEQUENCE: 138

Met Pro Leu Asn Gly Trp Thr Met Leu Ala Gln Val Glu Val Arg Ala
1               5                   10                  15

Met Thr Thr Thr Thr Gly Thr Asp Leu Ala Pro Arg Leu Arg Ala Phe
            20                  25                  30

Lys His Arg Leu Asp Pro Asn Pro Ala Gln Ala Thr Leu Leu Ala Gln
        35                  40                  45

Tyr Ala Gly Ala Ala Arg Val Ala Tyr Asn Met Leu Ile Ala His Asn
    50                  55                  60

Arg Ala Ala Leu Ala Ala Gly Ala Ala Arg Arg Thr Glu Leu Ala Glu
65                  70                  75                  80

Thr Gly Leu Ala Gly Pro Glu Leu Ala Ala Arg Met Lys Ala Glu Arg
                85                  90                  95

Ala Ala Asp Pro Thr Leu Arg Val Ala Ser Tyr Gln Ser Tyr Ala Thr
            100                 105                 110

Ala His Leu Thr Pro Leu Ile Arg Arg His Arg Glu Ala Ala Ala Ala
        115                 120                 125
```

-continued

Ile Ala Ala Gly Ala Asp Pro Ala Glu Ala Trp Thr Asp Glu Arg Tyr
    130                 135                 140

Ala Glu Pro Trp Met His Thr Val Pro Arg Arg Val Leu Val Ser Gly
145                 150                 155                 160

Leu Gln Asn Ala Ala Lys Ala Thr Glu Asn Trp Met Ala Ser Ala Ser
                165                 170                 175

Gly Thr Arg Ala Gly Ala Arg Val Gly Leu Pro Arg Phe Lys Lys Lys
            180                 185                 190

Gly Arg Ser Arg Asp Ser Phe Thr Ile Pro Ala Pro Glu Val Ile Gly
        195                 200                 205

Ala Ala Gly Thr Pro Tyr Lys Arg Gly Glu Pro Arg Arg Gly Val Ile
    210                 215                 220

Thr Asp His Arg His Leu Arg Leu Ala Ser Leu Gly Thr Ile Arg Thr
225                 230                 235                 240

Tyr Asp Lys Thr Ser Arg Leu Val Arg Ala Cys Arg Arg Gly Ala Gln
                245                 250                 255

Ile Arg Ser Met Thr Ile Ser Gln Ala Gly Gly Arg Trp Tyr Ala Ser
            260                 265                 270

Ile Leu Val Ala Asp Pro Thr Pro Ile Arg Thr Gly Pro Ser Arg Arg
        275                 280                 285

Gln Arg Ala Asn Gly Ala Val Gly Val Asp Leu Gly Val Lys His Leu
    290                 295                 300

Ala Ala Leu Ser Thr Gly Glu Val Ile Asp Asn Gly Arg Pro Gly Ala
305                 310                 315                 320

Arg Gln Ala Ala Arg Leu Thr Arg Leu Gln Arg Ala Tyr Ala Arg Thr
                325                 330                 335

Gln Pro Gly Ser Asn Arg Arg Glu Arg Val Arg Arg Gln Ile Ala Ala
            340                 345                 350

Leu Gln His Gly Ile Ala Leu Arg Arg Ala Gly Leu Leu His Gln Val
        355                 360                 365

Ser Thr Arg Leu Ala Thr Asp Phe Ala Val Val Ala Leu Glu Asp Leu
    370                 375                 380

Asn Val Ala Gly Met Thr Arg Ser Ala Arg Gly Thr Leu Glu Ala Pro
385                 390                 395                 400

Gly Arg Asn Val Ala Ala Lys Ser Gly Leu Asn Arg Ala Ile Leu Asp
                405                 410                 415

Ala Gly Leu Gly Met Leu Arg Arg Gln Leu Asp Tyr Lys Thr Ser Trp
            420                 425                 430

Ala Gly Ser Gln Val Lys Met Ile Asp Arg Phe Ala Pro Ser Ser Lys
        435                 440                 445

Ala Cys Ser Arg Cys Gly Thr Val Lys Ser Thr Leu Ser Leu Ala Glu
    450                 455                 460

Arg Thr Phe Glu Cys Glu Ala Cys His Leu Val Ile Asp Arg Asp Val
465                 470                 475                 480

Asn Ala Ala Ile Asn Ile Arg Ala Trp Ala Val Gln Glu Glu Arg Gly
                485                 490                 495

Ala Gly Val Glu Leu Ala Arg Gly Arg Arg Glu Ser Arg Asn Gly Arg
            500                 505                 510

Gly Ala Ala Val Ser Gly Pro Pro Ser Gly Gly Ala Ala Gly Gln Gly
        515                 520                 525

Arg Gly Ser Val Lys Pro Ala Pro Gln Gly Val Gly Met Ser Ser Arg
    530                 535                 540

Ala Thr Gly Trp Ser Ser Gln Pro Pro Ser Thr Glu Gly Glu Ser Ala
545 550 555 560

Val Arg Gly Ala Ser Ala Leu Ala Arg
565

<210> SEQ ID NO 139
<211> LENGTH: 670
<212> TYPE: PRT
<213> ORGANISM: Bacillus cereus

<400> SEQUENCE: 139

Met Ser Thr Ile Thr Ile Gln Cys Arg Leu Val Ala Pro Glu Ala Thr
1 5 10 15

Arg Gln Ala Leu Trp Gln Leu Met Ala Gln Lys Asn Thr Pro Leu Val
20 25 30

Ser Glu Leu Leu Arg Gln Val Ala Gln His Pro Asp Phe Glu Thr Trp
35 40 45

Arg Gln Gln Gly Lys Leu Glu Ala Gly Ile Ile Lys Lys Leu Cys Glu
50 55 60

Pro Leu Lys Lys Asp Pro Arg Phe Tyr Glu Gln Pro Ala Arg Phe Tyr
65 70 75 80

Thr Ser Ala Ile Ser Leu Val Asp Tyr Ile Tyr Lys Ser Trp Leu Lys
85 90 95

Val Gln Arg Arg Leu Gln Asn Lys Leu Glu Gly Gln Asn Arg Trp Leu
100 105 110

Val Met Leu Lys Ser Asp Glu Glu Leu Val Gln Ile Ser Gln Ser Ser
115 120 125

Leu Glu Thr Ile Gln Ala Lys Ala Thr Asp Ile Leu Ser Thr Leu Lys
130 135 140

Pro Glu Lys Pro Asp Lys Phe Pro Glu Thr Ser Thr Thr Lys Gly Lys
145 150 155 160

Lys Ser Lys Lys Tyr Lys Asn Asn Asn Ser Leu Phe Thr Gln Leu Tyr
165 170 175

Asn Leu Tyr Glu Lys Ala Asp Asp Thr Leu Thr His Cys Ala Ile Arg
180 185 190

Tyr Leu Leu Lys Asn Gly Cys Lys Ile Pro Gln Lys Pro Glu Asp Pro
195 200 205

Glu Lys Phe Ala Gln Arg Arg Arg Lys Val Glu Ile Lys Ile Glu Arg
210 215 220

Ile Ile Glu Gln Ile Glu Ser Ser Ile Pro Gln Gly Arg Asp Leu Thr
225 230 235 240

Gly Asp Ser Trp Leu Glu Thr Leu Ile Ile Ala Ala Asn Thr Ala Thr
245 250 255

Val Glu Ala Ser Glu Ile Lys Ser Trp Gln Asp Lys Leu Leu Ser Gln
260 265 270

Ser Lys Ser Ile Pro Tyr Pro Val Ala Tyr Glu Thr Asn Glu Asp Leu
275 280 285

Thr Trp Ser Ile Asn Glu Lys Gly Arg Leu Cys Val Arg Phe Asn Gly
290 295 300

Leu Gly Lys His Thr Phe Gln Ile Tyr Cys Asp Gln Arg Gln Leu Lys
305 310 315 320

Trp Phe Gln Arg Phe Tyr Glu Asp Gln Gln Ile Lys Lys Asp Gly Lys
325 330 335

Asp His His Ser Ser Ala Leu Phe Ser Leu Arg Ser Gly Arg Ile Val
340 345 350

```
Trp Gln Glu Gly Leu Gly Lys Gly Lys Pro Trp Asn Ile His Arg Leu
        355                 360                 365

Thr Leu His Cys Ser Leu Asp Thr Arg Phe Trp Thr Glu Glu Gly Thr
    370                 375                 380

Gln Gln Val Gln Gln Glu Lys Ser Lys Lys Phe Gln Thr Asn Arg Leu
385                 390                 395                 400

Arg Met Lys Pro Glu Leu Thr Phe Ser Ile Phe Phe Arg Ser Gln Thr
                405                 410                 415

Leu Glu Thr Tyr Leu Gln Val Trp Leu Val Ile Thr Ala Tyr Arg Leu
            420                 425                 430

Gln Ser Phe Leu Asp Lys Gly Asn Val Ala Lys Ala His Gln Glu Phe
        435                 440                 445

Gln Lys Ala Ile Lys Arg Asn Glu Ser Ser Leu Gln Lys Ile Thr Ser
    450                 455                 460

Ser Tyr Asn Arg Pro His Lys Thr Leu Tyr Gln Gly Lys Ser His Ile
465                 470                 475                 480

Phe Val Gly Val Ala Met Gly Leu Glu Lys Pro Ala Thr Val Ala Val
                485                 490                 495

Val Asp Gly Thr Thr Gly Lys Ala Ile Ala Tyr Arg Ser Leu Lys Gln
            500                 505                 510

Leu Leu Gly Asn Asn Tyr His Leu Phe Asn Arg Gln Gly Lys Gln Lys
        515                 520                 525

Gln Asn Thr Ser His Gln Arg His Lys Ser Gln Lys His Phe Ala Asp
    530                 535                 540

Asn Gln Phe Gly Glu Ser Gln Leu Gly Gln Tyr Ile Asp Cys Leu Leu
545                 550                 555                 560

Ala Lys Ala Ile Ile Ser Val Ala Gln Thr Tyr Cys Ala Gly Ser Ile
                565                 570                 575

Val Val Pro Lys Leu Lys Asp Met Arg Glu Leu Ile Gln Ser Glu Ile
            580                 585                 590

Gln Ala Lys Ala Glu Ala Lys Ile Pro Gly Tyr Val Glu Gly Gln Ala
        595                 600                 605

Lys Tyr Ala Lys Ser Tyr Arg Val Gln Val His Gln Trp Ser His Gly
    610                 615                 620

Arg Leu Ile Asp Asn Ile Thr Ser Gln Ala Ser Lys Phe Asn Ile Thr
625                 630                 635                 640

Val Glu Glu Gly Glu Gln Pro His Gln Gly Asn Pro Gln Asp Lys Ala
                645                 650                 655

Lys Leu Leu Ala Ile Ala Ala Tyr His Ser Arg Leu Cys Ala
            660                 665                 670
```

<210> SEQ ID NO 140
<211> LENGTH: 667
<212> TYPE: PRT
<213> ORGANISM: Cyanothece sp.

<400> SEQUENCE: 140

```
Met Ser Thr Ile Thr Ile Gln Cys Arg Leu Val Ala Pro Glu Ala Thr
1               5                   10                  15

Arg Gln Ala Leu Trp Gln Leu Met Ala Gln Lys Asn Thr Pro Leu Val
            20                  25                  30

Ser Glu Leu Leu Arg Gln Val Ala Gln His Pro Asp Phe Glu Thr Trp
        35                  40                  45

Arg Gln Gln Gly Lys Leu Glu Ala Gly Ile Ile Lys Lys Leu Cys Glu
```

-continued

```
    50                  55                  60

Pro Leu Lys Lys Asp Pro Arg Phe Asn Glu Gln Pro Ala Arg Phe Tyr
65                  70                  75                  80

Thr Ser Ala Ile Ala Leu Val Asp Tyr Ile Tyr Lys Ser Trp Leu Lys
                85                  90                  95

Leu Gln Gln Arg Leu Gln Arg Lys Leu Glu Gly Gln Asn Arg Trp Leu
            100                 105                 110

Ala Met Leu Lys Ser Asp Asp Glu Leu Ile Gln Ile Ser Gln Thr Asn
        115                 120                 125

Ile Glu Ile Ile Gln Ala Lys Ala Thr Glu Ile Leu Ser Thr Leu Gln
    130                 135                 140

Pro Gln Asp Arg Glu Gln Ser Ser Lys Lys Lys Ala Lys Lys Cys Lys
145                 150                 155                 160

Lys Ser Thr Asn Lys Asn Ser Leu Phe Ser Gln Leu Asp Lys Leu Tyr
                165                 170                 175

Asn Glu Ile Asn Asn Asn Leu Thr His Cys Ala Ile Arg Tyr Leu Leu
            180                 185                 190

Lys Asn Gly Gly Lys Ile Pro Gln Arg Pro Glu Asp Thr Glu Lys Phe
        195                 200                 205

Ala Gln Arg Arg Arg Lys Val Glu Ile Lys Ile Glu Arg Ile Ile Glu
    210                 215                 220

Gln Ile Glu Ser Ser Ile Pro Gln Gly Arg Asp Leu Thr Gly Asp Ser
225                 230                 235                 240

Trp Leu Glu Thr Leu Ile Ile Ala Ala Asn Thr Ala Thr Val Glu Ala
                245                 250                 255

Glu Asp Val Lys Ser Trp Gln Asp Lys Leu Leu Ser Gln Ser Lys Ser
            260                 265                 270

Ile Pro Tyr Pro Val Ala Tyr Glu Thr Asn Glu Asp Leu Thr Trp Ser
        275                 280                 285

Ile Asn Glu Lys Gly Arg Leu Cys Val Arg Phe Asn Gly Leu Gly Lys
    290                 295                 300

His Thr Phe Gln Ile Tyr Cys Asp Gln Arg Gln Leu Lys Trp Phe Gln
305                 310                 315                 320

Arg Phe Tyr Glu Asp Gln Gln Ile Lys Lys Asp Gly Lys Asp His His
                325                 330                 335

Ser Ser Ala Leu Phe Ser Leu Arg Ser Gly Arg Ile Val Trp Gln Glu
            340                 345                 350

Gly Leu Gly Lys Gly Lys Pro Trp Asn Ile His Arg Leu Thr Leu His
        355                 360                 365

Cys Ser Leu Asp Thr Arg Phe Trp Thr Glu Glu Gly Thr Gln Gln Val
    370                 375                 380

Gln Gln Glu Lys Ser Lys Lys Phe Gln Thr Asn Arg Leu Arg Met Lys
385                 390                 395                 400

Pro Glu Leu Thr Phe Ser Ile Phe Phe Arg Ser Gln Thr Leu Glu Thr
                405                 410                 415

Tyr Leu Gln Val Trp Leu Val Ile Thr Ala Tyr Arg Leu Gln Ser Phe
            420                 425                 430

Leu Asp Lys Gly Asn Val Ala Lys Ala His Gln Glu Phe Gln Lys Ala
        435                 440                 445

Ile Lys Arg Asn Glu Ser Ser Leu Gln Lys Ile Thr Ser Ser Tyr Asn
    450                 455                 460

Arg Pro His Lys Thr Leu Tyr Gln Gly Lys Ser His Ile Phe Val Gly
465                 470                 475                 480
```

Val Ala Met Gly Leu Glu Lys Pro Ala Thr Val Ala Val Val Asp Gly
485 490 495

Thr Thr Gly Lys Ala Ile Ala Tyr Arg Ser Leu Lys Gln Leu Leu Gly
500 505 510

Asn Asn Tyr His Leu Phe Asn Arg Gln Gly Lys Gln Lys Gln Asn Thr
515 520 525

Ser His Gln Arg His Lys Ser Gln Lys His Phe Ala Asp Asn Gln Phe
530 535 540

Gly Glu Ser Gln Leu Gly Gln Tyr Ile Asp Cys Leu Leu Ala Lys Ala
545 550 555 560

Ile Ile Ser Val Ala Gln Thr Tyr Cys Ala Gly Ser Ile Val Val Pro
565 570 575

Lys Leu Lys Asp Met Arg Glu Leu Ile Gln Ser Glu Ile Gln Ala Lys
580 585 590

Ala Glu Ala Lys Ile Pro Gly Tyr Val Glu Gly Gln Ala Lys Tyr Ala
595 600 605

Lys Ser Tyr Arg Val Gln Val His Gln Trp Ser His Gly Arg Leu Ile
610 615 620

Asp Asn Ile Thr Ser Gln Ala Ser Lys Phe Asn Ile Thr Val Glu Glu
625 630 635 640

Gly Glu Gln Pro His Gln Gly Asn Pro Gln Asp Lys Ala Lys Leu Leu
645 650 655

Ala Ile Ala Ala Tyr His Ser Arg Leu Cys Ala
660 665

<210> SEQ ID NO 141
<211> LENGTH: 642
<212> TYPE: PRT
<213> ORGANISM: Streptococcus parasanguinis

<400> SEQUENCE: 141

Met Ser Val Ile Thr Ile Gln Cys Arg Leu Val Ala Glu Glu Asp Ser
1 5 10 15

Leu Arg Gln Leu Trp Glu Leu Met Thr Glu Lys Asn Thr Pro Phe Ile
20 25 30

Asn Glu Ile Leu Leu His Leu Gly Lys His Pro Glu Phe Glu Thr Trp
35 40 45

Leu Glu Lys Gly Arg Ile Pro Ala Glu Ser Leu Lys Thr Leu Gly Asn
50 55 60

Ser Leu Lys Thr Gln Glu Pro Phe Thr Gly Gln Pro Gly Arg Phe Tyr
65 70 75 80

Thr Ser Ala Ile Ala Leu Val Asp Tyr Leu Tyr Lys Ser Trp Phe Ala
85 90 95

Leu Gln Lys Arg Arg Lys Asn Gln Ile Glu Gly Lys Gln Arg Trp Leu
100 105 110

Lys Met Leu Lys Ser Asp Pro Glu Leu Glu Gln Glu Ser Gln Ser Ser
115 120 125

Leu Glu Val Ile Arg Thr Lys Ala Thr Glu Leu Phe Ser Lys Phe Thr
130 135 140

Pro Gln Ser Asp Ser Glu Ala Leu Arg Arg Asn Gln Asn Asp Lys Ser
145 150 155 160

Lys Lys Gly Lys Lys Thr Lys Lys Pro Thr Lys Ala Lys Thr Ser Ser
165 170 175

Ile Phe Lys Ile Leu Leu Asn Thr Tyr Glu Glu Ala Glu Asp Pro Leu

```
            180                 185                 190

Thr Arg Cys Ala Leu Ala Tyr Leu Leu Lys Asn Asn Cys Gln Ile Ser
        195                 200                 205

Glu Leu Asp Glu Asn Pro Glu Glu Phe Thr Arg Asn Lys Arg Arg Lys
    210                 215                 220

Glu Ile Glu Ile Glu Arg Leu Lys Asp Gln Leu Gln Ser Arg Ile Pro
225                 230                 235                 240

Lys Gly Arg Asp Leu Thr Gly Glu Gln Trp Leu Glu Thr Leu Glu Ile
                245                 250                 255

Ala Thr Val Lys Val Pro Gln Asn Glu Asn Glu Ala Lys Ala Trp Gln
            260                 265                 270

Ala Ala Leu Leu Arg Lys Thr Ala Asn Val Pro Phe Pro Val Ala Tyr
        275                 280                 285

Glu Ser Asn Glu Asp Met Thr Trp Leu Lys Asn Asp Lys Asn Arg Leu
    290                 295                 300

Phe Val Arg Phe Asn Gly Leu Gly Lys Leu Asn Phe Glu Ile Tyr Cys
305                 310                 315                 320

Asp Lys Arg His Leu His Tyr Phe Gln Arg Phe Leu Glu Asp Gln Glu
                325                 330                 335

Ile Leu Arg Ser Ser Lys Arg Gln His Ser Ser Ser Leu Phe Thr Leu
            340                 345                 350

Arg Ser Gly Arg Ile Ala Trp Leu Pro Gly Glu Glu Lys Gly Glu His
        355                 360                 365

Trp Lys Val Asn Gln Leu Asn Phe Tyr Cys Ser Leu Asp Thr Arg Met
    370                 375                 380

Leu Thr Thr Glu Gly Thr Gln Gln Val Val Glu Glu Lys Val Thr Ala
385                 390                 395                 400

Ile Thr Glu Ile Leu Thr Lys Thr Lys Gln Lys Asp Asp Leu Asn Asp
                405                 410                 415

Lys Gln Gln Ala Phe Ile Thr Arg Gln Gln Ser Thr Leu Ser Arg Ile
            420                 425                 430

Asn Asn Pro Phe Pro Arg Pro Ser Lys Pro Asn Tyr Gln Gly Lys Ser
        435                 440                 445

Ser Ile Leu Ile Gly Val Ser Phe Gly Leu Glu Lys Pro Val Thr Val
    450                 455                 460

Ala Val Val Asp Val Val Lys Asn Gln Val Ile Ala Tyr Arg Ser Val
465                 470                 475                 480

Lys Gln Leu Leu Gly Glu Asn Tyr Asn Leu Leu Asn Arg Gln Arg Gln
                485                 490                 495

Gln Gln Gln Arg Leu Ser His Glu Arg His Lys Ala Gln Lys Gln Asn
            500                 505                 510

Ala Pro Asn Ser Phe Gly Glu Ser Glu Leu Gly Gln Tyr Val Asp Arg
        515                 520                 525

Leu Leu Ala Asp Ala Ile Ile Ala Ile Ala Lys Lys Tyr Gln Ala Gly
    530                 535                 540

Ser Ile Val Leu Pro Lys Leu Arg Asp Met Arg Glu Gln Ile Ser Ser
545                 550                 555                 560

Glu Ile Gln Ser Arg Ala Glu Asn Gln Cys Pro Gly Tyr Lys Glu Gly
                565                 570                 575

Gln Gln Lys Tyr Ala Lys Glu Tyr Arg Ile Asn Val His Arg Trp Ser
            580                 585                 590

Tyr Gly Arg Leu Ile Glu Ser Ile Lys Ser Gln Ala Ala Gln Ala Gly
        595                 600                 605
```

Ile Ala Ile Glu Thr Gly Thr Gln Pro Ile Arg Ala Ser Pro Gln Glu
    610                 615                 620

Lys Ala Arg Asp Leu Ala Leu Phe Ala Tyr Gln Glu Arg Gln Ala Ala
625                 630                 635                 640

Leu Ile

<210> SEQ ID NO 142
<211> LENGTH: 642
<212> TYPE: PRT
<213> ORGANISM: Anabaena cylindrica

<400> SEQUENCE: 142

Met Ser Val Ile Thr Ile Gln Cys Arg Leu Val Ala Glu Glu Asp Ser
1               5                   10                  15

Leu Arg Gln Leu Trp Glu Leu Met Ser Glu Lys Asn Thr Pro Phe Ile
            20                  25                  30

Asn Glu Ile Leu Leu Gln Ile Gly Lys His Pro Glu Phe Glu Thr Trp
        35                  40                  45

Leu Glu Lys Gly Arg Ile Pro Ala Glu Leu Leu Lys Thr Leu Gly Asn
    50                  55                  60

Ser Leu Lys Thr Gln Glu Pro Phe Thr Gly Gln Pro Gly Arg Phe Tyr
65                  70                  75                  80

Thr Ser Ala Ile Thr Leu Val Asp Tyr Leu Tyr Lys Ser Trp Phe Ala
                85                  90                  95

Leu Gln Lys Arg Arg Lys Gln Gln Ile Glu Gly Lys Gln Arg Trp Leu
            100                 105                 110

Lys Met Leu Lys Ser Asp Gln Glu Leu Glu Gln Glu Ser Gln Ser Ser
        115                 120                 125

Leu Glu Val Ile Arg Asn Lys Ala Thr Glu Leu Phe Ser Lys Phe Thr
    130                 135                 140

Pro Gln Ser Asp Ser Glu Ala Leu Arg Arg Asn Gln Asn Asp Lys Gln
145                 150                 155                 160

Lys Lys Val Lys Lys Thr Lys Lys Ser Thr Lys Pro Lys Thr Ser Ser
                165                 170                 175

Ile Phe Lys Ile Phe Leu Ser Thr Tyr Glu Glu Ala Glu Glu Pro Leu
            180                 185                 190

Thr Arg Cys Ala Leu Ala Tyr Leu Leu Lys Asn Asn Cys Gln Ile Ser
        195                 200                 205

Glu Leu Asp Glu Asn Pro Glu Glu Phe Thr Arg Asn Lys Arg Arg Lys
    210                 215                 220

Glu Ile Glu Ile Glu Arg Leu Lys Asp Gln Leu Gln Ser Arg Ile Pro
225                 230                 235                 240

Lys Gly Arg Asp Leu Thr Gly Glu Glu Trp Leu Glu Thr Leu Glu Ile
                245                 250                 255

Ala Thr Phe Asn Val Pro Gln Asn Glu Asn Glu Ala Lys Ala Trp Gln
            260                 265                 270

Ala Ala Leu Leu Arg Lys Thr Ala Asn Val Pro Phe Pro Val Ala Tyr
        275                 280                 285

Glu Ser Asn Glu Asp Met Thr Trp Leu Lys Asn Asp Lys Asn Arg Leu
    290                 295                 300

Phe Val Arg Phe Asn Gly Leu Gly Lys Leu Thr Phe Glu Ile Tyr Cys
305                 310                 315                 320

Asp Lys Arg His Leu His Tyr Phe Gln Arg Phe Leu Glu Asp Gln Glu
                325                 330                 335

Ile Leu Arg Asn Ser Lys Arg Gln His Ser Ser Ser Leu Phe Thr Leu
340 345 350

Arg Ser Gly Arg Ile Ala Trp Leu Pro Gly Glu Glu Lys Gly Glu His
355 360 365

Trp Lys Val Asn Gln Leu Asn Phe Tyr Cys Ser Leu Asp Thr Arg Met
370 375 380

Leu Thr Thr Glu Gly Thr Gln Gln Val Val Glu Glu Lys Val Thr Ala
385 390 395 400

Ile Thr Glu Ile Leu Asn Lys Thr Lys Gln Lys Asp Asp Leu Asn Asp
405 410 415

Lys Gln Gln Ala Phe Ile Thr Arg Gln Gln Ser Thr Leu Ala Arg Ile
420 425 430

Asn Asn Pro Phe Pro Arg Pro Ser Lys Pro Asn Tyr Gln Gly Lys Ser
435 440 445

Ser Ile Leu Ile Gly Val Ser Phe Gly Leu Glu Lys Pro Val Thr Val
450 455 460

Ala Val Val Asp Val Val Lys Asn Lys Val Ile Ala Tyr Arg Ser Val
465 470 475 480

Lys Gln Leu Leu Gly Glu Asn Tyr Asn Leu Leu Asn Arg Gln Arg Gln
485 490 495

Gln Gln Gln Arg Leu Ser His Glu Arg His Lys Ala Gln Lys Gln Asn
500 505 510

Ala Pro Asn Ser Phe Gly Glu Ser Glu Leu Gly Gln Tyr Val Asp Arg
515 520 525

Leu Leu Ala Asp Ala Ile Ile Ala Ile Ala Lys Lys Tyr Gln Ala Gly
530 535 540

Ser Ile Val Leu Pro Lys Leu Arg Asp Met Arg Glu Gln Ile Ser Ser
545 550 555 560

Glu Ile Gln Ser Arg Ala Glu Asn Gln Cys Pro Gly Tyr Lys Glu Gly
565 570 575

Gln Gln Lys Tyr Ala Lys Glu Tyr Arg Ile Asn Val His Arg Trp Ser
580 585 590

Tyr Gly Arg Leu Ile Glu Ser Ile Lys Ser Gln Ala Ala Gln Ala Gly
595 600 605

Ile Ala Ile Glu Thr Gly Lys Gln Ser Ile Arg Gly Ser Pro Gln Glu
610 615 620

Lys Ala Arg Asp Leu Ala Val Phe Thr Tyr Gln Glu Arg Gln Ala Ala
625 630 635 640

Leu Ile

<210> SEQ ID NO 143
<211> LENGTH: 638
<212> TYPE: PRT
<213> ORGANISM: Nocardiopsis synnemataformans

<400> SEQUENCE: 143

Met Thr Gln Ile Thr Val Gln Cys Arg Leu Val Ala Thr Glu Thr Thr
1 5 10 15

Arg Gln Glu Leu Trp Asp Leu Met Ala Asp Lys Asn Thr Pro Leu Ile
20 25 30

Asn Glu Leu Leu Lys Gln Val Ala Glu His Ser Asp Phe Glu Ala Trp
35 40 45

Arg Gln Lys Gly Lys Ile Pro Thr Gly Thr Ile Lys Gln Leu Cys Glu
50 55 60

```
Pro Leu Lys Thr Asp Ser Arg Phe Ile Gly Gln Pro Gly Arg Phe Tyr
65                  70                  75                  80

Thr Ser Ala Ile Ala Leu Val Ser Tyr Ile Tyr Lys Ser Trp Leu Ala
                85                  90                  95

Leu Met Lys Arg Leu Gln Tyr Lys Leu Glu Gly Lys Ile His Trp Leu
            100                 105                 110

Glu Met Leu Lys Ser Asp Glu Glu Leu Val Glu Ile Ser Gly Val Asn
        115                 120                 125

Leu Glu Ala Leu Arg Ser Lys Ala Ala Glu Ile Leu Ala Gln Phe Ser
    130                 135                 140

Pro Gln Ile Asp Thr Asn Asn Ser Gln Asn Lys Arg Lys Thr Lys Ser
145                 150                 155                 160

Lys Asn Ser Lys Lys Ser Lys Ser Ser Asp Ile Ser Lys Asn Leu Ser
                165                 170                 175

Gln Gln Leu Phe Asp Thr Tyr Arg Asp Thr Glu Asp Ile Val Thr His
            180                 185                 190

Cys Ala Ile Ser Tyr Leu Leu Lys Asn Gly Ser Lys Leu Pro Asn Lys
        195                 200                 205

Glu Glu Ser Pro Glu Lys Phe Thr Gln Arg Arg Arg Lys Ile Glu Ile
    210                 215                 220

Gln Ile Gln Arg Leu Arg Glu Gln Leu Glu Ala Arg Ile Pro His Gly
225                 230                 235                 240

Arg Asp Leu Thr Asp Leu Asn Trp Leu Asn Thr Leu Asp Ile Ala Thr
                245                 250                 255

Asn Gln Val Pro Gln Ser Glu Thr Glu Ala Lys Ser Trp Gln Asn Asn
            260                 265                 270

Leu Leu Arg Lys Ser His Ala Val Pro Phe Pro Val Ser Tyr Glu Thr
        275                 280                 285

Asn Glu Asp Met Thr Trp Phe Lys Asn Arg Lys Gly Arg Ile Cys Val
    290                 295                 300

Lys Phe Asn Gly Leu Ser Glu His Thr Phe Glu Ile Tyr Cys Asp Asn
305                 310                 315                 320

Arg Gln Leu His Trp Phe Lys Arg Phe Leu Ser Asp Gln Gln Ile Lys
                325                 330                 335

Lys Asn Ser Lys Asn Gln His Ser Ser Ser Leu Phe Thr Leu Arg Ser
            340                 345                 350

Gly Arg Ile Ser Trp Gln Glu Glu Val Gly Lys Asp Arg Pro Trp Asn
        355                 360                 365

Val Asn His Leu Lys Leu Asp Cys Thr Val Asp Thr Arg Leu Trp Thr
    370                 375                 380

Ala Glu Gly Thr Asn Gln Val Arg Glu Glu Lys Ala Glu Glu Ile Ala
385                 390                 395                 400

Lys Thr Ile Thr Lys Ser Lys Glu Lys Gly Glu Leu Asn Asp Arg Gln
                405                 410                 415

Leu Ala His Ile Lys Arg Lys Gln Ser Thr Leu Asp Arg Ile Asn Asn
            420                 425                 430

Pro Tyr Pro Arg Pro Asn Lys Pro Leu Tyr Lys Gly Leu Ser Asn Ile
        435                 440                 445

Leu Val Gly Val Ser Leu Gly Leu Glu Lys Thr Ala Thr Val Ala Ile
    450                 455                 460

Leu Asp Ala Ser Thr Asp Lys Val Val Thr Tyr Arg Ser Ile Lys Gln
465                 470                 475                 480
```

-continued

Leu Leu Gly Glu Asn Tyr Lys Leu Leu Asn Arg Gln Arg Gln Gln Lys
485 490 495

Gly Glu Leu Ser His Gln Arg Lys Ile Ala Gln Thr Gln Ala Ala Ser
500 505 510

Asn Gln Tyr Gly Glu Ser Glu Leu Gly Gln Tyr Ile Asp Arg Leu Leu
515 520 525

Ala Lys Glu Ile Val Ala Ile Ala Gln Lys Tyr Ser Ala Gly Ser Ile
530 535 540

Val Leu Pro Lys Leu Ser Asp Met Arg Glu Gln Ile Asn Ser Glu Ile
545 550 555 560

Gln Ala Lys Ala Leu Glu Lys Cys Pro Asp Cys Ile Glu Ala Gln Lys
565 570 575

Lys Tyr Ala Lys Gln Tyr Arg Arg Ser Val Asn Gln Trp Ser Tyr Gly
580 585 590

Arg Leu Ile Glu Asn Ile Lys Ser Gln Ala Ile Lys Thr Gly Ile Val
595 600 605

Ile Glu Glu Ser Lys Gln Pro Ile Arg Gly Ser Ser Gln Asp Lys Ala
610 615 620

Lys Glu Leu Ala Thr Thr Ala Tyr Lys Ser Arg Lys Lys Ser
625 630 635

<210> SEQ ID NO 144
<211> LENGTH: 635
<212> TYPE: PRT
<213> ORGANISM: Clostridium ultunense

<400> SEQUENCE: 144

Met Ser Val Ile Thr Ile Gln Cys Arg Leu Val Ala Glu Glu Asp Thr
1 5 10 15

Leu Arg Gln Val Trp Glu Leu Met Thr Asp Lys Asn Thr Pro Leu Val
20 25 30

Asn Glu Leu Leu Ala Gln Val Gly Lys His Pro Glu Phe Glu Thr Trp
35 40 45

Leu Glu Lys Gly Lys Ile Pro Thr Glu Phe Leu Lys Thr Leu Val Asn
50 55 60

Ser Leu Lys Asn Gln Glu Arg Phe Ser Asp Gln Pro Gly Arg Phe Tyr
65 70 75 80

Thr Ser Ala Ile Ala Leu Val Asp Tyr Val Tyr Lys Ser Trp Phe Ala
85 90 95

Leu Gln Lys Arg Arg Lys Arg Gln Ile Glu Gly Lys Glu Arg Trp Leu
100 105 110

Ile Ile Leu Lys Ser Asp Leu Gln Leu Glu Gln Glu Ser Gln Cys Ser
115 120 125

Leu Asn Val Ile Arg Thr Glu Ala Asn Glu Ile Leu Ala Lys Phe Thr
130 135 140

Pro Gln Ser Asp Gln Asn Lys Asn Gln Arg Lys Ser Lys Arg Thr Arg
145 150 155 160

Lys Ser Ala Lys Leu Gln Thr Pro Ser Leu Phe Gln Asn Leu Leu Asn
165 170 175

Thr Tyr Glu Gln Thr Gln Glu Thr Leu Thr Arg Cys Ala Ile Ala Tyr
180 185 190

Leu Leu Lys Asn Asn Cys Gln Ile Ser Glu Arg Asp Glu Asp Pro Glu
195 200 205

Glu Phe Asn Arg Asn Arg Arg Lys Lys Glu Ile Glu Ile Glu Arg Leu
210 215 220

-continued

```
Lys Asp Gln Leu Gln Ser Arg Ile Pro Lys Gly Arg Asp Leu Thr Gly
225                 230                 235                 240

Glu Glu Trp Leu Lys Thr Leu Glu Ile Ala Thr Thr Asn Val Pro Gln
                245                 250                 255

Asn Glu Asn Glu Ala Lys Ala Trp Gln Ala Ala Leu Leu Arg Lys Pro
            260                 265                 270

Ala Asp Val Pro Phe Pro Val Ala Tyr Glu Ser Asn Glu Asp Met Thr
        275                 280                 285

Trp Leu Gln Asn Asp Lys Gly Arg Leu Phe Val Arg Phe Asn Gly Leu
    290                 295                 300

Gly Lys Leu Thr Phe Glu Ile Tyr Cys Asp Lys Arg His Leu His Tyr
305                 310                 315                 320

Phe Lys Arg Phe Leu Glu Asp Gln Glu Leu Lys Arg Asn Ser Lys Asn
                325                 330                 335

Gln His Ser Ser Ser Leu Phe Thr Leu Arg Ser Gly Arg Ile Ala Trp
            340                 345                 350

Ser Leu Gly Glu Glu Lys Gly Glu Pro Trp Lys Val Asn Lys Leu His
        355                 360                 365

Leu Tyr Cys Thr Leu Asp Thr Arg Met Trp Thr Ile Glu Gly Thr Gln
    370                 375                 380

Gln Val Val Ser Glu Lys Thr Thr Lys Ile Thr Glu Thr Leu Asn Gln
385                 390                 395                 400

Ala Lys Arg Lys Asp Val Leu Asn Asp Lys Gln Gln Ala Phe Val Thr
                405                 410                 415

Arg Gln Gln Ser Thr Leu Asp Arg Ile Asn Asn Pro Phe Pro Arg Pro
            420                 425                 430

Ser Lys Pro Asn Tyr Gln Gly Gln Pro Ser Ile Leu Val Gly Val Ser
        435                 440                 445

Phe Gly Leu Glu Lys Pro Val Thr Leu Ala Val Val Asp Val Ile Lys
    450                 455                 460

Asn Glu Val Leu Ala Tyr Arg Thr Val Lys Gln Leu Leu Gly Lys Asn
465                 470                 475                 480

Tyr Asn Leu Leu Asn Arg Gln Arg Gln Gln Gln Gln Arg Leu Ser His
                485                 490                 495

Glu Arg His Lys Val Gln Lys Arg Asn Ala Pro Asn Ser Phe Gly Glu
            500                 505                 510

Ser Glu Leu Gly Gln Tyr Val Asp Arg Leu Leu Ala Asp Ala Ile Ile
        515                 520                 525

Ala Ile Ala Lys Thr Tyr Gln Ala Gly Ser Ile Val Ile Pro Lys Leu
    530                 535                 540

Arg Asp Met Arg Glu Gln Ile Ser Ser Glu Ile Gln Ser Arg Ala Glu
545                 550                 555                 560

Lys Lys Cys Pro Gly Tyr Lys Glu Val Gln Gln Lys Tyr Ala Lys Glu
                565                 570                 575

Tyr Arg Met Ser Val His Arg Trp Gly Tyr Gly Arg Leu Ile Glu Ser
            580                 585                 590

Ile Lys Ser Gln Ala Ala Lys Ala Gly Ile Phe Thr Glu Ile Gly Thr
        595                 600                 605

Gln Pro Ile Arg Gly Ser Pro Gln Glu Lys Ala Arg Asp Leu Ala Val
    610                 615                 620

Phe Ala Tyr Gln Glu Arg Gln Ala Ala Leu Ile
625                 630                 635
```

<210> SEQ ID NO 145
<211> LENGTH: 612
<212> TYPE: PRT
<213> ORGANISM: Bacillus cereus

<400> SEQUENCE: 145

Met Ser Gln Ile Thr Ile Gln Cys Arg Leu Val Ala Lys Glu Pro Thr
1 5 10 15

Arg Gln Thr Leu Trp Gln Leu Met Ala Glu Leu Asn Thr Pro Phe Ile
20 25 30

Asn Glu Leu Leu Gln Lys Val Ala Gln Asn Pro Asp Phe Glu Gln Trp
35 40 45

Arg Gln Lys Gly Lys Leu Gln Lys Ser Val Ile Lys Gln Leu Gly Asp
50 55 60

Lys Leu Lys Lys Asp Pro Arg Tyr Leu Gly Gln Pro Ala Arg Phe Tyr
65 70 75 80

Thr Ser Gly Ile Ser Leu Val Glu Tyr Ile Phe Lys Ser Trp Leu Lys
85 90 95

Leu Gln Gln Arg Leu Gln Arg Lys Leu Asp Gly Lys Arg Arg Trp Leu
100 105 110

Thr Val Leu Lys Ser Asp Glu Glu Leu Ile Gln Gln Ser Gln Gln Asn
115 120 125

Leu Glu Ala Ile Arg His Lys Ala Ser Glu Ile Leu Gln Thr His Gln
130 135 140

Lys Thr Glu Lys Leu Phe Asn His Leu Phe Gln Leu Tyr Gln Glu Glu
145 150 155 160

Lys Asn Pro Phe Thr His Ile Ala Leu Cys Tyr Leu Leu Lys Asn Arg
165 170 175

Cys Lys Leu Pro Gln Lys Pro Glu Asp Pro Glu Lys Phe Thr Lys Arg
180 185 190

Arg Arg Lys Val Glu Ile Ala Ile Asp Arg Leu Gln Glu Gln Leu Glu
195 200 205

Gly Arg Leu Pro Gln Gly Arg Asp Leu Thr Asn His Asn Trp Leu Glu
210 215 220

Thr Leu Ser Ile Ala Cys Gln Thr Asp Pro Glu Asp Thr Ala Gln Ala
225 230 235 240

Arg Ser Trp Gln Asp Lys Leu Leu Ile Gln Ser Gln Ser Ile Pro Phe
245 250 255

Pro Ile Asn Tyr Glu Thr Asn Glu Asp Leu Thr Trp His Lys Asn Glu
260 265 270

Lys Gly Arg Leu Cys Val Lys Phe Asn Gly Ile Ser Asp Leu Ser Phe
275 280 285

Glu Ile Tyr Cys Asp Gln Arg Gln Leu Lys Trp Phe Gln Arg Phe Tyr
290 295 300

Glu Asp Gln Gln Ala Lys Lys Gly Ser Lys Asn Gln His Ser Ser Ala
305 310 315 320

Leu Phe Thr Leu Arg Ser Gly Arg Ile Leu Trp Gln Glu Gly Asn Glu
325 330 335

Lys Gly Gln Pro Trp Asn Ile His Arg Leu Ile Leu Gln Cys Thr Leu
340 345 350

Asp Thr Arg Leu Trp Thr Gln Glu Gly Thr Glu Glu Val Lys Gln Glu
355 360 365

Lys Ala Glu Glu Ile Ala Lys Val Leu Thr Ser Met Asn Glu Lys Gly
370 375 380

Asp Leu Thr Lys Asn Gln Gln Ala Phe Ile Lys Arg Lys Gln Ser Thr
385 390 395 400

Leu Asp Lys Leu Glu Asn Pro Phe Pro Arg Pro Ser Gln Pro Leu Tyr
405 410 415

Arg Gly Gln Ser Asn Ile Leu Val Gly Val Ser Met Gly Val Asp Lys
420 425 430

Pro Ala Thr Val Ala Val Val Asp Gly Ile Thr Gln Lys Thr Leu Thr
435 440 445

Ile Glu Tyr Ile Lys Gln Leu Leu Gly Asn Asn Tyr Pro Leu Ile Gln
450 455 460

Arg Gln Arg Gln Gln Lys Gln His Gln Ser His Gln Arg Asn Val Ala
465 470 475 480

Gln Arg Lys Glu Ala Phe Asn Gln Phe Gly Asp Ser Glu Leu Gly Glu
485 490 495

Tyr Ile Asp Arg Leu Leu Thr Lys Ala Ile Val Thr Leu Ala Lys Lys
500 505 510

Tyr Lys Ala Gly Ser Ile Val Val Pro Lys Leu Glu Asp Met Arg Glu
515 520 525

Ile Val Gln Thr Glu Ile Gln Thr Lys Ala Glu Glu Arg Ile Pro Asn
530 535 540

Cys Ile Glu Ala Gln Lys Asn Tyr Ala Lys Cys Tyr Arg Val Gln Val
545 550 555 560

His Gln Trp Ser Tyr Ser Arg Leu Ile Asp Asn Ile Glu Ala Gln Ala
565 570 575

Ser Lys Leu Gly Ile Val Leu Glu Ile Ser Gln Gln Pro Tyr Lys Gly
580 585 590

Thr Pro His Asp Lys Ala Ile Ala Leu Ala Leu Asn Ala Tyr Gln Ser
595 600 605

Arg Leu Ser Ala
610

<210> SEQ ID NO 146
<211> LENGTH: 682
<212> TYPE: PRT
<213> ORGANISM: Anoxybacillus flavithermus

<400> SEQUENCE: 146

Met Thr Leu Lys Thr Leu Glu Cys Arg Leu Tyr Ala Pro Ser Asp Thr
1 5 10 15

Leu Arg Tyr Leu Trp Leu Leu Met Ala Glu Lys Asn Thr Pro Leu Ile
20 25 30

Asn Glu Ile Ile Asn His Leu Ser Glu His Pro Asp Phe Asp Gln Trp
35 40 45

Phe Lys Ala Lys Gln Ile Pro Lys Ser Ala Ile Ser Asp Ile Cys Asn
50 55 60

Asp Leu Lys Ser Gln Glu Asn Tyr Gln Asn Gln Pro Gly Arg Phe Tyr
65 70 75 80

Ser Ser Ala Ile Ser Leu Thr His Tyr Met Phe Lys Ser Trp Phe Ala
85 90 95

Val His Lys Gln Leu Gln Arg Arg Ile Glu Gly Lys Arg Arg Trp Leu
100 105 110

Asn Leu Leu Lys Ser Asp Gln Glu Leu Glu Gln Asn Cys Gly Gln Ser
115 120 125

Leu Glu Ile Ile Ile Gln Lys Ala Glu Glu Ile Leu Lys Leu Met Asp

-continued

```
    130                 135                 140

Ser Glu Lys Ser Gln Ser Ser Ser Lys Pro Lys Lys Pro Lys Lys Pro
145                 150                 155                 160

Lys Lys Lys Lys Lys Ser Ser Ser Glu Glu Thr Ile Thr Leu Phe Asp
                165                 170                 175

Arg Leu Phe Lys Ala Tyr Asn Gln Gly Asn Asp Ser Leu Glu Ser Tyr
            180                 185                 190

Ala Leu Ala Tyr Leu Leu Lys Asn Asn Gly Gln Ile Pro Glu Asp Asp
        195                 200                 205

Glu Asp Leu Asp Lys Phe Ala Leu Arg Lys Arg Lys Lys Glu Ile Glu
    210                 215                 220

Ile Glu Arg Leu Gln Gln Gln Leu Glu Asn Arg Ile Pro Leu Gly Arg
225                 230                 235                 240

Asp Leu Thr Gly Glu Leu Trp Gln Glu Met Leu Thr Ile Val Asn Glu
                245                 250                 255

Ser Ile Pro Gln Asp Glu Asn Glu Ala Ser Ala Trp Gln Ala Lys Leu
            260                 265                 270

Leu Lys Lys Ser His Asn Ile Pro Tyr Pro Val Ala Tyr Glu Thr Asn
        275                 280                 285

Thr Asp Leu Lys Trp Ser Lys Asp Ser Arg Gly His Leu Leu Val Thr
    290                 295                 300

Phe Asn Gly Leu Val Glu Ser Leu Lys Lys Leu Asn Leu Asn Pro Glu
305                 310                 315                 320

Phe Glu Ile Arg Cys Asp Arg Arg His Leu Pro Trp Phe Gln Arg Phe
                325                 330                 335

Cys Lys Asp Gln Glu Ile Lys Ala Asn Asn Asp Gln His Ser Ser Ala
            340                 345                 350

Leu Phe Val Leu Arg Ser Ala Arg Leu Ile Trp Arg Glu Gly Gln Gly
        355                 360                 365

Lys Glu Asp Pro Trp Lys Ile His Gln Leu Tyr Leu Gln Cys Ser Val
    370                 375                 380

Glu Thr Gln Leu Trp Thr Glu Ala Gly Thr Lys Gln Val Gln Ser Glu
385                 390                 395                 400

Lys Met Val Glu Phe Gln Leu Asn Gln Leu Arg Met Lys Pro Glu Leu
                405                 410                 415

Thr Phe Pro Ile Phe Phe Arg Ser Gln Ser Leu Pro Thr Tyr Phe Asn
            420                 425                 430

Leu Trp Lys Val Ile Thr Ser Tyr Arg Ile Leu Lys Phe Leu Glu Lys
        435                 440                 445

Gly Asp Phe Thr Lys Ala Gln Lys Asn Phe Gln Asp Ala Ile Lys Arg
    450                 455                 460

Thr Glu Ser Cys Leu Glu Asn Leu Gln Ser Ser Tyr Leu Thr Ser Gln
465                 470                 475                 480

Lys Ser Leu Tyr Gln Gly Asn Pro Glu Ile Ile Met Gly Val Ala Met
                485                 490                 495

Gly Leu Ser Gln Pro Ala Thr Ile Ala Val Val Asn Val Val Thr Gln
            500                 505                 510

Glu Val Leu Thr Tyr Arg Ser Leu Lys Gln Leu Leu Gly Lys Asn Tyr
        515                 520                 525

Asn Leu Leu Asn Arg Gln Arg Gln Gln Lys Gln Lys Leu Ser His Gln
    530                 535                 540

Arg His Lys Ala Gln Lys Lys Asp Ala Phe Asn Gln Tyr Gly Glu Ser
545                 550                 555                 560
```

```
Glu Leu Gly Gln Tyr Val Asp Arg Leu Ile Ala Lys Ala Ile Val Gln
                565                 570                 575

Val Ala Lys Glu Tyr Gln Ala Asp Ser Ile Ala Val Pro Lys Ile Arg
            580                 585                 590

Gln Met Arg Glu Ile Ile Gln Ser Glu Val Gln Ala Arg Ala Glu Arg
        595                 600                 605

Lys Ile Gln Gly Tyr Lys Glu Gly Gln Lys Lys Tyr Ala Gln Gln Tyr
    610                 615                 620

Arg Glu Asn Val His Gln Trp Ser Tyr Gly Arg Leu Ile Glu Ser Ile
625                 630                 635                 640

His Gln Ala Ser Ala Lys Phe Gly Ile Arg Val Glu Ile Ala Ser Gln
                645                 650                 655

Ser Tyr Gln Gly Ser Phe Gln Glu Gln Ala Gln Asn Leu Ala Ile Ala
            660                 665                 670

Ala Tyr Thr Asn Arg Leu Glu Ala Val Gly
        675                 680


<210> SEQ ID NO 147
<211> LENGTH: 660
<212> TYPE: PRT
<213> ORGANISM: Anoxybacillus suryakundensis

<400> SEQUENCE: 147

Met Thr His Ile Thr Val Val Gln Cys Arg Leu Ile Ala Pro Glu Ser
1               5                   10                  15

Thr Leu Gln His Ile Trp Lys Met Met Ala Gln Gln Gln Thr Pro Leu
            20                  25                  30

Ile Asn Gln Leu Leu His Asp Ile Asn Thr His Pro Asp Ile Asn Thr
        35                  40                  45

Trp Leu Thr Ala Asn Gln Leu Pro Ser Lys Leu Val Glu Thr Leu Ala
    50                  55                  60

Gln Pro Leu Lys Thr Gln Ser Pro Tyr Gln Gly Leu Pro Gly Arg Phe
65                  70                  75                  80

Ile Thr Ser Ala Ile Ile Leu Val Lys Glu Met Tyr Ala Ser Trp Phe
                85                  90                  95

Ala Ile Gln Thr Gln Lys Arg Leu Ser Leu Glu Gly Lys Lys Arg Phe
            100                 105                 110

Leu Thr Ile Leu Lys Ser Asp Lys Gln Leu Ile Gln Asp Ser Gln Thr
        115                 120                 125

Asp Phe Leu Thr Leu Cys Tyr Lys Ala Gln Gln Leu Leu Lys Arg Thr
    130                 135                 140

Gln Asn Lys Leu Lys Leu Asp Glu Pro Gln His Ser Glu Lys Ala His
145                 150                 155                 160

Trp Ser Ile Ile Asn Ala Leu Tyr Pro Ala Tyr Asn Asn Ala Lys Thr
                165                 170                 175

Pro Ile Ser Arg Ala Ala Phe Ala Leu Leu Ile Lys Asn Asn Gly Gln
            180                 185                 190

Val Pro Asp Thr Pro Glu Asn Pro Asp Tyr Tyr Gln Gln Arg Arg Lys
        195                 200                 205

Arg Lys Glu Ile Gln Ile Arg Arg Leu Glu Glu Gln Leu Lys Ala Ser
    210                 215                 220

Leu Pro Lys Gly Arg Ile Leu Asp Ser Lys His Trp Glu Asn Thr Leu
225                 230                 235                 240

Lys Leu Ala Gln Thr Pro Ile Thr Thr Ile Glu Glu Ile Thr Ser Leu
```

-continued

```
                245                 250                 255

Gln Thr Gln Leu Leu Gln Lys Tyr Ser His Leu Pro Phe Pro Val Phe
            260                 265                 270

Tyr Gly Thr Asn Thr Asp Leu Thr Trp Phe Lys Asn Pro Gln Gly Arg
        275                 280                 285

Ile Cys Val Lys Phe Asn Gly Leu Asn Gln Tyr Pro Phe Gln Ile Ala
    290                 295                 300

Cys Asn Lys Arg Gln Tyr Pro Trp Phe Gln Arg Phe Phe Thr Asp Tyr
305                 310                 315                 320

Gln Ser Tyr Lys Ser His Lys Gln Gln Val Pro Thr Gly Leu Met Val
                325                 330                 335

Leu Arg Ser Ala Arg Leu Leu Trp Gln Pro Thr Asn Gly Gln Gly Glu
            340                 345                 350

Pro Trp Asn Thr His His Leu Ser Leu His Cys Ala Ile Asp Asn Asp
        355                 360                 365

Leu Trp Thr Ile Ser Gly Ile Gln Gln Val Lys Gln Gln Lys Ile Leu
    370                 375                 380

Gln Thr Glu Gln Lys Ile Ala Asn Phe His Ser Lys Ala Leu Glu Lys
385                 390                 395                 400

Glu Leu Thr Pro Asn Gln Gln Gln Arg Leu Lys Ala Ser Gln Thr Ser
                405                 410                 415

Leu Asn Leu Leu Lys Thr Phe Asp Ile Asn Glu Phe Phe Pro Ser Lys
            420                 425                 430

Cys Ser Leu Tyr Gln Gly Ser Pro Asp Ile Ile Leu Gly Val Ser Ile
        435                 440                 445

Gly Leu Glu Asn Pro Ala Thr Ile Ala Ile Ile Asn Ile Ser Thr Gln
    450                 455                 460

Glu Ile Leu Thr Tyr Arg Thr Thr Lys Gln Leu Leu Ser Arg Thr Arg
465                 470                 475                 480

Lys Val Arg Asn Lys Lys Pro Asn Ser Asn Asn Ser Asn Gln Ser Leu
                485                 490                 495

Ser Ser Ala Tyr Lys Gln Ile Ser Asn Tyr Glu Leu Phe Leu Gln Tyr
            500                 505                 510

Gln Gln Gln Lys His His Asn Gln His Gln Arg His Asn Ala Gln Ile
        515                 520                 525

Asn Asp Ala Asn Asn Asn Tyr Gly Glu Ala Asn Leu Gly Leu Tyr Leu
    530                 535                 540

Asn Arg Leu Leu Ala Lys Ala Ile Leu Glu Leu Ala Gln Gln Tyr Gln
545                 550                 555                 560

Val Ser Leu Ile Ile Leu Pro Ser Leu Lys Asn Lys Arg Glu Leu Ile
                565                 570                 575

Glu Ser Glu Ile Arg Ala Lys Ala Glu Leu Lys Tyr Pro Gly Cys Lys
            580                 585                 590

Glu Lys Gln Asp Ser Tyr Ala Lys Asp Tyr Arg Thr Asn Val His Gln
        595                 600                 605

Trp Ser Tyr Gln Gln Leu Ile Lys Cys Ile Glu Ser Lys Ala Ala Gln
    610                 615                 620

Ile Gly Ile Asp Thr Ala Thr Gly Lys Gln Met Asn Leu Glu Thr Ser
625                 630                 635                 640

Gln Asp Gln Ala Arg Asn Leu Val Leu Asn Phe Cys Gln Lys Phe Ser
                645                 650                 655

Pro Thr Gln Val
            660
```

<210> SEQ ID NO 148
<211> LENGTH: 648
<212> TYPE: PRT
<213> ORGANISM: Ammonifex degensii

<400> SEQUENCE: 148

```
Met Cys Phe Val Trp Tyr Phe Ile Phe Met Ser Gln Lys Thr Ile Gln
1               5                   10                  15

Cys Arg Leu Ile Ala Ser Glu Ser Thr Arg Gln Lys Leu Trp Lys Leu
            20                  25                  30

Met Ala Glu Ser Asn Thr Pro Leu Ile Asn Glu Leu Leu Gln Gln Leu
        35                  40                  45

Ser Lys His Pro Asp Phe Glu Lys Trp Arg Arg Asn Gly Lys Leu Pro
    50                  55                  60

Ser Thr Val Val Ser Gln Leu Cys Gln Pro Leu Lys Thr Asp Pro Ser
65                  70                  75                  80

Phe Thr Gly Gln Pro Ser Arg Phe Tyr Ile Ser Ala Ile His Ile Val
                85                  90                  95

Asp Tyr Ile Tyr Lys Ser Trp Leu Thr Ile Gln Lys Arg Leu Gln Gln
            100                 105                 110

Gln Leu Asp Gly Lys Leu Arg Trp Ile Glu Met Phe Asn Ser Asp Val
        115                 120                 125

Glu Leu Val Glu Ile Ser Gly Phe Ser Leu Glu Ala Ile Arg Thr Lys
    130                 135                 140

Ala Ser Glu Ile Leu Ala Ile Thr Thr Pro Glu Ser Asp Pro Lys Thr
145                 150                 155                 160

Leu Leu Thr Lys Arg Gly Lys Thr Lys Gln Ser Lys Lys Ser Ser Ala
                165                 170                 175

Ser Asn Pro Asp Arg Ser Leu Ser Arg Lys Leu Phe Asp Ala Tyr Gln
            180                 185                 190

Glu Thr Asp Asp Ile Leu Ser Arg Ser Ala Ile Ser Tyr Leu Leu Lys
        195                 200                 205

Asn Gly Cys Lys Leu Asn Asp Lys Glu Glu Asn Pro Glu Lys Phe Ala
    210                 215                 220

Lys Arg Arg Arg Lys Val Glu Ile Gln Ile Gln Arg Leu Thr Asp Lys
225                 230                 235                 240

Leu Thr Ser Arg Ile Pro Lys Gly Arg Asp Leu Thr Tyr Ser Lys Trp
                245                 250                 255

Leu Glu Thr Leu Phe Thr Ala Thr Thr Thr Val Pro Glu Asn Asn Ala
            260                 265                 270

Glu Ala Lys Arg Trp Gln Asp Ile Leu Leu Thr Arg Ser Ser Ser Ile
        275                 280                 285

Pro Phe Pro Val Val Phe Glu Thr Asn Glu Asp Leu Val Trp Ser Thr
    290                 295                 300

Asn Glu Lys Gly Arg Leu Cys Val His Phe Asn Gly Leu Ser Asp Leu
305                 310                 315                 320

Ile Phe Glu Val Tyr Cys Asp Ser Arg Gln Leu Tyr Trp Phe Lys Arg
                325                 330                 335

Phe Leu Glu Asp Gln Gln Thr Lys Arg Lys Ser Lys Asn Gln His Ser
            340                 345                 350

Ser Gly Leu Phe Thr Leu Arg Asn Gly Arg Leu Ala Trp Gln Gln Gly
        355                 360                 365

Glu Gly Lys Gly Glu Pro Trp Asn Ile Gly His Leu Ala Leu Tyr Cys
```

```
    370                 375                 380

Cys Val Asp Asn Arg Leu Trp Thr Ala Glu Gly Thr Glu Gln Val Arg
385                 390                 395                 400

Gln Glu Lys Ala Glu Glu Ile Thr Lys Phe Ile Thr Lys Met Lys Asp
                405                 410                 415

Lys Ser Asp Leu Ser Glu Thr Gln Leu Ala Phe Ile Lys Arg Lys Glu
            420                 425                 430

Ser Thr Leu Thr Arg Ile Asn Asn Ser Phe Asp Arg Pro Ser Lys Pro
        435                 440                 445

Leu Tyr Gln Gly Gln Ser His Ile Leu Val Gly Val Ser Leu Gly Leu
    450                 455                 460

Glu Lys Pro Ala Thr Ile Ala Val Val Asp Ala Ile Ala Gly Lys Val
465                 470                 475                 480

Leu Thr Tyr Arg Ser Leu Arg Gln Leu Leu Gly Asp Asn Tyr Glu Leu
                485                 490                 495

Leu Asn Arg Gln Arg Arg Gln Gln Arg Ser Leu Ser His Glu Arg His
            500                 505                 510

Lys Ala Gln Lys Ser Phe Ser Pro Asn Gln Phe Gly Ala Ser Glu Leu
        515                 520                 525

Gly Gln Tyr Val Asp Arg Leu Leu Ala Lys Glu Ile Val Ala Ile Ala
    530                 535                 540

Gln Thr Tyr Lys Ala Gly Ser Ile Val Leu Pro Lys Leu Gly Asp Ile
545                 550                 555                 560

Arg Glu Ile Val Gln Ser Glu Ile Gln Ala Ile Ala Glu Ala Lys Cys
                565                 570                 575

Pro Ser Ser Ser Glu Ile Gln Gln Lys Tyr Ala Lys Gln Tyr Arg Val
            580                 585                 590

Asn Val His Gln Trp Ser Tyr Gly Arg Leu Ile Gln Ser Ile Gln Ser
        595                 600                 605

Lys Ala Ala Gln Ile Gly Ile Val Ile Glu Glu Gly Lys Gln Pro Ile
    610                 615                 620

Arg Gly Ser Pro Gln Asp Lys Ala Lys Glu Leu Ala Leu Tyr Ala Tyr
625                 630                 635                 640

Ser Leu Arg Leu Ala Arg Arg Ser
                645


<210> SEQ ID NO 149
<211> LENGTH: 643
<212> TYPE: PRT
<213> ORGANISM: Campylobacter fetus venerealis

<400> SEQUENCE: 149

Met Ser Val Ile Thr Ile Gln Cys Arg Leu Ile Ala Ser Glu Ala Thr
1               5                   10                  15

Arg Ser Tyr Leu Trp Gln Leu Met Ala Gln Lys Asn Thr Pro Leu Ile
            20                  25                  30

Asn Glu Leu Ile Glu Gln Leu Gly Ile His Pro Glu Ile Glu Gln Trp
        35                  40                  45

Leu Lys Lys Gly Lys Leu Pro Asp Gly Val Val Lys Pro Leu Cys Asp
    50                  55                  60

Ser Leu Ile Thr Gln Glu Ser Phe Ala Asn Gln Pro Lys Arg Phe Asn
65                  70                  75                  80

Lys Ser Ala Ile Glu Val Val Glu Tyr Ile Tyr Lys Ser Trp Leu Ala
                85                  90                  95
```

```
Leu Gln Lys Glu Arg Gln Gln Thr Ile Asp Arg Lys Glu His Trp Leu
            100                 105                 110

Lys Met Leu Lys Ser Asp Val Glu Leu Glu Gln Glu Ser Lys Cys Thr
        115                 120                 125

Leu Asp Ala Ile Arg Ser Gln Ala Thr Lys Ile Leu Pro Lys Tyr Leu
    130                 135                 140

Ala Gln Ser Glu Gln Asn Asn Asn Gln Thr Gln Ser Gln Asn Lys Lys
145                 150                 155                 160

Lys Ser Lys Lys Ser Lys Thr Lys Asn Glu Asn Ser Thr Leu Phe Asp
                165                 170                 175

Ile Leu Phe Lys Ala Tyr Asp Lys Ala Lys Asn Pro Leu Asn Arg Cys
            180                 185                 190

Thr Leu Ala Tyr Leu Leu Lys Asn Asn Cys Gln Val Ser Gln Lys Asp
        195                 200                 205

Glu Asp Pro Asn Gln Tyr Ala Leu Arg Arg Ser Lys Lys Glu Lys Glu
    210                 215                 220

Ile Glu Arg Leu Lys Lys Gln Leu Gln Ser Arg Lys Pro Asn Gly Arg
225                 230                 235                 240

Asp Leu Thr Gly Arg Glu Trp Gln Gln Thr Leu Ile Met Ala Thr Ser
                245                 250                 255

Ser Val Pro Glu Ser Asn Asp Glu Ala Asn Ile Trp Gln Lys Arg Leu
            260                 265                 270

Leu Lys Lys Asp Ile Ser Leu Pro Phe Pro Ile Arg Phe Arg Thr Asn
        275                 280                 285

Glu Asp Leu Ile Trp Ser Lys Asn Glu Glu Gly Arg Ile Cys Val Ser
    290                 295                 300

Phe Ser Gly Glu Gly Leu Asn Asp His Ile Phe Glu Ile Tyr Cys Gly
305                 310                 315                 320

Asn Arg Gln Ile His Trp Phe Gln Arg Phe Leu Glu Asp Gln Asn Ile
                325                 330                 335

Lys Asn Asp Asn Asn Asp Gln His Ser Ser Ala Leu Phe Thr Leu Arg
            340                 345                 350

Ser Ala Ile Leu Ala Trp Gln Glu Asn Lys Gln His Lys Glu Asn Ser
        355                 360                 365

Leu Pro Trp Asn Thr Arg Arg Leu Thr Leu Tyr Cys Thr Leu Asp Thr
    370                 375                 380

Arg Leu Trp Thr Thr Asp Gly Thr Glu Lys Val Lys Gln Glu Lys Val
385                 390                 395                 400

Asp Glu Phe Thr Gln Gln Leu Ala Asn Met Glu Gln Lys Glu Asn Leu
                405                 410                 415

Asn Gln Asn Gln Gln Asn Tyr Val Lys Arg Leu Gln Ser Thr Leu Asn
            420                 425                 430

Lys Leu Asn Asn Ala Tyr Pro Arg His Asn His Asp Leu Tyr Gln Gly
        435                 440                 445

Lys Pro Ser Ile Leu Val Gly Val Ser Leu Gly Leu Glu Lys Pro Ala
    450                 455                 460

Thr Leu Ala Ile Val Asp Ser Ser Thr Asn Ile Val Leu Ala Tyr Arg
465                 470                 475                 480

Ser Ile Lys Gln Leu Leu Gly Asp Asn Tyr Lys Leu Leu Asn Arg Gln
                485                 490                 495

Arg Gln Gln Gln Gln Arg Asn Ser His Glu Arg His Lys Ala Gln Lys
            500                 505                 510

Ser Asn Met Pro Asn Lys Leu Ser Glu Ser Asp Leu Gly Lys Tyr Ile
```

```
        515                 520                 525

Asp Asn Leu Leu Ala Gln Ala Ile Ile Ala Leu Ala Lys Asn Tyr Gln
    530                 535                 540

Ala Gly Ser Ile Val Leu Pro Thr Met Lys Asn Val Arg Glu Ser Ile
545                 550                 555                 560

Gln Ser Glu Ile Glu Ala Arg Ala Val Lys Arg Cys Pro Asn Tyr Lys
                565                 570                 575

Glu Gly Gln Gln Gln Tyr Ala Lys Gln Tyr Arg Gln Ser Ile His Arg
            580                 585                 590

Trp Ser Tyr Asn Arg Leu Met Gln Phe Ile Gln Ser Gln Ala Val Lys
        595                 600                 605

Ala Asn Ile Ser Ile Glu Gln Gly Pro Gln Pro Ile Arg Gly Ser Ser
    610                 615                 620

Gln Glu Lys Ala Arg Asp Leu Ala Ile Ala Ala Tyr Tyr Leu Arg Gln
625                 630                 635                 640

Asn Lys Ser


<210> SEQ ID NO 150
<211> LENGTH: 642
<212> TYPE: PRT
<213> ORGANISM: Calothrix sp.

<400> SEQUENCE: 150

Met Ser Gln Ile Thr Ile Gln Cys Arg Leu Val Ala Ser Glu Pro Ser
1               5                   10                  15

Arg His Gln Leu Trp Lys Leu Met Val Asp Leu Asn Thr Pro Leu Ile
            20                  25                  30

Asn Glu Leu Leu Val Gln Val Ala Gln His Pro Glu Phe Glu Thr Trp
        35                  40                  45

Arg Gln Lys Gly Lys His Pro Ala Lys Ile Val Lys Glu Leu Cys Glu
    50                  55                  60

Pro Leu Arg Thr Asp Pro Arg Phe Ile Gly Gln Pro Gly Arg Phe Tyr
65                  70                  75                  80

Thr Ser Ala Ile Ala Thr Val Asn Tyr Ile Tyr Lys Ser Trp Phe Ala
                85                  90                  95

Leu Met Lys Arg Ser Gln Ser Gln Leu Glu Gly Lys Met Arg Trp Trp
            100                 105                 110

Glu Met Leu Lys Ser Asp Ala Glu Leu Val Glu Val Ser Gly Val Thr
        115                 120                 125

Leu Glu Ser Leu Arg Thr Lys Ala Ala Glu Ile Leu Ser Gln Phe Ala
    130                 135                 140

Pro Gln Pro Asp Thr Val Glu Ala Gln Pro Ala Lys Gly Lys Lys Arg
145                 150                 155                 160

Lys Lys Thr Lys Lys Ser Asp Gly Asp Cys Ala Glu Arg Thr Leu Arg
                165                 170                 175

Glu Arg Ser Ile Ser Asp Tyr Leu Phe Glu Ala Tyr Arg Asp Thr Glu
            180                 185                 190

Glu Ile Leu Thr Arg Cys Ala Ile Asn Tyr Leu Leu Lys Asn Gly Cys
        195                 200                 205

Lys Ile Ser Asn Lys Glu Glu Asn Ala Glu Lys Phe Ala Lys Arg Arg
    210                 215                 220

Arg Lys Leu Glu Ile Gln Ile Glu Arg Leu Arg Glu Lys Leu Glu Ala
225                 230                 235                 240

Arg Ile Pro Lys Gly Arg Asp Leu Thr Asp Ala Lys Trp Leu Glu Thr
```

-continued

```
                245                 250                 255

Leu Leu Leu Ala Thr Leu Asn Val Pro Glu Asn Glu Ala Glu Ala Lys
            260                 265                 270

Ser Trp Gln Asp Ser Leu Leu Lys Lys Ser Ile Thr Val Pro Phe Pro
        275                 280                 285

Val Ala Tyr Glu Thr Asn Glu Asp Met Thr Trp Phe Lys Asn Glu Arg
    290                 295                 300

Gly Arg Ile Cys Val Lys Phe Ser Gly Leu Ser Glu His Thr Phe Gln
305                 310                 315                 320

Val Tyr Cys Asp Ser Arg Gln Leu Gln Trp Phe Gln Arg Phe Leu Glu
                325                 330                 335

Asp Gln Gln Ile Lys Arg Asn Ser Lys Asn Gln His Ser Ser Ser Leu
            340                 345                 350

Phe Thr Leu Arg Ser Gly Arg Ile Ala Trp Gln Glu Gly Glu Gly Lys
        355                 360                 365

Ser Glu Pro Trp Lys Val Asn Arg Leu Ile Leu Tyr Cys Ser Val Asp
    370                 375                 380

Thr Arg Leu Trp Thr Ala Glu Gly Thr Asn Leu Val Arg Glu Glu Lys
385                 390                 395                 400

Ala Glu Glu Ile Ala Lys Ala Ile Ala Gln Thr Lys Ala Lys Gly Lys
                405                 410                 415

Leu Asn Asp Lys Gln Gln Ala His Ile Lys Arg Lys Asn Ser Ser Leu
            420                 425                 430

Ala Arg Ile Asn Asn Leu Phe Pro Arg Pro Ser Lys Pro Leu Tyr Lys
        435                 440                 445

Gly Gln Ser His Ile Leu Val Gly Val Ser Leu Gly Leu Glu Lys Pro
    450                 455                 460

Thr Thr Leu Ala Val Val Asp Gly Ser Ile Gly Lys Val Leu Thr Tyr
465                 470                 475                 480

Arg Asn Ile Lys Gln Leu Leu Gly Asp Asn Tyr Arg Leu Leu Asn Arg
                485                 490                 495

Gln Arg Gln Gln Lys His Thr Leu Ser His Gln Arg Gln Val Ala Gln
            500                 505                 510

Ile Leu Ala Ser Pro Asn Gln Leu Gly Glu Ser Glu Leu Gly Gln Tyr
        515                 520                 525

Val Asp Arg Leu Leu Ala Lys Glu Ile Val Ala Ile Thr Gln Thr Tyr
    530                 535                 540

Lys Ala Gly Ser Ile Val Leu Pro Lys Leu Gly Asp Met Arg Glu Gln
545                 550                 555                 560

Val Gln Ser Glu Ile Gln Ala Lys Ala Glu Gln Lys Ser Asp Leu Ile
                565                 570                 575

Glu Val Gln Gln Lys Tyr Ser Lys Gln Tyr Arg Val Ser Val His Gln
            580                 585                 590

Trp Ser Tyr Gly Arg Leu Ile Ala Ser Ile Arg Ser Ser Ala Ala Lys
        595                 600                 605

Val Gly Ile Val Ile Glu Glu Ser Lys Gln Pro Ile Arg Gly Ser Pro
    610                 615                 620

Gln Glu Lys Ala Arg Glu Leu Ala Ile Ala Ala Tyr Asn Ser Arg Arg
625                 630                 635                 640

Arg Thr
```

<210> SEQ ID NO 151
<211> LENGTH: 639

<212> TYPE: PRT
<213> ORGANISM: Anabaena variabilis

<400> SEQUENCE: 151

```
Met Ser Gln Ile Thr Ile Gln Cys Arg Leu Ile Ala Ser Glu Ser Thr
1               5                   10                  15

Arg Gln Lys Leu Trp Lys Leu Met Ala Thr Leu Asn Thr Pro Leu Ile
            20                  25                  30

Asn Glu Leu Ile Glu Gln Leu Gly Lys His Pro Asp Phe Glu Asn Trp
        35                  40                  45

Arg Gln Gln Gly Lys Leu Pro Thr Thr Val Val Ser Gln Leu Cys Gln
    50                  55                  60

Pro Leu Lys Thr Asp Pro Arg Phe Val Gly Gln Pro Ser Arg Leu Tyr
65                  70                  75                  80

Met Ser Ala Ile His Ile Val Asp Tyr Ile Tyr Lys Ser Trp Leu Ala
                85                  90                  95

Ile Gln Lys Arg Leu Gln Gln Gln Leu Asp Gly Lys Met Arg Trp Leu
            100                 105                 110

Glu Met Leu Asn Ser Asp Val Glu Leu Val Glu Thr Ser Gly Ser Ser
        115                 120                 125

Met Gly Ala Ile Arg Thr Lys Ala Ser Glu Ile Leu Ala Lys Ala Met
    130                 135                 140

Pro Thr Ser Asp Ser Asp Ser Ser Gln Pro Lys Thr Lys Lys Gly Lys
145                 150                 155                 160

Glu Ala Lys Lys Ser Ser Ser Ser Ser Ser Asp Arg Ser Leu Ser Asn
                165                 170                 175

Lys Leu Phe Glu Ala Tyr Gln Glu Thr Glu Asp Ile Leu Ser Arg Ser
            180                 185                 190

Ala Ile Ser Tyr Leu Leu Lys Asn Gly Cys Lys Leu Ser Asp Lys Glu
        195                 200                 205

Glu Asp Ser Glu Lys Phe Ala Lys Arg Arg Arg Gln Val Glu Ile Gln
    210                 215                 220

Ile Gln Arg Leu Thr Glu Lys Leu Ile Ser Arg Met Pro Lys Gly Arg
225                 230                 235                 240

Asp Leu Thr Asn Arg Lys Trp Leu Glu Thr Leu Phe Thr Ala Thr Thr
                245                 250                 255

Thr Phe Pro Glu Asp Asn Ala Glu Ala Lys Arg Trp Gln Asp Ile Leu
            260                 265                 270

Leu Thr Arg Pro Ser Ser Leu Pro Phe Pro Leu Val Phe Glu Thr Asn
        275                 280                 285

Glu Asp Met Val Trp Ser Lys Asn Gln Lys Gly Arg Leu Cys Val His
    290                 295                 300

Phe Asn Gly Leu Ser Asp Leu Ser Phe Glu Val Tyr Cys Asp Asn Arg
305                 310                 315                 320

Gln Leu His Trp Phe Gln Arg Phe Leu Glu Asp Gln Gln Thr Lys Arg
                325                 330                 335

Gln Ser Lys Ser Gln Tyr Ser Ser Gly Leu Phe Thr Leu Arg Asn Gly
            340                 345                 350

His Leu Val Trp Gln Glu Gly Glu Gly Lys Ser Glu Pro Trp Asn Leu
        355                 360                 365

Asn Arg Leu Asn Leu Tyr Cys Cys Val Asp Asn Arg Leu Trp Thr Ala
    370                 375                 380

Asp Gly Thr Glu Gln Val Arg Gln Glu Lys Ala Glu Glu Ile Ser Lys
385                 390                 395                 400
```

```
Leu Ile Thr Lys Met Lys Glu Lys Ser Asp Leu Lys Asp Thr Gln Lys
                405                 410                 415

Ala Phe Ile Gln Arg Lys Glu Ser Thr Leu Asn Arg Met Asn Asn Ser
            420                 425                 430

Phe Glu Arg Pro Ser Gln Pro Leu Tyr Gln Gly Gln Ser His Ile Leu
        435                 440                 445

Val Gly Val Ser Leu Gly Leu Glu Lys Pro Ala Thr Val Ala Val Val
    450                 455                 460

Asp Ala Ile Ala Gly Lys Val Leu Ala Tyr Arg Ser Ile Arg Gln Leu
465                 470                 475                 480

Leu Gly Asp Asn Tyr Glu Leu Leu Asn Arg Gln Arg Arg Gln Gln Arg
                485                 490                 495

Ser Ser Ser His Glu Arg His Lys Ala Gln Lys Ser Phe Ser Pro Asn
            500                 505                 510

Gln Phe Gly Thr Ser Glu Leu Gly Gln Tyr Val Asp Arg Leu Leu Ala
        515                 520                 525

Lys Glu Ile Ile Ala Ile Ala Gln Thr Tyr Lys Ala Gly Asn Ile Val
    530                 535                 540

Leu Pro Lys Leu Gly Asp Met Arg Glu Ile Val Gln Ser Glu Ile Gln
545                 550                 555                 560

Ala Ile Ala Glu Ala Lys Cys Pro Gly Ser Val Glu Val Gln Gln Lys
                565                 570                 575

Tyr Ala Lys Gln Tyr Arg Val Asn Val His Lys Trp Ser Tyr Gly Arg
            580                 585                 590

Leu Ile Gln Ser Ile Gln Ser Lys Gly Ser Gln Ala Gly Ile Val Ile
        595                 600                 605

Glu Glu Gly Lys Gln Pro Val Arg Gly Ser Pro His Glu Gln Ala Lys
    610                 615                 620

Glu Leu Ala Leu Ser Ala Tyr His Asp Arg Leu Ala Arg Arg Ser
625                 630                 635


<210> SEQ ID NO 152
<211> LENGTH: 639
<212> TYPE: PRT
<213> ORGANISM: Cellulosilyticum ruminicola

<400> SEQUENCE: 152

Met Ser Val Ile Thr Ile Gln Cys Arg Leu Val Ala Asp Glu Glu Thr
1               5                   10                  15

Leu Arg His Leu Trp Thr Leu Met Ala Glu Lys Asn Thr Pro Phe Ala
            20                  25                  30

Asn Glu Ile Leu Glu Gln Leu Ala Gln His Ala Glu Phe Glu Ser Trp
        35                  40                  45

Val Lys Asn Ser Arg Val Pro Ala Thr Val Ile Lys Glu Leu Cys Asp
    50                  55                  60

Ser Leu Lys Asn Gln Glu Leu Phe Ala Gly Gln Pro Gly Arg Phe Tyr
65                  70                  75                  80

Thr Ser Ala Thr Thr Leu Val Thr Tyr Ile Tyr Lys Ser Trp Leu Ala
                85                  90                  95

Val Asn Lys Arg Leu Gln Arg Lys Ile Glu Gly Lys Lys Gln Trp Leu
            100                 105                 110

Asp Met Leu Arg Ser Asp Thr Glu Leu Glu Gln Glu Ser Asn Ser Asn
        115                 120                 125

Leu Glu Lys Ile Arg Ala Lys Ala Thr Glu Ile Leu Asp Ser Phe Ala
```

-continued

```
    130                 135                 140

Thr Arg Gln Ile Asn Gln Val Asn Ser Lys Ser Lys Thr Ser Lys Asn
145                 150                 155                 160

Asn Lys Asn Lys Gln Glu Lys Glu Val Lys Ser Leu Ser Ile Gln Ser
                165                 170                 175

Asn Ile Leu Phe Glu Thr Tyr Arg Gln Thr Glu Asp Asn Leu Thr Lys
            180                 185                 190

Cys Ala Ile Val Tyr Leu Leu Lys Asn Asn Cys Glu Val Asn Asp Val
        195                 200                 205

Glu Glu Asp Ile Glu Glu Tyr Glu Lys Asn Lys Arg Lys Lys Glu Ile
    210                 215                 220

Gln Ile Lys Arg Leu Glu Asp Gln Leu Lys Ser Arg Val Pro Lys Gly
225                 230                 235                 240

Arg Asp Leu Thr Gly Glu Lys Trp Val Glu Val Leu Glu Lys Ala Val
                245                 250                 255

Asn Ser Val Pro Glu Ser Glu Asn Glu Ala Lys Ser Trp Gln Ala Ser
            260                 265                 270

Leu Leu Arg Lys Ser Ser Gln Ile Pro Phe Pro Val Val Tyr Glu Thr
        275                 280                 285

Asn Glu Asp Ile Lys Trp Ser Ile Asn Glu Lys Gly Arg Ile Phe Val
    290                 295                 300

Ser Phe Asn Gly Leu Gly Lys Leu Lys Phe Glu Ile Phe Cys Asp Lys
305                 310                 315                 320

Arg His Leu His Tyr Phe Gln Arg Phe Leu Glu Asp Gln Asp Ile Lys
                325                 330                 335

Arg Gln Gly Lys Asn Gln His Ser Ser Ser Leu Phe Thr Leu Arg Ser
            340                 345                 350

Gly Arg Ile Ser Trp Leu Glu Gln Pro Gly Lys Gly Lys Pro Trp Asn
        355                 360                 365

Ile Asn Arg Leu Leu Leu Phe Cys Ser Ile Asp Thr Arg Met Leu Thr
    370                 375                 380

Ala Glu Gly Thr Gln Gln Val Ile Glu Glu Lys Ile Ala Asp Thr Gln
385                 390                 395                 400

Asn Lys Ile Ala Lys Ala Gln Glu Lys Cys Glu Gly Glu Leu Asn Pro
                405                 410                 415

Asn Gln Gln Ala His Ile Asn Arg Lys Lys Ser Thr Leu Ala Arg Ile
            420                 425                 430

Asn Thr Pro Phe Pro Arg Pro Ser Lys Pro Leu Tyr Gln Gly Lys Ser
        435                 440                 445

His Ile Val Val Gly Val Ser Leu Gly Leu Lys Ala Thr Ala Thr Ile
    450                 455                 460

Ala Val Phe Asp Ala Met Asn Asn Gln Val Leu Ala Tyr Arg Ser Thr
465                 470                 475                 480

Lys Gln Leu Leu Gly Asp Asn Tyr Lys Leu Leu Asn Arg Gln Gln Gln
                485                 490                 495

Gln Lys Gln Arg Leu Ser Gln Gln Arg His Lys Ser Gln Lys Gln Phe
            500                 505                 510

Ala Ser Asn Ser Phe Gly Glu Ser Glu Leu Gly Gln Tyr Val Asp Arg
        515                 520                 525

Leu Leu Ala Lys Glu Ile Val Ala Val Ala Lys Asn Phe Gly Ala Gly
    530                 535                 540

Ser Ile Val Leu Pro Lys Leu Gly Asp Met Arg Glu Ile Ile Gln Ser
545                 550                 555                 560
```

Glu Val Gln Ala Lys Ala Glu Lys Lys Ile Pro Gly Phe Ile Glu Leu
565 570 575

Gln Lys Asn Tyr Ala Lys Glu Tyr Arg Lys Ser Ala His Asn Trp Ser
580 585 590

Tyr Gly Arg Leu Ile Glu Asn Ile Gln Ser Gln Ala Thr Lys Glu Gly
595 600 605

Ile Glu Ile Glu Thr Gly Lys Gln Pro Thr Arg Gly Ile Pro Gln Glu
610 615 620

Gln Ala Arg Asp Leu Ala Leu Phe Ala Tyr Gln Cys Arg Ile Ala
625 630 635

<210> SEQ ID NO 153
<211> LENGTH: 635
<212> TYPE: PRT
<213> ORGANISM: Chloroflexi bacterium

<400> SEQUENCE: 153

Met Ser Gln Ile Thr Ile Gln Cys Arg Leu Val Ala Ser Glu Thr Thr
1 5 10 15

Arg Gln Gln Leu Trp Gln Leu Met Ala Glu Lys Asn Thr Pro Leu Ile
20 25 30

Asn Glu Leu Leu Ser Gln Ile Gly Lys His Pro Glu Phe Glu Thr Trp
35 40 45

Arg Gln Lys Gly Lys His Pro Thr Gly Ile Val Lys Glu Leu Cys Glu
50 55 60

Pro Leu Lys Thr Asp Pro Arg Phe Ile Gly Gln Pro Ala Arg Phe Tyr
65 70 75 80

Thr Ser Ala Thr Ala Ser Val Asn Tyr Ile Tyr Glu Ser Trp Phe Ala
85 90 95

Leu Met Lys Arg Tyr Gln Ser Gln Leu Asp Gly Lys Leu Arg Trp Leu
100 105 110

Glu Met Phe Asn Ser Asp Ala Glu Leu Val Glu His Ser Gly Val Ser
115 120 125

Leu Asp Thr Leu Arg Ala Thr Ser Ala Glu Ile Leu Ala Gln Phe Ala
130 135 140

Pro Gln Asp Thr Asn Arg Asp Thr Ser Asn Lys Gly Lys Lys Ser Lys
145 150 155 160

Met Gly Lys Lys Ser Gln Lys Ser Asp Ser Glu Gly Asn Leu Ser Lys
165 170 175

Lys Leu Phe Asp Ala Tyr Ser Ser Ala Glu Asp Asn Leu Thr Arg Cys
180 185 190

Ala Ile Ser His Leu Leu Lys Asn Gly Cys Lys Val Ser Asn Lys Glu
195 200 205

Glu Asn Ser Glu Lys Phe Thr Gln Arg Arg Arg Lys Leu Glu Ile Gln
210 215 220

Ile Gln Arg Leu Thr Glu Lys Leu Ala Ala Arg Ile Pro Lys Gly Arg
225 230 235 240

Asp Leu Thr Asp Thr Gln Trp Leu Glu Thr Leu Phe Thr Ala Thr Tyr
245 250 255

Asn Val Pro Glu Asp Glu Thr Glu Ala Lys Leu Trp Gln Asn Ser Leu
260 265 270

Leu Arg Lys Phe Ser Ser Leu Pro Phe Pro Val Ala Tyr Glu Thr Asn
275 280 285

Glu Asp Leu Val Trp Ser Lys Asn Arg Phe Gly Arg Ile Cys Leu Thr

```
290                 295                 300

Phe Pro Thr Leu Arg Glu His Ile Phe Gln Ile Tyr Cys Asp Ser Arg
305                 310                 315                 320

Gln Leu His Trp Phe Gln Arg Phe Leu Glu Asp Gln Glu Ile Lys Lys
                325                 330                 335

Asn Ser Lys Asn Gln His Ser Ser Ala Leu Phe Thr Leu Arg Ser Gly
            340                 345                 350

Arg Ile Ala Trp Gln Glu Gly Glu Gly Lys Gly Glu Pro Trp Asp Ile
        355                 360                 365

His His Leu Thr Leu Tyr Cys Cys Val Asp Thr Arg Leu Trp Thr Glu
    370                 375                 380

Glu Gly Thr Asn Leu Val Lys Glu Glu Lys Ala Glu Glu Ile Ala Lys
385                 390                 395                 400

Thr Ile Thr Gln Thr Lys Ala Lys Gly Asp Leu Asn Asp Lys Gln Gln
                405                 410                 415

Ala His Leu Lys Arg Lys Asn Ser Ser Leu Ala Arg Ile Asn Asn Pro
            420                 425                 430

Phe Pro Arg Pro Ser Gln Pro Leu Tyr Lys Gly Gln Ser His Ile Leu
        435                 440                 445

Leu Gly Val Ser Leu Gly Leu Glu Lys Pro Ala Thr Val Ala Val Val
    450                 455                 460

Asp Gly Thr Thr Gly Lys Val Leu Thr Tyr Arg Asn Ile Lys Gln Leu
465                 470                 475                 480

Leu Gly Asp Asn Tyr Lys Leu Leu Asn Arg Gln Arg Gln Gln Lys His
                485                 490                 495

Leu Leu Ser His Gln Arg His Ile Ala Gln Arg Ile Ala Ala Pro Asn
            500                 505                 510

Asn Phe Gly Asp Ser Glu Leu Gly Glu Tyr Ile Asp Arg Leu Leu Ala
        515                 520                 525

Lys Glu Ile Ile Ala Ile Ala Gln Thr Tyr Gln Ala Gly Ser Ile Val
    530                 535                 540

Leu Pro Asn Leu Gly Asp Met Arg Glu Gln Ile Gln Ser Glu Ile Lys
545                 550                 555                 560

Ala Lys Ala Glu Gln Lys Ser Asp Leu Val Glu Val Gln Lys Lys Tyr
                565                 570                 575

Ala Lys Gln Tyr Pro Asn Ser Val His Gln Trp Ser Tyr Gly Arg Leu
            580                 585                 590

Ile Thr Asn Ile Gln Ser Gln Ser Lys Lys Ala Gly Ile Val Ile Glu
        595                 600                 605

Glu Gly Lys Gln Gln Ile Arg Ala Ser Pro Leu Glu Lys Ala Lys Glu
    610                 615                 620

Leu Ala Ile Asn Ala Tyr Gln Ser Arg Lys Ala
625                 630                 635
```

<210> SEQ ID NO 154
<211> LENGTH: 711
<212> TYPE: PRT
<213> ORGANISM: Crinalium epipsammum

<400> SEQUENCE: 154

```
Met Ser Asp Gln Thr Ser Gln Asn Asn Glu Ile Thr Ile Gln Ser Leu
1               5                   10                  15

Leu Glu Ala Pro Glu Glu Thr Leu Cys Phe Leu Trp Gln Leu Met Val
            20                  25                  30
```

-continued

```
Asn Val Thr Glu Leu Ile Asn Ser Leu Leu His His Ile Asn Thr His
        35                  40                  45

Pro Asp Phe Asp Ile Trp Leu Thr Gln Cys Ala Ile Pro Ala Ser Val
    50                  55                  60

Ile Asn Ser Phe Ile Lys Thr Ala Lys Thr Gln Ser Pro Tyr Arg Glu
65                  70                  75                  80

Met Pro Thr Arg Phe Ile Thr Ser Ala Gln Asn Leu Val Asn Glu Met
                85                  90                  95

Phe Lys Ser Trp Phe Glu Ile Gln Arg Leu Lys Arg Leu Ser Leu Lys
            100                 105                 110

Gly Lys Arg His Phe Phe Thr Ile Leu Lys Ser Asp Glu Glu Leu Gln
        115                 120                 125

Arg Glu Ser Asp Cys Thr Phe Asp Thr Leu Cys Gln Glu Ala Ala Ile
    130                 135                 140

Ile Leu Gln Gln Thr Gln Leu Gln Ile Glu Gln Lys Arg Leu Asp Ala
145                 150                 155                 160

Asn Gln Pro Pro Pro Thr Leu Asp Lys Gln Ala Phe Trp Glu Val Ala
                165                 170                 175

His Val Leu Tyr Lys Ala Tyr Asp Gln Ala Asp Thr Pro Leu Val Arg
            180                 185                 190

Ser Gly Ile Ala Leu Leu Leu Lys Asn Gln Asn Gln Val Pro Glu Gln
        195                 200                 205

Phe Glu Asp Pro Lys Lys Tyr Gln Gln Arg Arg Gln Ala Lys Gln Glu
    210                 215                 220

Glu Ile Glu Arg Leu Glu His Gln Leu Gln Ser Lys Ala Pro Lys Gly
225                 230                 235                 240

Arg Leu Thr Asp Gln Gln Glu Trp Leu Arg Ile Leu Glu Lys Ala Ser
                245                 250                 255

Gln Pro Ile Thr Glu Val Ala Glu Phe Arg Asp Ile Gln Ala Gln Leu
            260                 265                 270

Leu Arg Lys Phe Phe Ala Leu Val Tyr Pro Val Thr Phe Ser Thr Asn
        275                 280                 285

Thr Asp Leu Gln Trp Ser Thr Asn Gln Gln Gly Arg Ile Cys Val Gln
    290                 295                 300

Phe Tyr Gly Met Ser Lys Tyr Thr Phe Glu Ile Ala Cys Asp Arg Arg
305                 310                 315                 320

Gln Leu Asn Trp Phe Lys Arg Phe Leu Ala Asp Tyr Gln Leu Tyr Lys
                325                 330                 335

Gln His Lys Thr Gln Ile Pro Thr Gly Leu Met Pro Leu Arg Cys Ala
            340                 345                 350

Arg Leu Val Trp Thr Glu Gly Gln Asp Asp Phe Ala Leu Ile Val Ala
        355                 360                 365

Thr Trp Leu Leu Ile Ala Val Ile Gln His Lys Phe Tyr His Ile Ala
    370                 375                 380

Trp Leu Leu Leu Lys Asn His Arg Ile Ile Lys Ser Pro Pro Trp Arg
385                 390                 395                 400

Val His His Leu His Leu His Cys Ile Val Asp His Arg Leu Trp Thr
                405                 410                 415

Gln Glu Gly Lys Glu Ile Val Lys Ala Glu Lys Ile Pro Gln Thr Glu
            420                 425                 430

Lys Leu Ile Asn Asp Phe Gln Gln Lys Glu Arg Ile Gln Glu Asn Gly
        435                 440                 445

Leu Thr Thr Gly Gln Gln Gln Arg Leu Lys Ala Ser Glu Thr Ser Leu
```

```
    450                 455                 460

Arg Leu Leu Gln Asn Cys Asp His Phe Ala Ala Ser Lys Arg Ile Ser
465                 470                 475                 480

Tyr Arg Gly Gln Pro Asn Arg Ile Leu Gly Val Ser Ile Gly Leu His
                485                 490                 495

Glu Pro Val Thr Ile Met Ile Val Asn Thr Thr Thr Gly Lys Thr Leu
            500                 505                 510

Ala Ser Arg Asn Thr Lys Gln Leu Leu Asp Lys Lys Arg Arg Val Arg
        515                 520                 525

Asp Gln Gln Pro Glu Leu Pro Lys Tyr Glu Glu Arg Gln His Phe Thr
    530                 535                 540

Asn Ile Tyr Lys Glu Ile Ser Asp Tyr Glu Leu Phe Leu Phe Tyr Arg
545                 550                 555                 560

Gln Gln Lys Gln Gln His Gln His Gln Arg His Lys Ala Gln Ile Lys
                565                 570                 575

Ala Thr Pro Asp His Ser Lys Glu Ala Asn Leu Gly Leu Tyr Ile Asn
            580                 585                 590

Arg Leu Leu Ala Lys Ala Ile Ile Glu Phe Ala Gln Gln His Gln Val
        595                 600                 605

Ser Thr Ile Ile Leu Pro Asp Leu Lys Asn Lys Arg Glu Ser Ile Glu
    610                 615                 620

Ser Glu Ala Lys Ala Leu Ala Lys Leu Lys Ile Pro Lys Asp Lys Ser
625                 630                 635                 640

Arg Gln Gln Gln Tyr Thr Arg Asn Ile Leu Ser Glu Val Ser Gln Trp
                645                 650                 655

Ser Tyr Lys Gln Leu Ser Asp Cys Ile Ile Asn Lys Ala Ser Gln Ser
            660                 665                 670

Gly Ile Ala Ile Glu Ile Ile Gln Gln Ile Ser Gln Gly Asn Pro Tyr
        675                 680                 685

Gln Lys Ala Arg Asn Leu Ile Thr Thr Phe Thr Lys Asn Ser Gly Asn
    690                 695                 700

Lys Cys Ser Ala Lys Ile Glu
705                 710


<210> SEQ ID NO 155
<211> LENGTH: 678
<212> TYPE: PRT
<213> ORGANISM: Geobacillus sp.

<400> SEQUENCE: 155

Met Ser Arg Asp Arg Gln Lys Lys Ser Thr Ser Pro Ile His Arg Thr
1               5                   10                  15

Ile Arg Cys His Leu His Ala Ser Glu Asp Val Leu Arg Lys Val Trp
            20                  25                  30

Glu Glu Met Thr Gln Lys Asn Thr Pro Leu Ile Val Gln Leu Leu Lys
        35                  40                  45

Ser Val Ser Glu Gln Pro Glu Phe Glu Thr Asn Gln Glu Lys Gly Thr
    50                  55                  60

Ile Ser Lys Lys Glu Ile Thr Lys Leu Arg Lys Ala Leu Thr Asn Asp
65                  70                  75                  80

Ser Asp Leu Gln Gln Gln Ser Gly Arg Leu Gly Ser Ser Ala Asp Ser
                85                  90                  95

Leu Val Thr Glu Val Tyr Thr Ser Trp Leu Thr Leu Ser Gln Lys Ile
            100                 105                 110
```

```
Lys Lys Gln Lys Glu Gly Lys Glu Tyr Phe Leu Asn Asn Ile Leu Lys
        115                 120                 125

Ser Asp Val Glu Leu Val Gln Glu Ser Asn Cys Asp Leu Gln Thr Ile
    130                 135                 140

Arg Cys Lys Ala Gln Asp Ile Leu Ser Gln Pro Lys Glu Phe Leu Glu
145                 150                 155                 160

Gln Ile Thr Asn His Asp Ala Val Leu Asn Gln Thr Lys Ser Ala Arg
                165                 170                 175

Lys Lys Val Gln Asn Ser Ser Asn Glu Ile Asn Ala Ser Lys Gln Arg
            180                 185                 190

Glu Asn Ser Asp Tyr Gln Glu Asn Val Asp Lys Asn Ile Pro Glu Thr
        195                 200                 205

Leu Thr Glu Ile Leu Tyr Lys Ile His Lys Ile Thr Gln Asp Ile Leu
    210                 215                 220

Thr Gln Cys Ala Val Ala Tyr Leu Ile Lys Asn His Asn Gln Val Ser
225                 230                 235                 240

Asp Leu Glu Glu Asp Ile Lys Lys Leu Lys Lys Arg Arg Thr Glu Lys
                245                 250                 255

Gln Val Gln Ile Lys Arg Leu Glu Glu Gln Ile Gln Lys Asn Lys Leu
            260                 265                 270

Pro Asn Gly Arg Asp Ile Thr Gly Glu Arg Tyr Asn His Ala Phe Asp
        275                 280                 285

Asn Leu Ile Asn Gln Val Pro Gln Asn Asn Glu Glu Phe Ala Glu Trp
    290                 295                 300

Ile Ala Ser Leu Leu Asn Lys Val Ser Asp Leu Pro Tyr Pro Ile Asp
305                 310                 315                 320

Tyr Leu Tyr Ser Asp Leu Thr Trp Tyr Lys Asn Glu Gln Arg Lys Ile
                325                 330                 335

Cys Val Tyr Phe Asn Gly Trp Ala Lys Phe His Phe Gln Ile Cys Cys
            340                 345                 350

Asn Lys Arg Gln Leu His Phe Phe Lys Arg Phe Leu Glu Asp Tyr Lys
        355                 360                 365

Ala Leu Lys Glu Ser Glu Lys Gly Glu Ile Lys Leu Ser Gly Ser Leu
    370                 375                 380

Val Thr Leu Arg Ser Val Gln Leu Leu Trp Gln Gln Gly Glu Gly Ala
385                 390                 395                 400

Gly Glu Pro Trp Lys Val Asn Lys Leu Ala Leu His Cys Thr Tyr Asp
                405                 410                 415

Ala Arg Leu Leu Thr Ala Glu Gly Thr Glu Glu Val Arg Gln Glu Lys
            420                 425                 430

Thr Asp Thr Thr Gln Lys Gln Val Thr Lys Ala Glu Gly Asn Glu Asn
        435                 440                 445

Ile Asp Ser Asp Glu Gln Lys Asn Leu Asn Arg Asn Ile Ser Ser Leu
    450                 455                 460

Ser Arg Leu Asn Asn Ser Phe Ala Arg Pro Ser Lys Pro Ile Tyr Arg
465                 470                 475                 480

Gly Gln Ser Asn Ile Ile Val Gly Val Ser Phe His Pro Val Glu Leu
                485                 490                 495

Ala Thr Leu Val Val Val Asp Ile Ile Thr Lys Glu Lys Ile Ile Cys
            500                 505                 510

Lys Thr Val Lys Gln Leu Leu Gly Asp Ala Phe Ser Leu Leu Ser Arg
        515                 520                 525

Arg Arg Arg Gln Gln Val His Phe Arg Lys Glu Arg Glu Lys Ala Gln
```

```
    530                 535                 540

Lys Lys Asp Ser Pro Cys Asn Met Gly Glu Ser Gln Leu Gly Glu Tyr
545                 550                 555                 560

Val Asp Lys Leu Leu Ala Lys Arg Ile Val Glu Val Thr Lys Glu Tyr
                565                 570                 575

Lys Ala Ser Cys Ile Val Leu Pro Arg Leu Lys Asp Thr Arg Glu Ile
            580                 585                 590

Arg Thr Ser Val Ile Gln Ala Lys Ala Glu Ala Lys Phe Pro Gly Asp
        595                 600                 605

Val Asn Ala Gln Lys Ile Tyr Val Lys Glu Tyr Asn Arg Gln Ile His
    610                 615                 620

Asn Trp Ser Tyr Gly Arg Leu Gln Glu Ser Ile Lys Ser Lys Ala Ala
625                 630                 635                 640

Glu Phe Lys Ile Ser Ile Glu Phe Gly Met Gln Pro Ser Tyr Asp Asn
                645                 650                 655

Leu Gln Glu Gln Ala Ile Asn Leu Ala Leu Ser Ala Tyr Gln Cys Arg
            660                 665                 670

Ile Asn Thr Ile Gly Arg
        675


<210> SEQ ID NO 156
<211> LENGTH: 674
<212> TYPE: PRT
<213> ORGANISM: Nostoc sp.

<400> SEQUENCE: 156

Met Ser Arg Asp Arg Lys Lys Gly Ser Lys Ser Pro Ser Leu Arg Thr
1               5                   10                  15

Ile Arg Cys His Leu His Thr Lys Glu Asp Val Leu Arg Lys Val Trp
            20                  25                  30

Glu Glu Met Thr Gln Lys Asn Thr Pro Leu Ile Val Glu Leu Leu Lys
        35                  40                  45

Ser Val Ser Glu Gln Pro Glu Phe Glu Thr Asn Lys Glu Asn Gly Lys
    50                  55                  60

Ile Thr Lys Lys Glu Ile Thr Asn Leu Arg Lys Ser Leu Thr Gln Asp
65                  70                  75                  80

Ser Gly Arg Leu Tyr Ser Ser Val Asp Asn Leu Val Gln Glu Val Tyr
                85                  90                  95

Ser Ala Trp Leu Thr Leu Tyr Gln Lys Arg Lys Lys Gln Lys Glu Gly
            100                 105                 110

Lys Glu Tyr Phe Leu Asn Asn Ile Leu Lys Ser Asp Ile Glu Leu Val
        115                 120                 125

Glu Glu Ser Asn Cys Asp Leu Gln Ile Leu Arg Ala Lys Ala Gln Glu
    130                 135                 140

Ile Ile Ser Asn Pro Gln Asp Ile Leu Arg Gln Ile Thr Ile Asp Asn
145                 150                 155                 160

Pro Lys Asp Lys Pro Thr Lys Ser Ile Gln Lys Arg Val Arg Lys Asn
                165                 170                 175

Ile Asn Ala Ser Asn Ser Asp Thr Ala Lys Asn Asn Ile Leu Asn Ser
            180                 185                 190

Gln Glu Lys Thr Thr Glu Glu Asn Ile Ser Lys Ser Val Ile Glu Ile
        195                 200                 205

Leu Tyr Glu Ile His Lys Thr Thr Gln Asp Thr Ile Ile Arg Cys Ala
    210                 215                 220
```

-continued

```
Val Thr Tyr Leu Ile Lys Asn Tyr Thr Lys Ile Ser Asp Thr Glu Glu
225                 230                 235                 240

Asp Leu Asn Lys Leu Lys Glu Arg Arg Ala Glu Lys Glu Ile Glu Ile
                245                 250                 255

Lys Arg Leu Glu Lys Gln Ile Gln Asp Ser Arg Leu Pro Asn Gly Arg
            260                 265                 270

Asp Ile Thr Gly Ala Arg Tyr Leu Glu Ala Phe Asp Lys Leu Ile Asn
        275                 280                 285

Gln Val Pro Lys Asn Asn Glu Glu Phe Ala Asn Trp Ile Ala Asp Ala
    290                 295                 300

Ser Arg Lys Ile Ser Asn Leu Pro Tyr Pro Ile Asp Tyr Leu Tyr Ser
305                 310                 315                 320

Asp Leu Thr Trp Tyr Lys Asn Gln Asp Gly Lys Ile Phe Val Tyr Phe
                325                 330                 335

Asn Gly Trp Ser Lys Tyr His Phe Gln Ile Cys Cys Asn Lys Arg Gln
            340                 345                 350

Arg His Phe Phe Glu Arg Phe Leu Glu Asp His Lys Ala Trp Lys Glu
        355                 360                 365

Ser Glu Lys Gly Glu Val Lys Leu Ser Gly Ser Leu Val Thr Leu Arg
    370                 375                 380

Cys Val Gln Leu Leu Trp Gln Gln Gly Glu Gly Lys Gly Glu Pro Trp
385                 390                 395                 400

Lys Val Asn Lys Leu Ser Leu His Cys Thr Tyr Asp Thr Arg Leu Trp
                405                 410                 415

Thr Ala Glu Gly Thr Glu Glu Ala Arg Lys Glu Lys Ile Asn Lys Ile
            420                 425                 430

Gln Arg Gln Val Glu Gln Ala Glu Glu Thr Glu Asn Leu Asp Glu Gln
        435                 440                 445

Gln Gln Lys Gln Leu Lys Lys Asn Lys Ser Ser Leu Ser Arg Leu Asn
    450                 455                 460

Asn Ser Phe Asn Arg Pro Ile Gln Pro Ile Tyr Gln Gly Leu Ser Asn
465                 470                 475                 480

Met Ile Val Gly Val Ser Phe His Pro Val Glu Leu Ala Thr Val Ala
                485                 490                 495

Val Val Asp Thr Thr Thr Gln Lys Val Ile Ala Tyr Lys Thr Ile Asn
            500                 505                 510

Glu Leu Leu Asp Asn Ala Phe His Leu Leu Ser Arg Met Arg Arg Gln
        515                 520                 525

Gln Ile His Phe Arg Lys Glu Arg Lys Lys Ala Gln Lys Lys Asp Ser
    530                 535                 540

Pro Cys Asn Leu Gly Glu Ser Lys Leu Gly Glu Tyr Val Asp Lys Leu
545                 550                 555                 560

Leu Ala Lys Arg Ile Val Glu Val Ala Lys Glu Tyr Gln Ala Ile Cys
                565                 570                 575

Ile Val Leu Pro Lys Leu Lys Asp Met Lys Glu Ile Arg Thr Ser Val
            580                 585                 590

Ile Gln Ala Lys Ala Glu Thr Lys Phe Pro Gly Asn Val Asn Ala Gln
        595                 600                 605

Lys Leu Tyr Val Lys Glu Tyr Asn Arg Gln Val His Asn Trp Ser Tyr
    610                 615                 620

Asn Arg Leu Gln Glu Ser Ile Lys Ser Lys Ala Ala Glu Leu Lys Ile
625                 630                 635                 640

Ser Ile Glu Phe Gly Ile Gln Leu Ser Tyr Asp Thr Leu Gln Ala Gln
```

```
                645                 650                 655

Ala Arg Asp Leu Ala Leu Ser Ala Tyr Gln Cys Arg Ile His Thr Ile
            660                 665                 670

Asp Arg


<210> SEQ ID NO 157
<211> LENGTH: 649
<212> TYPE: PRT
<213> ORGANISM: Clostridioides difficile

<400> SEQUENCE: 157

Met Ser Ile Ile Thr Ile Gln Cys Arg Leu Val Ala Asn Asp Arg Thr
1               5                   10                  15

Leu Gln His Leu Trp Glu Leu Met Ala Glu Lys Asn Thr Pro Leu Ile
            20                  25                  30

Ser Glu Leu Leu Glu Gln Leu Gly Lys His Pro Asp Phe Glu Thr Trp
        35                  40                  45

Leu Lys Asn Gly Lys Val Pro Lys Asp Thr Ile Lys Ile Leu Cys Asp
    50                  55                  60

Ser Leu Lys Thr Gln Ser Arg Phe Ala Gly Gln Pro Gly Arg Phe Tyr
65                  70                  75                  80

Thr Ser Ala Ile Ser Gln Val Lys Glu Ile Tyr Lys Ser Trp Leu Thr
                85                  90                  95

Leu Gln Lys Arg Arg Gln Arg Gln Ile Glu Gly Lys Gln Arg Trp Leu
            100                 105                 110

Gly Met Leu Lys Ser Asp Val Glu Leu Gln Glu Glu Ser Asn Cys Ser
        115                 120                 125

Leu Glu Lys Ile Arg Ala Lys Gly Thr Glu Ile Leu Ala Glu Phe Val
    130                 135                 140

Ser Lys Phe Thr Lys Asp Thr Thr Lys Lys Ser Lys Thr Lys Ile Lys
145                 150                 155                 160

Ser Thr Lys Lys Ser Asn Lys Lys Thr Lys Lys Asp Thr Glu Glu Ser
                165                 170                 175

Asn Ser Thr Leu Phe Gln Ala Leu Cys Asp Ile Tyr Asp Lys Thr Glu
            180                 185                 190

Asp Thr Leu Ser Lys Cys Ala Ile Ile Tyr Leu Leu Lys Asn Asn Cys
        195                 200                 205

Gln Val Ile Asp Thr Glu Glu Asn Pro Asp Thr Phe Leu Lys Arg Lys
    210                 215                 220

Arg Ala Lys Glu Ile Glu Ile Lys Arg Leu Gln Asp Gln Ile Val Gly
225                 230                 235                 240

Arg Ile Pro Lys Gly Arg Asp Leu Thr Asp Lys Lys Trp Leu Asp Thr
                245                 250                 255

Ile Lys Leu Ala Ser Ser Gln Val Pro Gln Asp Glu Asn Glu Ala Lys
            260                 265                 270

Ser Trp Gln Asn Gln Leu Leu Lys Thr Ser Ser Ser Val Pro Tyr Ser
        275                 280                 285

Val Asp Tyr Glu Thr Asn Thr Asp Ile Lys Trp Val Lys His Asn Asn
    290                 295                 300

Gly Ser Ile Phe Val Asn Phe Asn Gly Leu Gly Glu His Gln Phe Glu
305                 310                 315                 320

Val Tyr Cys Asp Ser Arg Gln Leu Pro Tyr Phe Gln Arg Phe Cys Glu
                325                 330                 335

Asp Met Gln Ile Trp His Asn Asp Glu Glu Lys Tyr Ser Ser Ala Leu
```

```
            340                 345                 350

Phe Met Leu Arg Ser Ala Arg Leu Val Trp Leu Glu Lys Lys Gly Arg
        355                 360                 365

Gly Lys Pro Trp Asn Val Asn Tyr Leu Tyr Leu His Cys Ser Leu Asp
    370                 375                 380

Thr Ser Leu Trp Thr Ala Glu Gly Thr Glu Gln Ile Arg Ile Asn Lys
385                 390                 395                 400

Ile Asn Glu Thr Asp Glu Ala Ile Ala Lys Ala Lys Thr Lys Asp Lys
                405                 410                 415

Gln Glu Leu Thr Glu Asn Gln Leu Ala Tyr Leu Gln Arg Gln Gln Ser
            420                 425                 430

Thr Arg Asn Lys Leu Asn Asn Ser Phe Pro Gly Arg Pro Ser Lys Pro
        435                 440                 445

Ile Tyr Lys Gly Asn Ser His Ile Leu Val Gly Val Ser Leu Gly Leu
    450                 455                 460

Glu Lys Pro Val Thr Val Ala Ala Val Asp Val Val Ser Asn Lys Val
465                 470                 475                 480

Leu Ala Tyr Arg Ser Val Lys Gln Leu Leu Gly Gln Asn Tyr Lys Leu
                485                 490                 495

Leu Asn Arg Gln Arg Gln Gln Gln Lys His Leu Ala Gln Lys Arg His
            500                 505                 510

Glu Ser Gln Lys Lys Gln Ala Pro Asn Gln Phe Gly Glu Ser Glu Leu
        515                 520                 525

Gly Leu Tyr Val Asp Arg Leu Leu Ala Lys Ser Ile Ile Asn Phe Ala
    530                 535                 540

Lys Thr Tyr Gln Ala Ser Ser Ile Ala Leu Pro Lys Leu Arg Asp Met
545                 550                 555                 560

Arg Glu Ile Ile Gln Ser Glu Ile Gln Ala Lys Ala Glu Ser Lys Ile
                565                 570                 575

Pro Gly Tyr Lys Glu Gly Gln Glu Lys Tyr Ala Lys Glu Tyr Arg Met
            580                 585                 590

Ser Val His Arg Trp Ser Tyr Gly Arg Leu Ile Gly Asn Ile Gln Ala
        595                 600                 605

Gln Ala Ala Gln Ala Gly Ile Leu Ile Glu Thr Ser Ser Gly Gln Ile
    610                 615                 620

Arg Gly Ser Pro Gln Glu Gln Ala Lys His Leu Ala Ile Ser Ala Tyr
625                 630                 635                 640

Ile Glu Arg Gln Thr Ile Leu Asn Lys
                645


<210> SEQ ID NO 158
<211> LENGTH: 645
<212> TYPE: PRT
<213> ORGANISM: Pseudomonas sp.

<400> SEQUENCE: 158

Met Ser Thr Ile Thr Ile Gln Cys Arg Leu Val Ala Glu Glu Ala Thr
1               5                   10                  15

Leu Arg Tyr Phe Trp Glu Leu Met Ala Glu Lys Asn Thr Pro Leu Ile
            20                  25                  30

Asn Glu Leu Leu Glu Gln Leu Gly Gln His Pro Asp Phe Asp Thr Trp
        35                  40                  45

Val Gln Ala Gly Lys Met Pro Glu Lys Thr Val Glu Asn Leu Cys Lys
    50                  55                  60
```

-continued

Ser Leu Glu Asp Arg Glu Pro Phe Ala Asn Gln Pro Gly Arg Phe Arg
65 70 75 80

Thr Ser Ala Val Ala Leu Val Lys Tyr Ile Tyr Lys Ser Trp Phe Ala
85 90 95

Leu Gln Lys Arg Arg Ala Asp Arg Leu Glu Gly Lys Glu Arg Trp Leu
100 105 110

Lys Met Leu Lys Ser Asp Val Glu Leu Glu Arg Glu Ser Asn Cys Ser
115 120 125

Leu Asp Ile Ile Arg Ala Lys Ala Gly Glu Ile Leu Ala Lys Val Thr
130 135 140

Glu Gly Cys Ala Pro Ser Asn Gln Thr Ser Ser Lys Arg Lys Lys Lys
145 150 155 160

Lys Thr Lys Lys Ser Gln Ala Thr Lys Asp Leu Pro Thr Leu Phe Glu
165 170 175

Ile Ile Leu Lys Ala Tyr Glu Gln Ala Glu Glu Ser Leu Thr Arg Ala
180 185 190

Ala Leu Ala Tyr Leu Leu Lys Asn Asp Cys Glu Val Ser Glu Val Asp
195 200 205

Glu Asp Ser Glu Lys Phe Lys Lys Arg Arg Arg Lys Lys Glu Ile Glu
210 215 220

Ile Glu Arg Leu Arg Asn Gln Leu Lys Ser Arg Ile Pro Lys Gly Arg
225 230 235 240

Asp Leu Thr Gly Asp Lys Trp Leu Lys Thr Leu Glu Glu Ala Thr Arg
245 250 255

Asn Val Pro Glu Asn Glu Asp Glu Ala Lys Ala Trp Gln Ala Gln Leu
260 265 270

Leu Arg Glu Ala Ser Ser Val Pro Phe Pro Val Ala Tyr Glu Thr Ser
275 280 285

Glu Asp Met Thr Trp Phe Thr Asn Glu Gln Gly Arg Ile Phe Val Tyr
290 295 300

Phe Asn Gly Ser Ala Lys His Lys Phe Gln Val Tyr Cys Asp Arg Arg
305 310 315 320

Gln Leu His Trp Phe Gln Arg Phe Val Glu Asp Phe Gln Ile Lys Lys
325 330 335

Asn Gly Asp Lys Lys Gly Ser Glu Lys Glu Tyr Pro Ala Gly Leu Leu
340 345 350

Thr Leu Cys Ser Thr Arg Leu Arg Trp Lys Glu Ser Ala Glu Lys Gly
355 360 365

Asp Pro Trp Asn Val His Arg Leu Ile Leu Ser Cys Thr Ile Asp Thr
370 375 380

Arg Leu Trp Thr Leu Glu Gly Thr Glu Gln Val Arg Ala Glu Lys Ile
385 390 395 400

Ala Gln Val Glu Lys Thr Ile Ser Lys Arg Glu Gln Glu Val Asn Leu
405 410 415

Ser Lys Thr Gln Leu Glu Arg Leu Gln Ala Lys His Ser Glu Arg Glu
420 425 430

Arg Leu Asn Asn Ile Phe Pro Asn Arg Pro Ser Lys Pro Ser Tyr Arg
435 440 445

Gly Lys Ser His Ile Ala Ile Gly Val Ser Phe Ser Leu Glu Asn Pro
450 455 460

Ala Thr Val Ala Val Val Asp Val Ala Thr Lys Lys Val Leu Thr Tyr
465 470 475 480

Arg Ser Phe Lys Gln Leu Leu Gly Asp Asn Tyr Asn Leu Ala Asn Arg

```
                485                 490                 495

Leu Arg Gln Gln Lys Gln Arg Leu Ser His Glu Arg His Lys Ala Gln
            500                 505                 510

Lys Gln Gly Ala Pro Asn Ser Phe Gly Asp Ser Glu Leu Gly Gln Tyr
        515                 520                 525

Val Asp Arg Leu Leu Ala Lys Ser Ile Val Ala Ile Ala Lys Thr Tyr
    530                 535                 540

Gln Ala Ser Ser Ile Val Leu Pro Lys Leu Arg Tyr Met Arg Glu Ile
545                 550                 555                 560

Ile His Asn Glu Val Gln Ala Lys Ala Glu Lys Lys Ile Pro Gly Tyr
                565                 570                 575

Lys Glu Gly Gln Lys Gln Tyr Ala Lys Gln Tyr Arg Ile Ser Val His
            580                 585                 590

Gln Trp Ser Tyr Asn Arg Leu Ser Gln Ile Leu Glu Ser Gln Ala Thr
        595                 600                 605

Lys Ala Gly Ile Ser Ile Glu Arg Gly Ser Gln Val Ile Gln Gly Ser
    610                 615                 620

Ser Gln Glu Gln Ala Arg Asp Leu Ala Leu Phe Ala Tyr Asn Glu Arg
625                 630                 635                 640

Gln Leu Ser Leu Gly
                645


<210> SEQ ID NO 159
<211> LENGTH: 643
<212> TYPE: PRT
<213> ORGANISM: Cyanothece sp.

<400> SEQUENCE: 159

Met Ser Met Tyr Thr Ile His Cys His Leu Thr Ala Ser Glu Pro Val
1               5                   10                  15

Arg Arg His Leu Trp Tyr Leu Met Ala Gly Ser Asn Thr Pro Leu Val
            20                  25                  30

Asn Asn Leu Leu Lys Leu Val Ser Gln His Pro Asp Phe Glu Thr Trp
        35                  40                  45

Gln Arg Lys Gly Asp Ile Ser Lys Ser Ser Val Glu Ala Leu Cys Glu
    50                  55                  60

Pro Leu Lys Glu Thr Tyr Pro Gly Gln Pro Gly Arg Phe Tyr Ser Ser
65                  70                  75                  80

Ala Ile Leu Arg Val Thr Tyr Thr Tyr Lys Ser Trp Leu Ala Leu Gln
                85                  90                  95

Lys Asn Arg Arg Tyr Arg Leu Glu Gly Lys Gln Arg Trp Leu His Val
            100                 105                 110

Val Glu Ser Asp Ser Glu Leu Leu His Arg Ser Gly Ser Ser Ile Glu
        115                 120                 125

Thr Leu Lys Tyr Arg Ala Gln Asp Ile Leu Val Gln Leu Asn Val Glu
    130                 135                 140

Gln Gln Thr Gln Lys Thr Ser Val Thr Asp Ile Ser Thr Ile Thr Pro
145                 150                 155                 160

Glu Glu Thr Pro Ser Ser Lys Asn Glu Ser Leu Phe Pro Ser Leu Phe
                165                 170                 175

Arg Ala Tyr Asp Ser Glu Asp Asp Ile Leu Ser Arg Cys Ala Ile Ala
            180                 185                 190

Tyr Leu Ile Lys Asn Gly Gly Lys Ile Pro Glu Thr Glu Glu Asp Gln
        195                 200                 205
```

-continued

```
Glu Lys Phe Thr Gln Arg Val Asn Ser Lys Arg Glu Glu Ile Glu Gln
    210                 215                 220

Leu Glu Ile Glu Leu Ser Ala Arg Tyr Pro Lys Gly Arg Asp Leu Thr
225                 230                 235                 240

Gly Glu Glu Phe Leu Glu Thr Leu Ala Ile Ala Thr Gln Gln Leu Ser
                245                 250                 255

Glu Thr Val Ala Gln Ala Arg Glu Trp Asn Asp Lys Ile Leu Thr Gln
            260                 265                 270

Pro Lys Phe Met Pro Tyr Pro Ile Ile Tyr Gly Ser Ser Thr Asp Val
        275                 280                 285

Arg Trp Arg Lys Thr Ser Lys Ser Arg Ile Thr Val Ser Phe Asn Gly
    290                 295                 300

Ile Asp Lys Tyr Leu Lys Ala Ala Asp Pro Glu Ile Lys Ala Trp Phe
305                 310                 315                 320

Lys Asp His Gln Glu Tyr Pro Phe Arg Leu His Cys Asp Glu Arg Gln
                325                 330                 335

Leu Pro Phe Phe Gln Arg Phe Leu Glu Asp Trp Gln Phe Tyr Gln Ala
            340                 345                 350

Asn Lys Glu Thr Tyr Pro Ala Gly Leu Leu Thr Leu Ser Ser Thr Leu
        355                 360                 365

Leu Gly Trp Arg Glu Gly Glu Gly Lys Gly Asp Pro Trp Asn Val Asn
    370                 375                 380

Arg Leu Ala Leu Tyr Cys Thr Phe Asp Thr Arg Leu Met Thr Ala Glu
385                 390                 395                 400

Gly Thr Leu Asp Val Gln Lys Glu Lys Ser Glu Lys Ala Leu Lys Asn
                405                 410                 415

Leu Ala Lys Ala Lys Pro Asp Pro Arg Asn His Ser Thr Leu Asp Arg
            420                 425                 430

Leu Lys Asn Leu Pro Val Arg Pro Ser Arg Thr Pro Tyr Gln Gly Asn
        435                 440                 445

Pro Glu Ile Leu Val Gly Leu Arg Val Gly Leu Thr Asn Pro Ile Thr
    450                 455                 460

Ala Ala Val Val Asn Gly Arg Thr Gly Glu Val Leu Thr Tyr Arg Thr
465                 470                 475                 480

Pro Ser Thr Leu Leu Gly Asp Arg Tyr Asp Leu Phe Asn Arg His Arg
                485                 490                 495

His Gln Gln Glu Gln Asn Ala Leu Glu Arg His Lys Tyr Gln Lys Arg
            500                 505                 510

Gly Val Thr Tyr Gln Pro Ser Glu Ser Glu Leu Gly Lys Tyr Val Asp
        515                 520                 525

Arg Leu Leu Ala Lys Ala Ile Ile Glu Leu Ala Gln Thr Tyr Lys Ala
    530                 535                 540

Gly Ser Ile Val Ile Pro Cys Leu Thr His Leu Arg Glu Ile Leu Ala
545                 550                 555                 560

Ser Glu Ile Ala Ala Arg Ala Glu Glu Lys Cys Pro Gly Ser Val Glu
                565                 570                 575

Ala Gln Asp Asn Tyr Ala Lys Glu Tyr Arg Arg Lys Ile His Asn Trp
            580                 585                 590

Ser Tyr Asn Arg Leu Ile Ser Ala Ile Cys Ser Lys Ala Glu Gln Leu
        595                 600                 605

Gly Ile Ile Val Glu Ser Gly Phe Gln Pro Tyr Glu Gly Asp Ser Tyr
    610                 615                 620

Gln Gln Ala Lys Asp Leu Ala Ile Ala Val Tyr His Ser Arg Gln Leu
```

```
625                 630                 635                 640

Ala Leu Lys


<210> SEQ ID NO 160
<211> LENGTH: 641
<212> TYPE: PRT
<213> ORGANISM: Methanosarcina vacuolata

<400> SEQUENCE: 160

Met Ser Lys Ile Thr Ile Gln Cys Arg Leu Val Ala Ser Glu Ala Thr
1               5                   10                  15

Arg Gln Tyr Leu Trp His Leu Met Ala Asp Ile Tyr Thr Pro Phe Val
            20                  25                  30

Asn Glu Ile Leu Arg Gln Ile Arg Glu Asp Asp Asn Phe Glu Gln Trp
        35                  40                  45

Arg Gln Ser Gly Lys Ile Pro Ala Ser Val Phe Glu Asp Tyr Arg Lys
    50                  55                  60

Thr Leu Lys Thr Glu Ser Arg Phe Gln Gly Met Pro Gly Arg Trp Tyr
65                  70                  75                  80

Tyr Ala Gly Arg Glu Glu Val Lys Arg Ile Tyr Lys Ser Trp Leu Ala
                85                  90                  95

Leu Arg Arg Arg Leu Arg Asn Gln Leu Ala Gly Gln Asn Arg Trp Leu
            100                 105                 110

Glu Val Leu Gln Ser Asp Glu Thr Leu Met Glu Val Ser Gly Leu Asp
        115                 120                 125

Leu Ser Ala Leu Gln Ala Glu Ala Ser Gln Leu Leu Asn Ile Leu Gly
    130                 135                 140

Ser Lys Asn Lys Thr Ser Lys Asn Arg Ser Lys Lys Ala Lys Gly Lys
145                 150                 155                 160

Pro Lys Gly Lys Ser Ala Lys Asp Pro Thr Leu Tyr Gln Ala Leu Trp
                165                 170                 175

Glu Leu Tyr Arg Glu Thr Glu Asp Ile Ala Lys Lys Cys Val Ile Ala
            180                 185                 190

Tyr Leu Leu Lys His Lys Cys Gln Val Pro Asp Lys Pro Glu Asp Pro
        195                 200                 205

Lys Lys Phe Arg His Arg Arg Arg Glu Ala Glu Ile Arg Ala Glu Arg
    210                 215                 220

Leu Asn Glu Gln Leu Ile Lys Thr Arg Leu Pro Lys Gly Arg Asp Leu
225                 230                 235                 240

Thr Asn Glu Gln Trp Leu Gln Val Leu Glu Ile Ala Thr Arg Gln Val
                245                 250                 255

Pro Lys Asp Glu Asp Glu Ala Ala Ile Trp Gln Ser Arg Leu Leu Thr
            260                 265                 270

Asp Ala Ala Lys Phe Pro Phe Pro Val Ala Tyr Glu Thr Asn Glu Asp
        275                 280                 285

Leu Lys Trp Phe Leu Asn Gly Lys Gly Arg Leu Cys Val Ser Phe Asn
    290                 295                 300

Gly Leu Ser Glu His Thr Phe Glu Val Tyr Cys Gly Gln Arg Gln Leu
305                 310                 315                 320

Tyr Trp Phe Asn Arg Phe Leu Glu Asp Gln Gln Ile Lys Lys Glu Asn
                325                 330                 335

Gln Gly Glu Arg Ser Ala Gly Leu Phe Thr Leu Arg Ser Gly Arg Leu
            340                 345                 350

Val Trp Lys Pro Tyr Ser Ser Asp Ala Ser Arg Ser Asp Pro Trp Met
```

```
        355                 360                 365

Ala Asn Gln Leu Thr Leu Gln Cys Ser Val Asp Thr Arg Leu Trp Thr
    370                 375                 380

Ala Glu Gly Thr Glu Gln Val Arg Gln Glu Lys Ala Thr Ser Ile Ala
385                 390                 395                 400

Lys Val Ile Ala Gly Thr Lys Ala Lys Gly Asn Leu Asn Gln Lys Gln
                405                 410                 415

Gln Asp Phe Ile Thr Lys Arg Glu Lys Thr Leu Glu Leu Leu His Asn
            420                 425                 430

Pro Phe Pro Arg Pro Ser Lys Pro Leu Tyr Gln Gly Lys Pro Ser Ile
        435                 440                 445

Ile Ala Ala Val Ser Phe Gly Leu Glu Lys Pro Ala Thr Leu Ala Ile
    450                 455                 460

Val Asp Ile Val Thr Asp Lys Ala Ile Thr Tyr Arg Ser Ile Arg Gln
465                 470                 475                 480

Leu Leu Gly Gln Asn Tyr Lys Leu Phe Thr Lys His Arg Leu Lys Gln
                485                 490                 495

Gln Gln Cys Ala His Gln Arg His Gln Asn Gln Val Glu Ser Ala Glu
            500                 505                 510

Asn Arg Ile Ser Glu Gly Gly Leu Gly Glu His Leu Asp Ser Leu Ile
        515                 520                 525

Ala Lys Ala Ile Leu Glu Thr Ala Ala Glu Tyr Gly Ala Ser Ser Ile
    530                 535                 540

Val Leu Pro Glu Leu Gly Asn Ile Arg Glu Ile Ile His Ala Glu Ile
545                 550                 555                 560

Gln Ala Lys Ala Glu Arg Lys Ile Pro Gly Leu Lys Glu Lys Gln Asp
                565                 570                 575

Glu Tyr Ala Ala Lys Phe Arg Ala Ser Val His Arg Trp Ser Tyr Gly
            580                 585                 590

Arg Leu Ala Gln Lys Val Thr Thr Lys Ala Ser Leu His Gly Leu Glu
        595                 600                 605

Thr Glu Ser Thr Arg Gln Ser Leu Gln Gly Thr Pro Gln Glu Lys Ala
    610                 615                 620

Arg Asn Leu Ala Ile Ser Ala Tyr Glu Ser Arg Lys Val Ala Gln Arg
625                 630                 635                 640

Ala


<210> SEQ ID NO 161
<211> LENGTH: 639
<212> TYPE: PRT
<213> ORGANISM: Methylobacter whittenburyi

<400> SEQUENCE: 161

Met Ser Gln Ile Thr Ile Gln Cys Cys Leu Ile Ala Ser Glu Ser Thr
1               5                   10                  15

Arg Gln Lys Leu Trp Lys Leu Met Ala His Leu Asn Thr Pro Leu Ile
            20                  25                  30

Asn Glu Leu Leu Gln Gln Leu Ser Lys His Pro Asp Phe Glu Lys Trp
        35                  40                  45

Arg Lys Asn Gly Lys Leu Pro Ser Thr Val Val Asn Gln Leu Cys Gln
    50                  55                  60

Pro Leu Lys Thr Asp Pro Ser Phe Thr Gly Gln Pro Ser Arg Leu Tyr
65                  70                  75                  80

Leu Ser Ala Ile His Val Val Asp Tyr Ile Tyr Lys Ser Trp Leu Ala
```

```
                85                  90                  95

Ile Gln Lys Arg Leu Gln Gln Gln Leu Asp Gly Lys Ile Arg Trp Leu
            100                 105                 110

Glu Met Leu Asn Ser Asp Ala Glu Leu Ile Glu Ile Ser Gly Cys Ser
        115                 120                 125

Leu Glu Ala Ile Arg Thr Lys Ala Ala Glu Ile Leu Ala Ile Ala Thr
    130                 135                 140

Pro Asp Ser Asp Val Ala Ala Pro Leu Thr Lys Thr Gly Lys Ala Lys
145                 150                 155                 160

Lys Ser Lys Lys Ser Ser Ala Ser Asn Pro Asp Arg Ser Leu Ser His
                165                 170                 175

Lys Leu Phe Asp Ala Tyr Gln Glu Thr Asp Asp Ile Leu Ser Arg Ser
            180                 185                 190

Ala Ile Ser Tyr Leu Leu Arg Asn Gly Cys Lys Leu Asn Asp Lys Glu
        195                 200                 205

Glu Asp Leu Glu Lys Phe Ala Lys Arg Arg Arg Lys Val Glu Ile Gln
    210                 215                 220

Ile Gln Arg Leu Thr Asp Lys Leu Thr Ser Arg Ile Pro Lys Gly Arg
225                 230                 235                 240

Asp Leu Thr Asn Ala Lys Trp Leu Glu Thr Leu Phe Thr Ala Thr Thr
                245                 250                 255

Thr Val Pro Glu Asp Asn Val Glu Ala Lys Arg Trp Gln Asp Ile Leu
            260                 265                 270

Leu Thr Arg Ser Ser Ser Val Pro Phe Pro Leu Ile Phe Glu Thr Asn
        275                 280                 285

Glu Asp Leu Val Trp Ser Lys Asn Glu Lys Gly Arg Leu Cys Val His
    290                 295                 300

Phe Asn Gly Leu Ser Asp Leu Thr Phe Glu Val Tyr Cys Asp Arg Arg
305                 310                 315                 320

Gln Leu His Trp Phe Lys Arg Phe Leu Glu Asp Gln Gln Thr Lys Arg
                325                 330                 335

Lys Ser Lys Asn Gln His Ser Ser Gly Leu Phe Thr Leu Arg Asn Gly
            340                 345                 350

Arg Leu Ala Trp Gln Glu Gly Glu Gly Lys Gly Glu Pro Trp Gln Ile
        355                 360                 365

Asn Arg Leu Thr Leu Tyr Cys Cys Val Asp Asn Arg Leu Trp Ser Ala
    370                 375                 380

Glu Gly Thr Glu Gln Val Arg Gln Glu Lys Glu Glu Glu Ile Thr Lys
385                 390                 395                 400

Phe Ile Thr Lys Met Asn Glu Lys Ser Asp Leu Ser Glu Thr Gln Gln
                405                 410                 415

Ala Phe Ile Lys Arg Lys Glu Ser Thr Leu Thr Arg Ile Asn Asn Ser
            420                 425                 430

Phe Glu Arg Pro Ser Gln Phe Leu Tyr Gln Gly Gln Ser His Ile Leu
        435                 440                 445

Val Gly Val Ser Leu Gly Leu Glu Lys Pro Ala Thr Val Ala Val Val
    450                 455                 460

Asp Ala Ile Ala Gly Lys Val Leu Ala Tyr Arg Ser Ile Lys Gln Leu
465                 470                 475                 480

Leu Gly Asp Asn Tyr Glu Leu Leu Asn Arg Gln Arg Arg Gln Gln Gln
                485                 490                 495

Tyr Leu Ser His Glu Arg His Lys Ala Gln Lys Ser Phe Ser Pro Asn
            500                 505                 510
```

Gln Phe Gly Thr Ser Glu Leu Gly Gln Tyr Val Asp Arg Leu Leu Ala
515 520 525

Lys Glu Ile Ile Ala Ile Ala Gln Thr His Lys Ala Gly Ser Ile Val
530 535 540

Leu Pro Lys Leu Gly Asp Met Arg Glu Ile Val Gln Ser Glu Ile Gln
545 550 555 560

Ala Ile Ala Glu Glu Lys Phe Pro Gly Tyr Val Glu Gly Gln Gln Lys
565 570 575

Tyr Ala Lys Gln Tyr Arg Val Asn Val His Gly Trp Ser His Ser Arg
580 585 590

Leu Ile Gln Ser Ile Gln Ser Lys Ala Ala Gln Ile Gly Ile Val Ile
595 600 605

Glu Glu Gly Lys Gln Pro Ile Arg Gly Ser Pro Gln Asp Lys Ala Lys
610 615 620

Glu Leu Ala Leu Ser Ala Tyr Asn Leu Arg Leu Ala Arg Arg Ser
625 630 635

<210> SEQ ID NO 162
<211> LENGTH: 639
<212> TYPE: PRT
<213> ORGANISM: Streptomyces sp.

<400> SEQUENCE: 162

Met Ser Gln Ile Thr Ile Gln Ala Arg Leu Ile Ser Phe Glu Ser Asn
1 5 10 15

Arg Gln Gln Leu Trp Lys Leu Met Ala Asp Leu Asn Thr Pro Leu Ile
20 25 30

Asn Glu Leu Leu Cys Gln Leu Gly Gln His Pro Asp Phe Glu Lys Trp
35 40 45

Gln Gln Lys Gly Lys Leu Pro Ser Thr Val Val Ser Gln Leu Cys Gln
50 55 60

Pro Leu Lys Thr Asp Pro Arg Phe Ala Gly Gln Pro Ser Arg Leu Tyr
65 70 75 80

Met Ser Ala Ile His Ile Val Asp Tyr Ile Tyr Lys Ser Trp Leu Ala
85 90 95

Ile Gln Lys Arg Leu Gln Gln Gln Leu Asp Gly Lys Thr Arg Trp Leu
100 105 110

Glu Met Leu Asn Ser Asp Ala Glu Leu Val Glu Leu Ser Gly Asp Thr
115 120 125

Leu Glu Ala Ile Arg Val Lys Ala Ala Glu Ile Leu Ala Ile Ala Met
130 135 140

Pro Ala Ser Glu Ser Asp Ser Ala Ser Pro Lys Gly Lys Lys Gly Lys
145 150 155 160

Lys Glu Lys Lys Pro Ser Ser Ser Ser Pro Lys Arg Ser Leu Ser Lys
165 170 175

Thr Leu Phe Asp Ala Tyr Gln Glu Thr Glu Asp Ile Lys Ser Arg Ser
180 185 190

Ala Ile Ser Tyr Leu Leu Lys Asn Gly Cys Lys Leu Thr Asp Lys Glu
195 200 205

Glu Asp Ser Glu Lys Phe Ala Lys Arg Arg Arg Gln Val Glu Ile Gln
210 215 220

Ile Gln Arg Leu Thr Glu Lys Leu Ile Ser Arg Met Pro Lys Gly Arg
225 230 235 240

Asp Leu Thr Asn Ala Lys Trp Leu Glu Thr Leu Leu Thr Ala Thr Thr

```
                245                 250                 255

Thr Val Ala Glu Asp Asn Ala Gln Ala Lys Arg Trp Gln Asp Ile Leu
            260                 265                 270

Leu Thr Arg Ser Ser Ser Leu Pro Phe Pro Leu Val Phe Glu Thr Asn
        275                 280                 285

Glu Asp Met Val Trp Ser Lys Asn Gln Lys Gly Arg Leu Cys Val His
    290                 295                 300

Phe Asn Gly Leu Ser Asp Leu Ile Phe Glu Val Tyr Cys Gly Asn Arg
305                 310                 315                 320

Gln Leu His Trp Phe Gln Arg Phe Leu Glu Asp Gln Gln Thr Lys Arg
                325                 330                 335

Lys Ser Lys Asn Gln His Ser Ser Gly Leu Phe Thr Leu Arg Asn Gly
            340                 345                 350

His Leu Val Trp Leu Glu Gly Glu Gly Lys Gly Glu Pro Trp Asn Leu
        355                 360                 365

His His Leu Thr Leu Tyr Cys Cys Val Asp Asn Arg Leu Trp Thr Glu
    370                 375                 380

Glu Gly Thr Glu Ile Val Arg Gln Glu Lys Ala Asp Glu Ile Thr Lys
385                 390                 395                 400

Phe Ile Thr Asn Met Lys Lys Lys Ser Asp Leu Ser Asp Thr Gln Gln
                405                 410                 415

Ala Leu Ile Gln Arg Lys Gln Ser Thr Leu Thr Arg Ile Asn Asn Ser
            420                 425                 430

Phe Glu Arg Pro Ser Gln Pro Leu Tyr Gln Gly Gln Ser His Ile Leu
        435                 440                 445

Val Gly Val Ser Leu Gly Leu Glu Lys Pro Ala Thr Val Ala Val Val
    450                 455                 460

Asp Ala Ile Ala Asn Lys Val Leu Ala Tyr Arg Ser Ile Lys Gln Leu
465                 470                 475                 480

Leu Gly Asp Asn Tyr Glu Leu Leu Asn Arg Gln Arg Arg Gln Gln Gln
                485                 490                 495

Tyr Leu Ser His Glu Arg His Lys Ala Gln Lys Asn Phe Ser Pro Asn
            500                 505                 510

Gln Phe Gly Ala Ser Glu Leu Gly Gln His Ile Asp Arg Leu Leu Ala
        515                 520                 525

Lys Ala Ile Val Ala Leu Ala Arg Thr Tyr Lys Ala Gly Ser Ile Val
    530                 535                 540

Leu Pro Lys Leu Gly Asp Met Arg Glu Val Val Gln Ser Glu Ile Gln
545                 550                 555                 560

Ala Ile Ala Glu Gln Lys Phe Pro Gly Tyr Ile Glu Gly Gln Gln Lys
                565                 570                 575

Tyr Ala Lys Gln Tyr Arg Val Asn Val His Arg Trp Ser Tyr Gly Arg
            580                 585                 590

Leu Ile Gln Ser Ile Gln Ser Lys Ala Ala Gln Thr Gly Ile Val Ile
        595                 600                 605

Glu Glu Gly Lys Gln Pro Ile Arg Gly Ser Pro His Asp Lys Ala Lys
    610                 615                 620

Glu Leu Ala Leu Ser Ala Tyr Asn Leu Arg Leu Thr Arg Arg Ser
625                 630                 635
```

<210> SEQ ID NO 163
<211> LENGTH: 637
<212> TYPE: PRT
<213> ORGANISM: Microcoleus sp.

<400> SEQUENCE: 163

Met Ser Ile Ile Thr Val Gln Cys Gln Leu Lys Ala Thr Lys Asp Ser
1 5 10 15

Leu Arg His Leu Trp Ser Leu Met Val Glu Lys Asn Thr Leu Leu Val
20 25 30

Asn Glu Leu Leu Lys Gln Ile Asn Thr His Pro Asp Leu Glu Asn Trp
35 40 45

Leu Lys Val Gly Asn Ile Lys Ala Glu Val Ile Glu Gly Leu Cys Asp
50 55 60

Asn Leu Arg Thr Glu Ser Arg Phe Gln Asp Met Pro Gly Arg Phe Ala
65 70 75 80

Asn Ala Ala Glu Lys Leu Val Lys Asp Ile Tyr Lys Ser Trp Phe Ala
85 90 95

Leu Gln Glu Glu Arg Arg Phe Arg Leu Trp Arg Lys Gln Arg Trp Phe
100 105 110

Ser Leu Leu Arg Ser Asp Leu Glu Leu Glu Gln Glu Ser Gly Leu Ser
115 120 125

Leu Glu Lys Leu Arg Thr Glu Ala Thr Lys Ile Leu Ile Lys Ala Gln
130 135 140

Leu Glu Cys Ser Arg Glu Ala Glu Pro Asp Gln Ala Thr Thr Asp Asn
145 150 155 160

Ser Ser Ala Leu Trp Asp Asn Leu Phe Thr Ala Tyr Asp Lys Phe Lys
165 170 175

Ser Pro Arg Leu Arg Cys Val Ile Ala Tyr Leu Leu Lys Asn Gly Cys
180 185 190

Gln Val Asn Lys Val Glu Glu Asp Pro Glu Ala Tyr Gln Arg Arg Arg
195 200 205

Arg Lys Lys Glu Ile Gln Ile Glu Arg Leu Lys Glu Gln Leu Lys Ser
210 215 220

Arg Leu Pro Lys Gly Arg Asn Leu Ser Glu Gln Glu Trp Leu Glu Ala
225 230 235 240

Leu Glu Gln Ala Gln Gly Leu Ile Ile Asp Asp Glu His Leu Arg Gln
245 250 255

Val Gln Ala Ser Leu Thr Arg Lys Gln Ser Pro Val Pro Phe Ser Ile
260 265 270

Ser Tyr Glu Thr Ser Thr Asp Leu Arg Trp Ser Ser Asn Glu Gln Gly
275 280 285

Arg Ile Cys Val Ser Phe Asn Gly Lys Gly Ile Ser Lys His Thr Phe
290 295 300

Glu Val Phe Cys Asp Gln Arg Gln Leu His Trp Phe Glu Arg Phe Tyr
305 310 315 320

Glu Asp Tyr Lys Ile Phe Thr Gln Asn Lys Asp Gln Val Pro Ala Gly
325 330 335

Leu Leu Thr Leu Arg Ser Ala Arg Leu Val Trp Gln Glu Gly Glu Gly
340 345 350

Glu Gly Glu Pro Trp Gln Val His Arg Leu Leu Leu His Cys Ser Val
355 360 365

Glu Thr Arg Leu Trp Thr Ala Gln Gly Thr Glu Glu Val Arg Ala Glu
370 375 380

Lys Ile Ala Gln Thr Gln Ala Ala Ile Asp Arg Gln Lys Ala Lys Gly
385 390 395 400

Thr Gln Ser Lys Lys Leu Asn Thr Ser Leu Glu Arg Leu Lys Thr Phe

```
                405                 410                 415

Gln Gly Phe Ser Arg Pro Ser Arg Ala Ser Tyr Lys Gly Asn Cys Ser
            420                 425                 430

Ile Val Ile Gly Val Ser Phe Gly Arg Ala Lys Pro Ala Thr Val Ala
        435                 440                 445

Val Val Asn Val Glu Thr Gly Glu Val Leu Ala Tyr Arg Asp Val Lys
    450                 455                 460

Gln Leu Leu Asn Lys Pro Ile Lys Glu Gly Lys Thr Lys Lys Lys Lys
465                 470                 475                 480

Thr Gln Tyr Glu Tyr Leu Lys Arg Arg Gln Glu Gln Gln Arg Leu Asn
                485                 490                 495

Ser His Gln Arg His Asn Ala Gln Lys Asn Gly Ala Pro Cys Asn Phe
            500                 505                 510

Gly Glu Ser Lys Gln Gly Glu Tyr Val Asp Arg Leu Leu Ala Lys Ala
        515                 520                 525

Ile Val Glu Val Ala Ser Gln Tyr Arg Ala Ser Ser Ile Val Leu Pro
    530                 535                 540

Asp Leu Arg Asn Ile Glu Glu Ala Ala Glu Ser Glu Val Arg Ala Arg
545                 550                 555                 560

Ala Glu Gln Lys Phe Pro Gly Asn Gln Lys Leu Gln Asp Ser Tyr Ala
                565                 570                 575

Lys Asp Tyr Arg Ala Ser Ile His Cys Trp Ser Tyr Ser Arg Leu Ala
            580                 585                 590

Gln Cys Ile Glu Leu Lys Ala Gly Lys Ala Gly Ile Ala Thr Glu Lys
        595                 600                 605

Val His Gln Pro His Gly Asp Thr Pro Gln Glu Lys Ala Arg Asp Leu
    610                 615                 620

Val Leu Ala Ala Tyr Ala Asn Arg Lys Val Ser Val Ser
625                 630                 635


<210> SEQ ID NO 164
<211> LENGTH: 637
<212> TYPE: PRT
<213> ORGANISM: Meiothermus silvanus

<400> SEQUENCE: 164

Met Ser Gln Ile Thr Ile Gln Cys Arg Leu Val Ala Thr Glu Ser Ala
1               5                   10                  15

Arg Gln Gln Met Trp Arg Leu Met Ala Glu Ile Asn Thr Pro Leu Ile
            20                  25                  30

Asn Glu Leu Leu Ala Gln Val Gly Gln His Pro Asp Phe Glu Gln Trp
        35                  40                  45

Arg Gln Lys Gly Lys Leu Pro Ser Thr Phe Ile Ser Gln Leu Ser Gln
    50                  55                  60

Ser Phe Lys Ser Asp Pro Arg Phe Leu Gly Gln Pro Ser Arg Phe Tyr
65                  70                  75                  80

Lys Ser Ala Phe Asn Ala Val Glu Tyr Ile Tyr Lys Ser Trp Leu Ala
                85                  90                  95

Leu Asn Lys Arg Leu Gln Gln Gln Leu Asp Arg Lys Arg Arg Trp Leu
            100                 105                 110

Glu Ile Leu Gln Ser Asp Thr Glu Leu Ala Ala Asp Ser Asn Cys Ser
        115                 120                 125

Leu Asp Ala Ile Arg Ser Lys Ala Ala Glu Ile Leu Ser Gln Ala Ile
    130                 135                 140
```

-continued

```
Gln Ala Pro Ser Leu Asp Ser Ser Pro Pro Arg Gly Lys Lys Gly Lys
145                 150                 155                 160

Lys Ser Lys Gly Arg Ser Ser Ser Ser Pro Val Ser Ser Leu Phe Ala
                165                 170                 175

Asn Leu Phe Lys Ala Tyr Gln Glu Thr Asp Asp Ile Lys Cys Arg Cys
            180                 185                 190

Ala Ile Ser Tyr Leu Leu Lys Asn Asn Cys Gln Leu Ser Asp Arg Glu
        195                 200                 205

Glu Asp Pro Glu Lys Phe Ala Lys Arg Arg Arg Lys Val Glu Ile Arg
    210                 215                 220

Ile Gln Arg Leu Thr Glu Lys Leu Asn Ser Arg Met Pro Asn Gly Arg
225                 230                 235                 240

Asp Leu Thr Asn Thr Arg Trp Leu Glu Thr Leu Ala Ile Ala Thr Thr
                245                 250                 255

Ser Val Pro Gln Asp Glu Ala Gln Ala Arg Gln Trp Gln Asp Val Leu
            260                 265                 270

Leu Thr Lys Pro Lys Ser Leu Pro Phe Pro Leu Ile Phe Glu Thr Asn
        275                 280                 285

Glu Asp Leu Phe Trp Ser Lys Asn Gln Gln Asp Arg Leu Cys Val His
    290                 295                 300

Phe Pro Gly Leu Arg Asp Leu Ala Phe Gln Val Tyr Cys Asp Arg Arg
305                 310                 315                 320

Gln Leu His Trp Phe His Arg Phe Leu Glu Asp Gln Gln Thr Lys His
                325                 330                 335

Ser Ser Lys Asn Gln His Ser Ser Ser Leu Phe Thr Leu Arg Ser Ala
            340                 345                 350

Tyr Leu Ala Trp Gln Gln Gly Lys Glu Lys Gly Glu Pro Trp Asn Thr
        355                 360                 365

His Tyr Leu Ile Leu Tyr Cys Cys Val Asp Thr Arg Leu Trp Thr Ala
    370                 375                 380

Glu Gly Thr Glu Leu Val Arg Gln Glu Lys Thr Ala Glu Ile Glu Lys
385                 390                 395                 400

Val Ile Asn Arg Thr Lys Ala Lys Asn Asp Leu Thr Glu Thr Gln Gln
                405                 410                 415

Ala Phe Ile Gln Arg Gln Lys Ser Thr Leu Ala Arg Ile Lys Gly His
            420                 425                 430

Phe Asp Arg Pro Ser Gln Ser Ile Tyr Gln Gly Gln Ser His Ile Leu
        435                 440                 445

Val Gly Val Ser Leu Gly Leu Asp Lys Pro Ala Thr Val Ala Val Val
    450                 455                 460

Asp Ala Ile Ala Glu Lys Val Leu Ala Tyr Arg Asn Thr Arg Gln Leu
465                 470                 475                 480

Leu Gly Asp Asn Tyr Lys Leu Leu Asn Arg Gln Arg Arg Gln Gln Arg
                485                 490                 495

Ser Leu Ser His Lys Arg His Lys Ala Gln Lys Arg Ala Asp Thr Asn
            500                 505                 510

Gln Phe Gly Glu Ser Glu Leu Gly Gln Tyr Val Glu Arg Leu Leu Ala
        515                 520                 525

Lys Glu Ile Val Ala Ile Ser Gln Asn Tyr Arg Ala Gly Ser Ile Val
    530                 535                 540

Leu Pro Lys Leu Gly Asp Met Gln Glu Ile Leu Thr Ser Glu Ile Gln
545                 550                 555                 560

Ala Arg Ala Glu Ala Lys Cys Pro Asn Tyr Val Glu Gly Gln Gln Lys
```

```
                565                 570                 575

Tyr Ala Lys Gln Tyr Arg Ile Ser Ile His Lys Trp Ser Tyr Gly Arg
            580                 585                 590

Leu Met Gln Asn Ile Gln Ser Gln Ala Ala Gln Ala Glu Ile Val Val
        595                 600                 605

Glu Glu Gly Lys Gln Leu Ile Arg Gly Ser Pro Gln Glu Met Ala Lys
    610                 615                 620

Glu Leu Ala Ile Ala Ala Tyr Gln Ser Arg Gln Pro Gln
625                 630                 635


<210> SEQ ID NO 165
<211> LENGTH: 636
<212> TYPE: PRT
<213> ORGANISM: Pseudonocardia asaccharolytica

<400> SEQUENCE: 165

Met Ser Val Ile Thr Ile Gln Cys Lys Leu Val Ala Thr Glu Glu Thr
1               5                   10                  15

Arg Arg Ala Leu Trp His Leu Met Ala Glu Lys His Thr Pro Leu Ile
            20                  25                  30

Asn Glu Leu Leu Lys His Ile Ala Gln Asp Ser Arg Phe Glu Glu Trp
        35                  40                  45

Ser Leu Thr Gly Lys Leu Pro Arg Leu Val Val Ser Glu Ala Cys Asn
    50                  55                  60

Gln Leu Lys Gln Asp Pro Gln Phe Ser Gly Gln Pro Gly Arg Phe Tyr
65                  70                  75                  80

Ser Ser Ala Ile Ser Thr Val His Arg Ile Phe Leu Ser Trp Leu Ala
                85                  90                  95

Leu Gln Thr Arg Leu Arg Asn Gln Ile Ser Gly Gln Thr Arg Trp Leu
            100                 105                 110

Ala Met Leu Gln Ser Asp Asn Glu Leu Thr Ile Ala Ser Gln Thr Asp
        115                 120                 125

Ile Asn Thr Leu Arg Leu Lys Ala Ser Glu Leu Leu Thr His Leu Asn
    130                 135                 140

Glu Pro Ile Ser Glu Ser Asp Gln Pro Glu Val Lys Lys Thr Arg Ser
145                 150                 155                 160

Lys Lys Lys Asn Gln Thr Ser Asn Gln Ala Gly Ala Asn Val Ser Arg
                165                 170                 175

Thr Leu Phe Lys Leu Tyr Asp Glu Thr Glu Asp Pro Leu Thr Arg Cys
            180                 185                 190

Ala Ile Ala Tyr Leu Leu Lys Asn Gly Cys Lys Leu Pro Asp Gln Asn
        195                 200                 205

Glu Asn Pro Glu Lys Phe Ile Lys Arg Arg Arg Lys Thr Glu Ile Arg
    210                 215                 220

Leu Glu Arg Leu Met Asn Thr Phe Gln Thr Thr Arg Ile Pro Arg Gly
225                 230                 235                 240

Arg His Leu Ser Trp His Ser Trp Ile Glu Ala Leu Glu Thr Ala Thr
                245                 250                 255

Ser His Ile Pro Glu Asn Glu Glu Glu Ala Ala Gly Trp Gln Ala Arg
            260                 265                 270

Leu Leu Thr Lys Pro Ala Ile Leu Pro Phe Pro Val Asn Tyr Glu Thr
        275                 280                 285

Asn Glu Asp Leu Arg Trp Ser Leu Asn Ser Gln Gly Arg Ile Cys Val
    290                 295                 300
```

Ser Phe Asn Gly Leu Ser Glu His Phe Phe Glu Val Tyr Cys Asp Gln
305 310 315 320

Arg Asp Leu His Trp Phe Asn Arg Phe Leu Glu Asp Gln Glu Thr Lys
325 330 335

Lys Ala Ser Lys Asn Gln His Ser Ser Ser Leu Phe Ser Leu Arg Ser
340 345 350

Gly Gln Ile Ala Trp Gln Glu Gly Lys Gly Asp Ala Glu His Trp Val
355 360 365

Val His Arg Leu Val Leu Ser Cys Ser Ile Glu Thr Asp Thr Trp Thr
370 375 380

Gln Glu Gly Thr Glu Glu Ile Arg Gln Lys Lys Ala Ser Asp Cys Ala
385 390 395 400

Lys Val Ile Ala Ser Thr Lys Ala Lys Glu Asn Arg Ser Gln Asn Gln
405 410 415

Asp Ala Phe Ile Arg Arg Arg Glu Arg Met Leu Glu Leu Leu Glu Asn
420 425 430

Gln Phe Pro Arg Pro Ser Tyr Pro Leu Tyr Gln Gly Gln Pro Ser Ile
435 440 445

Leu Ala Gly Val Ser Tyr Gly Leu Asp Lys Pro Ala Thr Leu Ala Ile
450 455 460

Val Asn Ile Gln Thr Gly Lys Ala Ile Thr Tyr Arg Ser Ile Arg Gln
465 470 475 480

Ile Leu Gly Lys Asn Tyr Lys Leu Leu Asn Arg Tyr Arg Leu Asn Gln
485 490 495

Gln Arg Asn Ala His Lys Arg His Asn Asn Gln Arg Lys Gly Gly Ser
500 505 510

Ser Gln Leu Arg Glu Ser Asn Gln Gly Gln Tyr Leu Asp Arg Leu Ile
515 520 525

Ala His Glu Ile Val Ala Ile Ala Gln Glu Tyr Gln Val Ser Ser Leu
530 535 540

Ala Leu Pro Asp Leu Gly Asp Ile Arg Glu Ile Val Gln Ser Glu Val
545 550 555 560

Gln Ala Arg Ala Glu Gln Lys Ile Leu Gly Ser Ile Glu Gln Gln Arg
565 570 575

Lys Tyr Ala Arg Gln Tyr Arg Ala Ser Val His Arg Trp Arg Tyr Ala
580 585 590

Gln Leu Thr Gln Phe Ile Gln Ser Gln Ala Ala Gln Val Gly Ile Ser
595 600 605

Ile Glu Ile Thr Lys Gln Pro Leu Ser Gly Thr Pro Gln Glu Lys Ala
610 615 620

Arg Asn Leu Ala Ile Ala Ala Tyr Gln Ser Arg Lys
625 630 635

<210> SEQ ID NO 166
<211> LENGTH: 635
<212> TYPE: PRT
<213> ORGANISM: Microcoleus sp.

<400> SEQUENCE: 166

Met Ser Gln Ile Thr Ile Gln Cys Arg Leu Val Ala Asn Val Ser Thr
1 5 10 15

Arg His Gln Ile Trp Thr Leu Met Ala Glu Arg Asn Thr Pro Leu Ile
20 25 30

Asn Glu Leu Leu Glu Gln Ile Gly Gln His Pro Asp Phe Glu Thr Trp
35 40 45

Arg Gln Lys Arg Lys Ile Pro Ala Gly Ile Ile Lys Gln Leu Cys Glu
50 55 60

Pro Leu Arg Thr Asp Ser Arg Phe Ile Gly Gln Pro Gly Arg Phe Tyr
65 70 75 80

Ala Ser Ala Ser Ala Leu Val Asp Tyr Ile Tyr Lys Ser Trp Leu Lys
85 90 95

Val Gln Gln Arg Leu Gln Arg Lys Leu Glu Gly Gln Met Arg Trp Leu
100 105 110

Gly Met Leu Lys Ser Asp Glu Glu Leu Val Asn Gln Ser Gly Cys Thr
115 120 125

Leu Glu Val Ile Arg Thr Lys Ala Ser Glu Ile Leu Val Pro Leu Thr
130 135 140

Ser Lys Asn Glu Ser Pro Gln Pro Thr Gln Thr Lys Gly Lys Lys Ser
145 150 155 160

Lys Lys Pro Gln Asp Leu Gly Ser Asn Arg Ser Ile Ser Lys Thr Leu
165 170 175

Phe Gln Val Tyr Asp Asp Ile Glu Asp Leu Leu Thr Lys Asn Ala Ile
180 185 190

Cys Tyr Leu Leu Lys Asn Gly Cys Lys Ile Pro Asp Gln Glu Glu Asp
195 200 205

Lys Glu Lys Phe Ala Lys Arg Arg Arg Lys Thr Glu Ile Lys Ile Ser
210 215 220

Arg Leu Glu Glu Gln Leu Ala Ser Arg Ile Pro Lys Gly Arg Asn Leu
225 230 235 240

Thr Gly Glu Lys Trp Leu Glu Thr Leu Ile Ala Ala Thr Ser Thr Val
245 250 255

Pro Glu Asn Glu Ser Gln Ala Arg Ser Trp Gln Asp Arg Leu Leu Thr
260 265 270

Lys Pro Gln Ser Val Pro Phe Pro Val Thr Tyr Glu Ser Asn Glu Asp
275 280 285

Leu Thr Trp Ser Lys Asn Ser Lys Gly Arg Leu Cys Val Lys Phe Asn
290 295 300

Gly Leu Ser Glu His Thr Phe Gln Ile Tyr Cys Asp Gln Arg Gln Leu
305 310 315 320

Lys Trp Phe Gln Arg Phe Leu Glu Asp Gln Gln Ile Lys Arg Glu Ser
325 330 335

Lys Asp Gln His Ser Ser Ser Leu Phe Thr Leu Arg Ser Gly Gln Ile
340 345 350

Ala Trp Ala Leu Gly Lys Gly Lys Gly Asp Ala Trp Asn Ile His His
355 360 365

Leu Thr Leu Tyr Cys Thr Leu Asp Thr Arg Leu Trp Thr Ala Glu Gly
370 375 380

Thr Glu Gln Val Arg Gln Glu Lys Ala Asp Asp Ile Ala Lys Thr Leu
385 390 395 400

Ala Arg Met Lys Glu Lys Gly Asp Leu Asn Asp Lys Gln Gln Ala Phe
405 410 415

Ile Lys Arg Lys Asn Ser Thr Leu Ala Arg Leu Asn Asn Pro Phe Pro
420 425 430

Arg Pro Ser Gln Pro Leu Tyr Gln Gly Arg Ser His Ile Ala Val Gly
435 440 445

Ile Ser Leu Gly Leu Gly Lys Pro Ala Thr Ala Ala Ile Val Asp Gly
450 455 460

-continued

```
Thr Thr Gly Glu Ala Ile Ala Tyr Arg Ser Ile Arg Gln Leu Leu Gly
465                 470                 475                 480

Asp Asn Tyr Lys Leu Phe Asn Arg Gln Arg Gln Glu Lys Gln Arg Gln
                485                 490                 495

Ser His Gln Arg His Lys Ala Gln Lys Asn Ala Thr Ser Asn Gln Phe
            500                 505                 510

Gly Glu Ser Glu Leu Gly Glu Tyr Val Asp Arg Leu Leu Ala Lys Glu
        515                 520                 525

Ile Val Thr Leu Ala Gln Thr Tyr Gln Ala Gly Ser Ile Val Leu Pro
    530                 535                 540

Lys Leu Gly Asp Met Arg Glu Leu Val His Ser Glu Ile Gln Thr Arg
545                 550                 555                 560

Ala Glu Gln Lys Ile Pro Ser Tyr Val Glu Gly Gln Gln Lys Tyr Ala
                565                 570                 575

Lys Gln Tyr Arg Val Asn Val His Gln Trp Ser Tyr Gly Arg Leu Ile
            580                 585                 590

Glu Asn Ile Gln Val Gln Ala Ala Lys Ile Gly Ile Ser Ile Glu Gln
        595                 600                 605

Gly Gln Gln Pro Val Arg Gly Ser Pro Gln Glu Lys Ala Lys Glu Met
    610                 615                 620

Ala Ile Ala Ala Tyr His Ser Arg Leu Asn Pro
625                 630                 635


<210> SEQ ID NO 167
<211> LENGTH: 616
<212> TYPE: PRT
<213> ORGANISM: Clostridium novyi

<400> SEQUENCE: 167

Met Ala His Val Thr Ile Gln Cys Arg Leu Ile Ala Ser Arg Asp Thr
1               5                   10                  15

Arg Gln Phe Leu Trp Gln Leu Met Ala Gln Lys Asn Thr Pro Leu Ile
            20                  25                  30

Asn Glu Ile Leu Leu Arg Ile Lys Gln His Pro Asp Phe Pro His Trp
        35                  40                  45

Arg Thr Lys Lys Arg Leu Pro Lys Asp Phe Leu Ala Arg Gln Ile Ala
    50                  55                  60

Glu Leu Lys Asn Asn Tyr Pro Phe Glu Glu Gln Pro Ser Arg Phe Tyr
65                  70                  75                  80

Ala Ser Val Asn Lys Val Ile Asp Tyr Ile Tyr Lys Ser Trp Phe Glu
                85                  90                  95

Val Gln Lys Ala Leu Asp Trp Lys Leu Gln Gly Asn Leu Arg Trp Val
            100                 105                 110

Glu Met Leu Leu Pro Asp Thr Glu Leu Ile Lys His Phe Asp Asn Ser
        115                 120                 125

Leu Glu Ser Leu Gln Gln Gln Ala Thr Leu Ile Leu Asp Ser Ile Asp
    130                 135                 140

Ser Thr Val Ser His Asp Arg Ile Ser Thr Ile Leu Phe Glu Lys Cys
145                 150                 155                 160

Gly Lys Thr Lys Lys Pro Glu Ile Lys Ser Ala Ile Ile Tyr Leu Leu
                165                 170                 175

Lys Asn Gly Cys Thr Ile Pro Lys Lys Pro Glu Thr Thr Glu Lys Tyr
            180                 185                 190

Gln Asp Leu Lys Arg Lys Val Glu Ile Lys Ile Thr Lys Leu His Arg
        195                 200                 205
```

-continued

```
Gln Ile Glu Ser Arg Ile Pro Leu Gly Arg Asp Leu Glu Asp Lys Lys
    210                 215                 220

Trp Leu Asp Thr Leu Ile Thr Ala Ser Thr Thr Ala Pro Ile Asp Gln
225                 230                 235                 240

Thr Glu Ala Asn Thr Trp Phe Ser Ile Leu Lys Gln Asn Gln Ser Ser
                245                 250                 255

Ile Pro Tyr Pro Ile Leu Tyr Glu Thr Asn Glu Asp Leu Lys Trp Ser
            260                 265                 270

Leu Asn Glu Lys Asn Arg Leu Ser Ile Arg Phe Ser Gly Leu Gly Glu
        275                 280                 285

His Ser Phe Gln Leu Cys Cys Asp His Arg Gln Leu Pro Tyr Phe Gln
    290                 295                 300

Arg Phe Tyr Glu Asp Gln Glu Leu Lys Lys Ala Ser Lys Asp Gln Leu
305                 310                 315                 320

Ser Ser Ala Leu Phe Thr Leu Arg Ser Ala Met Ile Leu Trp Lys Glu
                325                 330                 335

Asp Glu Gly Lys Gly Glu Leu Trp Asp Arg His Lys Leu Tyr Leu His
            340                 345                 350

Cys Thr Phe Glu Thr Arg Cys Leu Thr Ala Glu Gly Thr Ser Thr Ile
        355                 360                 365

Val Glu Glu Lys Gln Lys Glu Val Thr Lys Ile Ile Asp Leu Met Lys
    370                 375                 380

Ala Lys Glu Glu Leu Ser Asp Ser Gln Gln Ala Phe Ile Arg Arg Lys
385                 390                 395                 400

Asn Ser Thr Leu Ala Lys Leu Asn Asn Thr Phe Pro Arg Pro Ser Lys
                405                 410                 415

Pro Val Tyr Gln Gly Lys Pro Asn Val His Leu Gly Ile Ala Met Gly
            420                 425                 430

Leu Glu Gln Pro Val Thr Ile Ala Ile Val Asp Ile Glu Thr Asp Lys
        435                 440                 445

Val Ile Thr Tyr Arg Asn Thr Lys Gln Leu Leu Arg Glu Asp Tyr Arg
    450                 455                 460

Leu Leu Arg Arg Arg Arg Ile Glu Lys Gln Lys Leu Ser His Gln Asn
465                 470                 475                 480

His Lys Ala Arg Lys Arg Phe Asn Phe Gln Gln Lys Gly Glu Ser Asn
                485                 490                 495

Leu Gly Glu Tyr Leu Asp Arg Leu Ile Ala Lys Ala Ile Leu Thr Val
            500                 505                 510

Ala Gln Glu Tyr Gln Val Ser Thr Ile Leu Ile Pro Arg Leu Arg Asp
        515                 520                 525

Met Arg Ser Ile Thr Glu Ala Glu Ile Gln Leu Arg Ala Glu Lys Lys
    530                 535                 540

Ile Pro Glu Tyr Lys Glu Gly Gln Lys Lys Tyr Ala Gln Asp Tyr Arg
545                 550                 555                 560

Val Gln Val His Gln Trp Ser Tyr Gly Arg Leu Ile Glu Asn Val Lys
                565                 570                 575

Leu Ile Cys Glu Lys Val Gly Ile Val Val Val Glu Ala Lys Gln Pro
            580                 585                 590

Lys Gln Gly Thr Leu Thr Glu Lys Ala Leu Gln Leu Val Leu Ser Ala
        595                 600                 605

Thr Glu Lys Asn Leu Lys Lys Lys
    610                 615
```

<210> SEQ ID NO 168
<211> LENGTH: 615
<212> TYPE: PRT
<213> ORGANISM: Sulfolobus islandicus

<400> SEQUENCE: 168

```
Met Ser Gln Asn Ala Ile Gln Cys Arg Leu Ile Ala Pro Glu Thr Thr
1               5                   10                  15

Arg Arg Gln Gln Trp Gln Leu Met Ala Glu Lys Asn Thr Pro Leu Ile
            20                  25                  30

Asn Glu Leu Leu Lys Gln Leu Ala Glu His Pro Glu Leu Glu Thr Trp
        35                  40                  45

Lys Arg Lys Gly Lys Ile Pro Pro Gly Thr Val Lys Asn Leu Cys Gln
    50                  55                  60

Pro Leu Arg Thr Cys Pro Gln Tyr Ile Asn Gln Pro Gly Arg Phe Tyr
65                  70                  75                  80

Ser Ser Val Ile Ser Leu Ala Glu Tyr Ile Tyr Arg Ser Trp Leu Lys
                85                  90                  95

Leu Gln Arg Arg Leu Ile Phe Arg Leu Asn Gly Gln Gln Arg Trp Leu
            100                 105                 110

Gln Met Leu Lys Ser Asp Glu Glu Leu Val Ala Glu Ser Gly Arg Ser
        115                 120                 125

Leu Lys Glu Ile Glu Ala Lys Ala Ser Glu Ala Leu Asp Arg Leu Asn
    130                 135                 140

Arg Glu Glu Asn Pro Ser Ile Ser Asn Arg Leu Phe Asp Leu Tyr Asp
145                 150                 155                 160

Glu Thr Glu Asp Ile Leu Ile Arg Ser Ala Ile Val Tyr Leu Leu Lys
                165                 170                 175

Asn Gly Cys Lys Ile Arg Gln Lys Pro Glu Asp Pro Lys Lys Phe Ala
            180                 185                 190

Arg Arg Arg Arg Lys Thr Glu Ile Arg Val Lys Arg Leu Gln Glu Lys
        195                 200                 205

Leu Asn Gly Lys Ala Pro Gln Gly Arg Asp Leu Thr Gly Glu Lys Trp
    210                 215                 220

Leu Asn Thr Leu Phe Thr Ala Thr Ser Gln Val Pro Gln Asp Glu Ala
225                 230                 235                 240

Gln Ala Lys Ser Trp Gln Asp Ile Leu Leu Thr Lys Ser Lys Leu Val
                245                 250                 255

Pro Tyr Pro Ile Val Tyr Glu Ser Asn Glu Asp Leu Thr Trp Ser Lys
            260                 265                 270

Asn Glu Arg Gly Arg Leu Cys Val Lys Phe Asn Gly Leu Ser Asp His
        275                 280                 285

Thr Phe Gln Ile Tyr Cys Asp Arg Arg Gln Leu Lys Ile Phe Asn Arg
    290                 295                 300

Phe Tyr Glu Asp Gln Gln Ile Lys Lys Ala Ser Lys Asn Ser His Ser
305                 310                 315                 320

Ser Ala Leu Phe Thr Leu Arg Ser Ala Thr Ile Ala Trp Gln Glu Gly
                325                 330                 335

Lys Gly Lys Gly Glu Pro Trp Asn Val Asn Arg Leu Ile Leu Tyr Cys
            340                 345                 350

Thr Phe Asp Asn Leu Leu Leu Thr Thr Glu Gly Thr Glu Val Val Arg
        355                 360                 365

Gln Glu Lys Ala Glu Ala Ile Ala Asn Thr Leu Thr Lys Ile Lys Glu
    370                 375                 380
```

```
Lys Gly Asp Leu Asn Gln Lys Gln Gln Ala Phe Ile Arg Arg Lys Glu
385                 390                 395                 400

Thr Ser Leu Ser Arg Ile Asn Asn Pro Phe Pro Arg Pro Ser Arg Pro
                405                 410                 415

Leu Tyr Lys Gly Lys Ser Asn Ile Leu Leu Gly Val Ala Ile Arg Leu
            420                 425                 430

Asp Lys Pro Ala Thr Val Ala Ile Val Asp Gly Ala Thr Asp Lys Ala
        435                 440                 445

Ile Ala Tyr Leu Ser Thr Lys Gln Leu Leu Gly Lys Asn Tyr His Leu
    450                 455                 460

Leu Asn Arg Lys Arg Gln Gln Gln His Ile Leu Ser His Gln Arg Asn
465                 470                 475                 480

Val Ala Gln Arg His His Ala Asn Asn Lys Phe Gly Glu Ser Glu Leu
                485                 490                 495

Gly Gln Tyr Ile Asp Arg Leu Leu Ala Lys Ala Ile Ile Gln Leu Ala
            500                 505                 510

Lys Asp Tyr Arg Val Gly Ser Ile Val Val Pro Tyr Met Glu Asp Thr
        515                 520                 525

Arg Glu Ile Ile Gln Ala Glu Val Gln Ala Arg Ala Glu Ala Lys Ile
    530                 535                 540

Pro Gly Cys Ile Glu Lys Gln Lys Glu Tyr Ala Lys Lys Tyr Arg Thr
545                 550                 555                 560

Asn Ile His Lys Trp Ser Tyr Gly Arg Leu Ile Asp Leu Ile Lys Ala
                565                 570                 575

Gln Ala Ala Lys Ala Gly Ile Val Ile Glu Glu Ser Lys Gln Ser Ile
            580                 585                 590

Arg Gly Asp Pro Lys Lys Gln Ala Lys Glu Ile Ala Val Cys Ala Tyr
        595                 600                 605

Arg Asp Arg Ile Val Pro Phe
    610                 615


<210> SEQ ID NO 169
<211> LENGTH: 614
<212> TYPE: PRT
<213> ORGANISM: Crinalium epipsammum

<400> SEQUENCE: 169

Met Ser Gln Ile Thr Val Gln Cys Arg Leu Val Ala Ser Glu Ser Thr
1               5                   10                  15

Arg His His Leu Trp Lys Leu Met Ala Asp Leu Asn Thr Pro Leu Ile
            20                  25                  30

Asn Glu Leu Leu Ala Arg Met Ala Gln His Gln Asp Phe Glu Thr Trp
        35                  40                  45

Arg Lys Lys Gly Lys Leu Pro Asp Gly Ile Val Lys Gln Leu Tyr Gln
    50                  55                  60

Pro Leu Lys Thr Asp Pro Arg Phe Thr Asn Gln Pro Gly Arg Phe Tyr
65                  70                  75                  80

Thr Ser Ala Ile Thr Val Val Asp Tyr Ile Tyr Lys Ser Trp Phe Lys
                85                  90                  95

Ile Gln Gln Arg Leu Glu Gln Lys Leu Lys Gly Gln Ile Arg Trp Leu
            100                 105                 110

Gly Met Leu Lys Ser Asp Glu Glu Leu Ala Ala Glu Ser Asn Thr Ser
        115                 120                 125

Ile Glu Val Ile Arg Thr Asn Ala Ala Glu Leu Ile Thr Ser Leu Ser
```

-continued

```
    130                 135                 140

Ser Glu Asp Gly Ser Val Ser Thr Arg Leu Trp Lys Thr Tyr Asp Glu
145                 150                 155                 160

Thr Asp Asp Ile Leu Thr His Cys Val Ile Cys Tyr Leu Leu Lys Asn
                165                 170                 175

Gly Ser Lys Val Pro Lys Lys Pro Glu Glu Asn Leu Glu Lys Phe Ala
            180                 185                 190

Lys Arg Arg Arg Lys Val Glu Ile Lys Ile Glu Arg Leu Arg Arg Gln
        195                 200                 205

Leu Glu Ser Arg Ile Pro Lys Gly Arg Asp Leu Thr Gly Lys Asn Trp
    210                 215                 220

Leu Glu Thr Leu Ala Ile Ala Ser Thr Thr Ala Pro Ala Asp Glu Pro
225                 230                 235                 240

Glu Ala Gln Ser Trp Gln Asp Thr Leu Leu Thr Glu Ser Lys Leu Val
                245                 250                 255

Pro Phe Pro Val Ala Tyr Glu Thr Asn Glu Asn Leu Thr Trp Ser Lys
            260                 265                 270

Asn Glu Lys Gly Arg Leu Cys Val Gln Ile Ser Gly Leu Ser Lys His
        275                 280                 285

Ile Phe Gln Ile Tyr Cys Asp Gln Arg Gln Leu Lys Trp Phe Gln Arg
    290                 295                 300

Phe Tyr Glu Asp Gln Glu Ile Lys Lys Ala Asn Lys Asp Gln Tyr Ser
305                 310                 315                 320

Ser Gly Leu Phe Thr Leu Arg Ser Gly Arg Ile Ala Trp Gln Glu Gly
                325                 330                 335

Thr Asp Lys Gly Glu Pro Trp Asn Ile His His Leu Ile Leu Tyr Cys
            340                 345                 350

Thr Val Asp Thr Arg Leu Trp Thr Ala Glu Gly Thr Glu Gln Val Cys
        355                 360                 365

Gln Glu Lys Ala Glu Asp Ile Ala Lys Thr Leu Thr Arg Met Lys Lys
    370                 375                 380

Lys Gly Asp Leu Asn Asp Arg Gln Gln Ala Phe Ile Arg Arg Gln Gln
385                 390                 395                 400

Ser Thr Leu Ala Arg Leu Asn Asn Pro Tyr Pro Arg Pro Ser Gln Pro
                405                 410                 415

Leu Tyr Gln Gly Gln Pro His Ile Leu Val Gly Leu Ala Phe Gly Leu
            420                 425                 430

Asp Lys Pro Ala Thr Ala Ala Val Val Asp Gly Thr Thr Gly Lys Ala
        435                 440                 445

Ile Thr Tyr Arg Ser Leu Lys Gln Leu Leu Gly Asp Asn Tyr Glu Leu
    450                 455                 460

Leu Asn Lys Gln Arg Lys Arg Lys Gln Gln Gln Ser His Gln Arg His
465                 470                 475                 480

Lys Ala Gln Ser Asn Gly Arg Ser Asn Gln Phe Gly Asp Ser Asp Leu
                485                 490                 495

Gly Glu Tyr Val Asp Arg Leu Leu Ala Lys Ala Leu Val Thr Leu Ala
            500                 505                 510

Gln Ser Tyr Gln Ala Gly Ser Ile Val Leu Pro Lys Leu Gly Asp Ile
        515                 520                 525

Arg Glu Leu Ile Gln Ser Glu Ile Gln Ala Lys Ala Glu Gln Lys Ile
    530                 535                 540

Pro Gly Tyr Ile Ala Gly Gln Glu Lys Tyr Ala Lys Gln Tyr Lys Ile
545                 550                 555                 560
```

Ser Val His Gln Trp Ser Tyr Gly Arg Leu Ile Asp Asn Ile Lys Ala
565 570 575

Gln Ala Ala Lys Ile Ser Ile Val Ile Glu Glu Gly Gln Gln Pro Ile
580 585 590

Arg Gly Ser Pro Gln Glu Lys Ala Lys Glu Met Ala Ile Ser Ala Tyr
595 600 605

Asp Asp Arg Thr Lys Ser
610

<210> SEQ ID NO 170
<211> LENGTH: 612
<212> TYPE: PRT
<213> ORGANISM: Dermacoccus sp.

<400> SEQUENCE: 170

Met Ser Gln Ile Thr Ile Gln Cys Arg Leu Val Ala Lys Glu Ala Thr
1 5 10 15

Arg Gln Thr Leu Trp Gln Leu Met Ala Glu Leu Asn Thr Pro Phe Ile
20 25 30

Asn Glu Leu Leu Gln Gln Val Ala Gln Tyr Pro Asp Phe Glu Gln Trp
35 40 45

Arg Gln Arg Gly Arg Leu Thr Ala Lys Val Ile Glu Gln Leu Gly Asn
50 55 60

Glu Leu Lys Lys Asp Pro Arg Phe Leu Gly Gln Pro Ala Arg Phe Tyr
65 70 75 80

Thr Ser Gly Ile Ser Leu Val Glu Tyr Ile Phe Lys Ser Trp Leu Lys
85 90 95

Leu Gln Gln Arg Leu Gln Arg Lys Leu Asp Gly Lys Arg Arg Trp Leu
100 105 110

Glu Val Leu Lys Ser Asp Glu Gln Leu Ile Lys Asp Ser Gln Thr Asp
115 120 125

Leu Glu Thr Ile Arg Gln Lys Ala Thr Glu Ile Leu Gln Ser Tyr Glu
130 135 140

Gly Thr Glu Arg Leu Phe Asn Ser Leu Phe Gln Ala Tyr Arg Asp Glu
145 150 155 160

Gln Asn Ile Leu Thr Gln Thr Ala Leu Asn Tyr Leu Leu Lys Asn Arg
165 170 175

Cys Gln Leu Pro Lys Lys Pro Glu Asp Ala Lys Lys Phe Ala Lys Arg
180 185 190

Arg Arg Lys Val Glu Ile Thr Ile Lys Arg Leu Gln Lys Gln Ile Asn
195 200 205

Gly Arg Leu Pro Gln Gly Arg Asp Leu Thr Asn Asp Asn Trp Leu Glu
210 215 220

Thr Leu Asn Leu Ala Cys Asp Thr Asp Pro Lys Asp Val Glu Gln Ser
225 230 235 240

Arg Thr Trp Gln Asp Lys Leu Leu Lys Lys Ser Gln Ser Ile Pro Phe
245 250 255

Pro Ile Asn Tyr Glu Thr Asn Glu Asp Leu Thr Trp Ser Lys Asn Glu
260 265 270

Lys Gly Arg Phe Cys Val Gln Phe Asn Gly Ile Ser Asp Leu Lys Phe
275 280 285

Glu Ile Tyr Cys Asp Gln Arg Gln Leu Lys Trp Ile Gln Arg Phe Tyr
290 295 300

Glu Asp Gln Gln Val Lys Lys Asp Gly Lys Asp Gln His Ser Ser Gly

-continued

```
305                 310                 315                 320

Leu Phe Thr Leu Arg Ser Gly Arg Ile Leu Trp Gln Glu Gly Lys Gly
                325                 330                 335

Lys Gly Glu Leu Trp Asp Ile His Arg Leu Thr Leu Gln Cys Thr Leu
            340                 345                 350

Glu Thr Arg Cys Trp Thr His Glu Gly Thr Glu Gln Val Lys Gln Glu
        355                 360                 365

Lys Ala Asp Glu Ile Ala Gly Ile Leu Thr Arg Met Asn Glu Lys Gly
    370                 375                 380

Asp Leu Thr Lys Asn Gln Lys Ala Phe Val Arg Arg Lys Gln Ser Thr
385                 390                 395                 400

Leu Asn Arg Leu Glu Lys Pro Phe Pro Arg Pro Ser Gln Pro Leu Tyr
                405                 410                 415

Gln Gly Lys Ser Asn Ile Leu Val Gly Val Ser Met Glu Leu Lys Lys
            420                 425                 430

Pro Ala Thr Ile Ala Val Ile Asp Gly Val Thr Arg Lys Val Leu Thr
        435                 440                 445

Tyr Arg Asn Ile Lys Gln Leu Leu Gly Lys Asn Tyr Pro Leu Leu Asn
    450                 455                 460

Arg Gln Gln Arg Gln Lys Gln Arg Gln Ser His Gln Arg Asn Ile Ala
465                 470                 475                 480

Gln Arg Lys Glu Ala Phe Asn Gln Phe Gly Asp Ser Glu Leu Gly Gln
                485                 490                 495

His Ile Asp Arg Leu Leu Ala Lys Ala Ile Ile Ser Ile Ala Gln Lys
            500                 505                 510

Tyr Gln Ala Gly Ser Ile Val Val Pro Lys Leu Glu Asp Ile Arg Glu
        515                 520                 525

Ala Thr Gln Ser Glu Ile Gln Ala Lys Ala Glu Ala Lys Ile Pro Asn
    530                 535                 540

Cys Ile Glu Ala Gln Ala Glu Tyr Ala Lys Lys Tyr Arg Met Gln Val
545                 550                 555                 560

His Glu Trp Ser Tyr Gly Arg Leu Ile Asp Asn Ile Gln Ala Gln Ala
                565                 570                 575

Ser Lys Leu Gly Ile Phe Ile Glu Glu Ser Gln Gln Pro Leu Gln Gly
            580                 585                 590

Thr Pro Leu Gln Lys Ala Ala Glu Leu Ala Phe Lys Ala Tyr Arg Ser
        595                 600                 605

Arg Leu Ser Ala
    610
```